US008415407B2

(12) United States Patent
Beyar et al.

(10) Patent No.: US 8,415,407 B2
(45) Date of Patent: Apr. 9, 2013

(54) METHODS, MATERIALS, AND APPARATUS FOR TREATING BONE AND OTHER TISSUE

(75) Inventors: Mordechay Beyar, Caesarea (IL); Oren Globerman, Kfar-Shmaryahu (IL); Ronen Shavit, Tel-Aviv (IL); Hila Wachsler-Avrahami, Tel-Aviv (IL)

(73) Assignee: DePuy Spine, Inc., Raynham, MA (US)

( * ) Notice: Subject to any disclaimer, the term of this patent is extended or adjusted under 35 U.S.C. 154(b) by 582 days.

(21) Appl. No.: 11/360,251

(22) Filed: Feb. 22, 2006

(65) Prior Publication Data

US 2007/0027230 A1    Feb. 1, 2007

Related U.S. Application Data

(63) Continuation-in-part of application No. 11/194,411, filed on Aug. 1, 2005, and a continuation-in-part of application No. PCT/IL2005/000812, filed on Jul. 31, 2005.

(60) Provisional application No. 60/765,484, filed on Feb. 2, 2006, provisional application No. 60/762,789, filed on Jan. 26, 2006, provisional application No. 60/763,003, filed on Jan. 26, 2006, provisional application No. 60/738,556, filed on Nov. 22, 2005, provisional application No. 60/729,505, filed on Oct. 25, 2005, provisional application No. 60/720,725, filed on Sep. 28, 2005, provisional application No. 60/721,094, filed on Sep. 28, 2005, provisional application No. 60/647,784, filed on Jan. 31, 2005, provisional application No. 60/592,149, filed on Jul. 30, 2004, provisional application No. 60/654,495, filed on Feb. 22, 2005.

(51) Int. Cl.
*A61B 17/58* (2006.01)

(52) U.S. Cl.
USPC .......................................... 523/117; 606/94

(58) Field of Classification Search .................. None
See application file for complete search history.

(56) References Cited

U.S. PATENT DOCUMENTS

| | | | |
|---|---|---|---|
| 229,932 A | 7/1880 | Witsil | |
| 370,335 A | 9/1887 | Hunter | |
| 817,973 A | 4/1906 | Hausman | |
| 833,044 A | 10/1906 | Goodhugh | |
| 843,587 A | 2/1907 | DePew | |
| 1,175,530 A | 3/1916 | Kirchoff | |
| 1,612,281 A | 12/1926 | Goetz | |
| 1,612,996 A | 1/1927 | Waagbo | |
| 1,733,516 A | 10/1929 | Jamison | |
| 1,894,274 A | 1/1933 | Jacques | |
| 2,123,712 A | 7/1938 | Clark | |
| 2,283,915 A | 5/1942 | Cole | |
| 2,394,488 A | 2/1946 | Rotter et al. | |
| 2,425,867 A | 8/1947 | Davis | |
| 2,435,647 A | 2/1948 | Engseth | |
| 2,497,762 A | 2/1950 | Davis | |
| 2,521,569 A | 9/1950 | Davis | |
| 2,567,960 A | 9/1951 | Meyers et al. | |
| 2,745,575 A | 5/1956 | Spencer | |
| 2,773,500 A | 12/1956 | Young | |
| 2,808,239 A | 10/1957 | Alfred | |
| 2,874,877 A | 2/1959 | Spencer | |
| 2,918,841 A | 12/1959 | Poupitch | |
| 2,928,574 A | 3/1960 | Wagner | |
| 2,970,773 A | 2/1961 | Horace et al. | |
| 3,058,413 A | 11/1962 | Cavalieri | |
| 3,063,449 A | 11/1962 | Schultz | |
| 3,075,746 A | 1/1963 | Yablonski et al. | |
| 3,108,593 A | 10/1963 | Glassman | |
| 3,151,847 A | 10/1964 | Broomall | |
| 3,198,194 A | 8/1965 | Wilburn | |
| 3,216,616 A | 11/1965 | Blankenship, Jr. | |
| 3,224,744 A | 12/1965 | Broomall | |
| 3,225,760 A | 12/1965 | DiCosola | |
| 3,254,494 A | 6/1966 | Chartouni | |
| 3,381,566 A | 5/1968 | Passer | |
| 3,426,364 A | 2/1969 | Lumb | |
| 3,515,873 A | 6/1970 | Higgins | |
| 3,568,885 A | 3/1971 | Spencer | |
| 3,572,556 A | 3/1971 | Pogacar | |
| 3,615,240 A | 10/1971 | Sanz | |
| 3,674,011 A | 7/1972 | Michel et al. | |
| 3,701,350 A | 10/1972 | Guenther | |
| 3,750,667 A | 8/1973 | Pshenichny et al. | |
| 3,789,727 A | 2/1974 | Moran | |
| 3,796,303 A | 3/1974 | Allet-Coche | |
| 3,798,982 A | 3/1974 | Lundquist | |
| 3,846,846 A | 11/1974 | Fischer | |
| 3,850,158 A | 11/1974 | Elias et al. | |
| 3,867,728 A | 2/1975 | Stubstad et al. | |
| 3,873,008 A | 3/1975 | Jahn | |
| 3,875,595 A | 4/1975 | Froning | |
| 3,896,504 A | 7/1975 | Fischer | |
| 3,901,408 A | 8/1975 | Boden et al. | |

(Continued)

FOREIGN PATENT DOCUMENTS

| | | |
|---|---|---|
| AU | 724544 | 11/1996 |
| AU | 9865136 | 9/1998 |

(Continued)

OTHER PUBLICATIONS

MEDSAFE PALACOS R® 2007. Data Sheet: PALACOS R® Bone Cement with Garamycin, pp. 1-7; http://www.medsafe.govt.nz/profs/datasheet/p/palacosbonecements.htm.*

(Continued)

*Primary Examiner* — Suzanne Ziska
(74) *Attorney, Agent, or Firm* — Nutter McClennen & Fish LLP

(57) ABSTRACT

A bone cement comprising a first component and a second component, wherein contacting the first component and the second component produces a mixture which attains a high viscosity an initial period and the viscosity of the mixture remains relatively stable for a working time of at least 5 minutes after the initial setting period, and the mixture is suitable for in-vivo use.

9 Claims, 57 Drawing Sheets

U.S. PATENT DOCUMENTS

| | | |
|---|---|---|
| 3,921,858 A | 11/1975 | Bemm |
| 3,931,914 A | 1/1976 | Hosaka et al. |
| 3,942,407 A | 3/1976 | Mortensen |
| 3,976,060 A | 8/1976 | Hildenbrandt et al. |
| 3,993,250 A | 11/1976 | Shure |
| 4,011,602 A | 3/1977 | Rybicki et al. |
| 4,077,494 A | 3/1978 | Spaude et al. |
| 4,079,917 A | 3/1978 | Popeil |
| 4,090,640 A | 5/1978 | Smith et al. |
| 4,093,576 A | 6/1978 | Dewijn |
| 4,105,145 A | 8/1978 | Capra |
| 4,115,346 A | 9/1978 | Gross et al. |
| 4,146,334 A | 3/1979 | Farrell |
| 4,168,787 A | 9/1979 | Stamper |
| 4,170,990 A | 10/1979 | Baumgart et al. |
| 4,185,072 A | 1/1980 | Puderbaugh et al. |
| 4,189,065 A | 2/1980 | Herold |
| 4,198,975 A | 4/1980 | Haller |
| 4,204,531 A | 5/1980 | Aginsky |
| 4,239,113 A | 12/1980 | Gross et al. |
| 4,250,887 A | 2/1981 | Dardik et al. |
| 4,257,540 A | 3/1981 | Wegmann et al. |
| 4,268,639 A | 5/1981 | Seidel et al. |
| 4,274,163 A | 6/1981 | Malcolm et al. |
| 4,276,878 A | 7/1981 | Storz |
| 4,277,184 A | 7/1981 | Solomon |
| 4,298,144 A | 11/1981 | Pressi |
| 4,309,777 A | 1/1982 | Patil |
| 4,312,343 A | 1/1982 | LeVeen et al. |
| 4,313,434 A | 2/1982 | Segal |
| 4,326,567 A | 4/1982 | Mistarz |
| 4,338,925 A | 7/1982 | Miller |
| 4,341,691 A | 7/1982 | Anuta |
| 4,346,708 A | 8/1982 | LeVeen et al. |
| 4,349,921 A | 9/1982 | Kuntz |
| 4,359,049 A | 11/1982 | Redl et al. |
| 4,373,217 A | 2/1983 | Draenert |
| 4,380,398 A | 4/1983 | Burgess |
| 4,400,170 A | 8/1983 | McNaughton et al. |
| 4,403,989 A | 9/1983 | Christensen et al. |
| 4,404,327 A | 9/1983 | Crugnola et al. |
| 4,405,249 A | 9/1983 | Scales |
| 4,409,966 A | 10/1983 | Lambrecht et al. |
| 4,453,539 A | 6/1984 | Raftopoulos et al. |
| 4,474,572 A | 10/1984 | McNaughton et al. |
| 4,475,856 A | 10/1984 | Toomingas |
| 4,476,866 A | 10/1984 | Chin |
| 4,487,602 A | 12/1984 | Christensen et al. |
| 4,494,535 A | 1/1985 | Haig |
| 4,500,658 A | 2/1985 | Fox |
| 4,503,169 A | 3/1985 | Randklev |
| 4,522,200 A | 6/1985 | Stednitz |
| D279,499 S | 7/1985 | Case |
| 4,543,966 A | 10/1985 | Islam et al. |
| 4,546,767 A | 10/1985 | Smith |
| 4,554,914 A | 11/1985 | Kapp et al. |
| 4,558,693 A | 12/1985 | Lash et al. |
| 4,562,598 A | 1/1986 | Kranz |
| 4,576,152 A | 3/1986 | Miller et al. |
| 4,588,583 A | 5/1986 | Pietsch et al. |
| 4,593,685 A | 6/1986 | McKay et al. |
| 4,595,006 A | 6/1986 | Burke et al. |
| 4,600,118 A | 7/1986 | Martin |
| 4,605,011 A | 8/1986 | Naslund |
| 4,632,101 A | 12/1986 | Freedland |
| 4,636,217 A | 1/1987 | Ogilivie et al. |
| 4,642,099 A | 2/1987 | Phillips et al. |
| 4,650,469 A | 3/1987 | Berg et al. |
| 4,651,904 A | 3/1987 | Schuckmann |
| 4,653,487 A | 3/1987 | Maale |
| 4,653,489 A | 3/1987 | Tronzo et al. |
| 4,664,298 A | 5/1987 | Shew |
| 4,664,655 A | 5/1987 | Orentreich et al. |
| 4,668,220 A | 5/1987 | Hawrylenko |
| 4,668,295 A | 5/1987 | Bajpai |
| 4,670,008 A | 6/1987 | Von Albertini |
| 4,671,263 A | 6/1987 | Draenert |
| 4,676,655 A | 6/1987 | Handler |
| 4,676,781 A | 6/1987 | Phillips et al. |
| 4,686,973 A | 8/1987 | Frisch |
| 4,697,584 A | 10/1987 | Haynes |
| 4,697,929 A | 10/1987 | Muller |
| 4,704,035 A | 11/1987 | Kowalczyk |
| 4,710,179 A | 12/1987 | Haber et al. |
| 4,714,721 A | 12/1987 | Franek et al. |
| 4,717,383 A | 1/1988 | Phillips et al. |
| 4,718,910 A | 1/1988 | Draenert |
| 4,722,948 A | 2/1988 | Sanderson |
| 4,735,616 A | 4/1988 | Eibl et al. |
| 4,737,151 A | 4/1988 | Clement et al. |
| 4,747,832 A | 5/1988 | Buffet |
| 4,758,096 A | 7/1988 | Gunnarsson |
| 4,758,234 A | 7/1988 | Orentreich et al. |
| 4,759,769 A | 7/1988 | Hedman et al. |
| 4,762,515 A | 8/1988 | Grimm |
| 4,767,033 A | 8/1988 | Gemperle |
| 4,772,287 A | 9/1988 | Ray et al. |
| 4,782,118 A | 11/1988 | Fontanille et al. |
| 4,786,184 A | 11/1988 | Berezkina et al. |
| 4,791,150 A | 12/1988 | Braden et al. |
| 4,792,577 A | 12/1988 | Chen et al. |
| 2,067,458 A | 2/1989 | Nichols |
| 4,804,023 A | 2/1989 | Frearson |
| 4,813,870 A | 3/1989 | Pitzen |
| 4,815,454 A | 3/1989 | Dozier |
| 4,815,632 A | 3/1989 | Ball et al. |
| 4,826,053 A | 5/1989 | Keller |
| 4,830,227 A | 5/1989 | Ball et al. |
| 4,837,279 A | 6/1989 | Arroyo |
| 4,854,312 A | 8/1989 | Raftopoulos et al. |
| 4,854,482 A | 8/1989 | Bergner |
| 4,863,072 A | 9/1989 | Perler |
| 4,869,906 A | 9/1989 | Dingeldein et al. |
| 4,872,936 A | 10/1989 | Engelbrecht |
| 4,892,231 A | 1/1990 | Ball |
| 4,892,550 A | 1/1990 | Huebsch |
| 4,902,649 A | 2/1990 | Kimura et al. |
| 4,904,260 A | 2/1990 | Ray et al. |
| 4,908,017 A | 3/1990 | Howson et al. |
| 4,910,259 A | 3/1990 | Kindt-Larsen et al. |
| 4,927,866 A | 5/1990 | Purrmann et al. |
| 4,932,969 A | 6/1990 | Frey et al. |
| 4,935,029 A | 6/1990 | Matsutani et al. |
| 4,944,065 A | 7/1990 | Svanberg et al. |
| 4,944,726 A | 7/1990 | Hilal et al. |
| 4,946,077 A | 8/1990 | Olsen |
| 4,946,285 A | 8/1990 | Vennemeyer |
| 4,946,901 A | 8/1990 | Lechner et al. |
| 4,961,647 A | 10/1990 | Coutts et al. |
| 4,966,601 A | 10/1990 | Draenet |
| 4,968,303 A | 11/1990 | Clarke et al. |
| 4,969,888 A | 11/1990 | Scholten et al. |
| 4,973,301 A | 11/1990 | Nissenkorn |
| 4,973,334 A | 11/1990 | Ziemann |
| 4,978,336 A | 12/1990 | Capozzi et al. |
| 4,983,164 A | 1/1991 | Hook et al. |
| 4,994,065 A | 2/1991 | Gibbs et al. |
| 4,995,868 A | 2/1991 | Brazier |
| 5,004,501 A | 4/1991 | Faccioli et al. |
| 5,006,112 A | 4/1991 | Metzner |
| 5,012,066 A | 4/1991 | Matsutani et al. |
| 5,015,233 A | 5/1991 | McGough et al. |
| 5,018,919 A | 5/1991 | Stephan |
| 5,022,563 A | 6/1991 | Marchito et al. |
| 5,024,232 A | 6/1991 | Smid et al. |
| 5,028,141 A | 7/1991 | Stiegelmann |
| 5,037,473 A | 8/1991 | Antonucci et al. |
| 5,049,157 A | 9/1991 | Mittelmeier et al. |
| 5,051,482 A | 9/1991 | Tepic |
| 5,059,193 A | 10/1991 | Kuslich |
| 5,059,199 A | 10/1991 | Okada et al. |
| 5,061,128 A | 10/1991 | Jahr et al. |
| 5,062,128 A | 10/1991 | Jahr et al. |
| 5,071,040 A | 12/1991 | Laptewicz, Jr. |
| 5,074,871 A | 12/1991 | Groshong |
| 5,078,919 A | 1/1992 | Ashley et al. |
| 5,092,888 A | 3/1992 | Iwamoto et al. |

| | | | | | |
|---|---|---|---|---|---|
| 5,102,413 A | 4/1992 | Poddar | 5,468,245 A | 11/1995 | Vargas, III |
| 5,108,403 A | 4/1992 | Stern | 5,480,400 A | 1/1996 | Berger |
| 5,108,404 A | 4/1992 | Scholten et al. | 5,480,403 A | 1/1996 | Lee |
| 5,112,333 A | 5/1992 | Fixel | 5,482,187 A | 1/1996 | Poulsen et al. |
| 5,114,240 A | 5/1992 | Kindt-Larsen et al. | 5,492,247 A | 2/1996 | Shu et al. |
| 5,116,335 A | 5/1992 | Hannon | 5,494,349 A | 2/1996 | Seddon |
| 5,122,400 A | 6/1992 | Stewart | 5,501,374 A | 3/1996 | Laufer et al. |
| 5,123,926 A | 6/1992 | Pisharodi | 5,501,520 A | 3/1996 | Lidgren et al. |
| 5,125,971 A | 6/1992 | Nonami et al. | 5,501,695 A | 3/1996 | Anspach, Jr. et al. |
| 5,131,382 A | 7/1992 | Meyer | 5,512,610 A | 4/1996 | Lin |
| 5,141,496 A | 8/1992 | Dalto et al. | 5,514,135 A | 5/1996 | Earle |
| 5,145,250 A | 9/1992 | Planck et al. | 5,514,137 A | 5/1996 | Coutts |
| 5,147,903 A | 9/1992 | Podszun et al. | 5,518,498 A | 5/1996 | Lindenberg et al. |
| 5,171,248 A | 12/1992 | Ellis | 5,520,690 A | 5/1996 | Errico et al. |
| 5,171,278 A | 12/1992 | Pisharodi | 5,522,816 A | 6/1996 | Dinello et al. |
| 5,181,918 A | 1/1993 | Brandhorst et al. | 5,522,899 A | 6/1996 | Michelson |
| 5,188,259 A | 2/1993 | Petit | 5,526,853 A | 6/1996 | McPhee et al. |
| 5,190,191 A | 3/1993 | Reyman | 5,534,028 A | 7/1996 | Bao et al. |
| 5,192,327 A | 3/1993 | Brantigan | 5,536,262 A | 7/1996 | Velasquez |
| 5,193,907 A | 3/1993 | Faccioli | 5,545,460 A | 8/1996 | Tanaka et al. |
| 5,209,753 A | 5/1993 | Beidermann et al. | 5,548,001 A | 8/1996 | Podszun et al. |
| 5,217,147 A | 6/1993 | Kaufman | 5,549,380 A | 8/1996 | Lidgren et al. |
| 5,219,897 A | 6/1993 | Murray | 5,549,381 A | 8/1996 | Hays et al. |
| 5,236,445 A | 8/1993 | Hayhurst et al. | 5,549,679 A | 8/1996 | Kuslich |
| 5,242,983 A | 9/1993 | Kennedy et al. | 5,551,778 A | 9/1996 | Hauke et al. |
| 5,252,301 A | 10/1993 | Nilson et al. | 5,554,101 A | 9/1996 | Matula et al. |
| 5,254,092 A | 10/1993 | Polyak | 5,556,201 A | 9/1996 | Veltrop et al. |
| 5,258,420 A | 11/1993 | Posey-Dowty et al. | 5,558,136 A | 9/1996 | Orrico |
| 5,264,215 A | 11/1993 | Nakabayashi et al. | 5,558,639 A | 9/1996 | Gangemi et al. |
| 5,268,001 A | 12/1993 | Nicholson et al. | 5,571,189 A | 11/1996 | Kuslich et al. |
| 5,269,762 A | 12/1993 | Armbruster et al. | 5,573,265 A | 11/1996 | Pradel |
| 5,275,214 A | 1/1994 | Rehberger | 5,578,035 A | 11/1996 | Lin |
| 5,276,070 A | 1/1994 | Arroyo | 5,586,821 A | 12/1996 | Bonitati et al. |
| 5,277,339 A | 1/1994 | Shew et al. | 5,588,745 A | 12/1996 | Tanaka et al. |
| 5,279,555 A | 1/1994 | Lifshey | 5,591,197 A | 1/1997 | Orth et al. |
| 5,290,260 A | 3/1994 | Stines | 5,601,557 A | 2/1997 | Hayhurst |
| 5,295,980 A | 3/1994 | Ersek | 5,603,701 A | 2/1997 | Fischer |
| 5,302,020 A | 4/1994 | Kruse | 5,609,637 A | 3/1997 | Biedermann et al. |
| 5,303,718 A | 4/1994 | Kajicek | 5,624,184 A | 4/1997 | Chan |
| 5,304,147 A | 4/1994 | Johnson et al. | 5,630,806 A | 5/1997 | Inagaki et al. |
| 5,328,262 A | 7/1994 | Lidgren et al. | 5,634,880 A | 6/1997 | Feldman et al. |
| 5,328,362 A | 7/1994 | Watson et al. | 5,637,097 A | 6/1997 | Yoon |
| 5,331,972 A | 7/1994 | Wadhwani et al. | 5,638,997 A | 6/1997 | Hawkins et al. |
| 5,333,951 A | 8/1994 | Wakoh | 5,641,010 A | 6/1997 | Maier |
| 5,334,184 A | 8/1994 | Bimman | 5,645,598 A | 7/1997 | Brosnahan, III |
| 5,334,626 A | 8/1994 | Lin | 5,647,856 A | 7/1997 | Eykmann |
| 5,336,699 A | 8/1994 | Cooke et al. | 5,653,686 A | 8/1997 | Coulter et al. |
| 5,336,700 A | 8/1994 | Murray | 5,658,310 A | 8/1997 | Berger |
| 5,344,232 A | 9/1994 | Nelson et al. | 5,660,186 A | 8/1997 | Bachir |
| 5,348,391 A | 9/1994 | Murray | 5,665,067 A | 9/1997 | Linder et al. |
| 5,348,548 A | 9/1994 | Meyer et al. | 5,681,317 A | 10/1997 | Caldarise |
| 5,350,372 A | 9/1994 | Ikeda et al. | 5,683,451 A | 11/1997 | Lenker et al. |
| 5,354,287 A | 10/1994 | Wacks | 5,685,826 A | 11/1997 | Bonutti |
| 5,356,382 A | 10/1994 | Picha et al. | 5,690,606 A | 11/1997 | Slotman |
| 5,368,046 A | 11/1994 | Scarfone et al. | 5,693,100 A | 12/1997 | Pisharodi |
| 5,368,386 A | 11/1994 | Murray | 5,697,977 A | 12/1997 | Pisharodi |
| 5,370,221 A | 12/1994 | Magnusson et al. | 5,698,611 A | 12/1997 | Okada et al. |
| 5,372,583 A | 12/1994 | Roberts | 5,702,448 A | 12/1997 | Buechel et al. |
| 5,374,427 A | 12/1994 | Stille et al. | 5,704,895 A | 1/1998 | Scott et al. |
| 5,376,123 A | 12/1994 | Klaue et al. | 5,707,390 A | 1/1998 | Bonutti |
| 5,380,772 A | 1/1995 | Hasegawa et al. | 5,718,707 A | 2/1998 | Mikhail |
| 5,385,081 A | 1/1995 | Sneddon | 5,720,753 A | 2/1998 | Sander et al. |
| 5,385,566 A | 1/1995 | Ullmaerk | 5,725,341 A | 3/1998 | Hofmeister |
| 5,387,191 A | 2/1995 | Hemstreet et al. | 5,725,529 A | 3/1998 | Nicholson et al. |
| 5,390,683 A | 2/1995 | Pisharodi | 5,747,553 A | 5/1998 | Guzauskas |
| 5,395,167 A | 3/1995 | Murray | 5,752,935 A | 5/1998 | Robinson et al. |
| 5,395,326 A | 3/1995 | Haber et al. | 5,752,969 A | 5/1998 | Cunci |
| 5,398,483 A | 3/1995 | Smith et al. | 5,752,974 A | 5/1998 | Rhee |
| 5,401,806 A | 3/1995 | Braden et al. | 5,755,732 A | 5/1998 | Green et al. |
| 5,411,180 A | 5/1995 | Dumelle | 5,759,186 A | 6/1998 | Bachmann et al. |
| 5,415,474 A | 5/1995 | Nelson et al. | 5,763,092 A | 6/1998 | Lee et al. |
| 5,423,850 A | 6/1995 | Berger | 5,779,356 A | 7/1998 | Chan |
| 5,431,654 A | 7/1995 | Nic | 5,782,713 A | 7/1998 | Yang |
| 5,435,645 A | 7/1995 | Faccioli | 5,782,747 A | 7/1998 | Zimmon |
| 5,443,182 A | 8/1995 | Tanaka et al. | 5,782,830 A | 7/1998 | Farris |
| 5,445,639 A | 8/1995 | Kuslich et al. | 5,782,838 A | 7/1998 | Beyar et al. |
| 5,450,924 A | 9/1995 | Tseng | 5,785,647 A | 7/1998 | Tompkins et al. |
| 5,454,365 A | 10/1995 | Bonutti | 5,792,044 A | 8/1998 | Foley |
| 5,456,267 A | 10/1995 | Stark | 5,795,922 A | 8/1998 | Demian et al. |

| | | | | | | |
|---|---|---|---|---|---|---|
| 5,797,678 | A | 8/1998 | Murray | 6,174,935 B1 | 1/2001 | Matsunae et al. |
| 5,800,169 | A | 9/1998 | Muhlbauer | 6,176,607 B1 | 1/2001 | Hajianpour |
| 5,800,409 | A | 9/1998 | Bruce | 6,183,441 B1 | 2/2001 | Kriesel et al. |
| 5,800,549 | A | 9/1998 | Bao et al. | 6,183,516 B1 | 2/2001 | Burkinshaw et al. |
| 5,800,550 | A | 9/1998 | Sertich | 6,187,015 B1 | 2/2001 | Brenneman |
| 5,820,321 | A | 10/1998 | Gruber | 6,190,381 B1 | 2/2001 | Olsen et al. |
| 5,824,087 | A | 10/1998 | Aspden et al. | 6,210,031 B1 | 4/2001 | Murray |
| 5,826,713 | A | 10/1998 | Sunago et al. | 6,214,012 B1 | 4/2001 | Karpman et al. |
| 5,826,753 | A | 10/1998 | Fehlig et al. | 6,214,016 B1 | 4/2001 | Williams et al. |
| 5,827,289 | A | 10/1998 | Reiley et al. | 6,214,037 B1 | 4/2001 | Mitchell et al. |
| 5,829,875 | A | 11/1998 | Hagel et al. | 6,217,566 B1 | 4/2001 | Ju et al. |
| 5,830,194 | A | 11/1998 | Anwar et al. | 6,217,581 B1 | 4/2001 | Tolson |
| 5,839,621 | A | 11/1998 | Tada | 6,217,608 B1 | 4/2001 | Penn et al. |
| 5,842,785 | A | 12/1998 | Brown et al. | 6,221,029 B1 | 4/2001 | Mathis et al. |
| 5,865,802 | A | 2/1999 | Yoon et al. | 6,224,604 B1 | 5/2001 | Suddaby |
| 5,876,116 | A | 3/1999 | Barker et al. | 6,228,068 B1 | 5/2001 | Yoon |
| 5,876,457 | A | 3/1999 | Picha et al. | 6,228,082 B1 | 5/2001 | Baker et al. |
| 5,882,340 | A | 3/1999 | Yoon et al. | 6,231,615 B1 | 5/2001 | Preissman |
| 5,884,818 | A | 3/1999 | Campbell | 6,235,043 B1 | 5/2001 | Reiley et al. |
| 5,893,488 | A | 4/1999 | Hoag et al. | 6,238,399 B1 | 5/2001 | Heller et al. |
| 5,893,850 | A | 4/1999 | Cachia | 6,241,734 B1 | 6/2001 | Scribner et al. |
| 5,902,839 | A | 5/1999 | Lautenschlager et al. | 6,245,101 B1 | 6/2001 | Drasler et al. |
| 5,911,721 | A | 6/1999 | Nicholson et al. | 6,248,110 B1 | 6/2001 | Reiley et al. |
| 5,918,702 | A | 7/1999 | Cheng et al. | 6,254,268 B1 | 7/2001 | Long |
| 5,918,770 | A | 7/1999 | Camm et al. | 6,261,289 B1 | 7/2001 | Levy |
| 5,925,051 | A | 7/1999 | Mikhail | 6,264,618 B1 | 7/2001 | Landi et al. |
| 5,928,239 | A | 7/1999 | Mirza | 6,264,659 B1 | 7/2001 | Ross et al. |
| 5,931,347 | A | 8/1999 | Haubrich | 6,264,660 B1 | 7/2001 | Schmidt et al. |
| 5,941,851 | A | 8/1999 | Coffey et al. | 6,273,916 B1 | 8/2001 | Murphy |
| 5,954,671 | A | 9/1999 | O'Neill | 6,281,271 B1 | 8/2001 | Rumphorst et al. |
| 5,954,728 | A | 9/1999 | Heller et al. | 6,309,395 B1 | 10/2001 | Smith et al. |
| 5,961,211 | A | 10/1999 | Barker et al. | 6,309,420 B1 | 10/2001 | Preissman |
| 5,968,008 | A | 10/1999 | Grams | 6,312,149 B1 | 11/2001 | Sjovall et al. |
| 5,968,044 | A | 10/1999 | Nicholson et al. | 6,325,812 B1 | 12/2001 | Dubrul et al. |
| 5,968,999 | A | 10/1999 | Ramp et al. | 6,348,055 B1 | 2/2002 | Preissman |
| 5,972,015 | A | 10/1999 | Scribner et al. | 6,348,518 B1 | 2/2002 | Montgomery |
| 5,980,527 | A | 11/1999 | Cohen et al. | 6,350,271 B1 | 2/2002 | Kurz et al. |
| 5,993,535 | A | 11/1999 | Sawamura et al. | 6,361,539 B1 | 3/2002 | Heller et al. |
| 5,997,544 | A | 12/1999 | Nies et al. | 6,367,962 B1 | 4/2002 | Mizutani et al. |
| 6,004,325 | A | 12/1999 | Vargas, III | 6,375,659 B1 | 4/2002 | Erbe et al. |
| 6,007,496 | A | 12/1999 | Brannon | 6,375,682 B1 | 4/2002 | Fleischmann et al. |
| 6,017,349 | A | 1/2000 | Heller et al. | 6,383,188 B2 | 5/2002 | Kuslich et al. |
| 6,019,765 | A | 2/2000 | Thornhill et al. | 6,383,190 B1 | 5/2002 | Preissman |
| 6,019,776 | A | 2/2000 | Preissman et al. | 6,395,007 B1 | 5/2002 | Bhatnagar |
| 6,019,789 | A | 2/2000 | Dinh et al. | 6,402,701 B1 | 6/2002 | Kaplan et al. |
| 6,020,396 | A | 2/2000 | Jacobs | 6,402,758 B1 | 6/2002 | Tolson |
| 6,033,105 | A | 3/2000 | Barker et al. | 6,406,175 B1 | 6/2002 | Marino |
| 6,033,411 | A | 3/2000 | Preissman | 6,409,972 B1 | 6/2002 | Chan |
| 6,039,761 | A | 3/2000 | Li et al. | 6,410,612 B1 | 6/2002 | Hatanaka |
| 6,040,408 | A | 3/2000 | Koole | 6,425,887 B1 | 7/2002 | McGuckin et al. |
| 6,041,977 | A | 3/2000 | Lisi | 6,431,743 B1 | 8/2002 | Mizutani et al. |
| 6,042,262 | A | 3/2000 | Hajianpour | 6,433,037 B1 | 8/2002 | Guzauskas |
| 6,045,555 | A | 4/2000 | Smith et al. | 6,436,143 B1 | 8/2002 | Ross et al. |
| 6,048,346 | A | 4/2000 | Reiley | 6,439,439 B1 | 8/2002 | Rickard |
| 6,049,026 | A | 4/2000 | Muschler | 6,443,334 B1 | 9/2002 | John et al. |
| 6,075,067 | A | 6/2000 | Lidgren | 6,447,478 B1 | 9/2002 | Maynards |
| 6,080,579 | A | 6/2000 | Hanley, Jr. | 6,450,973 B1 | 9/2002 | Murphy |
| 6,080,801 | A | 6/2000 | Draenert et al. | 6,458,117 B1 | 10/2002 | Pollins, Sr. |
| 6,080,811 | A | 6/2000 | Schehlmann et al. | 6,479,565 B1 | 11/2002 | Stanley |
| 6,083,229 | A | 7/2000 | Constantz et al. | 6,488,667 B1 | 12/2002 | Murphy |
| 6,086,594 | A | 7/2000 | Brown | 6,494,868 B2 | 12/2002 | Amar |
| 6,103,779 | A | 8/2000 | Guzauskas | 6,500,182 B2 | 12/2002 | Foster |
| 6,116,773 | A | 9/2000 | Murray | 6,502,608 B1 | 1/2003 | Burchett et al. |
| 6,120,174 | A | 9/2000 | Hoag et al. | 6,527,144 B2 | 3/2003 | Ritsche et al. |
| 6,124,373 | A | 9/2000 | Peter et al. | 6,550,957 B2 | 4/2003 | Mizutani et al. |
| 6,126,689 | A | 10/2000 | Brett | 6,554,833 B2 | 4/2003 | Levy et al. |
| 6,127,597 | A | 10/2000 | Beyar et al. | 6,572,256 B2 | 6/2003 | Seaton et al. |
| 6,129,763 | A | 10/2000 | Chauvin et al. | 6,575,331 B1 | 6/2003 | Peeler et al. |
| 6,132,396 | A | 10/2000 | Antanavich et al. | 6,575,919 B1 | 6/2003 | Reilley et al. |
| 6,136,038 | A | 10/2000 | Raab | 6,582,439 B1 | 6/2003 | Sproul |
| 6,139,509 | A | 10/2000 | Yuan et al. | 6,592,559 B1 | 7/2003 | Pakter et al. |
| 6,142,998 | A | 11/2000 | Smith et al. | 6,599,293 B2 | 7/2003 | Tague et al. |
| 6,146,401 | A | 11/2000 | Yoon et al. | 6,599,520 B2 | 7/2003 | Scarborough et al. |
| 6,149,651 | A | 11/2000 | Drewry et al. | 6,613,018 B2 | 9/2003 | Bagga |
| 6,149,655 | A | 11/2000 | Constantz et al. | 6,613,054 B2 | 9/2003 | Scribner et al. |
| 6,149,664 | A | 11/2000 | Kurz | 6,626,912 B2 | 9/2003 | Speitling |
| 6,160,033 | A | 12/2000 | Nies | 6,641,587 B2 | 11/2003 | Scribner et al. |
| 6,161,955 | A | 12/2000 | Rademaker | 6,645,213 B2 | 11/2003 | Sand et al. |
| 6,168,597 | B1 | 1/2001 | Biedermann et al. | 6,662,969 B2 | 12/2003 | Peeler et al. |

| | | |
|---|---|---|
| 6,676,664 B1 | 1/2004 | Al-Assir |
| 6,689,823 B1 | 2/2004 | Bellare et al. |
| 6,702,455 B2 | 3/2004 | Vendrely et al. |
| 6,712,853 B2 | 3/2004 | Kuslich |
| 6,716,216 B1 | 4/2004 | Boucher et al. |
| 6,719,761 B1 | 4/2004 | Reiley et al. |
| 6,720,417 B1 | 4/2004 | Walter |
| 6,730,095 B2 | 5/2004 | Olson, Jr. et al. |
| 6,752,180 B2 | 6/2004 | Delay |
| 6,758,837 B2 | 7/2004 | Peciat et al. |
| 6,759,449 B2 | 7/2004 | Kimura et al. |
| 6,767,973 B2 | 7/2004 | Suau et al. |
| 6,770,079 B2 | 8/2004 | Bhatnagar |
| 6,779,566 B2 | 8/2004 | Engel |
| 6,780,175 B1 | 8/2004 | Sachdeva et al. |
| 6,783,515 B1 | 8/2004 | Miller et al. |
| 6,787,584 B2 | 9/2004 | Jia et al. |
| 6,796,987 B2 | 9/2004 | Tague et al. |
| 6,852,439 B2 | 2/2005 | Frank |
| 6,874,927 B2 | 4/2005 | Foster |
| 6,875,219 B2 | 4/2005 | Arramon et al. |
| 6,887,246 B2 | 5/2005 | Bhatnagar |
| 6,916,308 B2 | 7/2005 | Dixon et al. |
| 6,957,747 B2 | 10/2005 | Peeler et al. |
| 6,974,247 B2 | 12/2005 | Frei et al. |
| 6,979,341 B2 | 12/2005 | Scribner et al. |
| 6,979,352 B2 | 12/2005 | Reynolds |
| 6,994,465 B2 | 2/2006 | Tague et al. |
| 6,997,930 B1 | 2/2006 | Jaggi |
| 7,008,433 B2 | 3/2006 | Voellmicke et al. |
| 7,025,771 B2 | 4/2006 | Kuslich et al. |
| 7,029,163 B2 | 4/2006 | Barker et al. |
| 7,044,954 B2 | 5/2006 | Reiley |
| 7,048,743 B2 | 5/2006 | Miller |
| 7,066,942 B2 | 6/2006 | Treace |
| 7,087,040 B2 | 8/2006 | McGuckin |
| 7,091,258 B2 | 8/2006 | Neubert et al. |
| 7,097,648 B1 | 8/2006 | Globerman et al. |
| 7,112,205 B2 | 9/2006 | Carrison |
| 7,116,121 B1 | 10/2006 | Holcombe et al. |
| 7,252,671 B2 | 8/2007 | Scribner |
| 7,270,667 B2 | 9/2007 | Faccioli |
| 7,278,778 B2 | 10/2007 | Sand |
| 7,326,203 B2 | 2/2008 | Papineau et al. |
| 7,456,024 B2 | 11/2008 | Dahm et al. |
| 7,572,263 B2 | 8/2009 | Preissman |
| 7,604,618 B2 | 10/2009 | Dixon et al. |
| 7,666,205 B2 | 2/2010 | Weikel et al. |
| 8,066,713 B2 | 11/2011 | DiMauro et al. |
| 2001/0012968 A1 | 8/2001 | Preissman |
| 2001/0034527 A1 | 10/2001 | Scribner et al. |
| 2002/0008122 A1 | 1/2002 | Ritsche et al. |
| 2002/0010471 A1 | 1/2002 | Wironen |
| 2002/0010472 A1 | 1/2002 | Kuslich et al. |
| 2002/0013553 A1 | 1/2002 | Pajunk |
| 2002/0049448 A1 | 4/2002 | Sand et al. |
| 2002/0049449 A1 | 4/2002 | Bhatnaagr et al. |
| 2002/0058947 A1 | 5/2002 | Hochschuler et al. |
| 2002/0067658 A1 | 6/2002 | Vendrely et al. |
| 2002/0068939 A1 | 6/2002 | Levy et al. |
| 2002/0068974 A1 | 6/2002 | Kuslich et al. |
| 2002/0068975 A1 | 6/2002 | Teitelbaum et al. |
| 2002/0072768 A1 | 6/2002 | Ginn |
| 2002/0099384 A1 | 7/2002 | Scribner et al. |
| 2002/0099385 A1 | 7/2002 | Ralph et al. |
| 2002/0118595 A1 | 8/2002 | Miller |
| 2002/0156483 A1 | 10/2002 | Voellmicke et al. |
| 2002/0161373 A1 | 10/2002 | Osorio et al. |
| 2002/0177866 A1 | 11/2002 | Weikel et al. |
| 2002/0188300 A1 | 12/2002 | Arramon |
| 2002/0191487 A1 | 12/2002 | Sand |
| 2003/0018339 A1 | 1/2003 | Higueras et al. |
| 2003/0031698 A1 | 2/2003 | Roeder et al. |
| 2003/0032929 A1 | 2/2003 | McGuckin et al. |
| 2003/0036763 A1 | 2/2003 | Bhatnager et al. |
| 2003/0040718 A1 | 2/2003 | Keahey et al. |
| 2003/0050644 A1 | 3/2003 | Boucher et al. |
| 2003/0050702 A1 | 3/2003 | Berger |
| 2003/0078589 A1 | 4/2003 | Preissman |
| 2003/0109883 A1 | 6/2003 | Matsuzaki et al. |
| 2003/0109884 A1 | 6/2003 | Tague et al. |
| 2003/0144742 A1 | 7/2003 | King et al. |
| 2003/0162864 A1 | 8/2003 | Pearson et al. |
| 2003/0174576 A1 | 9/2003 | Tague et al. |
| 2003/0181963 A1 | 9/2003 | Pellegrino et al. |
| 2003/0185093 A1 | 10/2003 | Vendrely et al. |
| 2003/0220414 A1 | 11/2003 | Axen et al. |
| 2003/0225364 A1 | 12/2003 | Kraft et al. |
| 2003/0231545 A1 | 12/2003 | Seaton |
| 2004/0010263 A1 | 1/2004 | Boucher et al. |
| 2004/0029996 A1 | 2/2004 | Kuhn |
| 2004/0054377 A1 | 3/2004 | Foster et al. |
| 2004/0059283 A1 | 3/2004 | Kirwan et al. |
| 2004/0068264 A1 | 4/2004 | Treace |
| 2004/0073139 A1 | 4/2004 | Hirsch et al. |
| 2004/0092946 A1 | 5/2004 | Bagga et al. |
| 2004/0098015 A1 | 5/2004 | Weikel et al. |
| 2004/0106913 A1 | 6/2004 | Eidenschink et al. |
| 2004/0122438 A1 | 6/2004 | Abrams |
| 2004/0132859 A1 | 7/2004 | Puckett Jr et al. |
| 2004/0133124 A1 | 7/2004 | Bates et al. |
| 2004/0133211 A1 | 7/2004 | Raskin et al. |
| 2004/0138759 A1 | 7/2004 | Muller et al. |
| 2004/0157952 A1* | 8/2004 | Soffiati et al. .................. 523/115 |
| 2004/0157954 A1 | 8/2004 | Imai et al. |
| 2004/0167532 A1 | 8/2004 | Olson et al. |
| 2004/0167562 A1 | 8/2004 | Osorio et al. |
| 2004/0167625 A1 | 8/2004 | Beyar et al. |
| 2004/0193171 A1 | 9/2004 | DiMauro et al. |
| 2004/0215202 A1 | 10/2004 | Preissman |
| 2004/0220672 A1 | 11/2004 | Shadduck |
| 2004/0226479 A1 | 11/2004 | Lyles et al. |
| 2004/0229972 A1 | 11/2004 | Klee et al. |
| 2004/0230309 A1 | 11/2004 | DiMauro et al. |
| 2004/0236313 A1 | 11/2004 | Klein |
| 2004/0249015 A1 | 12/2004 | Jia et al. |
| 2004/0249347 A1 | 12/2004 | Miller et al. |
| 2004/0260303 A1 | 12/2004 | Carrison |
| 2004/0260304 A1 | 12/2004 | Faccioli et al. |
| 2004/0267154 A1 | 12/2004 | Sutton et al. |
| 2005/0014273 A1 | 1/2005 | Dahm |
| 2005/0015148 A1 | 1/2005 | Jansen et al. |
| 2005/0025622 A1 | 2/2005 | Djeridane et al. |
| 2005/0058717 A1 | 3/2005 | Yetlinler |
| 2005/0060023 A1 | 3/2005 | Mitchell et al. |
| 2005/0070912 A1 | 3/2005 | Voellmicke |
| 2005/0070914 A1 | 3/2005 | Constantz et al. |
| 2005/0070915 A1 | 3/2005 | Mazzuca |
| 2005/0083782 A1 | 4/2005 | Gronau et al. |
| 2005/0113762 A1 | 5/2005 | Kay et al. |
| 2005/0143827 A1 | 6/2005 | Globerman et al. |
| 2005/0154081 A1 | 7/2005 | Yin et al. |
| 2005/0180806 A1 | 8/2005 | Green |
| 2005/0203206 A1 | 9/2005 | Trieu |
| 2005/0209695 A1 | 9/2005 | de Vries et al. |
| 2005/0216025 A1 | 9/2005 | Chern Lin et al. |
| 2005/0256220 A1 | 11/2005 | Lavergne et al. |
| 2005/0281132 A1 | 12/2005 | Armstrong et al. |
| 2006/0035997 A1 | 2/2006 | Orlowski et al. |
| 2006/0041033 A1 | 2/2006 | Bisig et al. |
| 2006/0052794 A1 | 3/2006 | McGill |
| 2006/0074433 A1 | 4/2006 | McGill et al. |
| 2006/0079905 A1 | 4/2006 | Beyar et al. |
| 2006/0116643 A1 | 6/2006 | Dixon et al. |
| 2006/0116689 A1 | 6/2006 | Albans et al. |
| 2006/0116690 A1 | 6/2006 | Pagano |
| 2006/0148923 A1 | 7/2006 | Ashman et al. |
| 2006/0167148 A1 | 7/2006 | Engqvist et al. |
| 2006/0235338 A1 | 10/2006 | Pacheco |
| 2006/0241644 A1 | 10/2006 | Osorio et al. |
| 2006/0264695 A1 | 11/2006 | Viole et al. |
| 2006/0264967 A1 | 11/2006 | Ferreyro et al. |
| 2006/0266372 A1 | 11/2006 | Miller et al. |
| 2006/0271061 A1 | 11/2006 | Beyar et al. |
| 2006/0276819 A1 | 12/2006 | Osorio et al. |
| 2007/0027230 A1 | 2/2007 | Beyar et al. |
| 2007/0032567 A1 | 2/2007 | Beyar et al. |
| 2007/0055266 A1 | 3/2007 | Osorio et al. |

| | | | | | |
|---|---|---|---|---|---|
| 2007/0055267 A1 | 3/2007 | Osorio et al. | EP | 1570873 | 9/2005 |
| 2007/0055278 A1 | 3/2007 | Osorio et al. | EP | 1598 015 | 11/2005 |
| 2007/0055280 A1 | 3/2007 | Osorio et al. | EP | 1148851 | 5/2006 |
| 2007/0055284 A1 | 3/2007 | Osorio et al. | EP | 1829518 | 9/2007 |
| 2007/0055285 A1 | 3/2007 | Osorio | EP | 1886647 | 2/2008 |
| 2007/0055300 A1 | 3/2007 | Osorio et al. | FR | 1548575 | 10/1968 |
| 2007/0060941 A1 | 3/2007 | Reiley et al. | FR | 2606282 | 5/1988 |
| 2007/0118142 A1 | 5/2007 | Krueger | FR | 2629337 | 10/1989 |
| 2007/0142842 A1 | 6/2007 | Krueger | FR | 2638972 | 5/1990 |
| 2007/0197935 A1 | 8/2007 | Reiley et al. | FR | 2674119 | 9/1992 |
| 2007/0198013 A1 | 8/2007 | Foley et al. | FR | 2690332 | 10/1993 |
| 2007/0198023 A1 | 8/2007 | Sand et al. | FR | 2712486 | 5/1995 |
| 2007/0198024 A1 | 8/2007 | Plishka et al. | FR | 2722679 | 1/1996 |
| 2007/0282443 A1 | 12/2007 | Globerman et al. | GB | 8331 | 0/1904 |
| 2008/0039856 A1 | 2/2008 | DiMauro | GB | 179502045 | 4/1795 |
| 2008/0044374 A1 | 2/2008 | Lavergne et al. | GB | 408668 | 4/1934 |
| 2008/0058827 A1 | 3/2008 | Osorio et al. | GB | 2114005 | 8/1983 |
| 2008/0065087 A1 | 3/2008 | Osorio et al. | GB | 2156824 | 10/1985 |
| 2008/0065089 A1 | 3/2008 | Osorio et al. | GB | 2197691 | 5/1988 |
| 2008/0065137 A1 | 3/2008 | Boucher et al. | GB | 2268068 | 1/1994 |
| 2008/0065142 A1 | 3/2008 | Reiley et al. | GB | 2276560 | 10/1994 |
| 2008/0065190 A1 | 3/2008 | Osorio et al. | GB | 2411849 | 9/2005 |
| 2008/0071283 A1 | 3/2008 | Osorio et al. | GB | 2413280 | 10/2005 |
| 2008/0086133 A1 | 4/2008 | Kuslich et al. | GB | 2469749 | 10/2010 |
| 2008/0132935 A1 | 6/2008 | Osorio et al. | JP | 54-009110 | 1/1979 |
| 2008/0140079 A1 | 6/2008 | Osorio et al. | JP | 55-109440 | 8/1980 |
| 2008/0140084 A1 | 6/2008 | Osorio et al. | JP | 62-068893 | 3/1987 |
| 2008/0200915 A1 | 8/2008 | Globerman et al. | JP | 02-122017 | 5/1990 |
| 2008/0212405 A1 | 9/2008 | Globerman et al. | JP | 02-166235 | 6/1990 |
| 2008/0228192 A1 | 9/2008 | Beyar et al. | JP | 4 329956 | 11/1992 |
| 2009/0264892 A1 | 10/2009 | Beyar et al. | JP | 07-000410 | 1/1995 |
| 2009/0264942 A1 | 10/2009 | Beyar et al. | JP | 8322848 | 12/1996 |
| 2009/0270872 A1 | 10/2009 | DiMauro | JP | 10146559 | 6/1998 |
| 2010/0065154 A1 | 3/2010 | Globerman | JP | 10-511569 | 10/1998 |
| 2010/0069786 A1 | 3/2010 | Globerman et al. | JP | 2004-16707 | 1/2004 |
| 2010/0152855 A1 | 6/2010 | Kuslich et al. | JP | 2008-55367 | 3/2008 |
| 2010/0168271 A1 | 7/2010 | Beyar | RO | 116784 | 6/2001 |
| 2010/0268231 A1 | 10/2010 | Kuslich et al. | RU | 662082 | 5/1979 |

FOREIGN PATENT DOCUMENTS

| | | | | | |
|---|---|---|---|---|---|
| | | | RU | 1011119 | 4/1983 |
| DE | 226956 | 3/1909 | RU | 1049050 | 10/1983 |
| DE | 1283448 | 11/1968 | WO | WO 90/00037 | 1/1990 |
| DE | 2821785 | 11/1979 | WO | WO 92/14423 | 9/1992 |
| DE | 3003947 | 8/1980 | WO | WO 94/12112 | 6/1994 |
| DE | 2947875 | 4/1981 | WO | WO 95/13862 | 5/1995 |
| DE | 3443167 | 6/1986 | WO | WO 96/11643 | 4/1996 |
| DE | 3817101 | 11/1989 | WO | WO 96/19940 | 7/1996 |
| DE | 3730298 | 2/1990 | WO | WO 96/32899 | 10/1996 |
| DE | 4104092 | 8/1991 | WO | WO 96/37170 | 11/1996 |
| DE | 293485 | 9/1991 | WO | WO 97/18769 | 5/1997 |
| DE | 4016135 | 3/1992 | WO | WO 97/28835 | 8/1997 |
| DE | 4315757 | 11/1994 | WO | WO 98/28035 | 7/1998 |
| DE | 19612276 | 10/1997 | WO | WO 98/38918 | 9/1998 |
| DE | 10258140 | 7/2004 | WO | WO 99/18866 | 4/1999 |
| EP | 20207 | 6/1908 | WO | WO 99/18894 | 4/1999 |
| EP | 486638 | 6/1938 | WO | WO 99/29253 | 6/1999 |
| EP | 0044877 | 2/1982 | WO | WO 99/37212 | 7/1999 |
| EP | 0190504 | 3/1986 | WO | WO 99/39661 | 8/1999 |
| EP | 0177781 | 4/1986 | WO | WO 99/49819 | 10/1999 |
| EP | 0235905 | 9/1987 | WO | WO 99/52446 | 10/1999 |
| EP | 0301759 | 7/1988 | WO | WO 00/06216 | 2/2000 |
| EP | 0242672 | 9/1989 | WO | WO 00/44319 | 8/2000 |
| EP | 0425200 | 10/1990 | WO | WO 00/44321 | 8/2000 |
| EP | 0423916 | 4/1991 | WO | WO 00/44946 | 8/2000 |
| EP | 0475077 | 3/1992 | WO | WO 00/54705 | 9/2000 |
| EP | 0511868 | 4/1992 | WO | WO 00/56254 | 9/2000 |
| EP | 0493789 | 7/1992 | WO | WO 01/08571 | 2/2001 |
| EP | 0581387 | 2/1994 | WO | WO 01/13822 | 3/2001 |
| EP | 0614653 | 9/1994 | WO | WO 01/54598 | 8/2001 |
| EP | 0669100 | 8/1995 | WO | WO 01/060270 | 8/2001 |
| EP | 0748615 | 12/1996 | WO | WO 01/60270 | 8/2001 |
| EP | 0763348 | 3/1997 | WO | WO 01/76514 | 10/2001 |
| EP | 1074231 | 2/2001 | WO | WO 02/00143 | 1/2002 |
| EP | 1095667 | 5/2001 | WO | WO 02/02033 | 1/2002 |
| EP | 1103237 | 5/2001 | WO | WO 02/19933 | 3/2002 |
| EP | 1104260 | 6/2001 | WO | WO 02/064062 | 8/2002 |
| EP | 1464292 | 10/2004 | WO | WO 02/064194 | 8/2002 |
| EP | 1148850 | 4/2005 | WO | WO 02/072156 | 9/2002 |
| EP | 1552797 | 7/2005 | WO | WO 02/096474 | 12/2002 |
| | | | WO | WO 03/007854 | 1/2003 |

| | | |
|---|---|---|
| WO | WO 03/015845 | 2/2003 |
| WO | WO 03/022165 | 3/2003 |
| WO | WO 03/061495 | 7/2003 |
| WO | WO 03/078041 | 9/2003 |
| WO | WO 03/101596 | 12/2003 |
| WO | WO 2004/002375 | 1/2004 |
| WO | WO 2004/001980 | 3/2004 |
| WO | WO 2004/019810 | 3/2004 |
| WO | WO 2004/071543 | 8/2004 |
| WO | WO 2004/075965 | 9/2004 |
| WO | WO 2004/0080357 | 9/2004 |
| WO | WO 2004/080357 | 9/2004 |
| WO | WO 2004/110292 | 12/2004 |
| WO | WO 2004/110300 | 12/2004 |
| WO | WO 05/000138 | 1/2005 |
| WO | WO 2005/048867 | 6/2005 |
| WO | WO 2005/051212 | 6/2005 |
| WO | WO 2005/110259 | 11/2005 |
| WO | WO 2006/011152 | 2/2006 |
| WO | WO 2005/032326 | 4/2006 |
| WO | WO 2006/039159 | 4/2006 |
| WO | WO 2006/090379 | 8/2006 |
| WO | WO 2007/015202 | 2/2007 |
| WO | WO 2007/036815 | 4/2007 |
| WO | WO 2007/148336 | 12/2007 |
| WO | WO 2008/004229 | 1/2008 |
| WO | WO 2008/032322 | 3/2008 |
| WO | WO 2008/047371 | 4/2008 |

OTHER PUBLICATIONS

HERAEUS PALACOS® R. 2008. PALACOS® R, High viscosity bone cement.*
Odian 1991. Principles of Polymerization. pp. 20-23.*
Rimnac et al, 1986. The effect of centrifugation on the fracture properties of acrylic bone cements. The Journal of Bone and Joint Surgery, vol. 68:281-287.*
Blinc et al, 2004. Methyl-methacrylate bone cememnt surface does not promote platelet aggregation or plasma coagulation in vitro. Thrombosis Research, vol. 114:179-184.*
HERAEUS PALACOS® 2008 (as provided in the Jan. 21, 2010 interview.*
Rimnac et al ("The Effect of Centrifugation on the Fracture Properties of Acrylic bone Cements," The journal of Bone and Joint Surgery, 68-A(2): 281-287, 1986).*
HERAEUS PALACOS® 2008 as provided in the Jan. 21, 2010 interview.*
Farrar et al (Biomaterials, vol. 22:3005-3013 (2001)).*
Hasenwinkel et al (J. Biomed. Materials Research, 1999, vol. 47(1):36-45).*
Blinc et al. "Methyl methacrylate bone cement surface does not promote platelet aggregation or plasma coagulation in vitro," Thrombosis Research (2004) 114, 179-184.*
Serbetci et a ("Thermal and mechanical properties of hydroxyapatite impregnanted acrylic bone cements," Polymer Testing 23 (2004) 145-155).*
Lewis ("Properties of Acrylic Bone Cement: State of the Art Review," 1997 John Wiley & Sons, Inc., pp. 155-182).*
Mousa et al ("Biological and mechanical properties of PMMA-based bioactive bone cements," Biomaterials 21 (2000) 2137-2146).*
Bohner, M. et al., "Theoretical and Experimental Model to Describe the Injection of a Polymethacrylate Cement into a Porous Structure," Biomaterials 24(16):2721-30 (2003).
Breusch, S. et al., "Knochenzemente auf Basis von Polymethylmethacrylat," Orthopade 32:41-50 (2003).
Carrodegus et al., "Injectable Acrylic Bone Cements for Vertebroplasty with Improved Properties," J. Biomed. Materials Res. 68(1):94-104 (Jan. 2004).
Gheduzzi, S. et al., "Mechanical Characterisation of Three Percutaneous Vertebroplasty Biomaterials," J. Mater Sci Mater Med 17(5):421-26 (2006).
Giannitsios, D. et al., "High Cement Viscosity Reduces Leakage Risk in Vertebroplasty," European Cells & Mat. 10 supp. 3:54 (2005).
Hasenwinkel, J. et al., "A Novel High-Viscosity, Two-Solution Acrylic Bone Cement: Effect of Chemical Composition on Properties," J. Biomed. Materials Research 47(1):36-45 (1999).
Hasenwinkel, J. et al., "Effect of Initiation Chemistry on the Fracture Toughness, Fatigue Strength, and Residual Monomer Content of a Novel High-Viscosity, Two-Solution Acrylic Bone Cement," J. Biomed. Materials Res. 59(3):411-21 (2001).
Lewis, G. et al., "Rheological Properties of Acrylic Bone Cement During Curing and the Role of the Size of the Powder Particles," J. Biomed. Mat. Res. Appl. Biomat. 63(2):191-99 (2002).
Pascual, B. et al., "New Aspects of the Effect of Size and Size Distribution on the Setting Parameters and Mechanical Properties of Acrylic Bone Cements," Biomaterials 17(5):509-16 (1996).
Robinson, R. et al., "Mechanical Properties of Poly(methyl methacrylate) Bone Cement," J. Biomed. Materials Res. 15(2):203-08 (2004).
Saha, S. et a., "Mechanical Properties of Bone Cement: A Review," J. Biomed. Materilas Res. 18(4):435-62 (1984).
Farrar, D.F. et al., "Rheological Properties of PMMA Bone Cements During Curing," Biomaterials 22:3005-13 (2001).
Mousa, W.F. et al., "Biological and Mechanical Properties of PMMA-Based Bioactive Bone Cements," Biomaterials 21:2137-46 (2000).
Serbetci, K. et al., "Thermal and Mechanical Properties of Hydroxyapatite Impregnated Acrylic Bone Cements," Polymer Testing 23:145-55 (2004).
Cole et al., "AIM Titanium Humeral Nail System," Surgical Technique. DePuy Orthopaedics 17P (2000).
Heini et al., "The Use of a Side-Opening Injection Cannula in Vertebroplasty," Spine 27(1):105-09 (2002).
Hernandez et al., "Influence of Powder Particle Size Distribution on Complex Viscosity and Other Properties of Acrylic Bone Cement for Vertebroplasty and Kyphoplasty," J. Biomed. Mat. Res. 77B:98-103 (2006).
Ishikawa et al., "Effects of Neutral Sodium Hydrogen Phosphate on Setting Reaction and Mechanical Strength of Hydroxyapatite Putty," J. Biomed. Mat. Res. 44:322-29 (199).
Ishikawa et al., "Non-Decay Type Fast-Setting Calcium Phosphate Cement: Hydroxyapatite Putty Containing an Increased Amount of Sodium Alginate," J. Biomed. Mat. Res. 36:393-99 (1997).
Krause et al., "The Viscosity of Acrylic Bone Cements," J. Biomed. Mat. Res. 16:219-43 (1982).
Lewis, "Properties of Ascrylic Bone Cement: State of the Art Review," J. Biomed. Mat. Res. Appl. Biomaterials 38(2):155-82 (p. 158 s.Viscosity) (1997).
Lewis, "Toward Standardization of Methods of Determination of Fracture Properties of Acrylic Bone Cement and Statistical Analysis of Test Results," J. Biomed. Research: Appl. Biomaterials 53(6):748-68 (2000).
Nussbaum et al., "The Chemistry of Acrylic Bone Cements and Implications for Clinical Use in Image-Guided Therapy," J. Vasc. Interv. Radiol. 15:121-26 (2004).
Steen, "Laser Surface Treatment," Laser Mat. Processing, Springer 2d ed. ch. 6:218-71 (2003).
Varela et al., "Closed Intramedullary Pinning of Metacarpal and Phalanx Fractures," Orthopaedics 13(2):213-15 (1990).
Weissman et al., "Trochanteric Fractures of the Femur Treatment with a Strong Nail and early Weight-Bearing," Clin. Ortho. & Related Res. 67:143-50 (1969).
Lewis, G., "Properties of Acrylic Bone Cement: State of the Art Review," J. Biomed. Mat. Res. 38(2):155-82 (1997).
Lewis, G., "Toward Standardization of Methods of Determination of Fracture Properties of Acrylic Bone Cement and Statistical Analysis of Test Results," J. Biomed. Mat. Res. 53(6):748-68 (2000).
Al-Assir, et al., "Percutaneous Vertebroplasty: A Special Syringe for Cement Injection," AJNR Am. J. Neuroradiol. 21:159-61 (Jan. 2000).
Amar, Arun P. et al., "Percutaneous Transpedicular Polymethylmethacrylate Vertebroplasty for the Treatment of Spinal Compression Fractures," Neurosurgery 49(5):1105-15 (2001).
Avalione & Baumeister III, Marks' Standard Handbook for Mechanical Engineers, 10 ed, pp. 5-6 (1996).
Baroud et al., "Injection Biomechanics of Bone Cements Used in Vertebroplasty," Biomed. Mat. & Eng. 00:1-18 (2004).
Barr, J.D., "Percutaneous Vertebroplasty for pain Relief and Spinal Stabilization," Spine 25(8):923-28 (2000).

Belkoff, S. et al., The Biomechanics of Vertebroplasty, the Effect of Cement Volume on Mechanical Behavior, SPINE 26(14):1537-41 (2001).

Belkoff, S.M. et al., "An Ex Vivo Biomechanical Evaluation of a Hydroxyapatite Cement for Use with Kyphoplasty," Am. J. Neurorad. 22:1212-16 (2001).

Belkoff, S.M. et al., "An Ex Vivo Biomechanical Evaluation of a Inflatable Bone Tamp Used in the Treatment of Compression Fracture," SPINE 26(2):151-56 (2001).

Belkoff, S.M. et al., "An In Vitro Biomechanical Evaluation of Bone Cements Used in Percutaneous Vertebroplasty, " Bone 25(2):23S-26S (1999).

Canale et al., "Campbell's operative orthopaedic-vol. 3-ninth ed", Mosby:P2097,2121,2184-85,2890-96, (1998) abstracts.

Combs, S. et al., "The Effects of Barium Sulfate on the Polymerization Temperature and Shear Strength of Surgical Simplex P," Clin. Ortho. and Related Res. pp. 287-291 (Jun. 4, 1979).

Cotton, A. et al., "Percutaneous Vertebroplasty: State of the Art," Scientific Exhibit, Radiographics 18:311-20 (1998).

Dean, J.R. et al., "The Strengthening Effect of Percutaneous Vertebroplasty," Clin Radiol. 55:471-76 (2000).

Deramond, H. et al, "Percutaneous Vertebroplasty with Polymethylmethacrylate, Technique Indications and Results," Radiologic Clinics of North America 36(3) (May 1988).

Deramond, H. et al., "Temperature Elevation Caused by Bone cement Polymerization During Vertbroplasty," Bone 25(2):17S-21S (1999).

DeWijn, J.R., Characterization of Bone Cements, The Institute of Dental Materials Science and Technology and the Dept of Ortho., Catholic University, Netherlands 46:38-51 (1975).

Edeland, "Some additional suggestions for an intervertebral disc prothesis," J. Biomed. Eng. XP008072822, 7(1):57-62 (1985.

European Search Report, from EP09151379.6, mailed Oct. 20, 2009.

European Search Report, from EP06780252.0, mailed Oct. 29, 2009.

Fessler, Richard D. et al., "Vertebroplasty," Neurosurgical Operative Atlas 9:233-240 (2000).

Gangi, A., "CT-Guided Interventional Procedures for Pain Management in the Lumbosacral Spine," Radiographics 18:621-33 (1998).

Gangi, A., "Computed Tomography CT and Fluoroscopy-Guided Vertebroplasty: Results and Complications in 187 Patients," Seminars in Interventional Radiology 16(2):137-42 (1999).

Gangi, A., "Percutaneous Vertebroplasty Guided by a Combination of CT and Fluoroscopy," AJNR 15:83-86 (1994).

Garfin, S. R. et al., "New Technologies in Spine, Kyphoplasty and Vertebroplasty for the Treatment of Painful Osteoporotic Compression Fractures," Spine 26(14:1511-15 (2001).

Grados F. et al.,"Long-Term Observations of Vertebral Osteoporotic Fractures Treated by Percutaneous Vertebroplasty," Rheumatology 39:1410-14 (2000).

Heini, P. et al., "Augmentation of Mechanical Properties in Osteoporatic Vertebral Bones—a Biomechanical Investigation of Vertebroplasty Efficacy With Different Bone Cements," EUR Spine J. v. 10, pp. 164-171, Springer-Verlag (2001).

Heini, P., "Percutaneous Transpedicular Vertebroplasty with PMMA: Operative Technique and Early Results," EUR Spine J. v. 9, pp. 445-450, Springer-Verlag (2000).

International Preliminary Report on Patentability, from PCT/IB06/053014, dated Apr. 10, 2008.

International Search Report, from PCT/IL07,00833, mailed Apr. 4, 2008.

International Search Report, from PCT/IL07/00484, mailed Apr. 17, 2008.

International Search Report, for PCT/MX03/000027, filed Mar. 14, 2003.

Jasper, L.E. et al., "The Effect of Monomer-to-Powder Ratio on the Material Properties of Cranioplastic," Bone 25(2):27S-29S (1999).

Jensen, Mary E. et al., "Percutaneous Polymethylmethacrylate Vertebroplasty in the Treatment of Osteoporotic Vertebral Body Compression Fractures: Technical Aspects," AJNR 18:1897-1904 (1997).

Jensen, Mary E. et al., "Percutaneous Vertebroplasty in the Treatment of Osteoporotic Compression Fractures," Spine Interventions 10(3):547-568 (2000).

Kallmes, D. et al., "Radiation Dose to the Operator During Vertebroplasty: Prospective Comparison of the Use of 1-cc Syringes Versus an Injection Device," AJNR Am. J. Neuroradiol. 24:1257-60 (2003).

Kaufmann et al, "Age of Fracture and Clinical Outcomes of Percutaneous Vertebroplasty," Am. J. Neuroradiology 22:1860-63 (2001).

Kuhn, Klaus-Dieter, Bone Cements—Uptodate Comparison of Physical and Chemical Properties of Commercial Materials, Springer-Verlag Heidelberg Germany p. 7-8, 17, 38 (2000).

Kyphom Medical Professionals, KyphXProducts (Nov. 8, 2001).

Li, C. et al., "Thermal Characterization of PMMA-Based Bone Cement Curing," J. Materials Sci.: Materials in Medicine 15:84-89 (2004).

Lieberman, I.H. et al., "Initial Outcome and Efficacy of Kyphoplasty in the Treatment of Painful Osteoporatic Vertebral Compression Fractures," Spine 26(14:1631-38 (2001).

Mathis, John et al., "Percutaneous Vertebroplasty: A Developing Standard of Care for Vertebral Compression Fractures," AJNR Am. J. Neurorad. 22:373-81 (2001).

O'Brien, J. et al., "Vertebroplasty in patients with Severe Vertebral Compression Fractures: A Technical Report," AJNR 21:1555-58 (2000).

Padovani, B. et al., "Pulmonary Embolism Caused by Acrylic Cement: A Rare Complication of Percutaneous Vertebroplasty," AJNR 20:375-77 (1999).

Parallax Medical, Inc., Exflow Cement Delivery System (May 16, 2000).

Shah, T., Radiopaque Polymer Formulations for Medical Devices; Medical Plastics and Biomaterials Special Section; Medical device & Diagnostic Industry pp. 102-111 (2000).

Vasconcelos, C., "Transient Arterial Hypotension Induced by Polymethyacrylated Injection During Percutaneous Vertebroplasty," Letter to the Editor, JVIR (Aug. 2001).

Wimhurst, J.A., et al., "The Effects of Particulate Bone Cements at the Bone-Implant Interface," J. Bone & Joint Surgery pp. 588-92 (2001).

Wimhurst, J.A. et al., "Inflammatory Responses of Human Primary Macrophages to Particulate Bone Cements in Vitro," J. Bone & Joint Surgery 83B:278-82 (2001).

International Search Report, from corresponding PCT/IL07/01257, dated Jul. 15, 2008.

Baroud, G., "Influence of Mixing Method on the Cement Temperature-Mixing Time History and Doughing Time of Three Acrylic Cements for Vertebroplasty," Wiley Periodicals Inc. 112-116 (2003).

European Search Report, from EP 10182769.9, mailed Mar. 2, 2011.

European Search Report, from EP 10182693.1, mailed Mar. 2, 2011.

European Search Report, from EP 10192302.7, mailed Mar. 24, 2011.

European Search Report, from EP 10192301.9, mailed Mar. 24, 2011.

European Search Report, from EP 10192300.1, mailed Mar. 24, 2011.

Hide, I. et al., "Percutaneous Vertebroplasty: History, Technique and current Perspectives," Clin. Radiology 59:461-67 (2004).

Hu, M. et al., "Kyphoplasty for Vertebral Compression Fracture Via a Uni-Pedicular Approach," Pain Phys. 8:363-67 (2005).

Liang, B. et al., "Preliminary Clinical Application of Percutaneous Vertebroplasty," Zhong Nan Da Xue Bao Yi Xue Ban 31(1):114-9 (2006)(abs. only).

Noetzel, J. et al., Calcium Phosphate Cements in Medicine and Denistry—A Review of Literature, Schweiz Monatsschr Zehmed 115(12):1148-56 (2005)(abs. only).

Supp. EP Search Report, from EP Appl. No. 07766863.0, dated Apr. 12, 2011.

International Search Report, for PCT/IL07/00808, issued Aug. 22, 2008.

Marks, Standard handbook for mechanical engineers, section 5 (Tenth ed. 1996).

Supp. EP Search Report, from EP 07766838.2, dated May 18, 2011.

Cromer, A., "Fluids," Physics for the Life Sciences, 2:136-37 (1977).

JP Office Action, from JP Appl No. 2008-532910, mailed Jul. 19, 2011.

Lindeburg, M., "External Pressurized Liquids," Mechanical Eng. Ref. Manual for the PE Exam, 10:15-14(May 1997).

Feldman, H., "Die Geschichte der Injektionen," Laryngo-Rhino-Othol 79:239-46 (2000).

Glasgow Medico-Chirurgical Society, The lancet 1364 (May 18, 1907).

Greenberg, "Filling Root Canals by an Injection Technique," Dental Digest 61-63 (Feb. 1963).

Greenberg, "Filling Root Canals in Deciduous Teeth by an Injection Technique," Dental Digest 574-575 (Dec. 1961).

Greig, D., "A New Syringe for Injecting Paraffin," The Lancet 611-12 (Aug. 29, 1903).

Lake, R., "The Restoration of the Inferior Turbinate Body by Paraffin Injections in the Treatment of Atrophic Rhinitis," The Lancet 168-69 (Jan. 17, 1903).

Paget, S., "The Uses of Paraffin in Plastic Surgery," The Lancet 1354 (May 16, 1903).

Walton, A, "Some Cases of Bone Cavities Treated by Stopping With Paraffin," The Lancet 155 (Jan. 18, 1908).

Andersen, M. et al., "Vertebroplastik, ny behandling of osteoporotiske columnafrakturer?", Ugeskr Laeger 166/6:463-66 (Feb. 2, 2004) [English Abstract Only].

Japanese Office Action issued Feb. 21, 2012 for Application No. 2009-516062 (6 Pages).

JP Office Action, from JP Appl No. 2009-517607, mailed Aug. 9, 2011.

Codman & Shurtleff, "V-MAX™ Mixing and Delivery Device," Catalog No. 43-1056 (2001).

European Search Report, from EP05763930.4; mailed Sep. 11, 2008.

International Search Report, from PCT/IL06/00239, mailed Jan. 26, 2007.

International Search Report, from PCT/IL05/00812, mailed Feb. 28, 2007.

International Search Report, from PCT/IB06/052612, mailed Oct. 2, 2007.

Ryu, K. S. et al., "Dose-Dependent Epidural Leakage of Polymethylmethacrylate after Percutaneous Vertebroplasty in Patients with Osteoporotic Vertebral Compression Fractures," J. Neuro: Spine 96:56-61 (2002).

Supp. EP Search Report, from EP Appl. No. 05763930.4, dated Sep. 11, 2008.

Supp. EP Search Report, from EP Appl. No. 067112219, dated Sep. 15, 2008.

Zapalowicz, K. et al., "Percutaneous Vertebroplasty with Bone Cement in the Treatment of Osteoporotic Vertebral Compression Fractures," Ortopedia Traumatologia Rehabilitacja NR Jan. 2003 (w/ Eng. Abs).

European Search Report, from EP07827231.7, mailed Sep. 12, 2011.

Japanese Office Action issued Dec. 6, 2011 for Application No. 2008-524651 (9 Pages).

Mendizabal et al., Modeling of the curing kinetics of an acrylic bone cement modified with hydroxyapatite. International Journal of Polymeric Materials. 2003;52:927-938.

Morejon et al., Kinetic effect of hydroxyapatite types on the polymerization of acrylic bone cements. International Journal of Polymeric Materials. 2003;52(7):637-654.

Sreeja et al., Studies on poly(methyl methacrylate)/polystyrene copolymers for potential bone cement applications. Metals Materials and Processes. 1996;8(4):315-322.

Yang et al., Polymerization of acrylic bone cement investigated by differential scanning calorimetry: Effects of heating rate and TCP content. Polymer Engineering and Science. Jul. 1997;1182-1187.

* cited by examiner

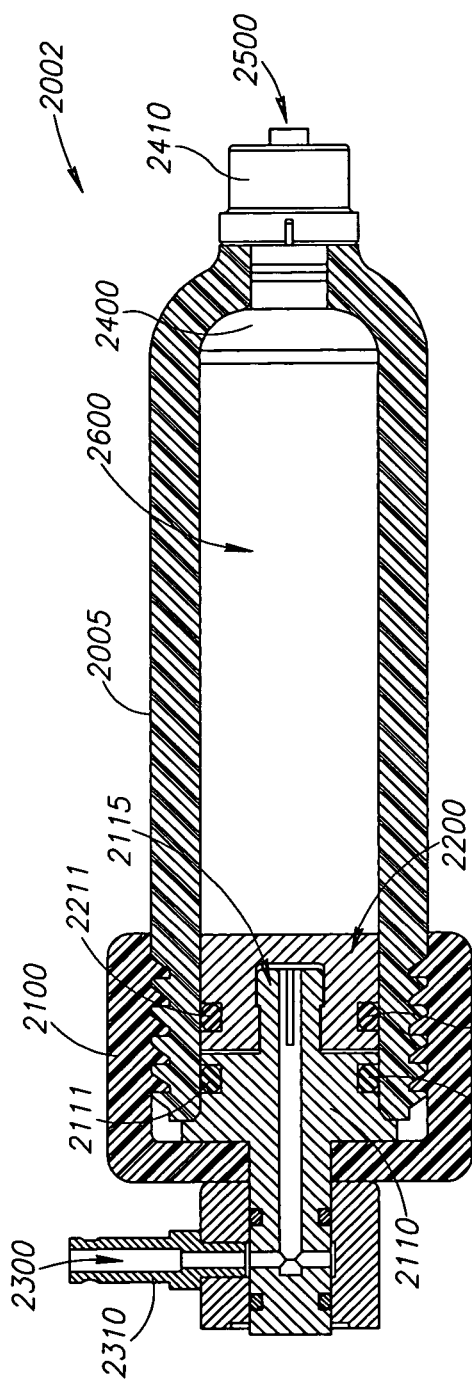
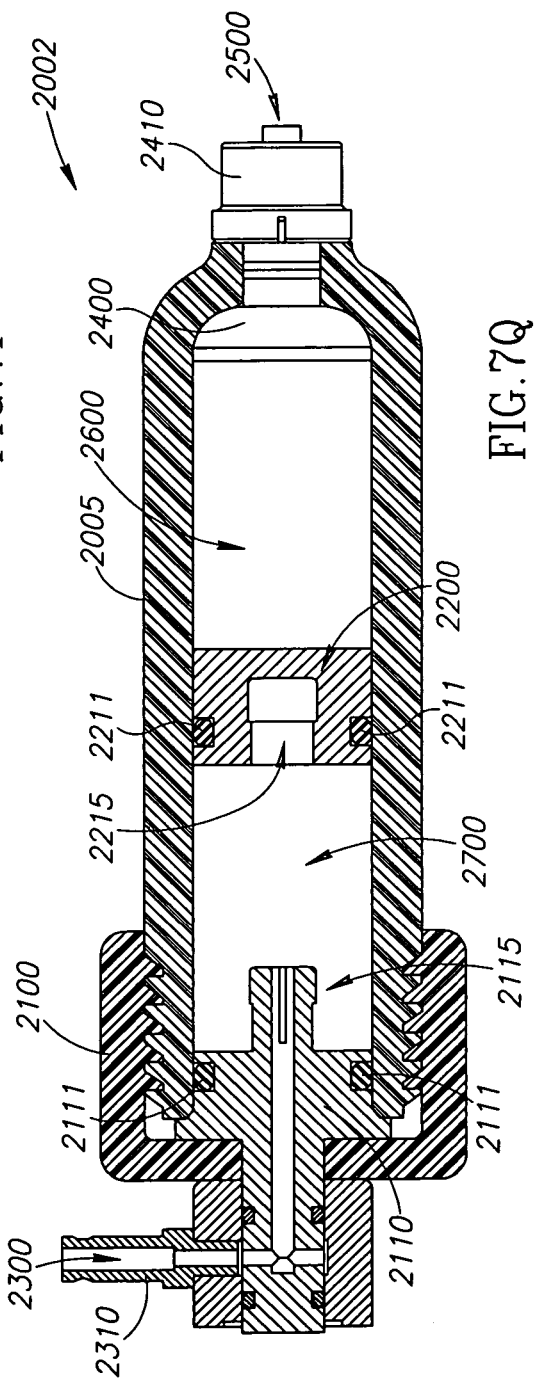
FIG.7P
FIG.7Q

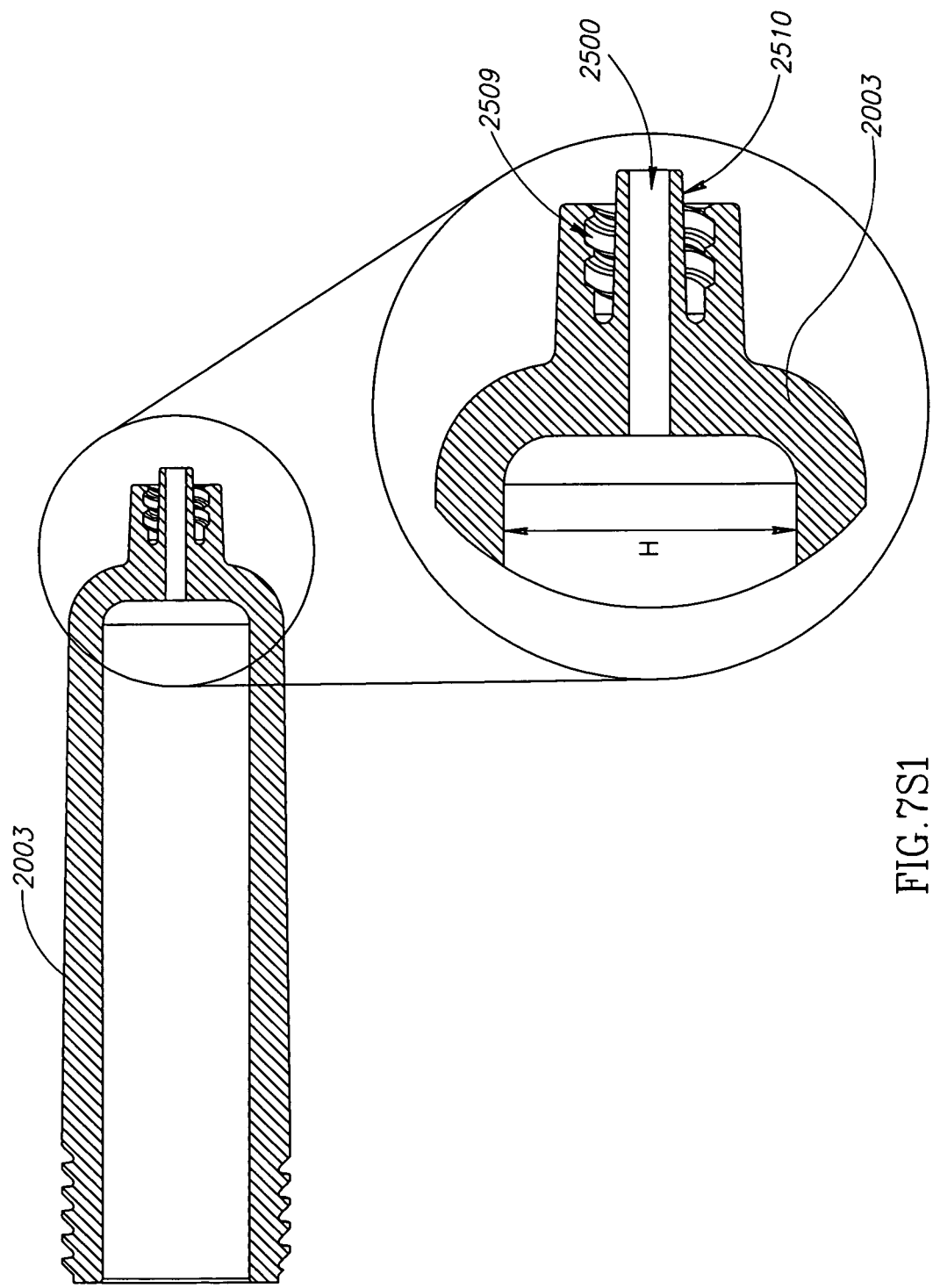
FIG.7S1

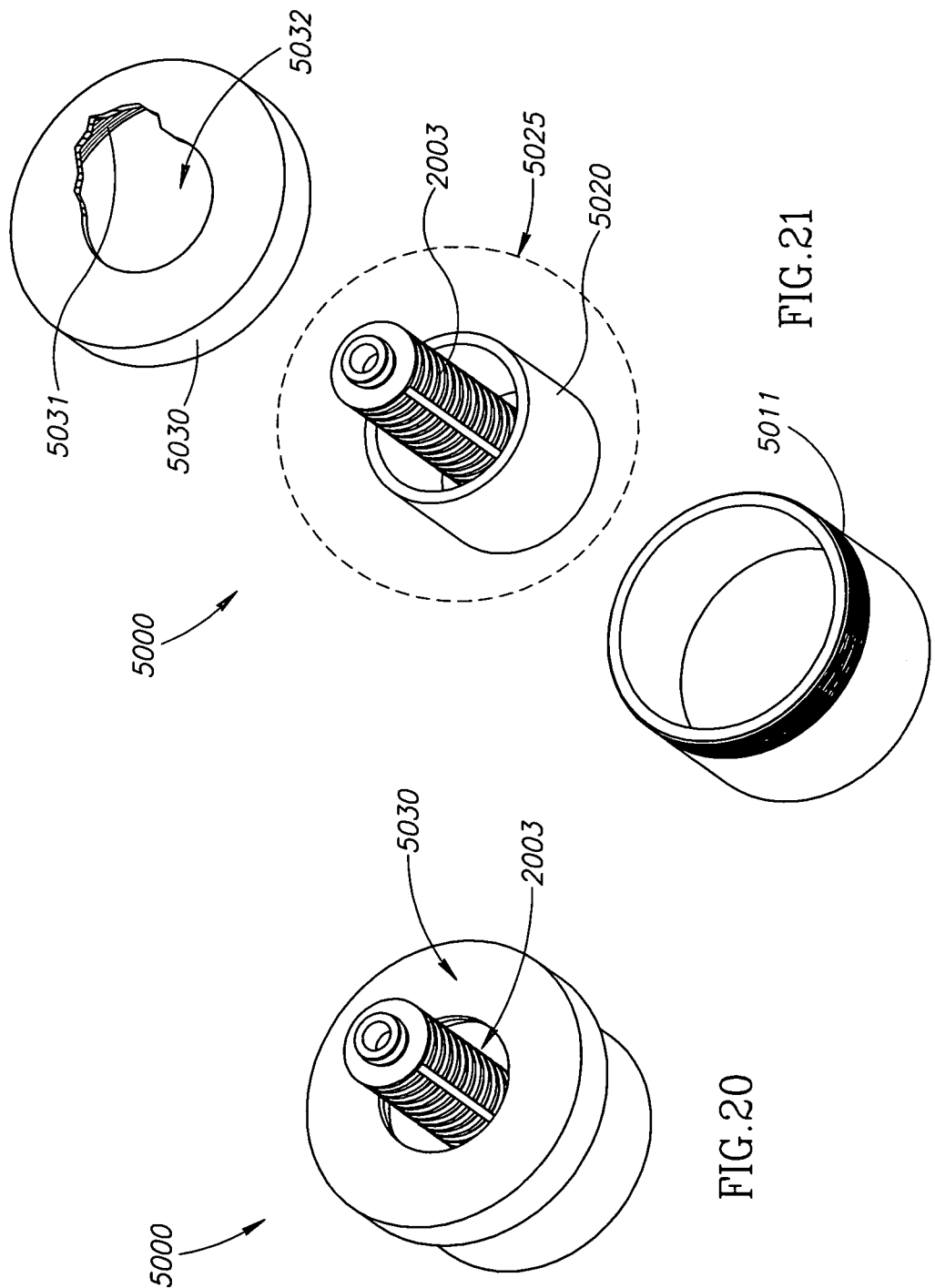

METHODS, MATERIALS, AND APPARATUS FOR TREATING BONE AND OTHER TISSUE

RELATED APPLICATIONS

The present application claims the benefit under 35 USC 119(e) of U.S. provisional applications identified as 60/765,484 filed on Feb. 2, 2006 and entitled "Methods, Materials and Apparatus for Treating Bone and Other Tissue"; 60/762,789 filed on Jan. 26, 2006 and entitled "Methods, Materials and Apparatus for Treating Bone and Other Tissue"; 60/763,003 entitled "Cannula" filed on Jan. 26, 2006; U.S. provisional application 60/738,556 filed Nov. 22, 2005 and entitled "Methods, Materials and Apparatus for Treating Bone and other Tissue"; 60/729,505 filed Oct. 25, 2005 and entitled "Methods, Materials and Apparatus for Treating Bone and other Tissue"; 60/720,725 filed on Sep. 28, 2005 and entitled "Tools and Methods for Treating Bones" and U.S. provisional application Nos. 60/721,094 filed on Sep. 28, 2005 and entitled "Tools and Methods for Material Delivery into the Body". The disclosures of these applications are incorporated herein by reference.

The present application is also a Continuation-in-Part of U.S. Ser. No. 11/194,411 filed Aug. 1, 2005 which claimed priority from IL 166017 filed Dec. 28, 2004 and IL 160987 filed Mar. 21, 2004 and also claimed the benefit under 35 USC 119(e) of U.S. Provisional Application No. 60/647,784 filed on Jan. 31, 2005 and U.S. Provisional Application No. 60/592,149 filed on Jul. 30, 2004. The present application is also a Continuation-in Part of PCT/IL2005/000812 of Jul. 31, 2005. The present application also claims the benefit under 35 USC 119(e) of U.S. provisional application No. 60/654,495 filed Feb. 22, 2005. The disclosures of these applications are incorporated herein by reference.

This application is related to PCT Application No. PCT/IL2004/000527 filed on Jun. 17, 2004, Israel Application No. 160987 filed on Mar. 21, 2004, U.S. Provisional Applications: 60/478,841 filed on Jun. 17, 2003; 60/529,612 filed on Dec. 16, 2003; 60/534,377 filed on Jan. 6, 2004 and 60/554,558 filed on Mar. 18, 2004; U.S. application Ser. No. 09/890,172 filed on Jul. 25, 2001, and U.S. application Ser. No. 09/890,318 filed on Jul. 25, 2001. The disclosures of all of these applications are incorporated herein by reference.

This application is also related to U.S. application Ser. No. 10/549,409 entitled "Hydraulic Device for the injection of Bone Cement in Percutaneous Vertebroplasty filed on Sep. 14, 2005, the disclosure of which is incorporated herein by reference.

FIELD OF THE INVENTION

The present invention relates to viscous materials, methods for injection of a viscous material into a living subject and/or to delivery systems for said injection.

BACKGROUND OF THE INVENTION

A common occurrence in older persons is compression fractures of the vertebrae, causing both pain and a shortening (or other distortion) of stature. One common treatment is vertebroplasty, in which cement is injected into a fractured vertebra. While this treatment fixes the fracture and reduces pain, it does not restore the vertebra and person to their original height. Another problem is that the cement is injected in a liquid phase so that it may be unintentionally injected outside of the vertebra and/or may migrate out through cracks in the vertebra. This may cause considerable bodily harm.

Another common treatment is kyphoplasty, in which the fracture is reduced, for example by first inflating a balloon inside the vertebra and then injecting a fixing material and/or an implant. The problem of cement migration is reduced, but not avoided, as a lower pressure can be used to inject the cement.

In general, polymeric cements becomes more viscous as the polymer chain grows by reacting directly with the double bond of a monomer. Polymerization begins by the "addition mechanism" in which a monomer becomes unstable by reacting with an initiator, a volatile molecule that is most commonly a radical (molecules that contain a single unpaired electron). Radicals bond with monomers, forming monomer radicals that can attack the double bond of the next monomer to propagate the polymer chain. Because radicals are so transient, initiators are often added in the form of an unreactive peroxide form that which is stable in solution. Radicals are formed when heat or light cleaves the peroxide molecule. For applications in which high temperatures are not practical (such as the use of bone cement in vivo), peroxide is cleaved by adding a chemical activator such as N,N-dimethyl-p-toluidine. (Nussbaum D A et al: "The Chemistry of Acrylic Bone Cement and Implication for Clinical Use in Image-guided Therapy", J Vasc Interv Radiol (2004); 15:121-126; the content of which is fully incorporated herein by reference).

Viscous cement is advantageous not only in reducing the risk of its leakage, but also, because of its ability to infiltrate into the intravertebral cancellous bone (interdigitaion) [see G Baroud et al, Injection biomechanics of bone cements used in vertebroplasty, Bio-Medical Materials and Engineering 00 (2004) 1-18]. Baroud also suggests that about 95% of the applied injection pressure is required to overcome friction in the cannula. In addition, viscous material may reduce the fracture.

Examples of commercially available viscous bone cements include, but are not limited to, CMW™ Nos. 1, 2 and 3 (DePuy Orthopaedics Inc.; Warsaw, Ind., USA) and Simplex®-P and -RO (Stryker Orthopaedics; Mahwah, N.J., USA). These cements are characterized by a liquid phase after mixing and prior to achieving a viscosity of 500 Pascal second. In a typical use scenario, these previously available cements are poured, while in a liquid phase, into a delivery device.

There have also been attempts to reduce cement migration by injecting more viscous cement, for example, during the doughing time and the beginning of polymerization. However, the injection methods suggested require higher pressures for the more viscous material. Also, some types of viscous materials, such as hardening PMMA, have a small workability window at high viscosities, as they harden very quickly once they reach a high viscosity. This has generally prevented very viscous materials and the associated very high pressures from being used. One possible reason is that as pressures increase, the physician is prevented from receiving feedback on the resistance of the body to the injection of the cement. Thus, over-injection can easily occur.

Some fixing materials, such as polymethylmethacrylate (PMMA), emit heat and possibly toxic materials while setting. These may further weaken the bone and possibly cause the cement to loosen and/or the bone to fracture.

It has recently been suggested that some fixing materials, being harder than bone, induce fractures in nearby bones.

It is also known to use bone-like repair materials, such as a slurry of bone chips, which apparently do not induce such fractures. However, injecting such materials is difficult due to their viscosity.

U.S. patents and applications U.S. Pat. No. 4,969,888, U.S. Pat. No. 5,108,404, U.S. Pat. No. 6,383,188, 2003/0109883, 2002/0068974, U.S. Pat. Nos. 6,348,055, 6,383,190, 4,494, 535, 4,653,489 and 4,653,487, the disclosures of which are incorporated herein by reference describe various tools and methods for treating bone.

An additional manner to deliver bone cement into the vertebra is using a tamping instrument (U.S. Pat. Nos. 6,241,734 and 6,613,054), comprising a cannula and a rod, which urges the material within the cannula into the bone.

U.S. patent application 20040260303, the disclosure of which is incorporated herein by reference, teaches an apparatus for delivering bone cement into a vertebra.

Cannulae with working sleeves are describe, for example, in U.S. Pat. Nos. 6,241,734 and 6,613,054, the disclosures of which are fully incorporated herein by reference.

SUMMARY OF THE INVENTION

An aspect of some embodiments of the invention relates to formulations of bone cement which provide a window of time during which the cement is suitably viscous for injection. In an exemplary embodiment of the invention, the cement achieves a high viscosity rapidly when components are mixed and then sets slowly. In an exemplary embodiment of the invention, the cement remains viscous when held above a threshold temperature and sets when cooled below the threshold temperature. In an exemplary embodiment of the invention, the cement is a non-setting cement. Optionally, there is no liquid phase when cement components are mixed.

An aspect of some embodiments of the invention relates to a viscous bone cement which has an enhanced high-viscosity window before it sets and where viscosity, while high, does not vary to a degree which influences injection parameters. Optionally, the viscosity in the window is 500, optionally 1,000, optionally 1,500, optionally 2,000 Pascal-sec or lesser or greater or intermediate values. Optionally, the cement is sufficiently viscous to move fractured bone, such as vertebral plates of a collapsed vertebra, as it is injected. In an exemplary embodiment of the invention, injection of viscous cement contributes to fracture reduction and/or restoration of vertebral height.

In an exemplary embodiment of the invention, mixture of polymer and monomer components produces a high viscosity material within 1 second, within 5 seconds, within 10 seconds, within 15 seconds, within 30 seconds, within 60 seconds, within 120 seconds or intermediate times. Optionally, once a high viscosity is achieved, the viscosity remains stable for 5 minutes or more. In an exemplary embodiment of the invention, this interval of stable viscosity provides a window of opportunity for performance of a medical procedure.

In an exemplary embodiment of the invention, the working window is at least 3 minutes, optionally at least 5 minutes, optionally at least 8 minutes, optionally at least 10 minutes, optionally at least 15 minutes, optionally at least 20 minutes. In an exemplary embodiment of the invention, increased viscosity is provided a short time after mixing of the cement, for example, zero time (for a pre-provided viscous material), less than 1 minutes or less than 2 or less than 3 minutes after mixing is complete.

In an exemplary embodiment of the invention, the cement may include an acrylic polymer, such as polymethylmethacrylate (PMMA) and/or styrene. In an exemplary embodiment of the invention, polymer bead size and/or molecular weight of the polymer prior to polymerization contribute to a final viscosity of the mixture. Optionally, an average molecular weight of the acrylic polymer is in excess of 60,000, optionally 70,000, optionally 80,000, optionally 90,000, optionally 100,000 Dalton. In an exemplary embodiment of the invention, the average molecular weight of the acrylic polymer in the beads is in the range of about 100,000 to 120,000, optionally about 110,000 Dalton. Optionally, the molecular weight of a portion of the acrylic polymer in the beads has a high molecular weight. Optionally, the portion includes 0.25%, 0.5%, 1%, 2%, 3% or lesser or intermediate or greater percentages of the total acrylic polymer in the beads. Optionally, high molecular weight acrylic polymer in the beads is 600,000, optionally 900,000, optionally 1,100,000 Dalton or intermediate or lesser or greater values. In an exemplary embodiment of the invention, approximately 1% of the PMMA in the beads is characterized by a molecular weight of 700,000 to 1,000,000 Dalton and the average molecular weight of the PMMA is approximately 110,000 Dalton. In an exemplary embodiment of the invention, bead diameter is in the range of was in the range of 10-200 microns, optionally, 20 to 150 microns, optionally with an average of about 60 microns or lesser or intermediate or greater sizes.

An aspect of some embodiments of the invention relates to the use of material that has a glass transition temperature higher than 37 degrees Celsius as a bone cement. In an exemplary embodiment of the invention, heating the material above the glass transition temperature transforms the material to a dough-like or putty-like state. Optionally, Dough-like indicates a viscosity of at least 500, optionally at least 900, optionally at least 1000 Pascal seconds or lesser or intermediate or greater values. In an exemplary embodiment of the invention, the dough-like state is characterized in that a pressure less than 200 atmospheres is sufficient to cause it to flow through a tube with with an ID of 3 mm and a length of 100 mm. Optionally, the dough-like material is suitable for delivery using a high-pressure fluid delivery system, for example as disclosed herein. In an exemplary embodiment of the invention, the temperature is lower than a maximum temperature allowed inside the human body, for example, being below 60 degrees Celsius, below, 50 degrees, 45 and/or below 40 degrees or intermediate or lesser temperatures. In an exemplary embodiment of the invention, a penetrating tube is subject to temperature control, for example by means of insulation. Optionally, a double-walled tube with vacuum pressure between its walls provides the isolation.

In an exemplary embodiment of the invention, the material (e.g., bone cement) includes processed bone (from human or animals origin) and/or synthetic bone. Optionally, the cement has osteoconductive and/or osteoinductive behavior.

In an exemplary embodiment of the invention, a bone cement is injected into a bone void as a preventive therapy or as a treatment for an existing condition.

In some exemplary embodiments of the invention, a temperature control unit is provided to facilitate heating and/or cooling of bone cement. Optionally, temperature control is applied to increase the handling and/or working time (e.g., heat may be applied to offset temerature changes resulting from high pressures). In various exemplary embodiments of the invention, the temperature control unit operates on cement in an external reservoir and/or cement in a delivery system reservoir.

An aspect of some embodiments of the invention relates to hydraulic systems for delivering viscous material into a bone. Optionally, delivery is via a small diameter tube such as a bone access cannula. In an exemplary embodiment of the invention, delivery is via a tube with an inner diameter of 1.5 mm, 2 mm, 3 mm, 4 mm or lesser or greater or intermediate values. In an exemplary embodiment of the invention, the system is operable by foot and/or is battery powered. In an exemplary embodiment of the invention, the system provides sufficient pressure to deliver at least 5 ml, optionally at least 10 ml, of a viscous bone cement as a single continuous aliquot.

In an exemplary embodiment of the invention, the system design assures the physician's hands are located outside an X-ray radiation zone. In an exemplary embodiment of the invention, a hand operable actuator for a pressure source is located 20 cm, 40 cm, 60 cm, 100 cm or intermediate or greater distances from a cement reservoir.

In an exemplary embodiment of the invention, the actuator for the pressure source employs a threaded steel rod which passes through a plastic nut. Optionally, this combination of materials reduces the friction coefficient. Optionally, reducing a diameter of the bolt reduces a radius-of-friction. Optionally, reducing a radius-of-friction reduces an applied moment. In an exemplary embodiment of the invention, a short actuation handle permits an operator to grasp the handle on both sides of the axis (bolt) so that moment is applied without generating undesired radial force.

In an exemplary embodiment of the invention, the pressure source includes a safety valve. In an exemplary embodiment of the invention, solidification of the cement contributes to increased pressure. Optionally, solidification of the cement increases pressure to a threshold which operates the safety valve. In an exemplary embodiment of the invention, the threshold is significantly below a maximum internal pressure which the system can withstand.

In an exemplary embodiment of the invention, the cement reservoir includes a floating piston. Optionally, the floating piston separates between cement and a hydraulic fluid. In an exemplary embodiment of the invention, the cement reservoir includes a piston mounted on a rod.

In various exemplary embodiments of the invention, the hydraulic actuator is operable by various means. Optionally, the pressure source includes a foot operable actuator. In an exemplary embodiment of the invention, the foot operable actuator includes a clutch plate with a hole with a varying aspect ration. In an exemplary embodiment of the invention, the pressure source provides a pressure of 50, optionally 100, optionally 150, optionally 200, optionally 300 atmospheres or lesser or greater or intermediate values. Optionally, the hydraulic actuator provides pressure amplification. In an exemplary embodiment of the invention, pressure amplification is provided by mechanical advantage (levers) and/or bolt thread step and/or a hydraulic amplification.

In an exemplary embodiment of the invention, mated threaded materials are chosen to reduce the friction coefficient ($\mu$). Optionally, the friction coefficient is 0.2 or less. Optionally, this friction coefficient increase maneuverability. Optionally, a cover serves as a nut and is made of a polymer/plastic. Optionally, a drive shaft serves as a bolt and is made of steel. Optionally, a Radius of Friction (R; bolt radius in this example) is reduced by reducing the thread diameter of the bolt and nut. In an exemplary embodiment of the invention, R is 2, optionally 3, optionally 4, optionally 5 mm or intermediate values.

According to various embodiments of the invention, the cannula may be equipped with one or more apertures for cement delivery at a distal end and/or near the distal end. In an exemplary embodiment of the invention, lateral openings on the cannula permit sideways injection to a desired target in a bone.

An aspect of some embodiments of the invention relates to an apparatus for mixing materials using a revolving paddle which does not rotate. Optionally, the paddle provides high shearing forces. Optionally, cement is easily removable from a flat paddle. Optionally, the mixer includes a delivery mechanism adapted to facilitate delivery of a viscous mixture from the mixer to an external reservoir. Optionally, the paddle presses materials against a wall of a container.

An aspect of some embodiment of the invention relates to the use of a high-pressure delivery system to fill a small diameter cannula with a high viscosity material. In an exemplary embodiment of the invention, pressure to fill the cannula is provided by a hydraulic delivery system. Optionally, once the cannula is filled, the cement may be injected into the body in various means, for example, using a tamping instrument including a rod adapted to comply with a lumen of the cannula. In an exemplary embodiment of the invention, pressure to fill the cannula is provided by a piston with a diameter greater than the cannula lumen. In an exemplary embodiment of the invention, a plurality of cannulae are pre-filled and used as needed. Optionally, the cannulae are provided into the body through an outer sheath which remains in place when the cannulae are changed. Alternatively or additionally, the cannula is refilled while inside the body.

An aspect of some embodiments of the invention relates to a bone cement cannula with a permanently closed distal tip. Optionally, delivery of cement is through one or more apertures on a lateral surface of the cannula near the distal tip. In an exemplary embodiment of the invention, an orientation marking on a proximal portion of the cannula facilitates correct orientation of the lateral aperture(s) after the distal tip of the cannula is inserted. Optionally, the cannula includes a depth marking or coining.

In an exemplary embodiment of the invention, the closed tip is used as a trocar tip for penetrating tissue and/or bone. Alternatively or additionally, the closed tip is used to aim cement delivery.

In an exemplary embodiment of the invention, there is provided a bone cement comprising:
  a first component; and
  a second component,
  wherein, contacting the first component and the second component produces a mixture which attains a viscosity greater than 500 Pascal seconds within an initial setting period,
  wherein the viscosity of the mixture remains between 500 and 2000 Pascal seconds for a working time of at least 5 minutes after the initial setting period, and
  wherein the mixture is suitable for in-vivo use.
  Optionally, the working time is at least 8 minutes long.
  Optionally, the initial setting period is less than 3 minutes.
  Optionally, the initial setting period does not exceed 1 minutes.
  Optionally, the mixture solidifies after the working time.
  Optionally, the initial setting period is less than 3 minutes and the mixture solidifies after the working time.
  Optionally, the first component includes PMMA and Barium Sulfate.
  Optionally, the second component includes MMA and DMPT.
  Optionally, the first component includes PMMA, Barium Sulfate, and Benzoyl Peroxide, and wherein the second component includes MMA, DMPT, and Hydroquinone.
  Optionally, the viscosity of greater than 500 Pascal-second results at least partly from a polymerization reaction.

In an exemplary embodiment of the invention, there is provided a bone cement comprising:
  a first component; and
  a second component, wherein, contacting the first component and the second component produces a mixture which attains a viscosity greater than 200 Pascal seconds within 1 minute, wherein the viscosity of the mixture remains between 200 and 2000 Pascal seconds for a working time of at least 5 minutes after the initial setting period, wherein the viscosity of said cement is changing by less than 10% in a period of 2 minutes within said working time, and wherein the mixture is suitable for in-vivo use.

In an exemplary embodiment of the invention, there is provided a bone cement comprising:

a mixture resulting from the contacting of a first component including PMMA with a second component including MMA, wherein a porton of the PMMA has a molecular weight between about 600,000 Dalton and about 1,200,000 Dalton.

Optionally, the first component contains about 69.4% w/w PMMA, about 30.1% Barium Sulfate, and about 0.5% Benzoyl Peroxide; and wherein the second component contains about 98.5% v/v MMA, about 1.5% DMPT, and about 20 ppm Hydroquinone.

Optionally, the average molecular weight of the PMMA is between about 80,000 Dalton and about 180,000 Dalton.

Optionally, the average molecular weight of the PMMA is about 110,000 Dalton.

Optionally, at least 80% of the PMMA has a bead size between 10 and 200 microns.

Optionally, the cement further comprises processed bone and/or synthetic bone that is mixed together with the first component and the second component.

In an exemplary embodiment of the invention, there is provided a bone cement kit comprising:

a first component including PMMA and a second component including MMA, wherein a porton of the PMMA has a molecular weight between about 600,000 Dalton and about 1,200,000 Dalton.

Optionally, the first component includes about 69.4% w/w PMMA, about 30.1% Barium Sulfate, and about 0.5% Benzoyl Peroxide; and the second component including about 98.5% v/v MMA, about 1.5% DMPT, and about 20 ppm Hydroquinone.

Optionally, the average molecular weight of the PMMA is between about 80,000 Dalton and about 180,000 Dalton.

Optionally, the average molecular weight of the PMMA is about 110,000 Dalton.

Optionally, at least 80% of the PMMA has a bead size between 10 and 200 microns.

In an exemplary embodiment of the invention, there is provided a vertebral implant comprising:

a quantity of cement characterized by a viscosity between 500 and 2000 Pascal seconds for at least 5 minutes, the cement injectable into a vertebral body during the at least 5 minutes, and capable of subsequent hardening therein.

Optionally, the at least 5 minutes is at least 8 minutes.

Optionally, the quantity of cement is at least 1 ml.

In an exemplary embodiment of the invention, there is provided an apparatus for injecting bone cement comprising:

a reservoir configured to hold at least 5 ml of unhardened bone cement, the reservoir having an outlet; and a hydraulically driven plunger configured to press the cement in the reservoir against the outlet with an internal pressure of at least 40 atm, so that at least a portion of the cement will be forced out of the reservoir through the outlet;

wherein the reservoir and the plunger are configured to withstand the internal pressure.

Optionally, the apparatus comprises a cannula configured to route the cement that is forced out of the outlet into a bone in a living subject.

Optionally, the pressure to operate the hydraulically driven plunger is generated by a hydraulic pressure source that is located at least 25 cm away from the plunger, and wherein the hydraulic pressure source has an actuator.

Optionally, each actuation of the actuator by a user causes the plunger to force a predetermined amount of cement out of the reservoir.

Optionally, the predetermined amount is between 0.15 and 0.5 ml.

Optionally, pressure to operate the hydraulically driven plunger is generated by a hydraulic pressure source including a foot-operable actuator.

Optionally, each actuation of the foot-operable actuator by a user causes the plunger to force a predetermined amount of cement out of the reservoir.

Optionally, the cannula has an inner diameter not exceeding 2.5 mm and a length of at least 100 mm.

Optionally, at least part of the reservoir is made of amorphous nylon.

Optionally, at least part of the reservoir is transparent.

Optionally, the reservoir is configured to hold at least 10 ml of cement.

Optionally, the internal pressure is at least 100 atm.

Optionally, the internal pressure is at least 200 atm.

In an exemplary embodiment of the invention, there is provided a method of delivering unhardened cement from a reservoir into a bone via a cannula, the cannula having an inlet and an outlet, the method comprising:

hydraulically generating a pressure of at least 40 atm in response to an actuation input; and using the pressure to force at least 5 ml of the cement out of the reservoir into the inlet of the cannula after the outlet of the cannula has been positioned in a desired location in the bone.

Optionally, the pressure is generated by a hydraulic pressure source that is located at least 25 cm away from the reservoir, and wherein the input originates from an actuator for the hydraulic pressure source.

Optionally, each actuation of the actuator by a user causes a predetermined amount of cement to be forced out of the reservoir.

Optionally, the predetermined amount is between 0.15 and 0.5 ml.

Optionally, the input originates from a foot-operable actuator for the hydraulic pressure source.

Optionally, each actuation of the foot-operable actuator by a user causes a predetermined amount of cement to be forced out of the reservoir.

Optionally, the pressure is at least 100 atm.

Optionally, the pressure is at least 200 atm.

In an exemplary embodiment of the invention, there is provided an apparatus for injecting bone cement comprising:

a reservoir configured to hold at least 5 ml of a bone cement having a viscosity of at least 900 Pascal seconds, the reservoir having an outlet; and a hydraulically actuated plunger configured to press the cement in the reservoir against the outlet with enough pressure to force at least some of the cement out of the reservoir in response to an actuation input.

Optionally, the apparatus comprises a cannula operatively configured to route cement from the outlet into a bone in a living subject.

Optionally, the pressure for operating the hydraulically actuated plunger is generated by a hydraulic pressure source located at least 25 cm away from the plunger.

Optionally, each actuation of the actuator by a user causes the plunger to force a predetermined amount of cement out of the reservoir.

Optionally, the predetermined amount is between 0.15 and 0.5 ml.

Optionally, the pressure for operating the hydraulically actuated plunger is generated by a hydraulic pressure source actuatable by a foot-operable actuator.

Optionally, each actuation of the foot-operable actuator by a user causes the plunger to force a predetermined amount of cement out of the reservoir.

Optionally, at least part of the reservoir is made of amorphous nylon.

Optionally, at least part of the reservoir is transparent.

Optionally, the reservoir is configured to hold at least 10 ml of cement.

In an exemplary embodiment of the invention, there is provided a method of flowing a viscous cement from a reservoir into a bone via a cannula, the method comprising:

generating a pressure within a cement having a viscosity of at least 900 Pascal seconds and residing in a reservoir in response to an actuation input;

wherein the pressure is generated using hydraulics and forces at least some of the cement out of the reservoir through an outlet.

Optionally, the pressure forces at least 5 ml of the cement into the inlet of a cannula operably connected to the outlet of the reservoir after a distal tip of the cannula has been positioned in a desired location in the bone.

Optionally, the pressure is generated by a hydraulic pressure source that is located at least 25 cm away from the reservoir.

Optionally, each actuation input causes a predetermined amount of cement to be forced out of the reservoir.

Optionally, the predetermined amount is between 0.15 and 0.5 ml.

Optionally, the pressure is generated by a hydraulic pressure source comprising a foot-operable actuator.

Optionally, each actuation of the foot-operable actuator causes a predetermined amount of cement to be forced out of the reservoir.

In an exemplary embodiment of the invention, there is provided a bone cement comprising:

a biocompatible material having a glass transition temperature above 37 degrees Celsius, wherein the biocompatible material is injectable into a bone when heated above its glass transition temperature.

Optionally, the material comprises polycaprolactone.

Optionally, the material comprises Polylactic acid (PLA).

Optionally, the material also includes ground bone.

In an exemplary embodiment of the invention, there is provided a vertebral implant comprising:

a quantity of a cement comprising a material having a glass transition temperature above 37 degrees Celsius, the cement injectable into a vertebral body so long as it remains at a temperature above the glass transition temperature, and capable of hardening within the vertebral body after injection therein and subsequent cooling.

Optionally, the cement is bioabsorbable.

Optionally, the cement also contains ground bone.

Optionally, the material comprises polycaprolactone.

Optionally, the material comprises Polylactic acid (PLA).

In an exemplary embodiment of the invention, there is provided an intra-medular nail comprising:

a quantity of a cement comprising a material having a glass transition temperature above 37 degrees Celsius, the cement injectable into a medullary canal of a long bone so long as it remains at a temperature above the glass transition temperature, and capable of hardening within the canal after injection therein and subsequent cooling.

Optionally, the cement is bioabsorbable.

Optionally, the cement also contains ground bone.

Optionally, the material comprises polycaprolactone.

Optionally, the material comprises Polylactic acid (PLA).

In an exemplary embodiment of the invention, there is provided a method of injecting bone cement, the method comprising:

(a) retaining a cement characterized by a viscosity of at least 500 Pascal-second within a reservoir; and (b) applying sufficient pressure to the cement in the reservoir to propel at least 5 ml of the material from the reservoir through a bone injection cannula operably connected to an outlet of the reservoir and having a distal tip inserted in a bone, the cannula characterized by an internal diameter not exceeding 4 mm.

In an exemplary embodiment of the invention, there is provided a method of injecting bone cement, the method comprising:

(a) retaining a cement characterized by a viscosity which requires a pressure of at least 20 atmosphere to cause the cement to flow through a cannula operably connected to an outlet of the reservoir and having a distal tip inserted in a bone and characterized by an internal diameter not exceeding 2.5 mm and by a length of at least 100 mm within a reservoir; and (b) applying the pressure.

In an exemplary embodiment of the invention, there is provided a cement comprising an acrylic polymer mixture, the cement achieving a viscosity of at least 500 Pascal-second within 180 seconds following initiation of mixing of a monomer component and a polymer component and characterized by sufficient biocompatability to permit injection into bone.

In an exemplary embodiment of the invention, there is provided a method of treating a bone, the method comprising:

delivering a bone cement which achieves a viscosity of at least 500 Pascal-second within 160 seconds from a time at which a polymer component and a monomer component of the cement are contacted one with another into a bone.

In an exemplary embodiment of the invention, there is provided a system for delivery of a viscous material into a bone, the system comprising:

(a) a reservoir containing a volume of a material characterized by a viscosity of at least 900 Pascal-second and operably connected to a pressure source;

(b) the pressure source adapted to apply sufficient pressure to the material in the reservoir by advancement of a piston within the reservoir to expel at least 5 ml of the material from the reservoir without retraction of the piston;

(c) an actuator operable to activate the pressure source; and (d) a tube adapted to deliver said pressure from said pressure source to said reservoir.

In an exemplary embodiment of the invention, there is provided an apparatus for mixing, the apparatus comprising:

(a) a container adapted to contain at least a polymer component and a monomer component of a bone cement to be mixed;

(b) a mixing paddle attachable to a drive mechanism via a mixing element axle; and (c) the drive mechanism adapted to move the mixing paddle along a travel path in the mixing container so that a reference point on the mixing element will face in a same direction at every point on the travel path.

In an exemplary embodiment of the invention, there is provided a method of treating a bone comprising introducing a material with a glass transition temperature above 37 degrees Celsius when the material is above the glass transition temperature.

In an exemplary embodiment of the invention, there is provided a use of a material with a glass transition temperature above 37 degrees Celsius in formulation of a bone cement.

In an exemplary embodiment of the invention, there is provided a method for treating vertebra, the method comprising:
(a) heating a bone cement including a material with a glass transition temperature above 37 degrees Celsius at least to its glass transition temperature; and
(b) flowing the bone cement into an interior of a vertebra while the material remains at least at the glass transition temperature.

In an exemplary embodiment of the invention, there is provided a method for treating long bones, the method comprising:
(a) heating a bone cement including a material with a glass transition temperature above 37 degrees Celsius at least to its glass transition temperature; and
(b) flowing the bone cement into an interior of a medullary canal of a long bone while the material remains at least at the glass transition temperature.

In an exemplary embodiment of the invention, there is provided a bone cement delivery cannula, the cannula comprising:
(a) an inner lumen adapted to provide a channel of fluid communication between a bone cement reservoir and at least one lateral cement ejection aperture; and
(b) a permanently axially closed distal tip.

In an exemplary embodiment of the invention, there is provided a method of delivering bone cement to a bone, the method comprising:
flowing bone cement through an inner lumen of a cannula characterized by a permanently axially closed distal tip so that the cement exits at least one lateral aperture of the cannula.

In an exemplary embodiment of the invention, there is provided an apparatus for filling an injection reservoir with a viscous material, the apparatus comprising:
(a) a container capable of containing a viscous material;
(b) a transfer piston insertable in the container so that the piston forms a circumferential seal with respect to the container, the transfer piston including a hole; and
(c) a mechanism for attaching an aperture of an injection reservoir to the hole in the transfer piston.

In an exemplary embodiment of the invention, there is provided an injection kit, the kit comprising:
a sterile package containing
(a) a hydraulic pressure source capable of delivering at least 50 atmospheres of pressure to an injection reservoir;
(b) a quantity of a fluid contained in the pressure source; and
(c) a connector adapted for connection to an injection reservoir.

In an exemplary embodiment of the invention, there is provided a method of restoring a height of a subject, the method comprising:
flowing a sufficient quantity of a material characterized by a viscosity of at least 500 Pascal second at the time of injection through a cannula characterized by an ejection port located within a vertebra to at least partially reduce a vertebral fracture.

In an exemplary embodiment of the invention, there is provided a system for injection of material into a bone, the system comprising:

(a) a reservoir containing material to be injected into a bone, said reservoir deployed external to a body of a subject;
(b) a pressure source adapted to apply sufficient pressure to the material in the reservoir to expel at least a portion of the material from the reservoir through a cannula;
(c) an actuator operable to activate the pressure source; and
(d) the cannula adapted for insertion into the bone, said cannula connectable to the external reservoir;
wherein an operator of the system may perform an injection touching only the actuator.

In an exemplary embodiment of the invention, there is provided a bone cement comprising an acrylic polymer mixture, the cement achieving a viscosity of at least 500 Pascal-second when 100% of a polymer component is wetted by a monomer component.

Optionally, the cement achieves a viscosity of at least 500 Pascal-second when 95% of a polymer component is wetted by a monomer component.

In an exemplary embodiment of the invention, there is provided a bone cement comprising:
a monomer containing component and a polymer containing component, the cement characterized in that when the monomer containing component and the polymer containing component contact one another so that the polymer component is wetted by the monomer component a high viscosity cement characterized by a relatively stable flowability for a period of at least 8 minutes results after an intitial setting period.

In an exemplary embodiment of the invention, there is provided a bone cement according to claim 95, wherein the initial setting period does not exceed 2 minutes.

Optionally, the initial setting period does not exceed 0.5 minutes.

Optionally, the initial setting period does not exceed 5 seconds.

Optionally, the high viscosity is at least 500 Pascal sec.
Optionally, the high viscosity is at least 900 Pascal sec.
Optionally, the stable flowability results from a change in viscosity of less than 200 Pascal sec.

In an exemplary embodiment of the invention, there is provided a bone cement comprising a monomer containing a monomer component and a polymer containing component, the cement characterized in that when the monomer containing component and the polymer containing component contact one another so that the polymer component is wetted by the monomer component a high viscosity cement is formed after an initial setting period, a viscosity of said high viscosity cement changing by less than 20% in a period of 5 minutes.

Optionally, the initial setting period does not exceed 2 minutes.

Optionally, the initial setting period does not exceed 0.5 minutes.

Optionally, the initial setting period does not exceed 5 seconds.

Optionally, the high viscosity is at least 500 Pascal sec.
Optionally, the high viscosity is at least 900 Pascal sec.
Optionally, the stable flowability results from a change in viscosity of less than 200 Pascal sec.

Optionally, the cement achieving a viscosity of at least 500 Pascal-second within 180 seconds following initial contact of a monomer component and a polymer component.

Optionally, the viscosity is at least 900 Pascal sec.
Optionally, the viscosity is at least 1500 Pascal sec.
Optionally, the viscosity is achieved within 2 minutes.
Optionally, the viscosity is achieved within 1 minute.
Optionally, the viscosity is achieved within 45 seconds.

In an exemplary embodiment of the invention, there is provided a bone cement, the cement achieving a putty like state when 95% of a polymer component is wetted by a monomer component.

Optionally, the putty like state is characterized by a viscosity of at least 500 Pascal sec.

Optionally, the putty like state is characterized by a viscosity of at least 900 Pascal sec.

Optionally, the 95% wetting occurs within 60 seconds of initial contact.

In an exemplary embodiment of the invention, there is provided a method of injecting bone cement, the method comprising:
(a) providing a reservoir containing a cement characterized by a viscosity of at least 500 Pascal-second; and
(b) applying sufficient pressure to the cement in the reservoir to propel at least 5 ml of the material from the reservoir through a bone injection cannula characterized by an internal diameter not exceeding 4 mm.

Optionally, providing includes mixing components so that they achieve a viscosity of at least 500 Pascal-second within 160 seconds from the beginning of mixing to form a viscous cement.

Optionally, mixing occurs in the reservoir.

Optionally, providing includes use of a non-setting cement characterized by a viscosity of at least 500 Pascal-second.

Optionally, the at least 5 ml flows through the cannula as an uninterrupted aliquot.

Optionally, the mixing occurs in a separate container and providing includes a transfer to the reservoir, the transfer performed after the cement reaches the viscosity of at least 500 Pascal-second.

Optionally, mixing components causes the cement to achieve a viscosity of at least 900 Pascal-second within 160 seconds from the beginning of mixing.

Optionally, the method includes introducing the cannula into an interior of a bone.

Optionally, said bone is a vertebra.

Optionally, said cannula is introduced into the bone via a working sleeve, the working sleeve having an inner diameter slightly larger than an outer diameter of the cannula.

In an exemplary embodiment of the invention, there is provided a method of injecting bone cement, the method comprising:
(a) providing a reservoir containing a cement characterized by a viscosity which requires a pressure of at least 20 atmosphere to cause the cement to flow through a cannula characterized by an internal diameter not exceeding 2.5 mm and by a length of at least 100 mm;
(b) applying the pressure.

Optionally, the applying the pressure begins within 60 seconds of an initiation of mixing of components of the cement.

Optionally, the applying the pressure begins within 120 seconds of an initiation of mixing of components of the cement.

Optionally, the applying the pressure begins within 180 seconds of an initiation of mixing of components of the cement.

In an exemplary embodiment of the invention, there is provided a bone cement comprising an acrylic polymer mixture, the cement achieving a viscosity of at least 500 Pascal-second within 180 seconds following initiation of mixing of a monomer component and a polymer component.

Optionally, the viscosity of at least 500 Pascal-second results at least partly from a polymerization reaction.

Optionally, the viscosity of at least 500 Pascal-second results at least partly from particles characterized by a large surface area provided in the cement.

Optionally, said particles characterized by a large surface area include Zirconium.

Optionally, said particles characterized by a large surface area include bone.

Optionally, said cement achieves the viscosity of at least 500 Pascal-second without passing through an apparent liquid phase.

Optionally, the cement achieves a viscosity of at least 500 Pascal-second within 120 seconds following initiation of mixing of monomer and polymer components.

Optionally, the cement achieves a viscosity of at least 500 Pascal-second within 60 seconds following initiation of mixing of monomer and polymer components.

Optionally, the cement achieves a viscosity of at least 500 Pascal-second within 45 seconds following initiation of mixing of monomer and polymer components.

Optionally, the cement achieves a viscosity of at least 500 Pascal-second within 30 seconds following initiation of mixing of monomer and polymer components.

Optionally, the cement achieves a viscosity of at least 500 Pascal-second within 15 seconds following initiation of mixing of monomer and polymer components.

Optionally, a bone cement according to the invention is used in a vertebroplasty and/or a kyphoplasty procedure.

Optionally, the viscosity of the cement changes by less than 10% within a subsequent 2 minutes.

Optionally, the viscosity changes by less than 20% within a subsequent 8 minutes.

Optionally, the viscosity changes by less than 200 Pascal-second during a window of at least two minutes after said mixing.

Optionally, the window begins 1 minute after said mixing.
Optionally, the window begins 2 minutes after said mixing.
Optionally, the window begins 3 minutes after said mixing.
Optionally, the window begins 6 minutes after said mixing.
Optionally, the window begins 8 minutes after said mixing.

Optionally, the portion of the polymer component of the mixture is characterized by a molecular weight in the range of 600,000 to 1,200,000 Dalton.

Optionally, the portion comprises at least 1% of said polymer component of the mixture.

Optionally, the portion comprises at least 2% of said polymer component of the mixture.

Optionally, the portion comprises at least 3% of said polymer component of the mixture.

Optionally, the portion comprises at least 5% of said polymer component of the mixture.

Optionally, the polymer component of the mixture includes PMMA.

Optionally, the polymer component of the mixture includes styrene.

In an exemplary embodiment of the invention, there is provided a method of treating a bone, the method comprising:
(a) preparing a bone cement which achieves a viscosity of at least 500 Pascal-second within 160 seconds from a time at which a polymer component and a monomer component of the cement are contacted one with another;
(b) delivering the bone cement into a bone.

Optionally, the cement achieves a viscosity of at least 500 Pascal-second within 90 seconds.

Optionally, the bone is a vertebra.

Optionally, the material is an acrylic polymer mixture.

In an exemplary embodiment of the invention, there is provided a system for delivery of a viscous material into a bone, the system comprising:
(a) a reservoir containing a volume of a material characterized by a viscosity of at least 900 Pascal-second;
(b) a pressure source adapted to apply sufficient pressure to the material in the reservoir to expel at least 5 ml of the material from the reservoir without retraction of a piston;
(c) an actuator operable to activate the pressure source; and
(d) a tube adapted to deliver said pressure from said pressure source to said reservoir.

Optionally, the volume is at least 5 ml.

Optionally, the volume is at least 10 ml.

Optionally, the reservoir contains a piston; said piston responsive to a pressure supplied by said pressure source.

Optionally, the reservoir is adapted for connection to a cannula with an inner diameter of not more than 5 mm.

Optionally, the pressure source includes a hydraulic mechanism.

Optionally, the hydraulic mechanism includes a sterile hydraulic fluid.

Optionally, the sterile hydraulic fluid is deployed in a manner which prevents the fluid from passing through the reservoir into the body of a subject.

Optionally, the actuator is adapted to provide hydraulic amplification.

Optionally, the actuator includes a ball screw connection.

Optionally, the actuator is manually operable.

Optionally, the actuator is operable by a foot.

Optionally, the actuator is electrically operable.

Optionally, the a battery provides electric power for the electric operation.

Optionally, the pressure source is adapted to generate a pressure of 50-300 atmospheres.

Optionally, the system includes at least one pressure limiting mechanism.

Optionally, the actuator is adapted to deliver defined aliquots of material in response to separate actuations.

Optionally, the aliquots of material have a volume in the range of 0.15 to 0.5 ml.

Optionally, the material is characterized by a viscosity of less than 2000 Pascal-second.

In an exemplary embodiment of the invention, there is provided an apparatus for mixing, the apparatus comprising:
(a) a container containing at least a polymer component and a monomer component of a bone cement to be mixed;
(b) a mixing paddle attachable to a drive mechanism via a mixing element axle; and
(c) the drive mechanism adapted to move the mixing paddle along a travel path so that a reference point on the mixing element will face in a same direction at every point on the travel path.

Optionally, operation of the drive mechanism causes the mixing paddle to press at least a portion of the material being mixed against a wall of the container.

Optionally, the drive mechanism includes at least one gear.

Optionally, the mixing paddle is characterized by a surface area of at least 600 square millimeters.

Optionally, the apparatus includes a transfer mechanism to transfer a viscous mixture out of the container of the apparatus.

In an exemplary embodiment of the invention, there is provided a bone cement with a glass transition temperature above 37 degrees Celsius.

Optionally, the cement includes polycaprolactone and/or Polylactic acid (PLA).

In an exemplary embodiment of the invention, material characterized by a glass transition temperature above 37 degrees Celsius is used in formulation of a bone cement.

In an exemplary embodiment of the invention, there is provided a method for treating bones, the method comprising:
(a) providing a bone cement including a material with a glass transition temperature above 37 degrees Celsius;
(b) heating the material at least to its glass transition temperature; and
(c) injecting the material into an interior of a vertebra preventing the material from cooling to a temperature below the glass transition temperature.

Optionally, the method includes permitting the material to cool to 37 degrees and set within the vertebra.

Optionally, the material is bioabsorbable.

Optionally, the method includes mixing the material with ground bone.

In an exemplary embodiment of the invention, there is provided a method for treating long bones, the method comprising:
(a) providing a material with a glass transition temperature above 37 degrees Celsius;
(b) heating the material to its glass transition temperature; and
(c) injecting the material into an interior of a medullary canal of a long bone while maintaining the material at the glass transition temperature.

Optionally, the inserting into a medullary canal of a long bone results in formation of an intra-medular nail.

In an exemplary embodiment of the invention, there is provided a bone cement delivery cannula, the cannula comprising:
(a) an inner lumen adapted to provide a channel of fluid communication between a bone cement reservoir and at least one lateral cement ejection aperture; and
(b) a permanently axially closed distal tip.

In an exemplary embodiment of the invention, there is provided a method of delivering bone cement to a bone, the method comprising:
(a) inserting a cannula characterized by an axially closed distal tip into a bone; and
(b) causing bone cement to flow through an inner lumen of the cannula and exit at least one lateral aperture of the cannula.

In an exemplary embodiment of the invention, there is provided an apparatus for filling an injection reservoir with a viscous material, the apparatus comprising:
(a) a container capable of containing a viscous material;
(b) a transfer piston insertable in the container so that the piston forms a circumferential seal with respect to the container, the transfer piston including a hole; and
(c) a mechanism for attaching an aperture of an injection reservoir to the hole in the transfer piston.

In an exemplary embodiment of the invention, there is provided an injection kit, the kit comprising;
(a) a hydraulic pressure source capable of delivering at least 50 atmospheres of pressure to an injection reservoir;
(b) a quantity of a fluid contained in the pressure source; and
(c) a connector adapted for connection to an injection reservoir.

Optionally, the connector includes at least 20 cm of a flexible tubing.

Optionally, the pressure source is capable of delivering at least 100 atmospheres of pressure.

Optionally, the pressure source is capable of delivering at least 200 atmospheres of pressure.

Optionally, the pressure source is capable of delivering at least 300 atmospheres of pressure.

In an exemplary embodiment of the invention, there is provided a method of restoring a height of a subject, the method comprising:

(a) inserting a cannula into a fractured vertebra; and (b) injecting a sufficient quantity of a material characterized by a viscosity of at least 500 Pascal second at the time of injection to at least partially reduce the fracture.

Optionally, the injecting is at a pressure sufficient to overcome a resistant pressure in the vertebra.

Optionally, the pressure is at least 50 atmospheres.
Optionally, the pressure is at least 100 atmospheres.
Optionally, the pressure is at least 200 atmospheres.
Optionally, the pressure is at least 300 atmospheres.

In an exemplary embodiment of the invention, there is provided a system for injection of material into a bone, the system comprising:

(a) a reservoir containing material to be injected into a bone, said reservoir deployed external to a body of a subject;

(b) a pressure source adapted to apply sufficient pressure to the material in the reservoir to expel at least a portion of the material from the reservoir through a cannula;

(c) an actuator operable to activate the pressure source; and (d) a cannula adapted for insertion into the bone, said cannula connectable to the external reservoir;

wherein an operator of the system may perform an injection touching only the actuator.

Optionally, the system is used to inject material in proximity to an implant to strengthen the implant.

Optionally, a method described herein is employed as a means of vertebroplasty.

Optionally, a system described herein is employed to perform a vertebroplasty procedure.

Optionally, a cement described herein is employed in a vertebroplasty procedure.

In an exemplary embodiment of the invention, there is provided a bone cement comprising an acrylic polymer mixture, the cement achieving a viscosity of at least 500 Pascal-second when 100% of a polymer component is wetted by a monomer component.

Optionally, the cement achieves a viscosity of at least 500 Pascal-second when 95% of a polymer component is wetted by a monomer component.

An aspect of some embodiments of the invention relates to both moving and supporting bone using a same material, which is not enclosed by a bag to prevent migration of the material. In an exemplary embodiment of the invention, a material which does not set to a hardened condition is injected into a bone which is fractured and the pressure of the injected material moves the fractured pieces of the bone. The injected material remains in the bone to provide support and prevent retrograde motion of the bone, for example, permanently or until the bone heals. Optionally, an additional material or implant may be provided to further support the bone, however, the injected material supports at least 20%, optionally 30%, optionally 40%, optionally 50% of the forces applied by the bone pieces, or smaller, intermediate or greater percentages. Optionally, the additional material is a cement which sets to a hardened condition.

In an exemplary embodiment of the invention, the material used is an artificial material. In an alternative embodiment of the invention, the material is natural.

In various embodiments of the invention, the following types of materials are used:

(a) Relatively (to bone) soft solid materials which can optionally undergo substantial plastic deformation without tearing and optionally include no cross-linking above type I. In an exemplary embodiment of the invention, these materials are compressed radially and provided through a narrow diameter aperture into the bone. In an alternative exemplary embodiment of the invention, the material is provided in a small profile condition and either compressed axially for loading into a delivery system or simply advanced into the bone without initial compression.

In an exemplary embodiment of the invention, the soft materials are plastically deforming materials. In the example of intra-vertebral use, at least 50%, 80%, 90%, 95% or more of deformation is optionally plastic deformation. Optionally, the materials have an elastic deformation of 0.1% or less. In an exemplary embodiment of the invention, for a material 1 mm in thickness, elastic spring-back is less than 0.1 mm, less than 0.05 mm or less.

(b) High viscosity fluids, such as bone slurry, semi-hardened cement and putty-like materials. These materials are flowed through the delivery system, optionally under a high pressure. In some cases, the fluids set to a hardened condition, for example, due to a polymerization process or due to contact with body fluids.

An aspect of some embodiments of the invention relates to fracture reduction (e.g., height restoration in a vertebra), using a soft material that is not constrained by an enclosure. In an exemplary embodiment of the invention, the material is a soft material softer than 60A, 70A, 80A, 90A or 100A shore. Optionally, the material is at least 10A shore or 20A shore, for example, at least 20A or 30A shore.

In an alternative exemplary embodiment of the invention, the material is a flowable material, for example, with a viscosity greater than 100 Pascal-second, 300 Pascal-second, 500 Pascal-second, 600 Pascal-second, 800 Pascal-second, 1000 Pascal-second or more. Optionally, the material has a viscosity of less than 4,000 Pascal-second, optionally less than 1,800 Pascal-second, optionally less than 1,400 Pascal-second, optionally less than 1,100 Pascal-second or smaller intermediate or larger values.

An aspect of some embodiments of the invention relates to the use of materials which do not set to a hardened condition for supporting bone. In an exemplary embodiment of the invention, the material is injected into a bone.

As used herein, the term "setting" is used to define materials whose mechanical properties, such as strength and/or hardness, increase for chemical reasons, for example, due to polymerization during and/or shortly after implantation, e.g., after a few hours, a few days or a few weeks. It should be noted that a material which sets to a non-hardened condition is a setting material. A pre-set soft material will also generally not set to a hardened condition.

As used herein the term "hardened condition" is used to describe materials that are 50% or more the hardness of cortical bone. In some cases it is desirable to compare the strength and/or young modulus of the material to cortical and/or trabecular bone, in which case, values within 110% or 120% or 130% or intermediate values of the values for the bone in question bone may be desirable.

In an exemplary embodiment of the invention, the injected material is selected to have a high viscosity or is a soft material which can undergo plastic deformation, for example, by the material not tearing during an injection via a small diameter tube. Optionally, the material is mechanically sheared during injection.

In an exemplary embodiment of the invention, the use of a non-hardening material allows more flexibility in injection methods, due to the relieving of time constraints typically involved in using a cement which sets to a hardened condition, such as PMMA, in which the time between mixing and setting and especially the time at a given viscosity range, constrains the physician. Optionally, a non-hardening material is more convenient to use, as it does not require the user to mix the material at the time of use. In an exemplary embodiment of the invention, the material is provided in a pre-loaded magazine or delivery system.

A potential property of using a viscous or soft solid material is that there is less danger of leakage out of the vertebra. Optionally, various components are added to the material, for example, a bone growth factor or a radio-opaque material.

A potential advantage of some pre-set or non-setting materials is that an exothermic setting reaction is avoided.

In an exemplary embodiment of the invention, the injected material is free of cross-linking or includes only type I cross-linking.

Optionally, the injected material softens over time.

In an exemplary embodiment of the invention, the material is formulated so that only hardens in the presence of water or other materials common in the body but does not set or harden outside the body. Thus the material can be pre-formulated and mixed and will only set after being introduced into the body. Optionally, the material sets after 10-30 minutes or longer.

An aspect of some embodiments of the invention relates to treatment of body tissues by injecting a non-solid or soft-solid material harder than 10A shore. In an exemplary embodiment of the invention, the injected material flows into or is forced into an intra-body space to be filled thereby. In an exemplary embodiment of the invention, the injected material is viscous enough or solid enough so it does not inadvertently migrate out of a tissue into which it is injected, for example, out of a vertebra. This viscosity level used may depend on the size and/or shape of voids leading out of the tissue being treated. Optionally, the material sets to a hardened condition. Alternatively, the material does not.

In an exemplary embodiment of the invention, the material is provided under a pressure of greater than 40 atmospheres.

An aspect of some embodiments of the invention relates to a method of providing a flowable or soft-solid material into the body, in discrete units, optionally of predetermined quantities. In an exemplary embodiment of the invention, a delivery system with a first quantity of material is provided and a user can select a discrete amount of this first quantity to be injected. This is in contrast to continuous methods in which material is injected until a user stops the injection or the material is all used up. Optionally, the material to be injected is provided in a magazine from which a unit of material can be selected for injection. Optionally, selection is by cutting the material away from the magazine.

In an exemplary embodiment of the invention, a treatment for a bone is provided by injecting two, three, four or more discrete units of material.

A potential advantage of working in discrete portions which are considerably smaller than a total therapeutic amount, in some embodiments of the invention, is that a friction between the material and a delivery system is reduced, as the amount of material advanced at each time is reduced.

An aspect of some embodiments of the invention relates to using a sleeve for delivering material or a device implant that have a high friction to a delivery system, to a site inside the body. In an exemplary embodiment of the invention, the sleeve is designed to reduce friction between the delivered material and a delivery system. Optionally, the sleeve is provided inside of a delivery tube. Optionally, force is applied directly on the sleeve to deliver the material or implant.

An aspect of some embodiments of the invention relates to a system for delivering material into a bone which system is adapted to travel over a guidewire. Optionally, the system travels over a guidewire when loaded. Alternatively or additionally, the system is loaded after being introduced into the body. In an exemplary embodiment of the invention, the system comprises a distal end adapted to penetrate bone, for example vertebral bone. In an exemplary embodiment of the invention, the system is adapted to deliver the material into a vertebra in a manner which will at least partially restore a height of said vertebra. In an exemplary embodiment of the invention, the material surrounds the guidewire.

An aspect of some embodiments of the invention relates to a system for delivering material into a bone under pressure, the system being adapted to penetrate bone. In an exemplary embodiment of the invention, the system comprises a distal tip adapted to penetrate bone. Optionally, an aperture is formed near the distal tip for delivering of said material.

An aspect of some embodiments of the invention relates to materials for use in the body for supporting hard tissue and which do not set to a hardened condition when in storage (e.g., for over 1 hour or over one day or 1 week). In an exemplary embodiment of the invention, the material comprises polymers without cross-linking or with type I cross-linking. Optionally, the composition of the material is a mixture of Laurylmethacrylate (LMA) and methylmethacrylate (MMA), for example in a ratio of between 90:10 and 10:90. Optionally, the material is thermoplastic rather than thermo-setting.

In an exemplary embodiment of the invention, the material is a putty-like material. In one example, the material is composed of a mixture of hydroxyapatite and sufficient sodium alginate, such that the mixture remains putty like after time, at least if not in contact with water.

In an exemplary embodiment of the invention, the material softens over time. Optionally, the material is composed of MMA and LMA with poly-hema added, and softens by the absorption of body fluids by the composition.

Alternatively or additionally, water soluble materials, such as salts or materials which degrade in body fluids, such as some sugars and plastics, are added and when they degrade, soften the material.

In an exemplary embodiment of the invention, the material hardens over time, but does not harden completely. Optionally, the material includes a solvent, such as NMP (N-methyl pyrolidone), which is soluble in water and as it is carried away, the material hardens somewhat.

Optionally, the actually injected material includes one or more added components. Optionally, one or more of a radio opaque marker, antibiotic, anti-inflammatory and/or bone growth factor, are provided as the added components. Optionally, an added component is added by volume of less than 30% of the material volume and in total less than 50% for all the added components.

Optionally, the added materials are chemically inert but may have a structural effect, for example, due to bulk thereof.

Optionally, non-inert materials are added, for example, 5% of a cement which sets to a hardened condition may be added. Optionally, such non-inert materials are mixed-in at a coarse grain.

An aspect of some embodiments of the invention relates to using a material which sets to a hardened condition, which maintains a high viscosity value during a substantial window of time. In an exemplary embodiment of the invention, the viscosity is between 600 Pascal-second and 1,800 Pascal-second during a period of at least 5 or at least 8 minutes or greater or intermediate values. In an exemplary embodiment of the invention, the material is composed of a mixture of PMMA beads and/or styrene beads and MMA monomers, with the increase in viscosity being provided by the size of the beads of, for example, 10-200 microns and/or by changing the ratio between beads and liquid MMA monomer, and/or by changing molecular weight of polymer in the beads. Optionally, as setting progresses, viscosity due to the beads is replaced/increased by viscosity due to the polymerization process. Alternatively or additionally, addition of Butyl Methacrylate to PMMA provides an increase in viscosity for any given ratio between monomer and polymer and/or for any given set of bead parameters.

An aspect of some embodiments of the invention relates to treating compression fractures by heating a compressed vertebra. Optionally, the heating is provided by a stand-alone tool. Optionally, the heating is provided to replace heating which is otherwise provided by the setting of a cement. Optionally, a thermocouple or other temperature sensor is used to control the amount of heating provided.

An aspect of some embodiments of the invention relates to a method of selecting mechanical properties of an implant to match those of a bone, cortical and/or trabecular, being treated. In an exemplary embodiment of the invention, one or more of hardness, strength and/or Young modulus are matched.

There is thus provided in accordance with an exemplary embodiment of the invention, a method of treating a vertebra, comprising:

(a) accessing an interior of a vertebra; and
(b) introducing a sufficient amount of artificial biocompatible material which does not set to a hardened condition in storage, into said bone, with sufficient force to move apart fractured portions of said bone.

Optionally, said material does not set to a hardened condition after introduction into the body.

In an exemplary embodiment of the invention, said material can be stored for over 1 day.

In an exemplary embodiment of the invention, said material softens after implantation.

In an exemplary embodiment of the invention, said material partly hardens after implantation.

In an exemplary embodiment of the invention, said material does set to a hardened condition after introduction into the body.

In an exemplary embodiment of the invention, said material does not set to a hardened condition in storage.

In an exemplary embodiment of the invention, said material is artificial.

In an exemplary embodiment of the invention, said material is a plastically deforming material. Optionally, said material has a hardness of between 10A shore and 100A shore and/or a Young modulus higher than 200 MPa. Alternatively or additionally, said material is free of cross-linking higher than type I. Alternatively or additionally, said material is thermoplastic. Alternatively or additionally, said material comprises LMA (lauryl methacrylate) and MMA (methyl methacrylate).

In an exemplary embodiment of the invention, said material is a viscous fluid. Optionally, said material has a viscosity between 600 Pascal-second and 1,800 Pascal-second.

In an exemplary embodiment of the invention, introducing comprises introducing at a pressure of at least 40 atmospheres.

In an exemplary embodiment of the invention, introducing comprises introducing at a pressure of at least 100 atmospheres.

In an exemplary embodiment of the invention, introducing comprises introducing through a delivery channel having a diameter of less than 6 mm and a length of at least 70 mm.

In an exemplary embodiment of the invention, introducing comprises introducing through an extrusion aperture having a minimum dimension of less than 3 mm.

In an exemplary embodiment of the invention, introducing comprises introducing through an extrusion aperture having a minimum dimension of less than 1.5 mm.

In an exemplary embodiment of the invention, introducing comprises introducing through a plurality of extrusion apertures simultaneously.

In an exemplary embodiment of the invention, introducing comprises changing an introduction direction during said introduction.

In an exemplary embodiment of the invention, introducing comprises changing an introduction position during said introduction.

In an exemplary embodiment of the invention, said material comprises at least one material adapted to function in a capacity other than structural support.

In an exemplary embodiment of the invention, introducing comprises advancing said material using a motor.

In an exemplary embodiment of the invention, introducing comprises advancing said material using a hydraulic source.

In an exemplary embodiment of the invention, introducing comprises introducing said material in discrete unit amounts. Optionally, at least some of the units have different mechanical properties form each other.

In an exemplary embodiment of the invention, introducing comprises cutting said material away from a delivery system.

In an exemplary embodiment of the invention, introducing comprises not twisting said material during said introducing.

In an exemplary embodiment of the invention, introducing comprises shaping an extrusion form of said material using an exit aperture.

In an exemplary embodiment of the invention, accessing comprises accessing using a guidewire and providing a delivery system over the guidewire.

In an exemplary embodiment of the invention, accessing comprises accessing using a delivery system of said material.

In an exemplary embodiment of the invention, introducing comprises introducing without a separate void forming act.

In an exemplary embodiment of the invention, introducing comprises introducing without a spatially constraining enclosure.

In an exemplary embodiment of the invention, introducing comprises introducing in a spatially constraining enclosure.

In an exemplary embodiment of the invention, introducing comprises also introducing at least 10% by volume of a material which sets to a hardened condition.

In an exemplary embodiment of the invention, the method comprises selecting said material to have at least one of hardness and Young modulus properties less than those of trabecular bone of said vertebra, after a week from said implantation.

In an exemplary embodiment of the invention, said introduced material is operative to support at least 30% of a weight of vertebra within a week after implantation.

There is also provided in accordance with an exemplary embodiment of the invention, a surgical set comprising:

at least one tool adapted to deliver a material into a vertebra; and
at least 1 cc of artificial biocompatible prepared material that does not set to a hardened condition outside the body. Optionally, said at least one tool comprises a pressure delivery mechanism capable of delivering said material at a pressure of above 100 atmospheres. Alternatively or additionally, said set comprises a disposable hydraulic actuator. Alternatively or additionally, said set comprises a replaceable magazine for storing said material.

There is also provided in accordance with an exemplary embodiment of the invention, a method of treating bone, comprising:

(a) accessing an interior of a bone; and (b) introducing a sufficient amount of biocompatible material into said bone, without an enclosure between said material and the bone, said introducing being with sufficient force to move apart fractured portions of said bone. Optionally, the method comprises leaving said material in said bone to resist at least 30% of a normative force which urges said portions together.

Optionally, said bone is a vertebra. Optionally, said material does not set to a hardened condition in storage. Alternatively or additionally, said material does not set to a hardened condition in the body.

There is also provided in accordance with an exemplary embodiment of the invention, a method of treating a vertebra, comprising:

(a) accessing an interior of a vertebra; and (b) introducing a sufficient amount of spatially unconstrained biocompatible soft material having a hardness of less than 100A Shore into said vertebra, with sufficient force to move apart fractured portions of said bone.

There is also provided in accordance with an exemplary embodiment of the invention, a surgical set comprising:

at least one tool adapted to deliver a material into a vertebra; and at least 1 cc of biocompatible prepared material that has a Young modulus of less than 120% of healthy vertebral trabecular bone and is prepared at least 1 day ahead of time.

There is also provided in accordance with an exemplary embodiment of the invention, a method of treating a bone, comprising:

(a) accessing an interior of a bone; and (b) introducing, via a delivery tube, into said bone an unconstrained plastically deformable solid material harder than 10A shore and softer than 100A shore.

There is also provided in accordance with an exemplary embodiment of the invention, apparatus for delivering a material or an implant into a bone, comprising:

(a) a delivery tube having a lumen and a distal end adapted for insertion into a body;

(b) a payload comprising at least one of material and an implant inside said lumen;

(c) a lining disposed between said tube and said payload; and (d) an advancing mechanism adapted to move said liner and said payload to said distal end, wherein said liner reduces a friction of said payload against said delivery tube. Optionally, the apparatus comprises a splitter which splits said sleeve.

In an exemplary embodiment of the invention, said mechanism pulls said sleeve.

In an exemplary embodiment of the invention, said mechanism pushes said payload.

In an exemplary embodiment of the invention, said sleeve folds over said delivery tube.

There is also provided in accordance with an exemplary embodiment of the invention, a biocompatible material which does not set to a hardened condition and does not include cross-linking of a type greater than type I and formed of MMA (methyl methacrylate). Optionally, said material is formed of a mixture of MMA and LMA (lauryl methacrylate)

There is also provided in accordance with an exemplary embodiment of the invention, a second medical use of PMMA for height restoration of vertebral bones when applied directly into a vertebra. Optionally, said PMMA is applied during setting while at a viscosity higher than 400 Pascal-second.

There is also provided in accordance with an exemplary embodiment of the invention, a second medical use of bone putty for vertebral treatment when applied under pressure through a tubular delivery system into a vertebral bone.

There is also provided in accordance with an exemplary embodiment of the invention, a polymerizing composition, comprising:

(a) a first quantity of beads having a set of sizes; and (b) a second quantity of monomer, wherein said quantities are selected so that a mixture of said quantities results in a setting material having a workability window of at least 5 minutes at a viscosity between 500 and 2000 Pascal-second.

There is also provided in accordance with an exemplary embodiment of the invention, a method of treating bone, comprising providing a heat source into a vertebra in a controlled manner.

There is also provided in accordance with an exemplary embodiment of the invention, a composite tool for accessing bone, comprising:

an elongate body having:

(a) a head adapted to penetrate bone;

(b) an aperture adapted to extrude material into bone, near said head; and (c) a lumen adapted to deliver material to said aperture; and a source of material under pressure. Optionally, the tool comprises a lumen for a guidewire.

There is also provided in accordance with an exemplary embodiment of the invention, a composite tool for accessing bone comprising:

a drill tool including a lumen;

a separable guidewire adapted to fit in said lumen; and a handle adapted to control the relative positions of said drill tool and said guidewire.

There is also provided in accordance with an exemplary embodiment of the invention, bone cement comprising:

a polymer component; and a monomer component, wherein, when the two components are mixed together, the resulting mixture attains, within a period of up to 2 minutes, a putty-like consistency wherein the viscosity of the resulting mixture remains approximately constant during a period of time of at least 5 minutes.

BRIEF DESCRIPTION OF THE FIGURES

Exemplary non-limiting embodiments of the invention will be described with reference to the following description of embodiments in conjunction with the figures. Identical structures, elements or parts which appear in more than one figure are generally labeled with a same or similar number in all the figures in which they appear, in which:

FIGS. 7P and 7Q are cross sectional views of a cement reservoir illustrating a floating piston according to some exemplary embodiments of the invention;

FIG. 7S1 is a cross sectional view of a cement reservoir according to an additional exemplary embodiment of the invention;

FIGS. 14C1, 14C2, 14C3 and 14C4 are a series of top views illustrating an exemplary travel path of a mixing element within a mixing well of the exemplary apparatus of FIGS. 14A and 14B;

FIGS. 18, 19, 20 and 21 are perspective views of an exemplary embodiment of a transfer apparatus for loading a viscous material into a container.

DETAILED DESCRIPTION OF EXEMPLARY EMBODIMENTS

Overview of Exemplary Process

Figure 1A:
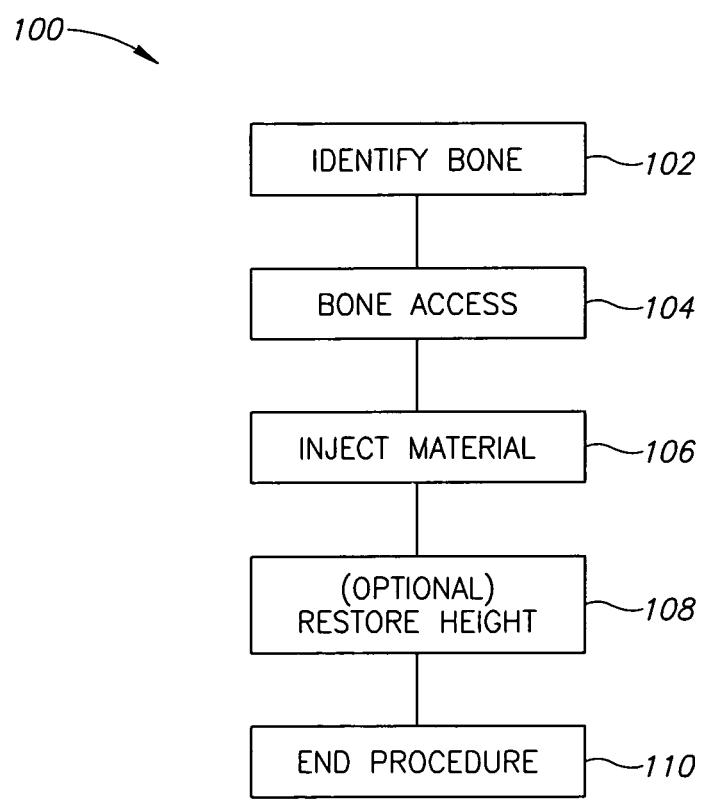
FIG. 1A is a general flowchart of a process of treating a compression fracture, in accordance with an exemplary embodiment of the invention.

FIG. 1A is a general flowchart 100 of a process of treating a compression fracture, in accordance with an exemplary embodiment of the invention.

At 102, a bone to be treated is identified. In the case of a vertebra, this usually involves X-ray or CT images to identify a vertebra or other bone that is fractured, for example by a compression fracture. The following description focuses on vertebral compression fractures but some embodiments of the invention are not limited to such cases.

In an exemplary embodiment of the invention, the access is minimally invasive, for example, only a single channel is formed into the body. Optionally, the procedure is carried out via a cannula having a diameter of, for example of 5 mm, 4 mm or less in diameter is inserted into the body. In some cases, multiple openings into the body are formed. The procedure can also be carried out using a surgical or key-hole incision; however, this may require a longer recuperation period by the patient. Optionally, the cannula (and corresponding length of a delivery tube described below) is at least 50 mm, 70 mm, 100 mm or more or intermediate or smaller values.

At 104, the vertebra is accessed.

At 106, a material, having a high viscosity in some embodiments of the invention, is injected into the vertebra. Optionally, the vertebra is fractured due to weakening caused by osteoporosis or other pathological conditions.

At 108, material is optionally provided in a manner and/or amount which restores at least part of the height of the vertebra, for example, 20%, 40%, 50% or intermediate or a higher percentage of a pre-compression height. A particular feature of some embodiments of the invention is that the provided material is of sufficient viscosity or sufficiently solid that leakage from the vertebra is reduced or prevented, as compared to liquid PMMA cement. A pressure used to advance the material may be higher than what is known in the art to match the increased viscosity.

At 110, the procedure is completed and the tube is removed.

Exemplary Bone Access Set

Figure 2:
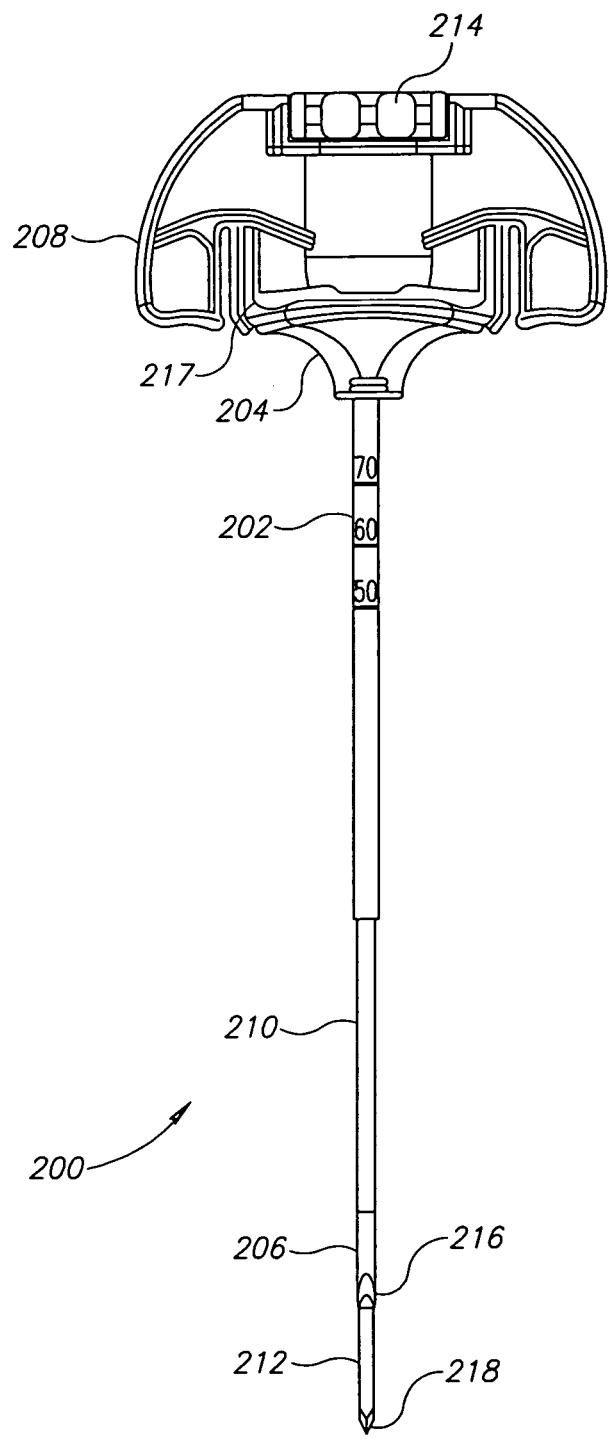
FIG. 2 shows a composite tool for accessing a vertebra, in accordance with an exemplary embodiment of the invention.

Before going into the details of the procedure, the tools used are first described. FIG. 2 shows a composite tool 200 optionally used for accessing the bone, in accordance with an exemplary embodiment of the invention. In an exemplary embodiment of the invention, the access tools used comprise a set of component tools that interlock to act, selectively, as a single tool or as separate tools. In an exemplary embodiment of the invention, this composite set/tool serves as a one step access system in which only a single insertion of objects into the body is required. Optionally, as described below, the delivery system is also inserted at the same time. Optionally, a cannula portion of the tool is omitted, for example as described in the embodiments of FIGS. 12A-12C.

In an exemplary embodiment of the invention, the components of tool 200 are coaxially matched components, which fit one within the lumen of the next.

An optional cannula 202 comprises a handle 204 and a body including a lumen.

An optional drill tool 206 includes an elongate body adapted for drilling and a handle 208. Optionally, handle 208 selectively rotationally locks to handle 204, for manipulation using a single hand, optionally using a snap-lock 217. The body of tool 206 fits in the lumen of cannula 202. Optionally, a section 210 of tool 206 is marked to be visible on an x-ray image, even in contrast to cannula 202. Optionally, this allows the difference in diameters between cannula 202 and drill tool 206 to be minimal. Absent such a marker, in some cases, the difference in diameters may not be visible on an x-ray image and the two tools cannot be distinguished.

An optional guidewire 212 is provided inside a lumen of drill tool 206. Optionally, a knob or other control 214 is provided for selective advancing and/or retracting of guidewire 212 relative to drill 216. The knob may be marked with relative or absolute positions.

Optional depth marking are provided on cannula 202.

Figure 1B:
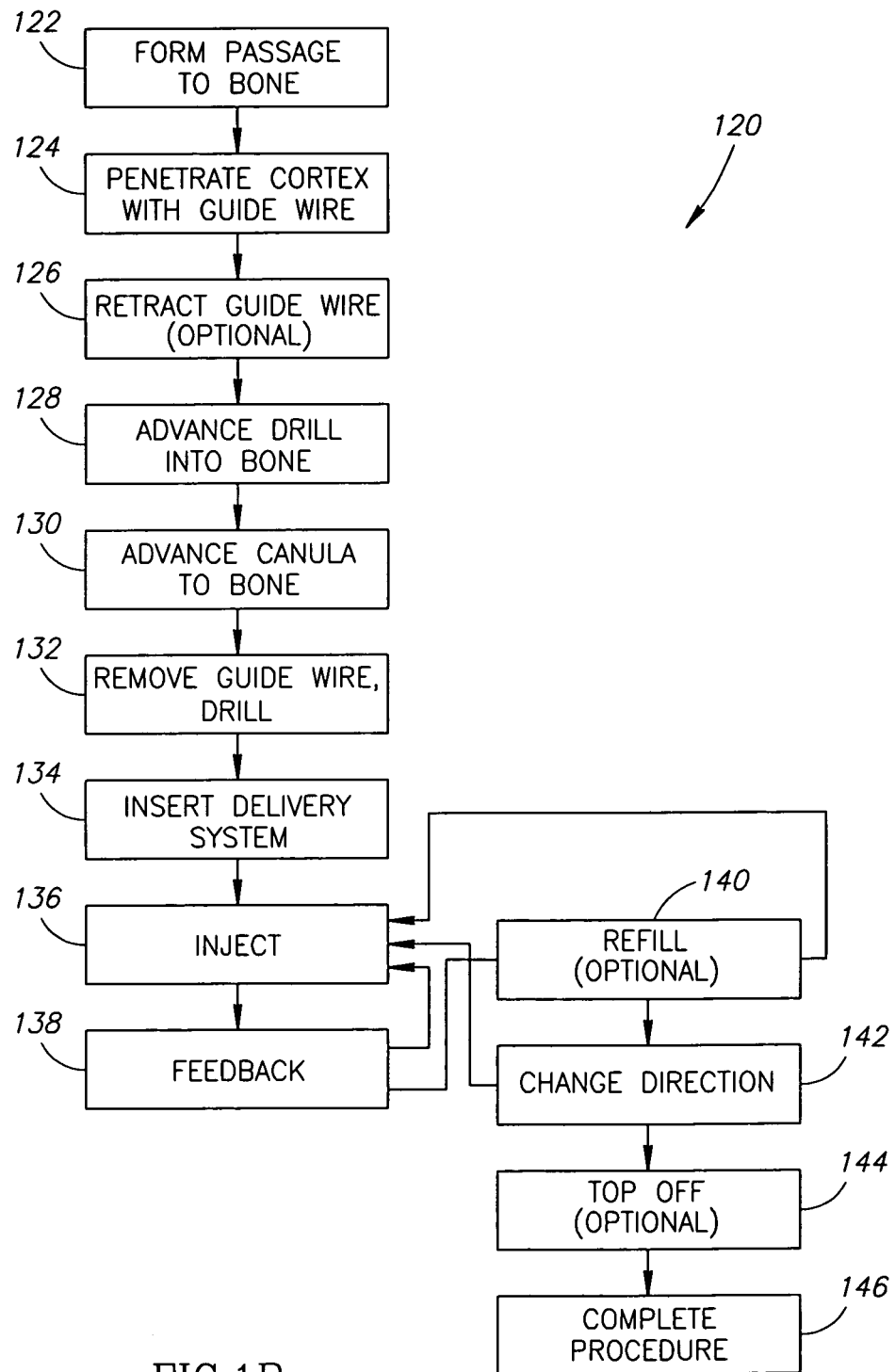
FIG. 1B is a more detailed flowchart of a process of treating a compression fracture, in accordance with an exemplary embodiment of the invention.

An exemplary use of these tools will be described below, in which FIGS. 3A-3F schematically show the progress as a vertebra 300 having a compression fracture 306 is being treated, paralleling a detailed flowchart 120 shown in FIG. 1B.

Penetrate to Bone

At 122 (FIG. 1B), a passage is formed to the bone through a skin layer 312 and intervening tissue, such as muscle and fat. Optionally, the passage is formed by advancing composite tool/set 200 until a tip 218 of guidewire 212 contacts the bone. In some embodiments, tip 218 is designed to drill in soft tissue (e.g., includes a cutting edge). Alternatively or additionally, tip 218 includes a puncturing point adapted to form a puncture in soft tissue.

Figure 3A:
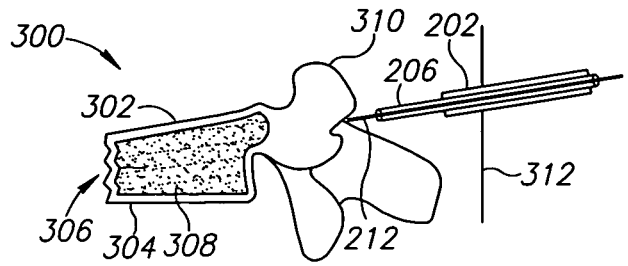
FIGS. 3A-3F show stages of a method of treatment according to FIGS. 1A and 1B, in an exemplary implementation of the method.

This is shown in FIG. 3A. Also shown are cortical plates 302 and 304 of the vertebra and a cancellous bone interior 308.

A single pedicle 310 is shown, due to the view being cross-sectional. Optionally, the access to the vertebra is via a pedicle. Optionally, the access is via both pedicles. Optionally, an extrapedicular approach is used. Optionally, the access point or points are selected to assist in an even lifting of the vertebra.

Penetrate Bone

Figure 3B:
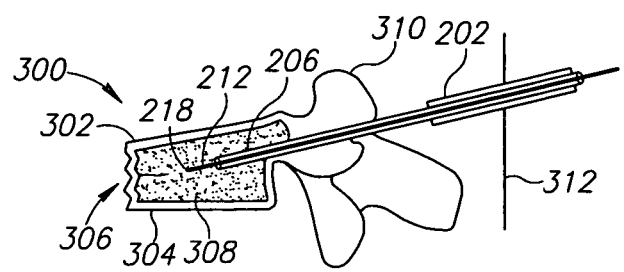

At 124, tip 218 penetrates through the cortex of the bone being treated (FIG. 3B). In an exemplary embodiment of the invention, tip 218 is separately manipulated from the rest of composite tool 200. Optionally, tip 218 is advanced until it contacts a far side of the vertebra.

In an exemplary embodiment of the invention, tip 218 of guidewire 212 is formed to drill in bone and is advanced through the vertebral cortex by rotation or vibration. Optionally, it is advanced by tapping thereon or applying pressure thereto.

Optionally, a relative position of the guidewire and the cannula is noted, to assist in determining the inner extent of the vertebra.

At 126, the guidewire is optionally retracted. Optionally, the guidewire is axially locked to drill tool 206. Optionally, guidewire 212 and drill tool 206 align so that tip 218 and a tip 216 of the drill tool form a single drilling tip.

Figure 3C:
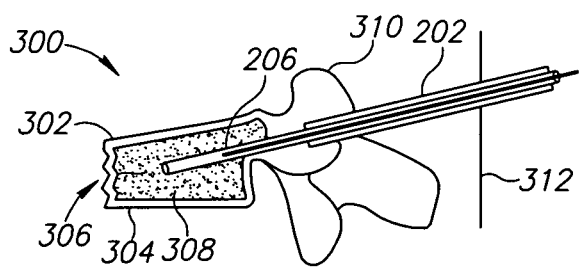

At 128, drill tool 206 is advanced into the bone (FIG. 3C). Optionally, tip 216 of drill tool 206 designed for drilling and/or is advanced, for example, by tapping, rotation and/or vibration. Optionally, the drill tool is advanced to the far side of the vertebra. Optionally, the previous depth marking of the guidewire is used to limit this advance. Optionally, the guidewire is not retracted at 126. Instead, drill tool 206 is advanced over the guidewire until it reaches the end of the guidewire.

At 130, cannula 202 is optionally advanced to the bone over the drill. Optionally, the leading edge of the cannula is threaded or otherwise adapted to engage the bone at or about the bore formed by the drill tool. Optionally, the cannula is inserted into the bone.

Figure 3D:
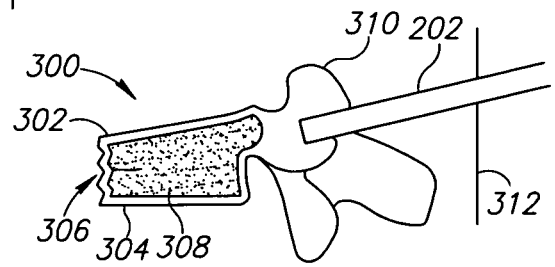

At 132, the guidewire and/or drill tool are optionally removed (FIG. 3D).

In some embodiments, the cannula is not advanced all the way to the bone. In others, the cannula may be advanced into the bone, for example, to prevent contact between the treatment and cortical bone and/or weak or fractured bone. Optionally, the cannula is advanced past the pedicle and to the vertebral interior 308.

Optionally, a reamer (not shown) is inserted into the cannula and used to remove tissue from interior 308.

Inject Material

Figure 3E:
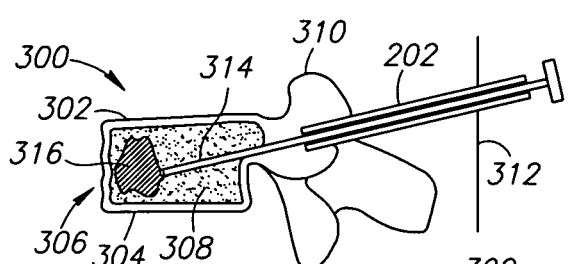

At 134, a material delivery system 314 is provided into cannula 202 (shown in FIG. 3E). Optionally, the delivery system delivers material to a side thereof (described below).

At 136, system 134 is activated to inject material 316 into interior 308. FIG. 3E shows that when enough material is injected, vertebral height may be partially or completely restored. The injected material may partially or completely compress interior 308.

Feedback

At 138, feedback is optionally provided to an operator, to decide if injection is completed. Optionally, feedback is provided by fluoroscopic imaging of the site. However, other imaging methods may be used.

Optionally, non-imaging feedback is provided, for example a pressure inside the vertebra, using a pressure sensor (not shown), or using an indicator (visual or audio) for the amount of material injected.

Optionally, the feedback is used to decide if the procedure is progressing as desired, e.g., desired amount of height restoration (if any), verify a lack of material leakage, determine symmetry or asymmetry and/or the presence of new fractures in bone.

Repeat and/or Change

Optionally, the material is provided in a magazine having a fixed amount (described below). If that magazine is finished and additional material is required, a refill may be provided (140), for example by replacing the magazine with a new one.

Optionally, a property of the delivery of material is changed, for example one or more of a delivery pressure, a delivery rate, an amount of delivery when delivery is in discrete units, a viscosity, composition and/or type of the delivered material, a pre-heating or pre-cooling of the material, a location of provision inside the vertebra, a spatial pattern of provision and/or a direction of provision in the vertebra.

Optionally, the direction of provision of the material is changed (142), for example, to assist in maintaining symmetry of lifting or to point in the injection of material away from a fracture or towards an empty space. Optionally, the direction of provision is changed by rotating delivery system 314. Alternatively or additionally, injection is continued through a new access hole in the vertebra. Optionally, the cannula is moved axially.

Optionally, a different material is used to top off the procedure, for example, a cement which sets to a hardened condition (e.g., PMMA) is used to seal the entry hole and/or stiffen the non-hardening material (144).

Complete Procedure

Figure 3F:
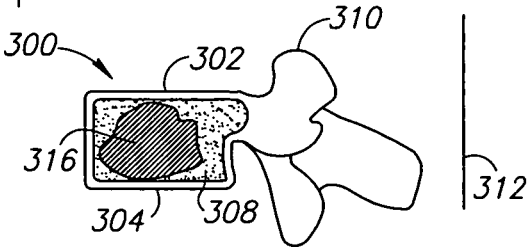

At 146, the tools are removed. FIG. 3F shows vertebra 300 after the procedure is completed. Optionally, the entry incision is sealed, for example, using tissue glue or a suture.

Exemplary Basic Delivery System

Figure 4A:
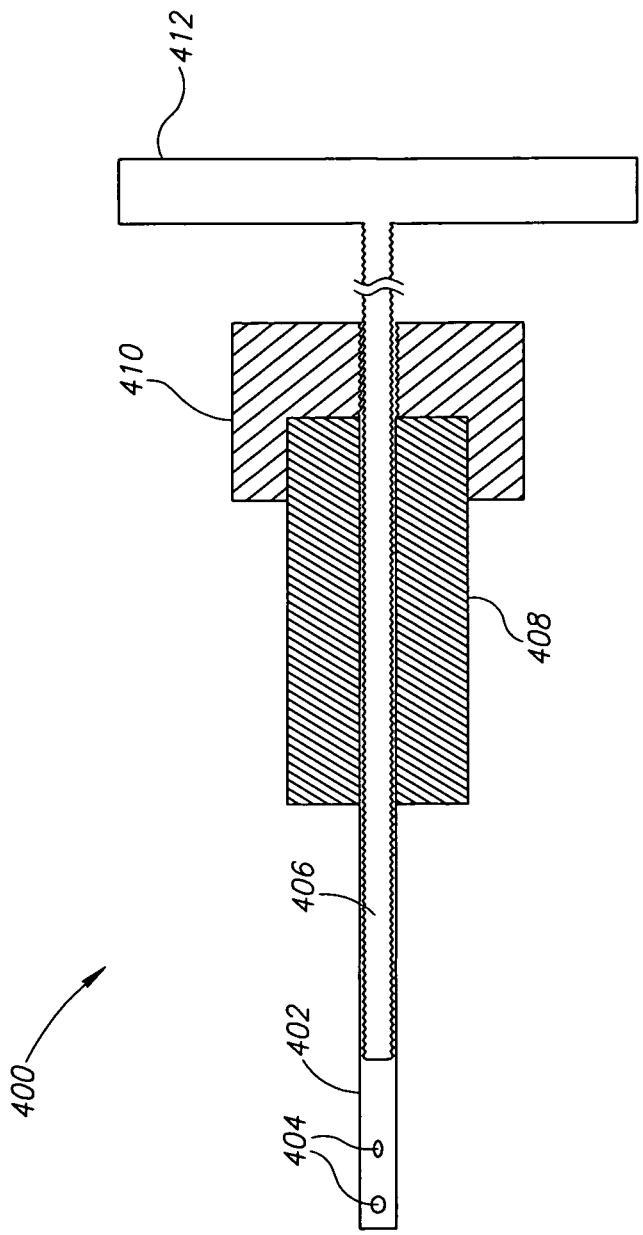
FIGS. 4A and 4B illustrate basic material delivery systems, in accordance with exemplary embodiments of the invention.
Figure 4B:
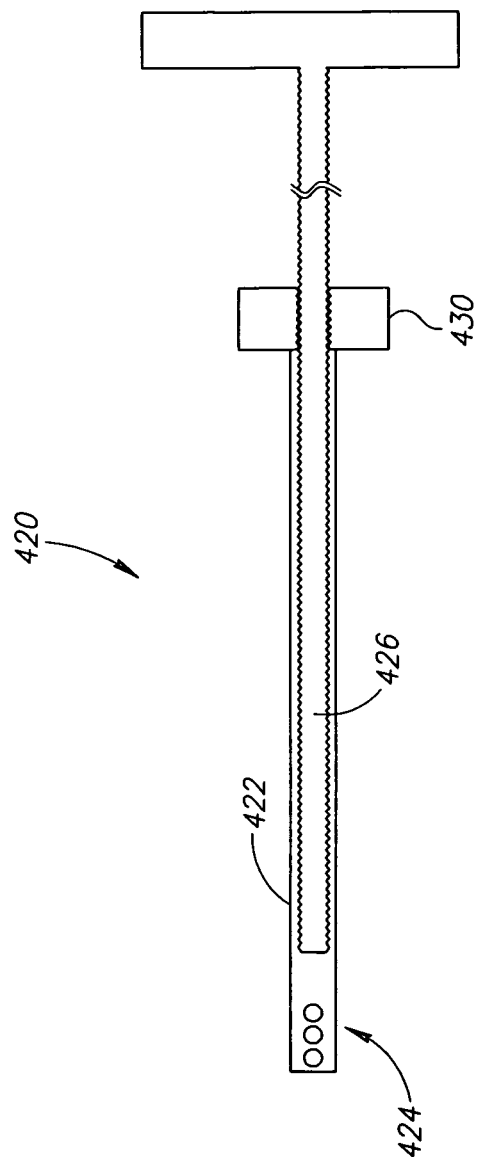

FIGS. 4A and 4B illustrate basic delivery systems, in accordance with exemplary embodiments of the invention FIG. 4A is a cross-sectional view of a delivery system 400, comprising generally of a delivery tube 402 having one or more extrusion apertures 404. Optionally, the distal end of tube 402 is sealed. Alternatively it may be at least partially open, so forward injection of material is provided. It is noted that when the end is sealed, there may be less force acting to retract the delivery system from the vertebra. Material inside tube 402 is advanced by a threaded pusher 406.

In the design shown, tube 402 is attached to a barrel 408 with a permanent or temporary attachment method. Threading (not shown) may be provided inside of barrel 408, to match the threading on pusher 406. Alternatively (not shown), the inner diameter of barrel 408 is greater than that of tube 402. Optionally, barrel 408 and/or tube 402 serve as a reservoir of material.

A body 410 which acts as a nut and includes an inner threading engages pusher 406. In an exemplary embodiment of the invention, when a handle 412 of pusher 402 is rotated (while holding on to body/nut 410), pusher 406 is advanced, injecting material out of apertures 404 into the body. Optionally, barrel 408 is detachable from body 410, for example, for replacing barrel 408 with a material-filled barrel, when one barrel is emptied. The coupling can be, for example, a threading or a quick connect, for example, a rotate-snap fit. Optionally, tube 402 is detachable from barrel 408, for example using the same type of coupling.

In an exemplary embodiment of the invention, when the distal tip of pusher 406 goes past apertures 404 (in embodiments where it is that long), the passage cuts the material in front of the pusher away from the material exiting the aperture, releasing the exiting material from the delivery system.

FIG. 4B shows an alternative embodiment of a delivery system, 420, in which a different design of apertures 424 is used. In the embodiment, a delivery tube 422 serves as a barrel and storage for the material and is optionally detachable from a threaded nut body 430. Optionally, tube 422 is long enough to include an amount of material sufficient for injection, for example, 8-10 cc. Optionally; body 430 includes a pistol or other grip (not shown) and, as above, may be threaded to engage a pusher 426.

In an exemplary embodiment of the invention, the delivery system is made of metal, for example, stainless steel. Alternatively or additionally, at least some of the components are made of a polymer material, for example, PEEK, PTFE, Nylon and/or polypropylene. Optionally, one or more components are formed of coated metal, for example, a coating with Teflon to reduce friction.

In an exemplary embodiment of the invention, the threading of the pusher is made of Nitronic 60 (Aramco) or Gall-Tough (Carpenter) stainless steels.

In an exemplary embodiment of the invention, instead of a standard threading, a ball screw is used. Optionally, the use of a ball screw increases energy efficiency and makes operation easier for manual systems as shown in FIGS. 4A and 4B. Optionally, a gasket is provided to separate the balls from the material.

In an exemplary embodiment of the invention, the delivered material is provided as an elongate sausage with a diameter similar to that of the delivery tube and/or aperture(s). Optionally, a long delivery tube is provided. Alternatively, a plurality of such strings/sausages are implanted. Optionally, the material is provided in a diameter smaller than that of the delivery tube, for example, 0.1-0.01 mm smaller so that there is reduced friction.

Exemplary Extrusion Details

Referring back to FIG. 4A, it is noted that the more proximal extrusion aperture 404 is optionally smaller than the more distal one. Optionally, the relative sizes are selected so that the extrusion rate and/or forces at the two holes is the same. Alternatively, the holes are designed so that the rates and/or forces are different. Referring to FIG. 4B, three axially spaced apertures may be provided and the profile of extrusion can be that a greatest extrusion and/or force is applied at the middle hole.

In an exemplary embodiment of the invention, the sizes of apertures are selected so that the total amount of material ejected is as desired, taking into account the possible sealing of some of the apertures by the advance of the pusher.

In an exemplary embodiment of the invention, the apertures are designed so that the extruded material is ejected perpendicular to the delivery system. Optionally, the delivery system is shaped so that the ejection is at an angle, for example, an angle in the plane of the axis and/or an angle in a plane perpendicular to the axis. Optionally, the angle is selected to offset forces which tend to push the delivery system out of the vertebra. Alternatively or additionally, the angle is selected to match a desired lifting direction of the vertebra or, for example, to prevent direct lifting by the extruded material. Optionally, the delivery system is inserted at a desired angle into the vertebra. Optionally, the angles of different apertures, for example, apertures on opposite sides of the delivery tube, are different, for example, defining a 180 degree angle between the apertures on opposite sides or a more acute (towards the proximal side) or oblique angle. In an exemplary embodiment of the invention, the extrusion angle is 30 degrees, 45 degrees, 60 degrees, 80 degrees or smaller, intermediate or larger angles to the tube axis. Optionally, the material is extruded with a bend radius of 1 mm, 2 mm, 3 mm, 4 mm, 5 mm, 10 mm or intermediate, smaller or larger radii.

The radial arrangement of the extrusion apertures can be of various designs. In one example, for example to ensure even filling of space 308, three, four or more axial rows of apertures are provided. Each row can have, for example, one, two, three or more apertures. In another example, apertures are provided only on opposing sides, so that, for example, a user can select if to extrude towards cortical plates 302 and/or 304, or not.

Rather than rows, a staggered arrangement may be used. One possible advantage for a staggered arrangement is that the delivery tube may be overly weakened by aligned rows of apertures.

Figure 5A:
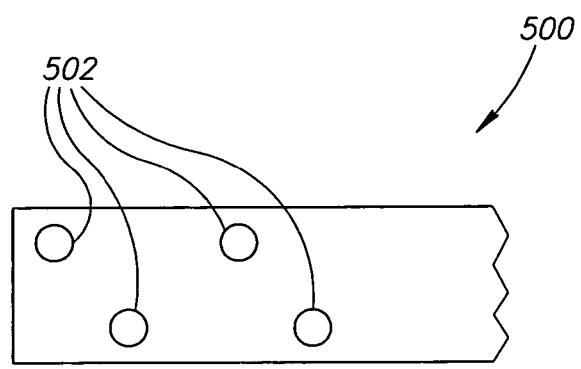
FIGS. 5A and 5B show details of material extruder tips, in accordance with exemplary embodiments of the invention.
Figure 5B:
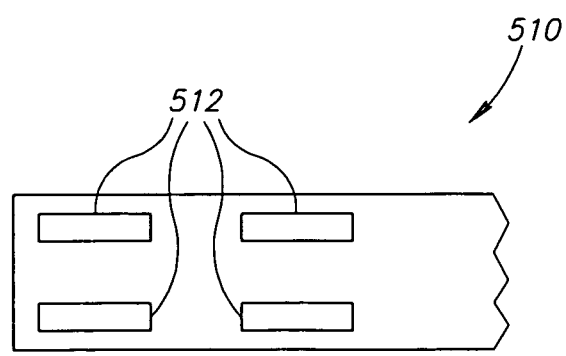

FIG. 5A shows a design of a delivery tip 500 in which round apertures 502 in a staggered row design are used. FIG. 5B shows a design of a delivery tip 510 in which elongated rectangular apertures 512 are arranged in a non-staggered manner.

As shown, the shape of the apertures can be various, for example, round, ellipsoid, rectangular, axially symmetric or asymmetric, parallel to the tube axis or not and/or elongate. Optionally, the edges of the apertures are jagged. Optionally, the shape of the apertures is selected for one or more of the following reasons: shape of extrusion, preventing failure of the aperture and/or preventing failure of the delivery tip. Optionally, the apertures have a lip (optionally pointing inwards), which may assist in shaping the extrusion. For example, the lip may be between 0.1 and 1 mm in width, for example, 0.3 mm or 0.5 mm.

In an exemplary embodiment of the invention, the delivery tube is rigid. Optionally, the delivery tube is flexible or is mechanically shaped (e.g., using a vise) before insertion. In an exemplary embodiment of the invention, the cannula is flexible and allows the insertion of a delivery tube which is curved at its end.

In an exemplary embodiment of the invention, the type of delivery tip used is selected by a user. Optionally, the delivery tip is replaceable, for example attached by a threading to the delivery system.

Optionally, an overtube or ring is selectively provided over part of the delivery system to selectively block one or more of the apertures.

Figure 7A:
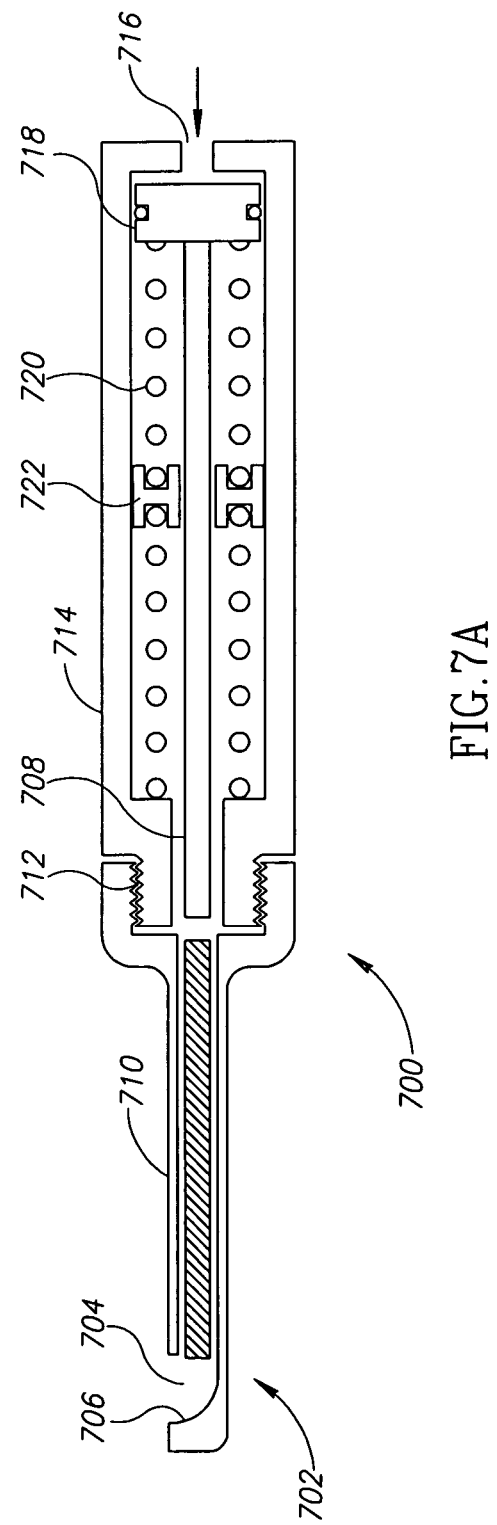
FIG. 7A illustrates a hydraulic delivery system, in accordance with an exemplary embodiment of the invention.

Referring briefly to FIG. 7A, a closed distal tip 702 of cannula 710 is shown, in which a guiding incline 706 is provided to guide the ejected material out of a lateral aperture 704. Optionally, the use of such an incline reduces turbulence in the flow/distortion of the material and/or may assist in reducing friction and/or improving control over the shape of the extrusion. Also to be noted is that material extrusion is provided on only one side of the delivery system. This may allow better control over the force vectors inside the vertebra, caused by the extrusion. In an exemplary embodiment of the invention, the angles defined by the guiding incline (90 degrees and in the plane of the tube axis) help determine the extrusion direction.

Also shown in FIG. 7A is a non-twisting pusher 708, which may reduce turbulence, friction and/or other difficulties in extruding the material, such as voids.

Figure 5C:
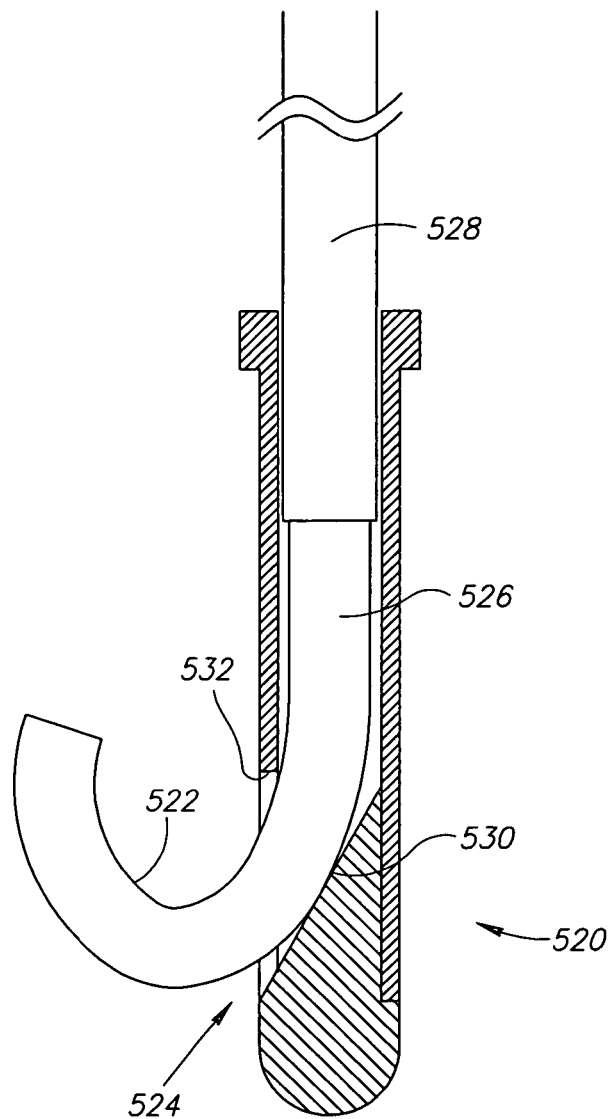
FIG. 5C shows an elongated and curved extrusion of material, in accordance with an exemplary embodiment of the invention.

FIG. 5C shows a cannula delivery tip 520, from which a material 526 is extruded by a pusher 528 in a curved extrusion shape 522. In an exemplary embodiment of the invention, the curvature is controlled by controlling the relative friction on a proximal side 532 and on a distal side 530 of a lateral aperture 524. Alternatively or additionally, the degree of curvature depends on the size of the aperture and the shape of the incline. Optionally, the material is plastically deformed by the extrusion and may maintain a shape conferred thereby barring contact with a deforming surface (e.g., a bone plate). In an exemplary embodiment of the invention, a distal tip of the cannula is closed, optionally permanently closed, so that cement 522 is forced laterally outwards via aperture 524.

Alternatively or additionally, extrusion 522 can be curved or bent due to axial or rotational motion of tip 520. Optionally, the rotation is used to more uniformly fill space 308.

In an exemplary embodiment of the invention, the delivery tube moves and/or rotates during delivery. Optionally, a gear mechanism couples movement of the pusher with rotation and/or axial motion of the tube. Optionally, a manual motion is provided by an operator. Optionally, a vibrator is coupled to the delivery system.

Figure 6C:
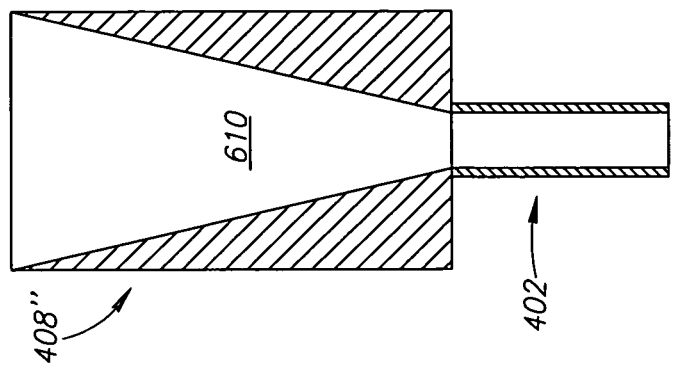
FIGS. 6A-6C illustrate narrowing lumen sections of a delivery system, in accordance with an exemplary embodiment of the invention.

One consideration mentioned above, is that the amount of material in barrel 408 may not be sufficient for a complete procedure. A matching design is illustrated in FIG. 6A, in which the diameter of an inner lumen 602 of barrel 408 is the same as the diameter of an inner lumen 604 of delivery tube 402. A longer delivery tube/barrel maybe required to reduce the number of barrel changes.

Figure 6B:
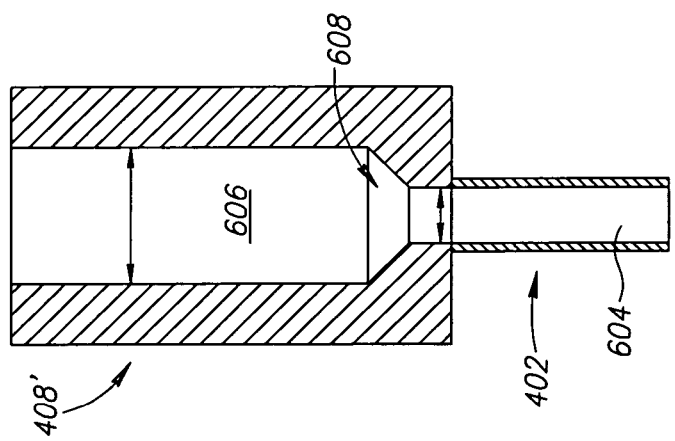
Figure 6A:
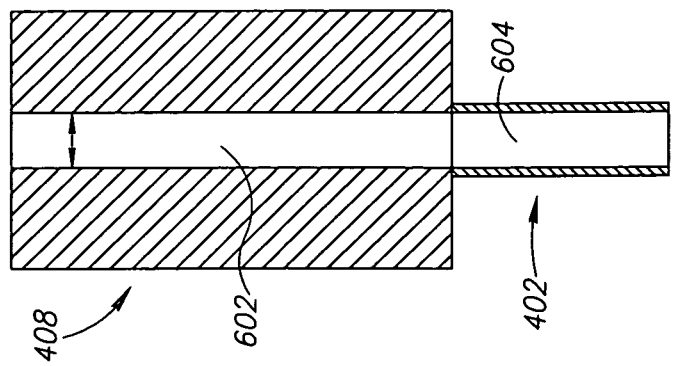

FIG. 6B shows an alternative design, in which a barrel 408' has a lumen 606 with a greater inner diameter and thus a greater storage volume. Optionally, the greater diameter provides an additional hydraulic amplification factor as the diameter changes. Optionally, a sudden change in diameter may cause turbulence, resistance and/or void creation. In some materials, diameter change requires compression of the material. Optionally, as shown, a gradual change in diameter is provided, with an intermediate sloped section 608 with an inner diameter varying between the diameters of lumen 606 and 604. Optionally, the pusher has a diameter matching lumen 606 and does not fit into lumen 604. Optionally, an extension is provided to the pusher, which extension does fit in lumen 604.

Referring to FIG. 6C, a gradually changing lumen 610 is provided in a barrel 408". Optionally, the distal end of the pusher is made of a flexible material, which can conform to the change in diameter. Optionally, the flexible material is harder than the injected material. Alternatively or additionally, the distal end of the pusher is shaped to match the geometry of lumen 610.

In an exemplary embodiment of the invention, the lumen of the barrel is larger than the diameter of the pusher, at least in a proximal section of the barrel. After the pusher advances an amount of material into the bone, the pusher is retracted and the material remaining in the barrel is rearranged so that the next advance of the pusher will advance it. Optionally, the rearranging is by advancing a second plunger having a diameter similar to that of the barrel. Optionally, this plunger is coaxial with the pusher.

The delivery tube may have various cross-sectional shapes, for example, circular, rectangular, arcuate and/or square. Optionally, the cross-section is matched to the shape of extrusion apertures. Optionally, the inside of the apertures is made sharp to cut the extruded material as it is advanced, instead of or in addition to plastically deforming or shearing it.

Exemplary Viscosity/Plasticity and Pressure

In an exemplary embodiment of the invention, the viscosity of the bone cement is 500, optionally 1,000, optionally 1,500, optionally 2,000 Pascal-sec or lesser or greater or intermediate values at the time of loading to an injection system, optionally 3, or 2 or 1 minutes or lesser or intermediate values after mixing. Optionally, a cement with viscosity in this range is useful in vertebral repair, for example in vertebroplasty and/or kyphoplasty procedures. In an exemplary embodiment of the invention, use of a cement which is viscous at the time of injection reduces the risk of material leakage. Reduced leakage optionally contributes to increased likelihood of a positive clinical outcome.

In an exemplary embodiment of the invention, cement is sufficiently viscous to move the bone as it is injected. Optionally, moving of the bone contributes to fracture reduction and/or restoration of vertebral height.

In an exemplary embodiment of the invention, the provided material has a viscosity of above 600 Pascal-second. Optionally, the material is advanced into the body using a pressure of at least 40 atmospheres or higher, for example, 100 or 200 atmospheres or more. If the material is plastic, it may have a hardness, for example, of between 10A shore and 100A shore and/or a Young modulus higher than 200 MPa.

In an exemplary embodiment of the invention, pressure requirements are relaxed at a beginning of a procedure, for example, if a void is created by bone access or by rotation of the delivery system.

In an exemplary embodiment of the invention, the outer diameter of the delivery system is, for example, 2 mm, 3 mm, 4 mm, 5 mm or intermediate or smaller or larger diameters. Optionally, the wall thickness of the delivery system is 0.2 or 0.3 mm. Optionally, the wall thickness increases towards the distal tip It should be noted that the pressure used for delivery may depend on one or more of: the friction between the material and the delivery system, the length of material being pushed, the pressure applied to the material, the pressure desired to be applied by the material to the vertebra, the manner in which the extrusion applies pressure against the vertebra, the viscosity of the material, an area of contact between the material and the cylinder and/or other causes of resistance to motion of the material.

Lower pressures may be used, for example, if it is deemed that the vertebra may be damaged or material leakage possible.

The volume injected may be, for example, 2-4 cc for a typical vertebra and as high as 8-12 cc or higher. Other volumes may be appropriate, depending for example, on the volume of space 308 and the desired effect of the injection.

In an exemplary embodiment of the invention, the rate of injection is 0.25 cc/sec. Higher or lower rates may be provided, for example, between 25 cc/sec and 0.1 cc/sec or less, and between 25 cc/sec and 1 cc/sec or more. Optionally, the rate is controlled using electronic or mechanical circuitry. Optionally, the rate is decided by an operator responsive to expected or imaged bone deformation in response to the pressure. Optionally, the rate is changed over the length of the procedure, for example, being higher at a beginning and lower at an end. Optionally, the rate of injection is controlled by the operator (or automatically) responsive to a feedback mechanism, such as fluoroscopy.

Fast Setting Cement.

Figure 15:
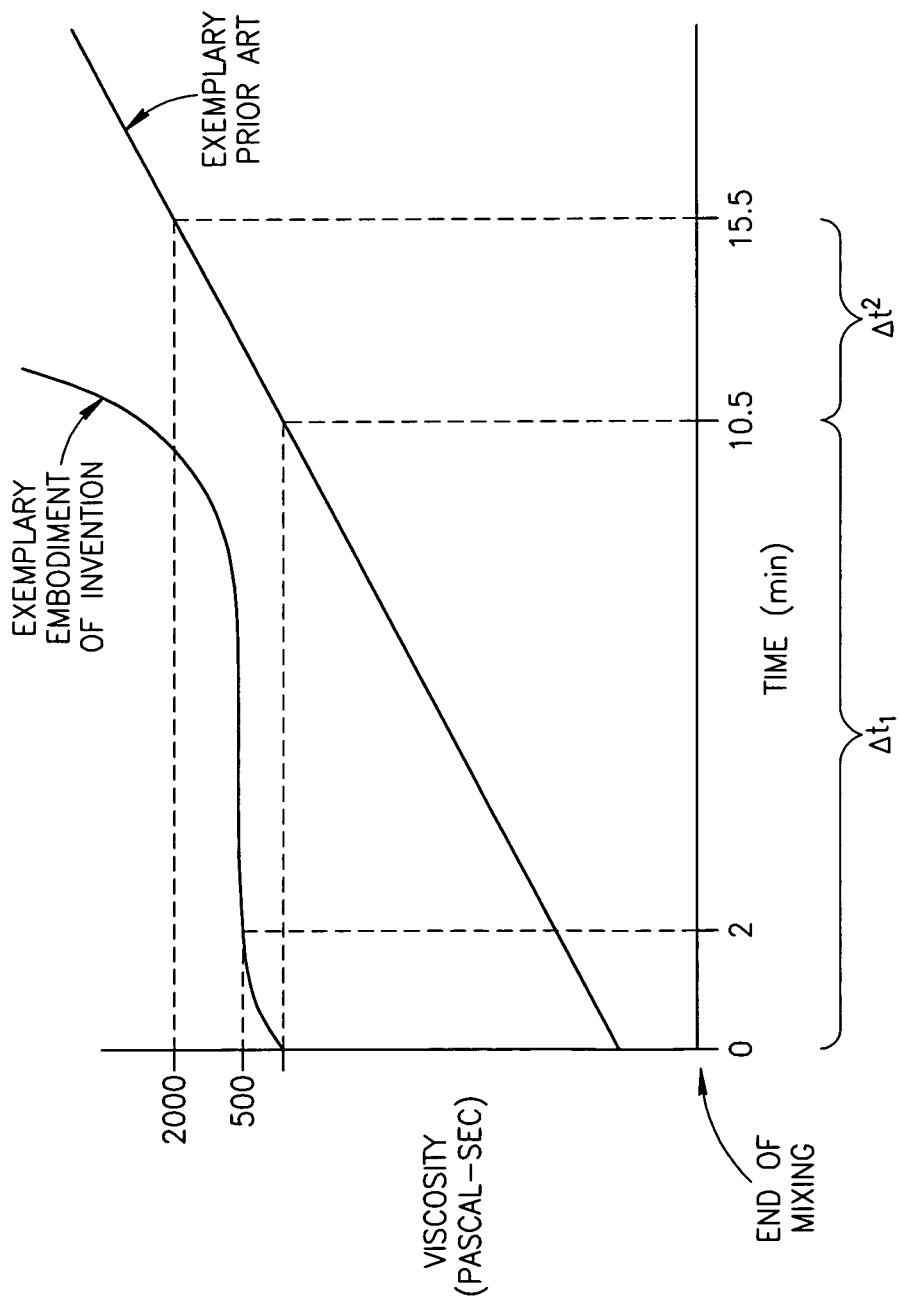
FIG. 15 is a graph of viscosity (Pascal Sec) as a function of time (minutes) for an exemplary cement according to the invention and an exemplary prior art cement.

FIG. 15 is a plot of viscosity as a function of time for an exemplary bone cement according to the present invention. The figure is not drawn to scale and is provided to illustrate the principles of the invention. The end of a mixing process is denoted as time 0. In an exemplary embodiment of the invention, bone cement according to the invention enters a plastic phase upon mixing so that it has substantially no liquid phase. Optionally, mixture of polymer and monomer components produces a material with viscosity of about 500 Pascal-second or more within 15, optionally 30, optionally 60, optionally 90, optionally 120 seconds or lesser or greater or intermediate times. In an exemplary embodiment of the invention, the material reaches a viscosity higher than 500 Pa-s within about 30 seconds after its components mixing. Optionally, once a high viscosity is achieved, the viscosity remains relatively stable for 2, optionally 5, optionally 8 minutes or more. In an exemplary embodiment of the invention, this interval of stable viscosity provides a window of opportunity for performance of a medical procedure. In an exemplary embodiment of the invention, stable viscosity means that the viscosity of the cement changes by less than 200 Pascal-second during a window of at least 2 minutes optionally at least 4 minutes after mixing is complete. Optionally, the window begins 1, 2, 3, 6, or 8 minutes after mixing is complete or lesser or intermediate times. In an exemplary embodiment of the invention, the viscosity of the cement remains below 1500 Pascal-second for at least 4, optionally at least 6, optionally at least 8 optionally at least 10 minutes or intermediate or greater times.

In an exemplary embodiment of the invention, an applied injection pressure in the cement reservoir is reduced as the cement flows through the cannula. Optionally, friction between the cement and the cannula walls reduces pressure.

In an exemplary embodiment of the invention, injection of cement is continuous. The term continuous as used here indicates that the greatest interruption in a flow of cement exiting a distal tip of the cannula is less than 5, optionally less than 2, optionally less than 1, optionally less than 0.5, optionally less than 0.1 seconds or lesser or intermediate times.

In FIG. 15 the end of a mixing process is denoted as time 0. Mixing is deemed to end when all acrylic polymer beads have been wetted with monomer.

For purposes of comparison, the graph illustrates that an exemplary prior art cement reaches a viscosity suitable for injection at a time of approximately 10.5 minutes post mixing and is completely set by about 15.5 minutes.

A window of opportunity for injection with an exemplary cement according to the invention ($\Delta t_1$) is both longer and earlier than a comparable window for an exemplary prior art cement ($\Delta t_2$). Optionally, ($\Delta t_1$) begins substantially as soon as mixing is complete. In an exemplary embodiment of the invention, the cement has substantially no time in a liquid phase before entering a plastic phase.

Viscosity Measurements Over Time for Exemplary Fast Setting Cements

In order to evaluate the viscosity profile of different exemplary batches of cement according to some embodiments of the invention, a bulk of pre-mixed bone cement is placed inside a Stainless Steel injector body (e.g. 2002 of FIGS. 7P and 7Q). Krause et al. described a method for calculating viscosity in terms of applied force. ("The viscosity of acrylic bone cements", Journal of Biomedical Materials Research, (1982): 16:219-243). This article is fully incorporated herein by reference.

In the experimental apparatus inner diameter of injection chamber 2600 is approximately 18 mm. The distal cylindrical outlet 2500 has inner diameter of approximately 3 mm and a length of more than 4 mm. This configuration simulates a connection to standard bone cement delivery cannula/Jamshidi needle. A piston 2200 applies force (F), thus causing the bone cement to flow through outlet 2500. Piston 2200 is set to move with constant velocity of approximately 3 mm/min. As a result, piston deflection is indicative of elapsed time.

The experimental procedure serves as a kind of capillary extrusion rheometer. The Rheometer measures the pressure difference from a end to end of the capillary tube. The device is made of a 18 mm cylindrical reservoir and a piston. The distal end of the reservoir consist of 4 mm long 3 mm hole. Assuming steady flow, isothermal conditions and incompressibility of the tested material, the viscose force resisting the motion of the fluid in the capillary is equal to the applied force acting on the piston measured by a load cell. Results are presented as force vs displacement. As displacement rate was constant and set to 3 mm/min, the shear rate was constant as well. In order to measure the time elapses from test beginning, the displacement rate is divided by 3 (jog speed).

Figure 16:
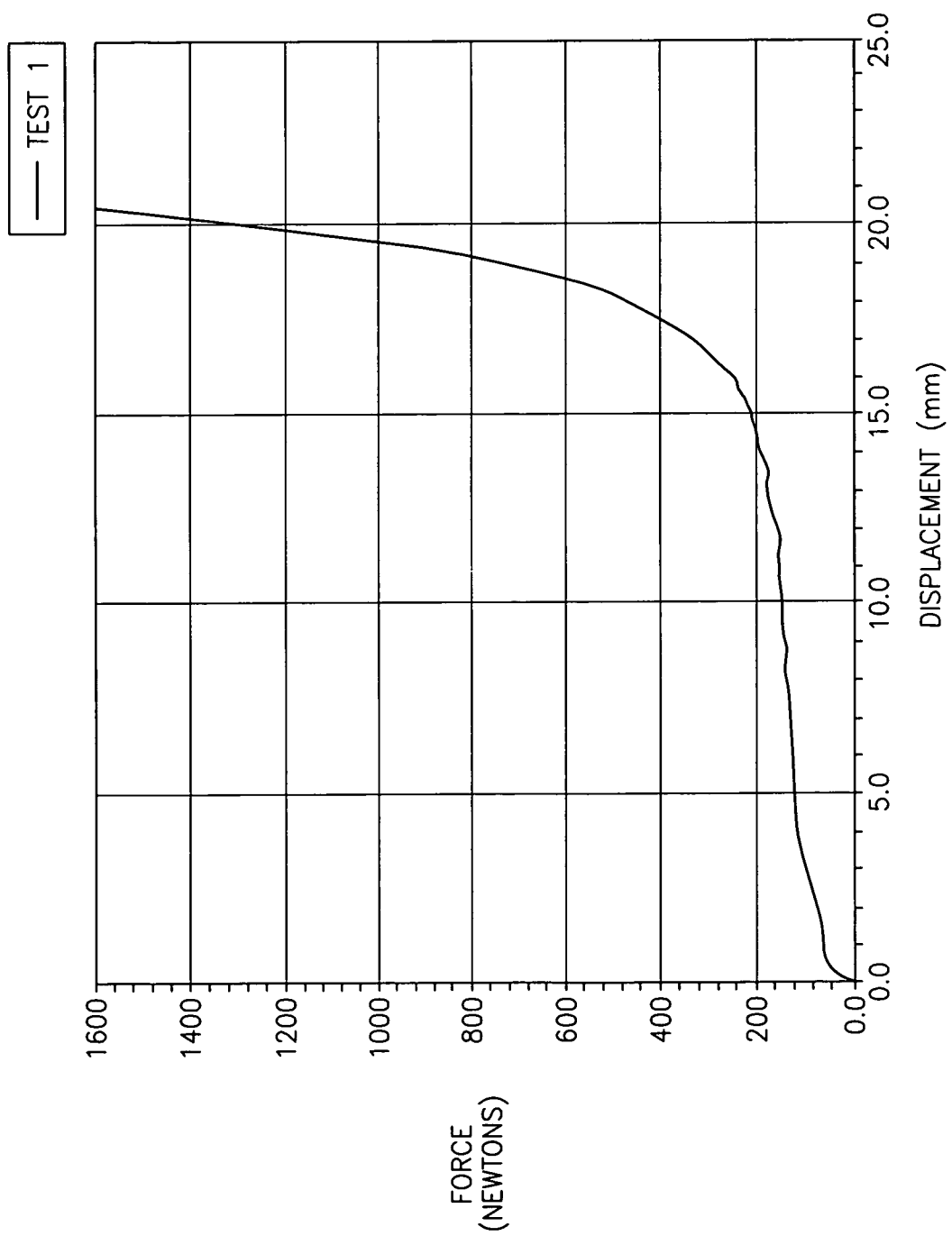
FIGS. 16 and 17 are graphs indicating viscosity as Newtons of applied force per unit displacement (mm) under defined conditions for exemplary cements according to the invention and illustrate the time window for injection which is both early and long.

FIG. 16 indicates a viscosity profile of a first exemplary batch of cement according to the invention as force (Newtons) vs displacement (mm). The cement used in this experiment included a liquid component containing approximately 98.5% v/v MMA, approximately 1.5% DMPT and approximately 20 ppm of Hydroquinone and a powder component containing approximately 69.39% w/w PMMA, approximately 30.07% Barium Sulphate and approximately 0.54% of Benzoyl Peroxide. The average molecular weight of the PMMA was approximately 110,000 Dalton. Approximately 1% of the PMMA had a molecular weight of 700,000 to 1,000,000 Dalton. The bead size was in the range of 10-200 microns.

In this test (Average temperature: 22.3° C.; Relative Humidity: app. 48%) the cement was mixed for 30-60 seconds, then manipulated by hand and placed inside injector 2002. Force was applied via piston 2200 approximately 150 seconds after end of mixing, and measurements of force and piston deflection were taken.

At a time of 2.5 minutes after mixing (0 mm deflection) the force applied was higher than 30 N.

At a time of 6.5 minutes after mixing (12 mm deflection) the force applied was about 150 N.

At a time of 7.5 minutes after mixing (15 mm deflection) the force applied was higher than 200 N.

At a time of 8.5 minutes after mixing (18 mm deflection) the force applied was higher than 500 N.

At a time of 9.17 minutes after mixing (20 mm deflection) the force applied was higher than 1300 N.

Figure 17:
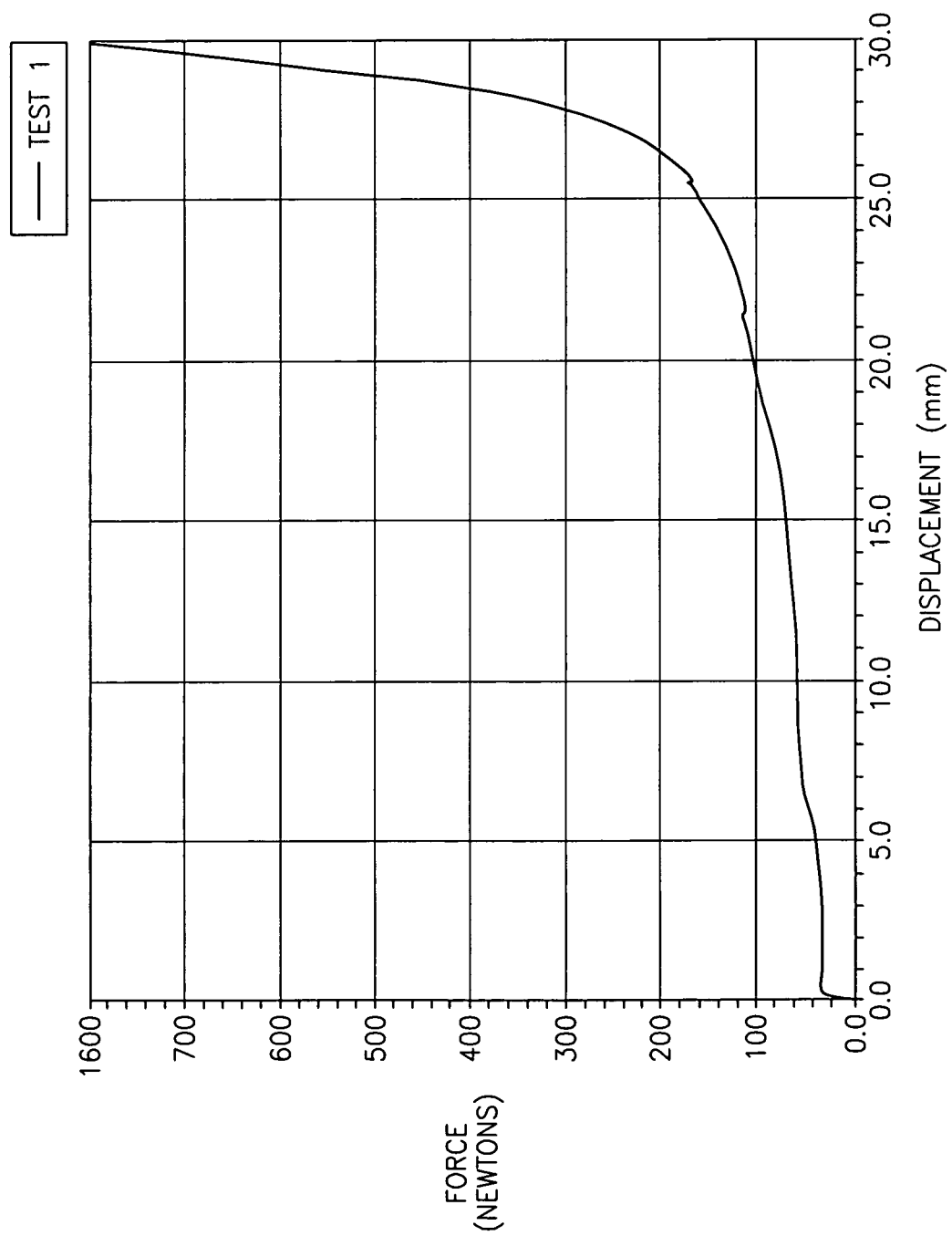

FIG. 17 indicates a viscosity profile of an additional exemplary batch of cement according to the invention as force (Newtons) vs displacement (mm). The cement in this test was prepared according to the same formula described for the experiment of FIG. 16. In this test (Average 21.1° C.; Relative Humidity: app. 43%) the cement was mixed for approximately 45 seconds, then manipulated by hand and placed inside injector 2002. Force was applied via piston 2200 approximately 150 seconds after end of mixing, and measurements of force and piston deflection were taken.

At a time of 2.25 minutes after mixing (0 mm deflection) the force applied was higher than 30 N.

At a time of 8.25 minutes after mixing (18 mm deflection) the force applied was about 90 N.

At a time of 10.3 minutes after mixing (25 mm deflection) the force applied was higher than 150 N.

At a time of 11.4 minutes after mixing (28.5 mm deflection) the force applied was higher than 500 N.

At a time of 12.25 minutes after mixing (30 mm deflection) the force applied was higher than 800 N.

Results shown in FIGS. 16 and 17 and summarized hereinabove illustrate that exemplary bone cements according to some embodiments the invention are ready for injection in as little as 2.25 minutes after mixing is completed. Alternatively or additionally, these cements are characterized by short mixing time (i.e. transition to plastic phase in 30 to 60 seconds). The exemplary cements provide a "working window" for injection of 4.5 to 6.3 minutes, optionally longer if more pressure is applied. These times correspond to delivery volumes of 14.9 and 20.8 ml respectively. These volumes are sufficient for most vertebral repair procedures. These results comply with the desired characteristics described in FIG. 15. Differences between the two experiments reflect the influence of temperature and humidity on reaction kinetics.

Hydraulic Material Provision System

FIG. 7A shows a delivery system 700 which is powered hydraulically. A cannula 710 is filled with material to be ejected into the body. Cannula 710 is optionally detachable via a connection 712 to a body 714. Optionally, the connection is by threading. Alternatively, a fast connection method, such as a snap connection, is used.

Body 714 converts hydraulic pressure provided via an input port 716 into an advance of a pusher rod 708. Optionally, body 714 is integral with tube 710, but this prevents replacing tube 710 when the material to be ejected is exhausted.

In an exemplary embodiment of the invention, incoming hydraulic (or pneumatic) fluid pushes against a piston 718, which advances pusher 708 directly. Optionally, a hydraulic advantage is provided by the ratios of the piston and the pusher. Optionally, a spring 720 is provided for retracting pusher 708 when the fluid pressure is released.

Optionally, one or more spacers 722 are provided surrounding pusher 708, to prevent buckling thereof. Optionally, the spacers are mounted on spring 720. Optionally, spacers are provided at several axial locations. Alternatively to spacers, fins may extend from pusher 708 to body 714.

Optionally, in use, when material is used up, pressure is reduced, pusher 708 retracts and delivery tube 710 is replaced. Optionally, a barrel filled with material for injection, separate from tube 710 is provided, so that tip 702 does not need to be removed from the body.

Figure 7B:
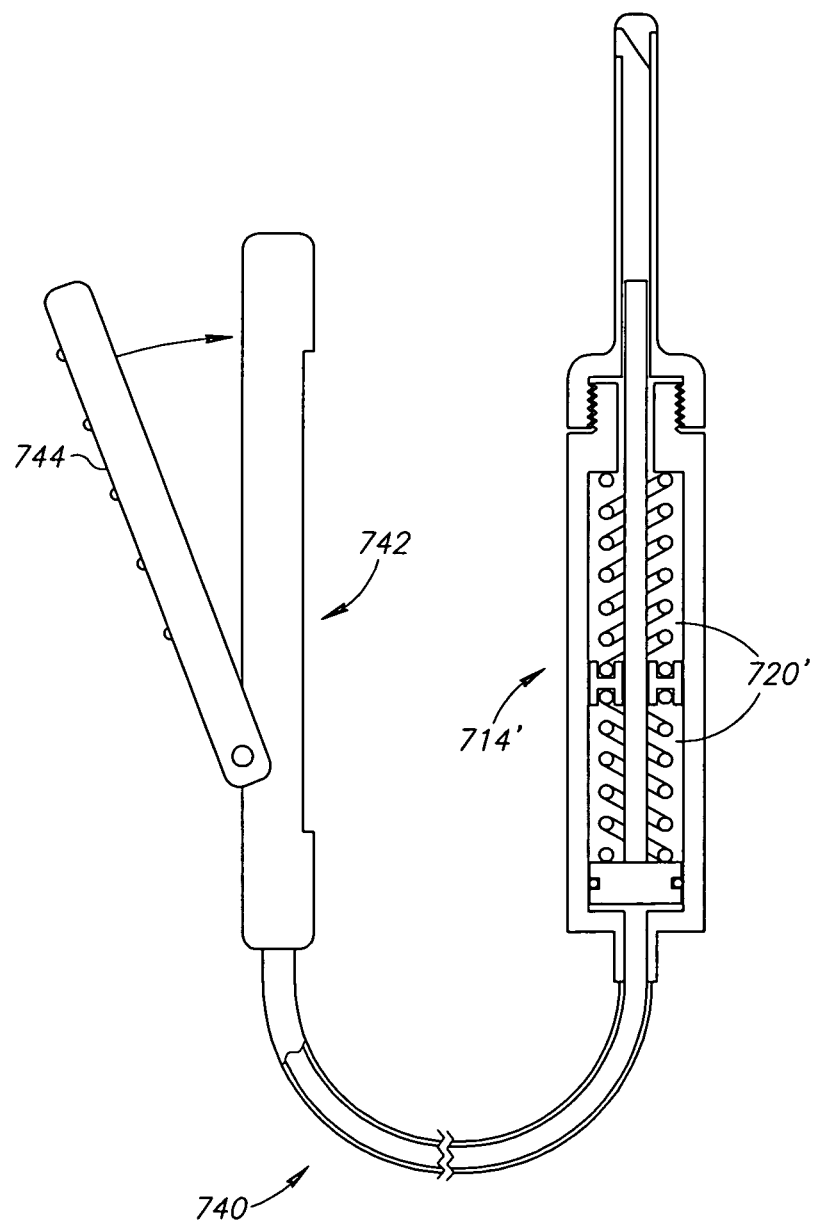
FIGS. 7B and 7C show alternative methods of providing hydraulic power to the system of FIG. 7A, in accordance with exemplary embodiments of the invention.
Figure 7C:
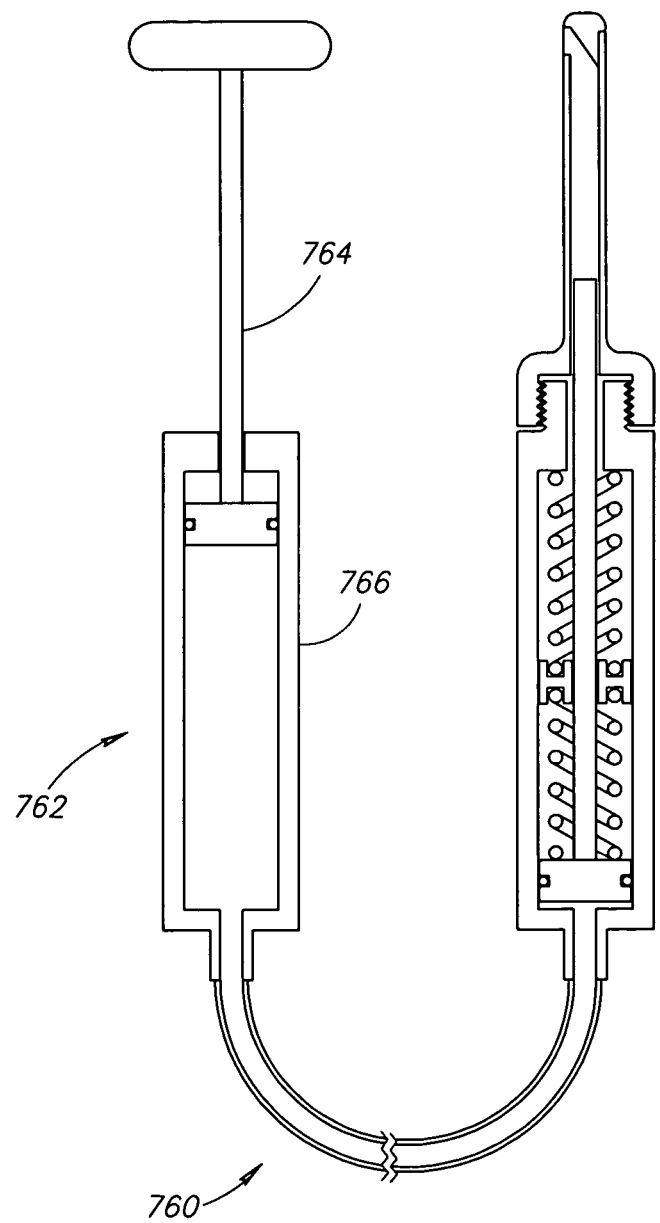

FIGS. 7B and 7C show two alternative methods of providing hydraulic power. In FIG. 7B, a foot pedal pump 740 is used, in which a user places his foot on a pedal 744 and depresses it against a plate 742. Various foot pumps are known in the art. Optionally, a long press releases the pressure. Optionally, the hydraulic subsystem is a sealed system which is provided ready to use (e.g., including fluid) to the user and/or distributor. Exemplary lengths of the flexible tubing are between 0.2 and 3 meters, for example, between 1 and 2 meters. However, greater lengths can be used as well.

In an exemplary embodiment of the invention, a foot operable actuator employs a 1.5 m, optionally 2 m, optionally 2.5 m tube or a tube of lesser or intermediate or greater length (see FIG. 7B).

In an exemplary embodiment of the invention, a hand operable actuator employs a 0.25 m, optionally 0.5 m, optionally 1.0 m tube or a tube of lesser or intermediate or greater length.

Also shown in FIG. 7B is a variant of body 714, indicated as 714'. Instead of a single spring 720, two springs 720' are shown, with the spacer(s) between the springs. Optionally, the use of multiple springs helps maintain the spacers near a middle (or other relative length unit) of the pusher in danger of buckling.

FIG. 7C shows an alternative embodiment, in which a hand pump 760 is used, which pump can be of any type known in the art, for example, a mechanism 762 comprising a piston 764 and a cylinder 766. Optionally, the pumping is by rotating piston 764 elative to cylinder 766, which components include matching threading. Alternatively, linear motion is used. Optionally, a hydraulic gain is achieved between the pump and the delivery mechanism, for example a gain of 1:3, 1:5, 1:10 or any smaller, intermediate or greater gain.

In an exemplary embodiment of the invention, the hydraulic system is provided as a disposable unit, with a non-disposable (or a disposable) foot pump.

Figure 7D:
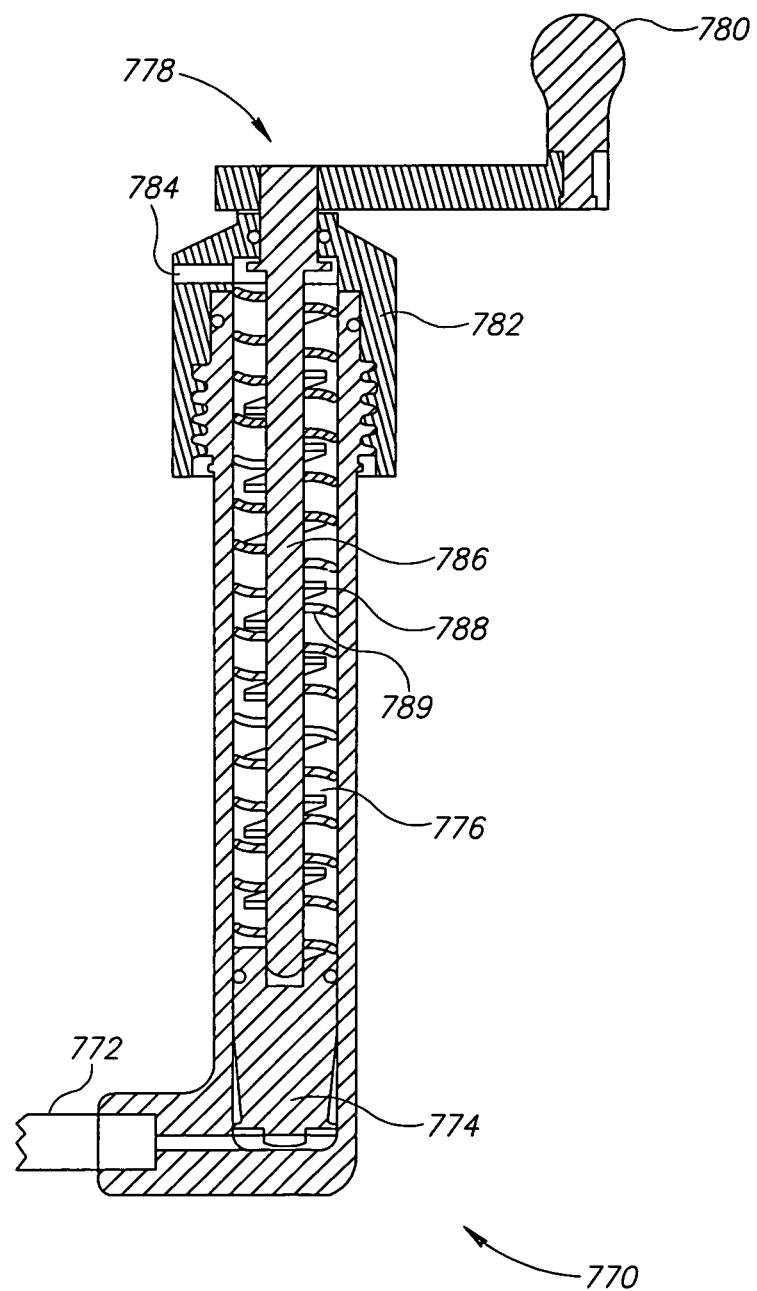
FIGS. 7D and 7E illustrate an exemplary hydraulic system including a disposable unit, in accordance with an exemplary embodiment of the invention.
Figure 7E:
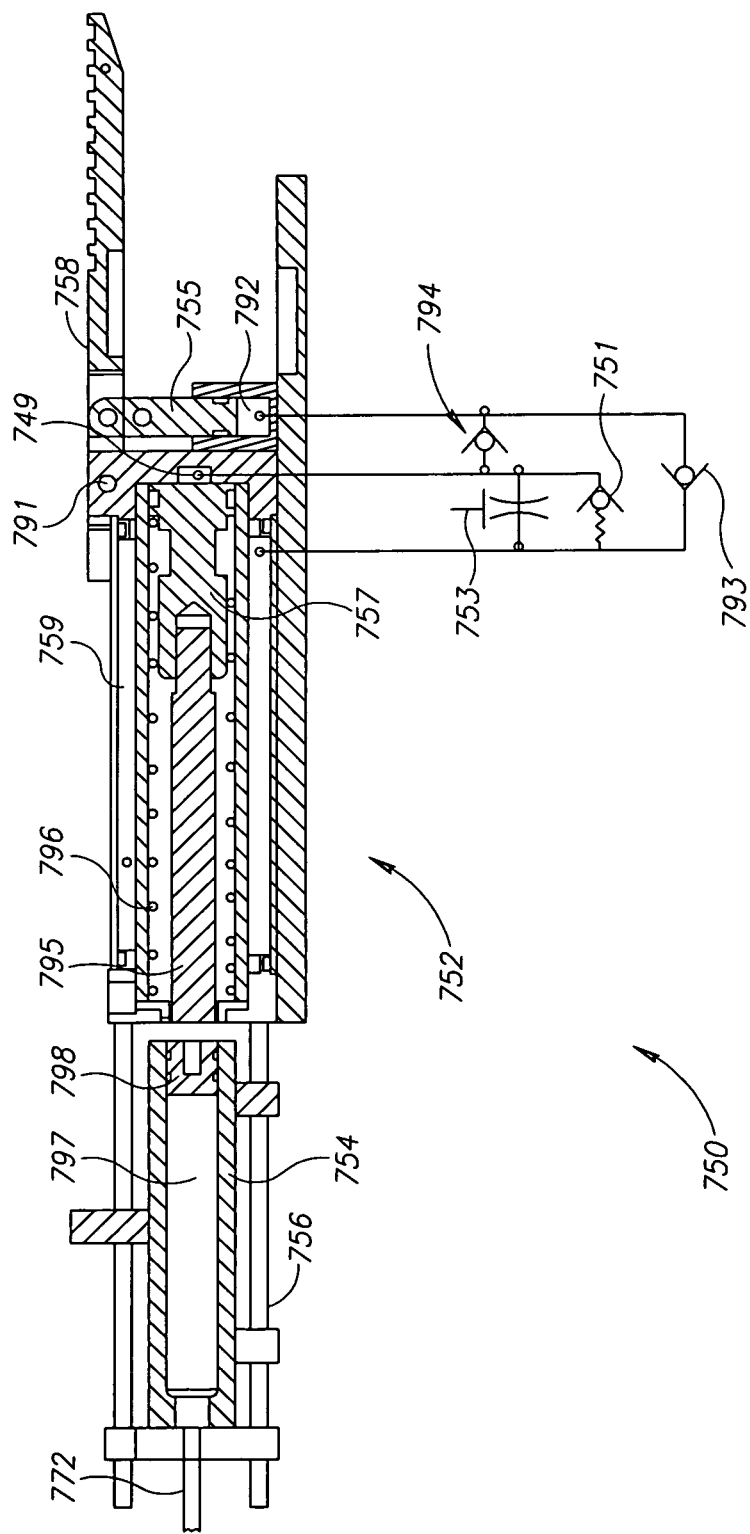

FIG. 7D shows a disposable mixing and storage chamber 770 and FIG. 7E shows a reusable pump 750 with a disposable hydraulic capsule 754.

Referring to FIG. 7D, a same capsule 770 is optionally used both for mixing and for storage/delivery of a material.

Optionally, the material is a setting cement such as PMMA. In the embodiment of a hydraulic delivery stream, a flexible tube 772 is optionally permanently connected to a pump (FIG. 7E). When fluid is provided through tube 772, a piston 774 moves through a cylinder volume 776 and pushes the material out (e.g., and into a delivery system). In the figure, the capsule is shown loaded with a mixer 778. Optionally, materials are provided into volume 776 using a detachable funnel (not shown) and then the funnel is removed and mixer 778 inserted instead. In the exemplary mixer shown, a cap 782 covers cylinder 776. When mixing is completed, this cap may be replaced by a fitting adapted to couple to the delivery tube.

In use, a handle 780 is rotated, rotating a shaft 786 having a rotor 788 defined thereof, for example, as a helix. An optional stator 789 is provided. An optional vent 784 may be connected to a vacuum source, to suck out toxic and/or bad smelling fumes caused by the setting of the material. Optionally, a viscosity of the materials is estimated by the difficulty in turning the handle. Optionally, the handle includes a clutch (not shown) that skips when a desired viscosity is reached. Optionally, the clutch is settable. Optionally, a viscosity meter is used or viscosity is estimated based on temperature, formulation and time from mixing.

Cap 782 optionally includes a squeegee or other wiper, to wipe material off of mixer 778 when it is removed from capsule 770.

Referring to FIG. 7E, tube 772 connects to a capsule 754 which includes a piston 798 and a volume 797, pre-filled with fluid. In an exemplary embodiment of the invention, a frame 756 is provided attached to pump 750 for selectively receiving capsule 754.

Pump 750 is, for example, a hydraulic oil based pump-mechanism 752 that extends a pushing rod 795 which advances piston 798.

In the embodiment shown, a foot pedal 758, attached to an axis 791, forces a piston 755 into a cylinder 792. A one way valve 794 allows the fluid in cylinder 792 to flow into a volume 749 where it pushes against a piston 757. When pedal 758 is released, a spring (not shown) pulls it back to an upward position and allows a hydraulic fluid to flow from a storage chamber 759 (e.g., which surrounds the pump) through a one way valve 793 into cylinder 792.

A pressure relief valve 751 is optionally provided to prevent over pressurizing of cylinder 749. In an exemplary embodiment of the invention, a spring 796 is provided to push back piston 757 and pusher 795 with it, when pressure is released. Optionally, pressure is released using a bypass valve 753, which is manually operated. Once pusher rod 795 is retracted, capsule 740 is optionally removed.

Figure 7F:
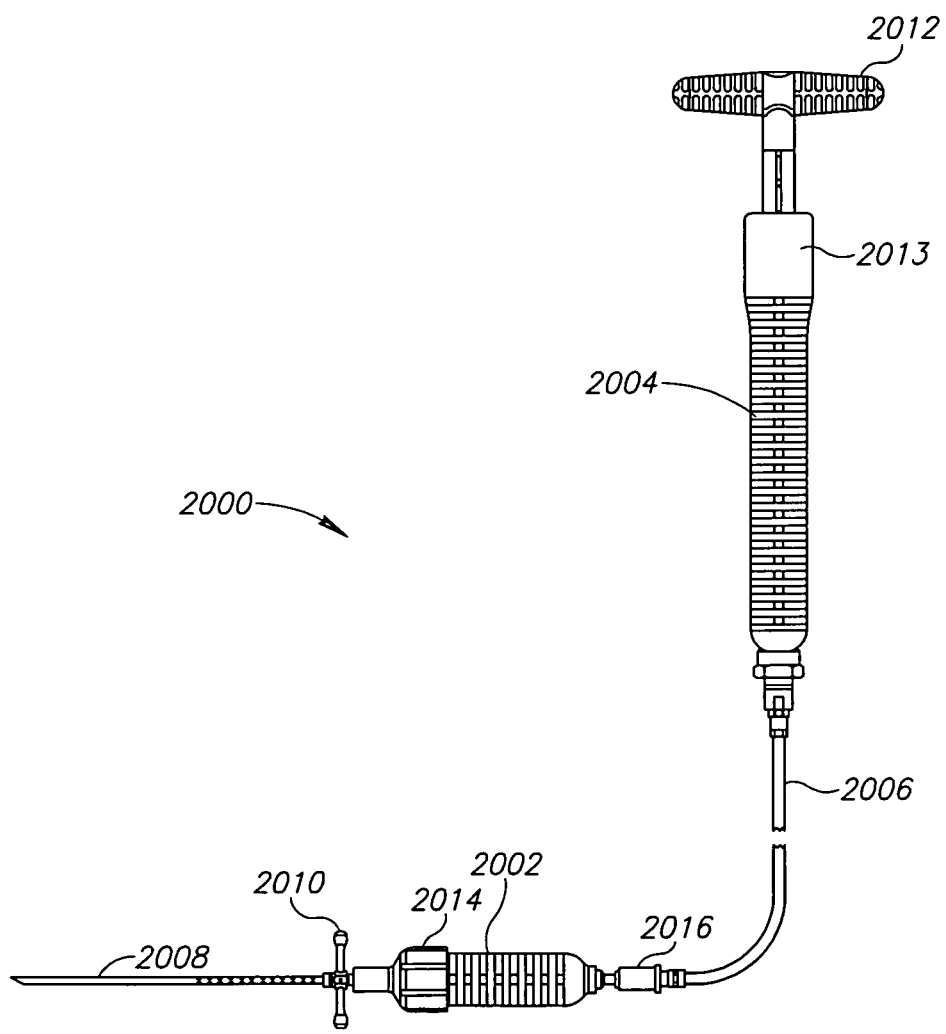
FIGS. 7F-7G illustrate an exemplary hydraulic delivery system, in accordance with an exemplary embodiment of the invention.

FIGS. 7F (side view) and 7G (cross section) illustrate a hydraulic delivery system 2000, comprising a reservoir 2002 for material (e.g. bone cement) and a pressure source 2004. Optionally a flexible tube 2006 which connects reservoir 2002 and pressure source 2004 is included in system 2000. Reservoir 2002 is connectable to a cannula 2008. Cannula 2008 can optionally be introduced into a bone prior to injection of material from reservoir 2002. Reservoir 2002 and cannula 2008 may be connected using, for example, a luer lock connector 2010 and/or threaded connector 2014. Alternately, reservoir 2002 and cannula 2008 may be fashioned as a single piece. Optionally, cannula 2008 is compatible with a stylet (not shown).

In an exemplary embodiment of the invention, cannula 2008 is a plastically deformable cannula, optionally a slitted cannula. Plastically deformable cannulae in general, and slitted cannulae in particular are described in detail in co-pending U.S. application 60/721,094 entitled "Tools and Methods for Material Delivery into the Body", and in co-pending application entitled "Cannula" identified as and filed concurrently with the instant application, the disclosures of which are fully incorporated herein by reference. Optionally, use of a plastically deformable cannula 2008 facilitates positioning of reservoir 2002 outside of an X-ray imaging field.

In an exemplary embodiment of the invention, pressure source 2004 is a hydraulic pressure source. Pressure source 2004 may be filled with any liquid. In an exemplary embodiment of the invention, pressure source 2004 is filled is filled with a sterile liquid 2026 (FIG. 7G), such as saline or water. Optionally, filling is via flexible tube 2006. Optionally, an outlet of tube 2006 is immersed in the liquid, and hydraulic actuator 2012 is operated to fill pressure source 2004 with liquid. In the exemplary embodiment of FIGS. 7F and 7G, the actuator is depicted as a ball screw connection 2013 equipped with a rotating handle 2012. According to this embodiment, handle 2012 is rotated to fill pressure source 2004 with liquid.

In an exemplary embodiment of the invention, pressure source 2004 is provided as a prefilled unit. Optionally the prefilled unit includes body 2004, tube 2006 and/or cap 2013 and/or handle 2012 with drive shaft 2022. Optionally the prefilled unit includes body 2004, optionally with tube 2006 and is provided with temporary seals at each end. In an exemplary embodiment of the invention, the seals are removed or broken when additional system components are connected.

Although an exemplary manually operable actuator is pictured, hydraulic actuator 2012 may be operable by, for example, a foot pedal (see FIG. 7T described hereinbelow) or an electric actuator, such as a linear actuator or a motor. Electric operation may be achieved, for example, by employing a battery (as described hereinbelow) and/or mains supply. In an exemplary embodiment of the invention, the hydraulic actuator causes pressures source 2004 to generate a pressure of 50, optionally 100, optionally 150, optionally 200, optionally 300 atmospheres or lesser or greater or intermediate values.

Optionally, a safety mechanism (described in greater detail hereinbelow) limits pressure. In an exemplary embodiment of the invention, the safety mechanism includes a valve with a defined pressure threshold. In an exemplary embodiment of the invention, the threshold is set to prevent injection of cement after it has solidified and/or to protect the system from being damaged by attempts to inject solidified cement.

For example if a particular cement formulation is flowable at a pressure of 150 atmospheres during the "working window", a valve threshold may be set at 170 atmospheres. In such a case, the system would be designed to withstand a greater internal pressure, such as 200 atmospheres. This arrangement reduces the chance that the system will be damaged when cement solidifies.

Optionally, the pressure threshold is 150 or 210 atmospheres or lesser or greater or intermediate values. In an exemplary embodiment of the invention, the safety mechanism may be used to release trapped gases (e.g. air) and/or cement. In an exemplary embodiment of the invention, each activation of the hydraulic actuator (e.g., handle rotation, foot pedal pressing) results in injection of defined amount of cement. Optionally, the hydraulic actuator provides pressure amplification.

Optionally, air is removed from pressure source 2004 and/or tube 2006 prior to connection of pressure source 2004 to reservoir 2002. One or more connectors 2016 can be optionally employed to connect of reservoir 2002 to pressure source 2004, optionally via tube 2006. Connectors 2016 may be, for example, luer lock connectors, quick release connectors or threaded connectors.

Figure 7G:
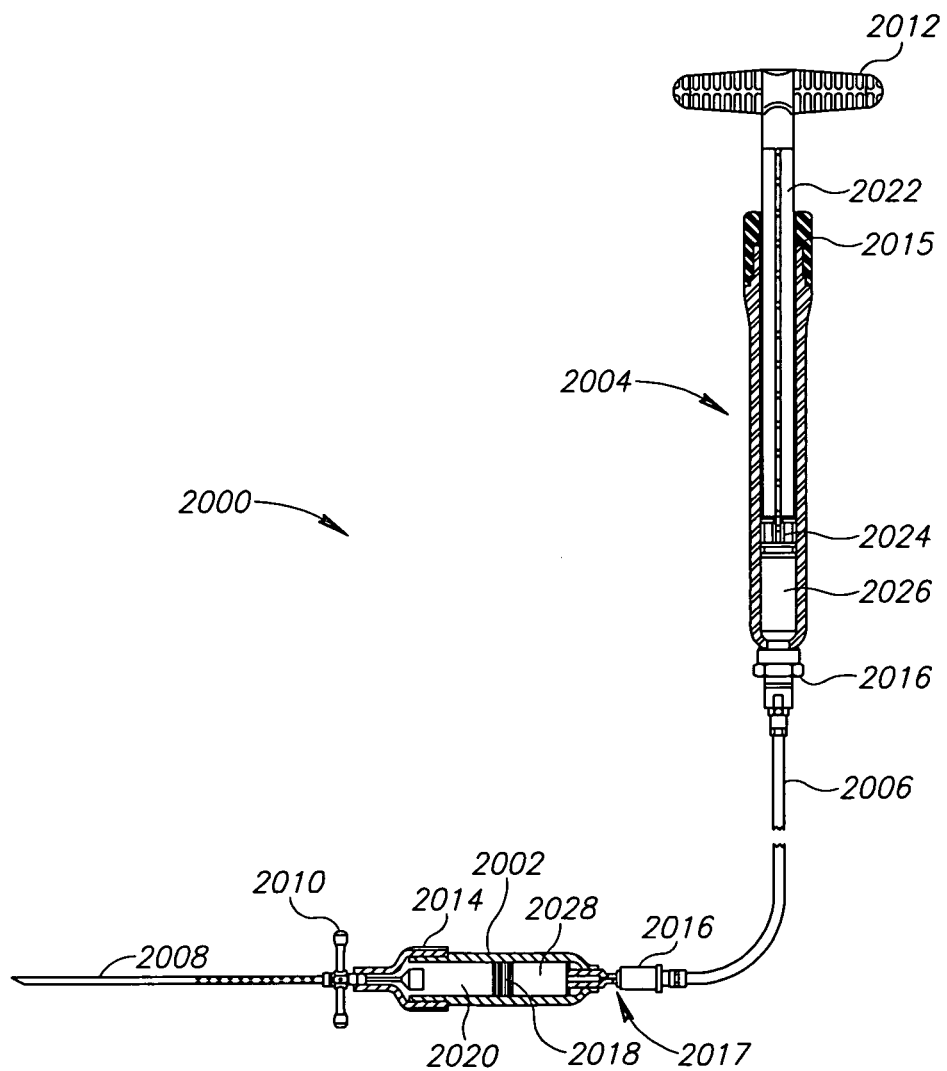

In an exemplary embodiment of the invention, delivery system 2000 is employed to deliver a viscous material, optionally a viscous bone cement. In an exemplary embodiment of the invention, cement components (e.g. powder and liquid) are mixed. The mixture is loaded into reservoir 2002, optionally via a reservoir cap 2014. Optionally cap 2014 is unscrewed and reservoir 2002 is filled with bone cement 2020 (FIG. 7G). According to various embodiments of the invention, cement 2020 may be inserted into reservoir 2002 manually or by use of a tool or filling device. In an exemplary embodiment of the invention, cement 2020 is sufficiently viscous that it may be preformed to a size and shape which permit easy insertion into reservoir 2002. After cement 2020 is inserted in reservoir 2002, cap 2014 is replaced. Pressure source 2004 is connected to reservoir 2002, optionally via flexible tube 2006, via connector(s) 2016. In an exemplary embodiment of the invention, pump 2004, tube 2006, connector 2016 and fluid 2026 are provided as a pre-assembled sterile unit. Optionally, air is removed from the system via a pressure release valve 2017, optionally on connector 2016. Optionally rotation of handle 2012 increases pressure in the system and drives air out. Optionally, air is released through valve 2017 or is expelled via cannula 2008 prior to insertion of the cannula in the body.

Optionally, mixing of cement components is performed under vacuum to prevent air bubbles from being entrapped in the cement.

Reservoir 2002 is connected to cannula 2008 via connector 2010. In an exemplary embodiment of the invention, connector 2010 serves as an orientation marker which indicates an ejection direction of cement injected through the cannula. Operation of handle 2012 delivers cement 2020 from reservoir 2002 to cannula 2008. In an exemplary embodiment of the invention, rotation of handle 2012 rotates pump thread 2022 and advances piston 2024. Advancing piston 2024 applies pressure to liquid 2026 within pressure source 2004 and causes liquid 2026 to advance into reservoir 2002, optionally via tube 2006. Liquid 2028 in reservoir 2002 applies pressure to a piston 2018 within reservoir 2002. As piston 2018 advances through reservoir 2002, it causes cement 2020 to advance and exit reservoir 2002 via the cannula 2008.

According to various embodiments of the invention, 2008 cannula may be equipped with one or more apertures for cement delivery. Optionally, these apertures are located at a distal end and/or near the distal end of cannula 2008. Optionally, the apertures face axially and/or radially with respect to the cannula. Optionally, the cannula distal end is closed. In an exemplary embodiment of the invention, one or more lateral openings on the cannula permit sideways injection to a desired target in a bone from a cannula with a permanently closed distal tip.

In an exemplary embodiment of the invention, the injection procedure is monitored by a medical imaging system (e.g. fluoroscopy). When a desired amount of cement 2020 has been delivered through cannula 2008, injection is stopped. Optionally, reservoir 2002 is disconnected from cannula 2008 and/or tube 2006 and/or pressure source 2004. Cannula 2008 is removed from the bone, and the operation site is closed.

In an exemplary embodiment of the invention, cannula 2008 and/or cement 2020 are composed of biocompatible materials. In an exemplary embodiment of the invention, components of system 2000 which contact cement 2020 are not adversely affected by the cement. For example if MMA is employed as a component of the cement, reservoir 2002 may be constructed of an MMA monomer resistant polymer/Plastic while cannula 2008 may be constructed of Stainless Steel. In various exemplary embodiments of the invention, reservoir 2002 may be made of, for example, nylon, pressure source 2004 may be made of, for example, metal and/or plastic (e.g. polycarbonate), and the flexible tube 2006 is made of, for instance, nylon or Teflon®.

In an exemplary embodiment of the invention, reservoir 2002 and/or pressure source 2004 are constructed of Amorphous Nylon (e.g. Nylon Nos. 6, 6/6 or 12, e.g. Grilamid 90 or Durethan) and/or of a Cyclic Olefin Copolymer (COC) (e.g., Topas®; Ticona GmbH, Kelsterbach, Germany). These materials are resistant to cement components, including the monomer component.

In an exemplary embodiment of the invention, the reservoir 2002 is designed to withstand pressures in the range of 100 to 300 atmospheres. Optionally, a reservoir with an internal diameter of 18 mm wis constructed with a wall thickness of 5 mm so that the outer diameter is 28 mm. Optionally, the walls are ribbed to increase strength and/or reduce weight.

The pressure source 2004 will come in contact only with the hydraulic fluid, such as water or a saline solution. Optionally, pressure source 2004 is constructed of Polycarbonate and/or polysulphone and/or PEEK or other materials which are not corroded by the hydraulic fluid.

Optionally, system 2000 employs a pressure of at least 100, optionally 150, optionally, optionally 200, optionally 300 atmospheres or lesser or intermediate or greater values to inject cement 2020. In an exemplary embodiment of the invention, system 2000 is constructed to withstand these operational pressures. The actual pressure which accumulates in the system may vary, for example as the viscosity of cement 2020 varies. Various types of connectors and/or pressure sources and/or reservoirs and/or cannulae may be employed depending upon an anticipated pressure. One of ordinary skill in the art will be able to select commercially available components such as connectors, tubing and O-rings which are suitable for use in construction of a system 2000 with a given anticipated operating pressure. In some exemplary embodiments of the invention, pressure is provided by a tamping instrument including a rod adapted to comply with a lumen of the cannula (see FIG. 7A). In other exemplary embodiments of the invention, pressure is provided by a piston (e.g. 2018 in FIG. 7G) with a diameter wider than the cannula lumen.

It is stressed that the combination of high viscosity cements employed in the context of the invention and the small diameter of the cannula to be filled renders standard syringes or other non-amplifying pressure sources ill suited for cannula filling. Optionally, the viscous cement is manually manipulated to facilitate loading of the delivery device reservoir as described hereinbelow under "Transfer of viscous materials".

In those embodiments of the invention in which a tamping rod is employed, it may optionally be introduced into the vertebra via a working sleeve characterized by a slightly larger diameter than the cannula diameter.

Optionally, reservoir 2002 is transparent to permit visualization of cement 2020. In an exemplary embodiment of the invention, a transparent reservoir 2002 is marked with graduations indicating the amount cement 2020 in the reservoir. Optionally, this permits a user to ascertain how much cement is being injected.

In an exemplary embodiment of the invention, pressure source 2004, optionally attached to tube 2006, are provided filled with liquid. Optionally, air has already been flushed from these components. Such an embodiment may expedite operating room procedures. According to this embodiment, a quick connector 2016, connecting the reservoir 2002 to the flexible tube 2006, is equipped with a uni-directional valve 2017 that seals the tube 2006 until it is connected to the reservoir 2002.

Optionally, a uni-directional valve (not shown in the Figures) is incorporated into the reservoir piston 2018, and is opened/released toward reservoir portion that does not contain cement 2028. For example, systems of the type illustrated in FIG. 7G, the cement is loaded from a distal side (covered by cap 2014) of container 2002. Prior to attaching connector 2016, air can be drained by a one-way valve in piston 2018, so entrapped air can flow from container 2020 through the one-way valve in piston 2018, and through escape valve 2017.

In an exemplary embodiment of the invention, (FIGS. 7p; 7S) air escapes from opening 2500 directly. Optionally, no valves are provided.

Although a hand operated handle is pictured, according to additional exemplary embodiments of the invention, handle 2012 may be replaced by a foot pedal that is used to actuate piston 2024. Alternatively or additionally, pressure source 2004 may rely upon electric power for actuation. Electric power may be supplied, for example, by a battery. In an exemplary embodiment of the invention, a battery powered motor turns screw threads 2022 to advance piston 2024.

The construction and operation of exemplary hydraulic pressure sources for use in systems of the general type depicted in FIGS. 7F and 7G is depicted in greater detail in FIGS. 7I through 7O.

Exemplary Pressure Source

Figure 7H:
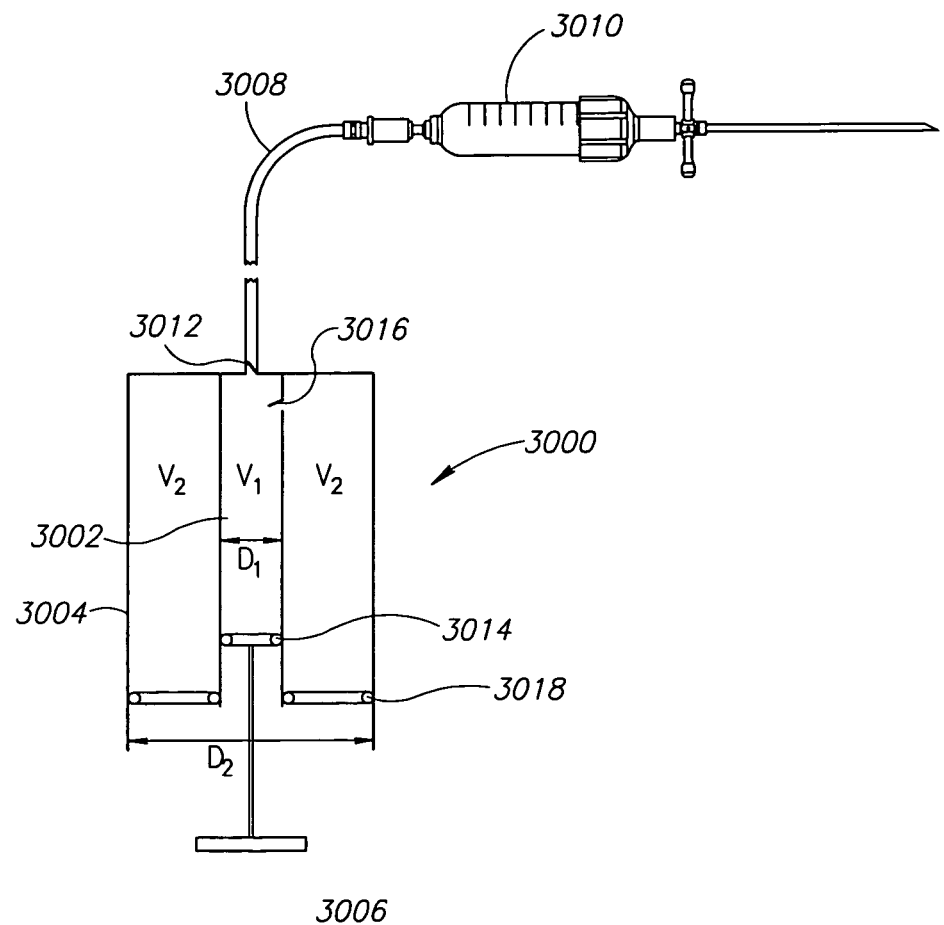
FIG. 7H illustrates an exemplary hydraulic delivery system, in accordance with an exemplary embodiment of the invention.
Figure 7I:
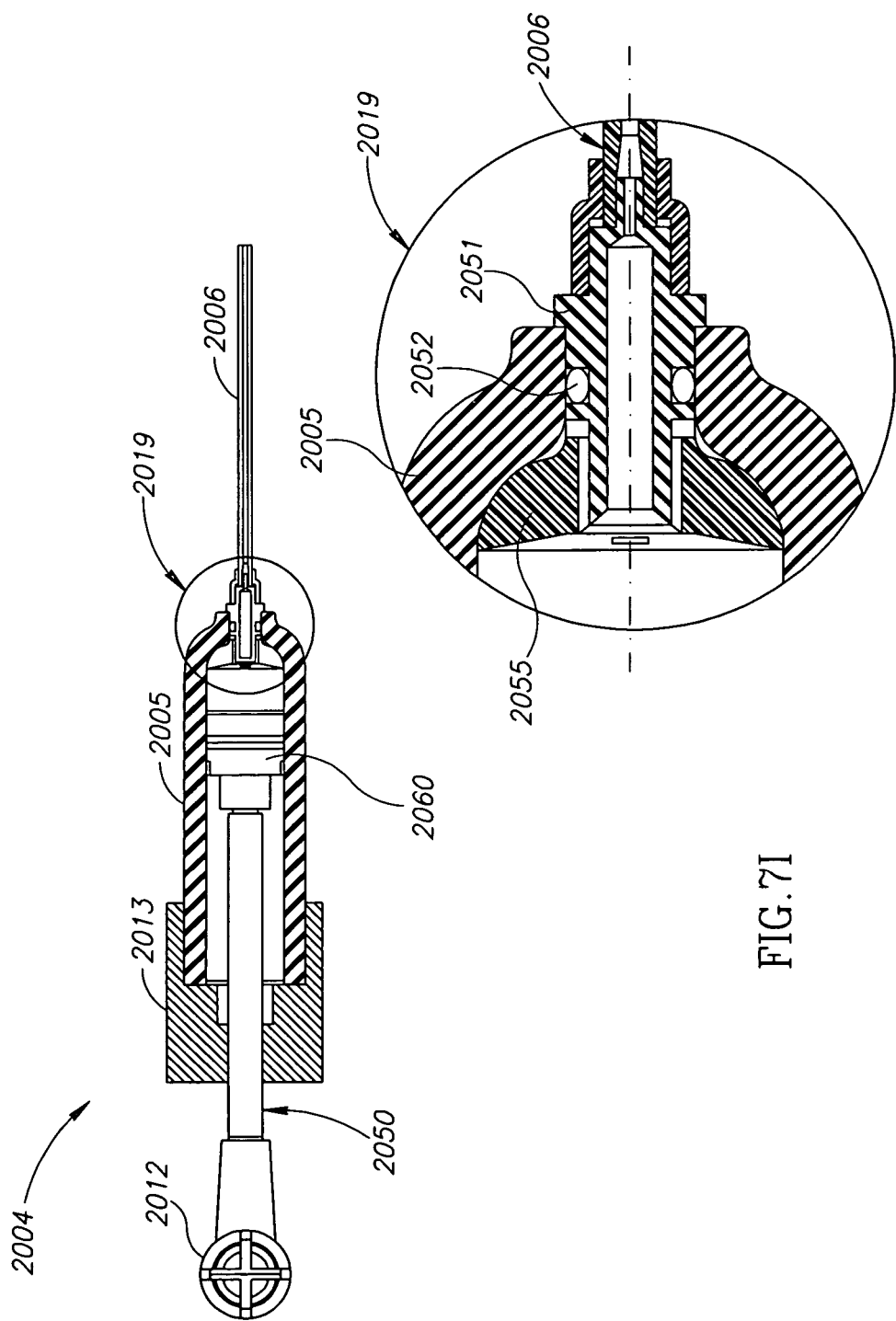
FIG. 7I is a cross sectional view of a hydraulic actuator for a delivery system in accordance with an exemplary embodiment of the invention; the inset shows a portion of the actuator in greater detail.

FIG. 7I illustrates a hydraulic pressure source 2004 including an actuation handle 2012 connected to a drive shaft 2050 and piston 2060. Drive shaft 2050 passes through hydraulic chamber cap 2013 and is insertable in hydraulic pressure body 2005. Piston 2060 is connected to, or constructed as part of, a distal end of drive shaft 2050. Piston 2060 forms a circumferential seal with respect to an inner surface of a lumen of hydraulic pressure body 2005. In an exemplary embodiment of the invention, hydraulic pressure body 2005 is constructed of Amorphous Nylon or Polycarbonate.

In an exemplary embodiment of the invention, a small step of the threading (eg 1 mm/rotation), a small radius of bolt (eg 4 mm) and materials employed in construction for bolt and nut (eg Nylon for nut 2013 and stainless steel for bolt 2050) produce a low friction coefficient.

Amorphous Nylon provides the requisite strength to resist high internal pressures with a low weight when compared to previously available steel hydraulic pressure sources. In an exemplary embodiment of the invention, an amorphous nylon reservoir with an OD Of 20, optionally 25, optionally 30, optionally 35 mm (or lesser or intermediate or greater values) resists an internal pressure of as much as 300 atmospheres or more. Optionally, it can be transparent. Optionally, a transparent pressure body 2005 allows an operator to observe progress of piston 2060. In an exemplary embodiment of the invention, progress of the piston is gauged against calibration markings on body 2005.

In an exemplary embodiment of the invention, pressure body 2005 is connectable to a flexible tube 2006. Optionally, tube 2006 is glued to reservoir 2002 directly (eg by UV curing glue). The inset 2019 shows an exemplary embodiment of this connection in greater detail. A funnel 2055 is seated in a distal aperture of hydraulic pressure body 2005 and sealed by means of an O-ring 2052 and adapter plug 2051. According to this exemplary embodiment of the invention, as pressure on hydraulic fluid in hydraulic pressure body 2005 increases, funnel 2055 is more firmly seated against the distal aperture of hydraulic pressure body 2005. Optionally, this arrangement spreads the stresses radially over a distal end of the reservoir. Optionally, this arrangement prevents leaks at operating pressures of 100 to 300 atmospheres. The liquid is forced through tube 2006 as the pressure increases. In an exemplary embodiment of the invention, a hydraulic unit including body 2005, cap 2013, drive shaft 2050 and piston 2060 is provided as a unit pre-filled with a sterile liquid. Optionally, walls 2005 are transparent so that piston 2060 is visible to an operator of the unit. In an exemplary embodiment of the invention, transparent walls 2005 are marked with graduations which indicate an injected volume of cement.

In an exemplary embodiment of the invention, specific materials for the cover 2013 and drive shaft 2050 are chosen to reduce the friction coefficient ($\mu$). Optionally, cover 2013 is made of a polymer/plastic while shaft 2050 is made of steel. Optionally, Radius of Friction (R) is reduced by reducing the thread diameter on shaft 2050 and/or cap 2013.

$$M = R \cdot f$$

$$f = \mu \cdot F$$

So $M = R * \mu * f$. Therefore, a reduction in the moment the moment needed for every normal force F is optionally achieved by reducing R and/or $\mu$ Working moment (M) is the product of R and the radial force (f) of the hydraulic liquid. The force (F) between cap 2013 and shaft 2050 is the axial force applied on the piston 2060.

Figure 7J:
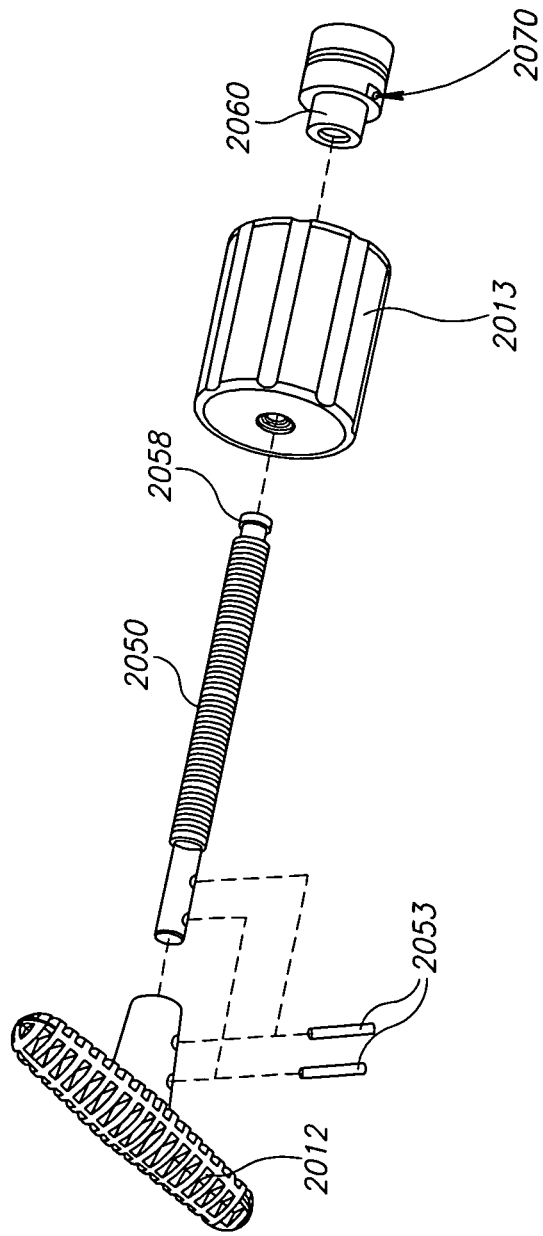
FIGS. 7J and 7K are exploded and cross sectional views respectively of a portion of a hydraulic actuator for a delivery system in accordance with an exemplary embodiment of the invention.

FIG. 7J is an exploded view of a handle and piston assembly as depicted in the exemplary embodiment of FIG. 7I. According to this embodiment, pins 2053 anchor handle 2012 to drive shaft 2050. Optionally pins 2053 are designed to break if excessive torque is applied. In an exemplary embodiment of the invention, breaking of pins 2053 is a safety feature. Cap 2013 and shaft 2050 are each threaded so that rotation of handle 2012 can cause shaft 2050 to advance or recede through cap 2013. Optionally, cap 2013 is constructed of a plastic polymer. Optionally, shaft 2050 is constructed of metal, for example stainless steel. In an exemplary embodiment of the invention, threaded shaft 2050 is constructed of stainless steel and has a diameter of 6 mm, optionally 5 mm, optionally, 4 mm or lesser or greater or intermediate diameters. Optionally, stainless steel threads mated to plastic polymer threads provide a low friction connection which makes it easy to operate handle 2012 manually. In an exemplary embodiment of the invention, a narrow diameter drive shaft 2050 is employed as a means of reducing the amount of friction against threads of cap 2013. In an exemplary embodiment of the invention, threads on shaft 2050 and 2013 each engage a set of ball bearings to provide a ball screw mechanism. In this figure, an optional pressure release port 2070 on piston 2060 is visible.

Figure 7K:
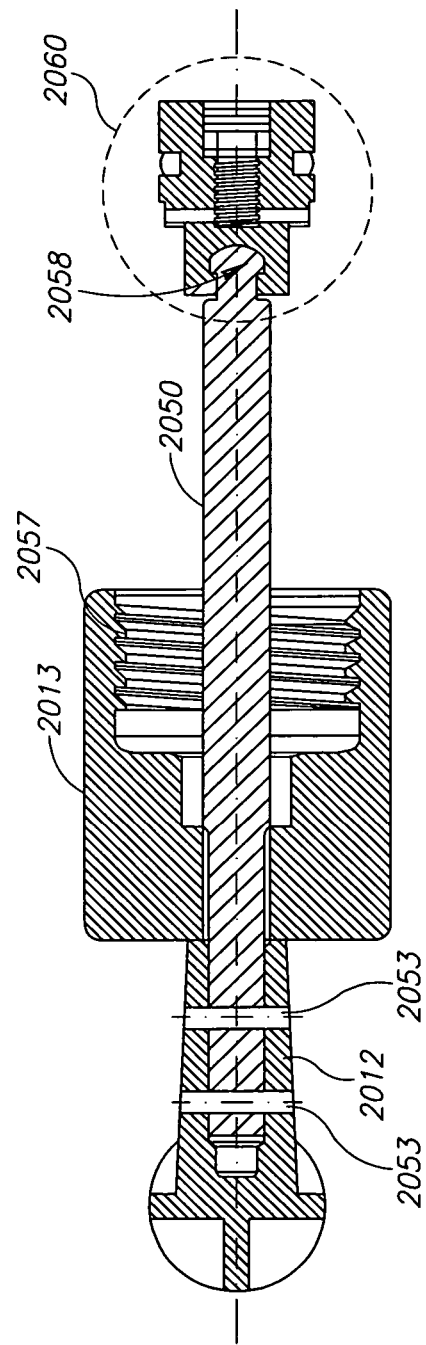

FIG. 7K is a cross sectional view of a handle and piston assembly as depicted in FIG. 7J FIG. 7K shows a second set of threads 2057 on cap 2013. Threads 2057 are one exemplary means to engage cap 2013 to hydraulic pressure body 2005. Once cap 2013 is engaged to hydraulic pressure body 2005, operation of handle 2012 will cause advancement of piston 2060 in hydraulic pressure body 2005. Optionally, threads 2057 are in the same direction, as threads on shaft 2050 to prevent disassembly. Optionally, threads 2057 are locked once the cap 2013 is completely on.

FIG. 7K also shows an exemplary engagement mechanism by which drive shaft 2050 may be coupled to piston 2060. The pictured engagement mechanism relies upon a ball 2058 which snaps into a matching socket (2059; FIG. 7M) in piston 2060. In an exemplary embodiment of the invention, this arrangement assures that piston 2o60 remains attached to ball 2058 as shaft 2050 advances. Optionally, a ball/socket connection of this type permits piston 2060 to advance without rotating as bolt 2050 rotates. In an exemplary embodiment of the invention, this lack of piston rotation increases valve life and improves sealing. Optionally, the ball/socket type connection provides a sufficiently strong engagement force so that back turning of shaft 2050 will retract piston 2060. Optionally, a ball socket connection is economical yet reliable.

In an exemplary embodiment of the invention, operation of handle 2012 in an opposite direction will cause retreat of piston 2060 in hydraulic pressure body 2005. Optionally, operation in a reverse direction ceases injection of cement.

Pressure Source Safety Valve

Figure 7L:
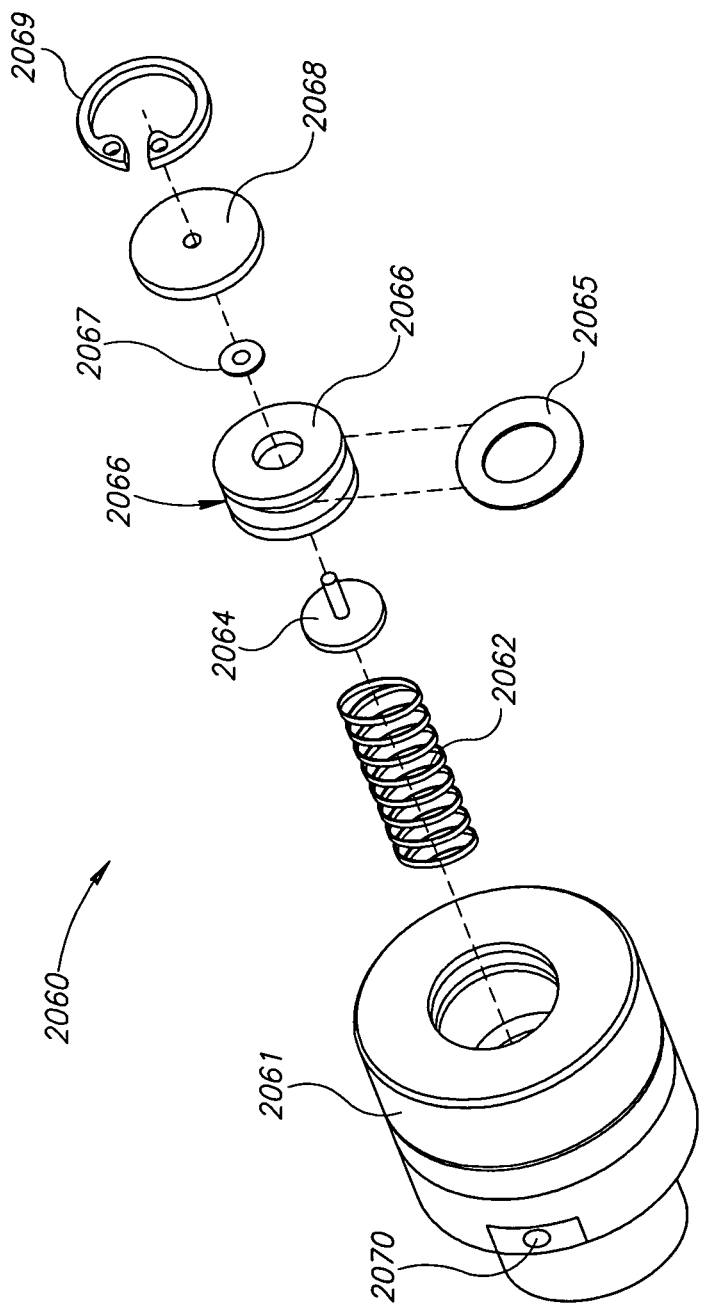
FIG. 7L is an exploded view of a pressure release valve for a delivery system in accordance with an exemplary embodiment of the invention.
Figure 7M:
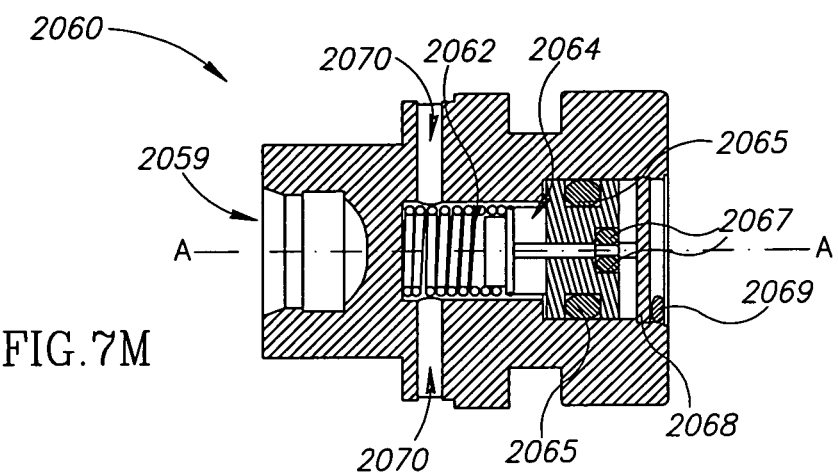
FIGS. 7M, 7N and 7O are cross sectional views and a side view of a pressure release valve for a delivery system in operation in accordance with an exemplary embodiment of the invention.

FIG. 7L is an exploded view of a piston 2060 including a pressure release valve which can relieve excess pressure of hydraulic fluid by venting hydraulic fluid through one or more release ports 2070 on piston 2060. In an exemplary embodiment of the invention, the pressure relief valve includes a spring 2062, a pressure release aperture element 2064, and a sealing gasket 2067. In the figure, optional washers 2065, 2066, 2068 and 2069 are depicted. In an exemplary embodiment of the invention, the pressure release valve is triggered at a pressure of 160 Atmospheres. Optionally, a threshold pressure of 160 atmospheres protects a system designed to withstand 200 atmospheres.

Figure 7N:
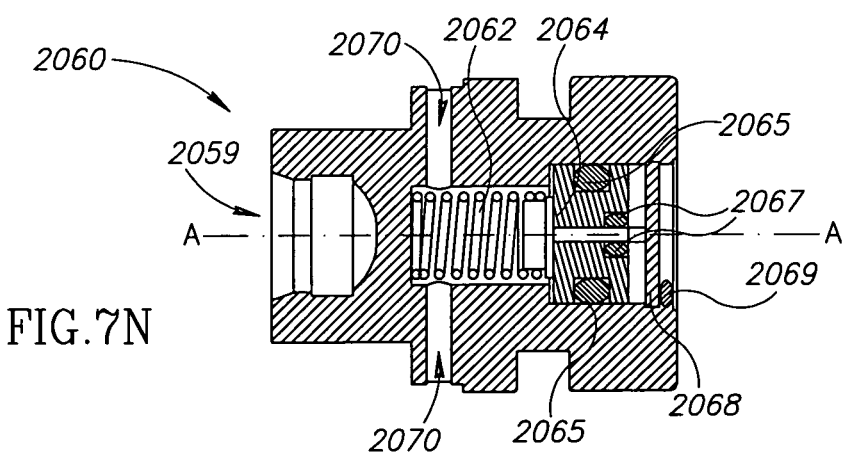

FIGS. 7M and 7N are cross sectional views of the valve of FIG. 7L in an open and a closed operational state respectively. FIG. 7N shows spring 2062 in a fully extended configuration. As distal end 2058 of drive mechanism is forced into receptacle 2059, piston 2060 advances through hydraulic pressure body 2005. Advancement of piston 2060 causes an increase in pressure of a fluid residing in hydraulic pressure body 2005. Advancement of piston 2060 causes an increase in pressure of a fluid residing in hydraulic pressure body 2005. When the pressure inside the hydraulic pressure body 2005 reaches a predetermined_threshold (e.g., 150, 160 or 210 atmospheres), the retraction of spring 2062 causes apertured element 2064 to protrude through seal 2067. Apertured element 2064 provides a channel of fluid communication between pressurized fluid 2020 (FIG. 7G) and lower pressure compartment (2028). This permits hydraulic fluid to flow to the rear chamber 2028 behind piston 2060 via release ports 2070. Release of hydraulic fluid causes the pressure to drop below the threshold, spring 2062 to expand and seal the valve. In an exemplary embodiment of the invention, released hydraulic fluid is visible in transparent pressure body 2005.

Figure 7O:
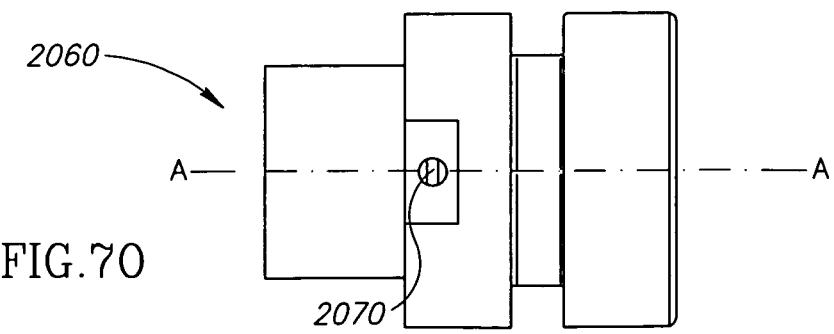

FIG. 7O is a side view of an exemplary embodiment of piston 2060 showing release port 2070. In an exemplary embodiment of the invention, opening of the valve reduces the hydraulic pressure to the threshold pressure.

In an exemplary embodiment of the invention, pressure at the defined threshold, indicates that the procedure should be stopped because the cement has solidified. If the physician wants to continue with the procedure, replacement of reservoir 2002 is indicated.

Injection Reservoir

FIGS. 7P and 7Q are side cross-sectional views of an injection reservoir 2002 according to an exemplary embodiment of the invention. Reservoir 2002 may be constructed of, for example, amorphous nylon e.g. Durethan® (LANXESS, Leverkuzen, Germany), Grilamid® (EMS-Grivory, Reichenauerstrasse, Switzerland) or Topas® (Ticona GmbH, Kelsterbach, Germany). In an exemplary embodiment of the invention, materials for construction of reservoir 2002 are selected so that they are not corroded by the relevant cement.

In an exemplary embodiment of the invention, the amorphous nylon is transparent. In an exemplary embodiment of the invention, the thickness of walls 2003 of reservoir 2002 is greater than 3 mm, optionally greater than 4 mm, optionally greater than 5 mm optionally greater than 6 mm or intermediate or greater values. In an exemplary embodiment of the invention, reservoir 2002 is characterized by a wall thickness to internal diameter ratio of about 0.23, optionally 0.25, optionally, 0.27, optionally 0.29 (e.g., wall thickness of about 5 mm and ID of about 18 mm), This ratio provides sufficient strength to withstand pressures of 100 to 300 atmospheres.

In an exemplary embodiment of the invention, walls 2003 of reservoir 2002 are transparent and marked with a scale indicating volume. Optionally, this permits an operator of the system to ascertain how much cement has been injected at any given moment. Optionally, ribs provided to add strength serve as a scale indicating volume.

In an exemplary embodiment of the invention, cement reservoir 2002 is loadable with sufficient cement to treat at least one vertebra with a single injected aliquot. Optionally, 5 ml optionally 10 ml or intermediate or greater volumes are typically employed to treat a single vertebra. Optionally, cement reservoir 2002 is loadable with sufficient cement to treat at least two vertebrae, optionally at least 3, optionally at least 4 vertebrae without re-filling. Optionally, this reduces a number of access procedures for each vertebra, optionally to a single access procedure. In an exemplary embodiment of the invention, a single access procedure is employed to treat at least two locations in a vertebra.

In an exemplary embodiment of the invention, reservoir 2002 is loaded with a cement characterized by a long "working window" during which the cement is characterized by a viscosity above 500 Pascal second but is not yet solidified. Optionally, the working window is greater than 5, optionally 8, optionally 12, optionally 15 minutes or intermediate or greater times.

In an exemplary embodiment of the invention, reservoir 2002 serves also as a mixing chamber. Optionally, a polymer component and a monomer component of the cement are mixable in reservoir 2002. Alternatively, mixing is performed in a separate mixing apparatus and cement is transferred to the reservoir after mixing is complete.

Reservoir Assembly

FIG. 7P illustrates assembly of an exemplary injection reservoir for injection of bone cement. While this reservoir is suited for use in a system of the general type depicted in FIGS. 7F and 7G, the exemplary embodiment of FIG. 7P features a proximal reservoir cap 2100 as opposed to the distal reservoir cap of FIGS. 7F and 7G.

A reservoir cap 2100 includes a connector plug 2110 equipped with a tube connection 2310 to facilitate connection to tube 2006 which contains hydraulic fluid. Plug 2110 and tube connection 2310 form a contiguous lumen 2300 which facilitates delivery of hydraulic fluid from tube 2006. Plug 2110 optionally rotates within cap 2100 so that an angle of tube connection 2310 with respect to reservoir 2002 can be adjusted.

In an exemplary embodiment of the invention, the angle of connection 2310 with respect to reservoir 2002 is adjusted so that tube 2006 is out of the field of view of an X-ray imaging device. In an exemplary embodiment of the invention, rotation of plug 2110 makes connection of 2006 more convenient. Plug 2110 optionally includes a coupling portion 2115 which mates with a complementary coupling portion 2215 (FIG. 7Q) on delivery piston 2200. Optionally, piston 2200 is mounted on plug 2110 during assembly by snap coupling portions 2115 and 2215.

Cement reservoir 2600 is optionally filled with cement prior to closing of reservoir body 2003 with cap 2100. Cap 2100 can then be attached to body 2003 by means of, for example, mated threads on the two pieces. At this stage, both plug 2100 and piston 2200 are sealed to an inner side of walls 2003, for example by O-rings 2211. During operation, hydraulic actuator 2004 causes a fluid to flow through tube 2006 under pressure and enter lumen 2300. As the applied pressure increases, this fluid accumulates in portion 2700 of reservoir 2002 (FIG. 7Q). In an exemplary embodiment of the invention, plug 2100 and piston 2200 disengage when the fluid pressure developed in 2700 supplies enough force to advance piston 2200 against resistance supplied by cement in portion 2600 of reservoir 2002.

At the distal end of reservoir 2002, an optional inner plug 2400 engages an outer connector 2410 and holds outer connector 2410 to the distal end of the injection reservoir. Outer connector 2410 is constructed to engage an injection cannula and to remain engaged at a relevant operating pressure of the delivery system. Inner plug 2400 and outer connector 2410 form a channel of fluid communication 2500 which can facilitate a flow of cement from reservoir 2600 to an inner lumen of a cannula connected to connector 2410. The function of plug 2400 during filling of reservoir 2002 is described with regard to FIGS. 7R and 7S, hereinbelow.

FIG. 7Q shows that fluid 2700 accumulates within 2005 and pushes piston 2200 away from plug 2110 and towards plug 2400. As the volume of fluid 2700 increases, the volume of cement 2600 decreases and the cement is pushed outwards through channel 2500 into a cannula (not shown in this figure). In an exemplary embodiment of the invention, piston 2200 is a floating piston which is moved by a column of fluid 2700. Optionally, walls 2005 are transparent so that piston 2200 is visible to an operator of the unit, for example as an indicator of cement volume. In an exemplary embodiment of the invention, transparent walls 2003 are marked with graduations which indicate an injected volume of cement.

Figure 7R:
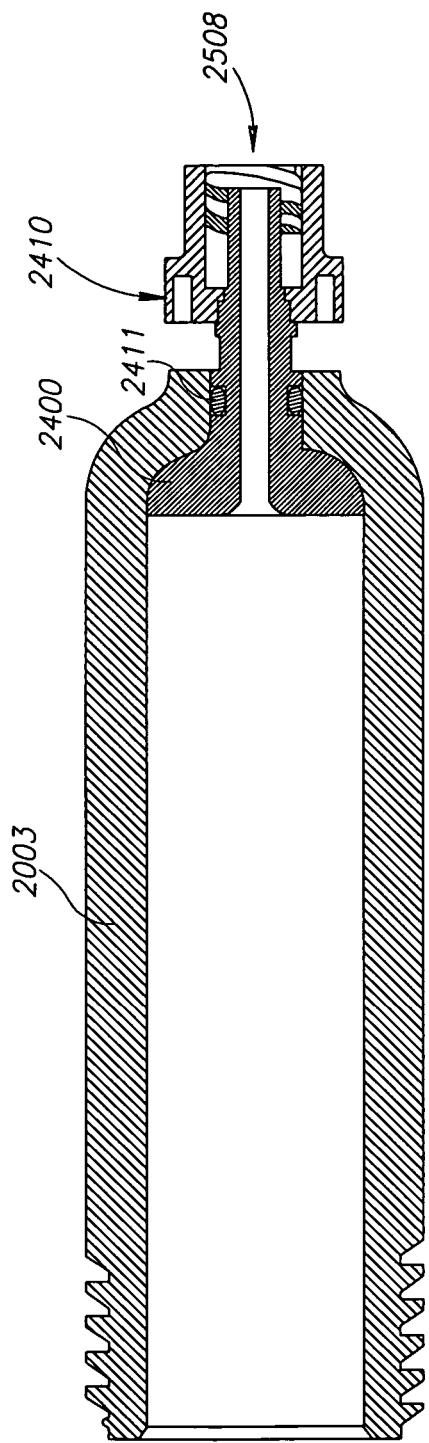
FIGS. 7R and 7S are cross sectional views of a cement reservoir illustrating assembly of a distal injection port according to some exemplary embodiments of the invention.
Figure 7S:
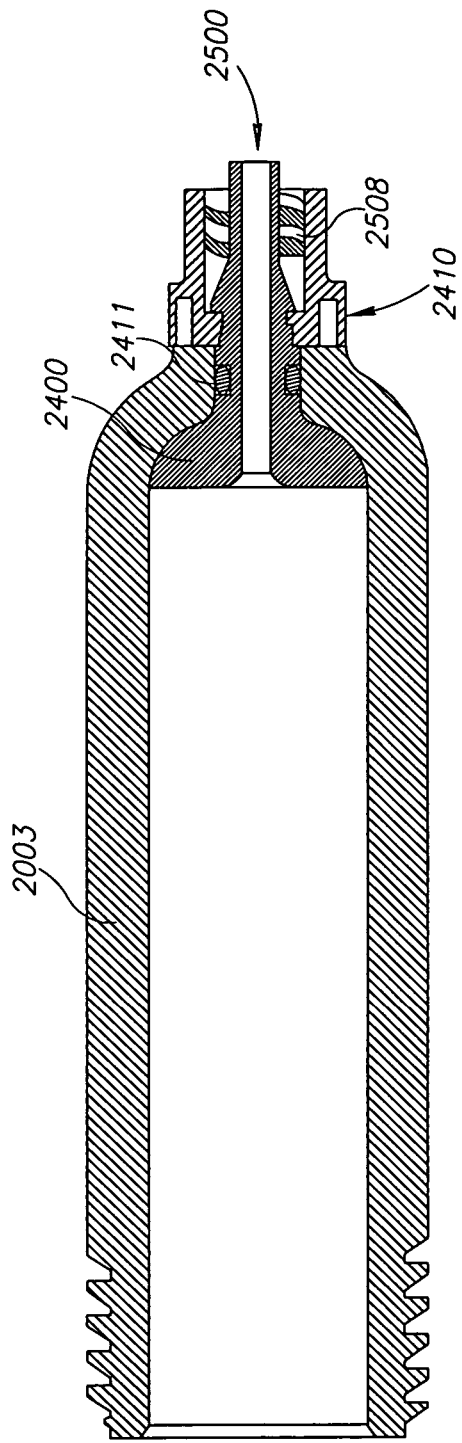

In an exemplary embodiment of the invention, cement reservoir 2600 is supplied as a separate unit comprising walls 2003, inner plug 2400 (FIG. 7R) and outer connector 2410. FIGS. 7R and 7S illustrate one embodiment of this exemplary type. Plug 2400 contains an aperture 2500 which is initially covered by connector 2410 during filling of the reservoir with cement and subsequently opened to permit attachment of a cannula.

FIG. 7R illustrates outer connector 2410, inner plug 2400 and walls 2003 in cross section. In this figure, connector 2410 is only partially pressed onto a protruding portion of plug 2400. Seal 2508 remains unbroken. O-ring 2411 provides a tight seal between walls 2003 and plug 2400. This arrangement permits introduction of cement into the reservoir from a proximal end before cap 2100 (FIG. Q) is attached. Once the reservoir is filled, cap 2100 may be applied as described above. Optionally, this arrangement permits a more efficient seal to a cannula and/or provides the possibility to rotate the cannula with respect to the reservoir In an exemplary embodiment of the invention, the cannula may be deformed from a straight line and/or be directional.

Once the reservoir is filled and capped, seal 2508 may be broken (FIG. 7S) by advancing connector 2410 towards plug 2400. Breaking of seal 2508 creates channel of fluid communication 2500 which can facilitate a flow of cement outwards from the reservoir into a cannula (not shown in this figure) connected to connector 2410. In an exemplary embodiment of the invention, breaking of seal 2508 exposes a threaded and/or luer connection which is adapted to engage a cannula.

FIG. 7S1 depicts an exemplary embodiment of reservoir 2600 in which walls 2003 are formed as a contiguous unit which includes some of the functional characteristics of outer connector 2410, inner plug 2400 in FIG. 7S. In the exemplary embodiment of FIG. 7S1, aperture 2500 is not sealed. Walls 2003 include threads 2509 and/or luer connector 2510 for attachment to a cannula.

Foot Operable Actuator

Figure 7T:
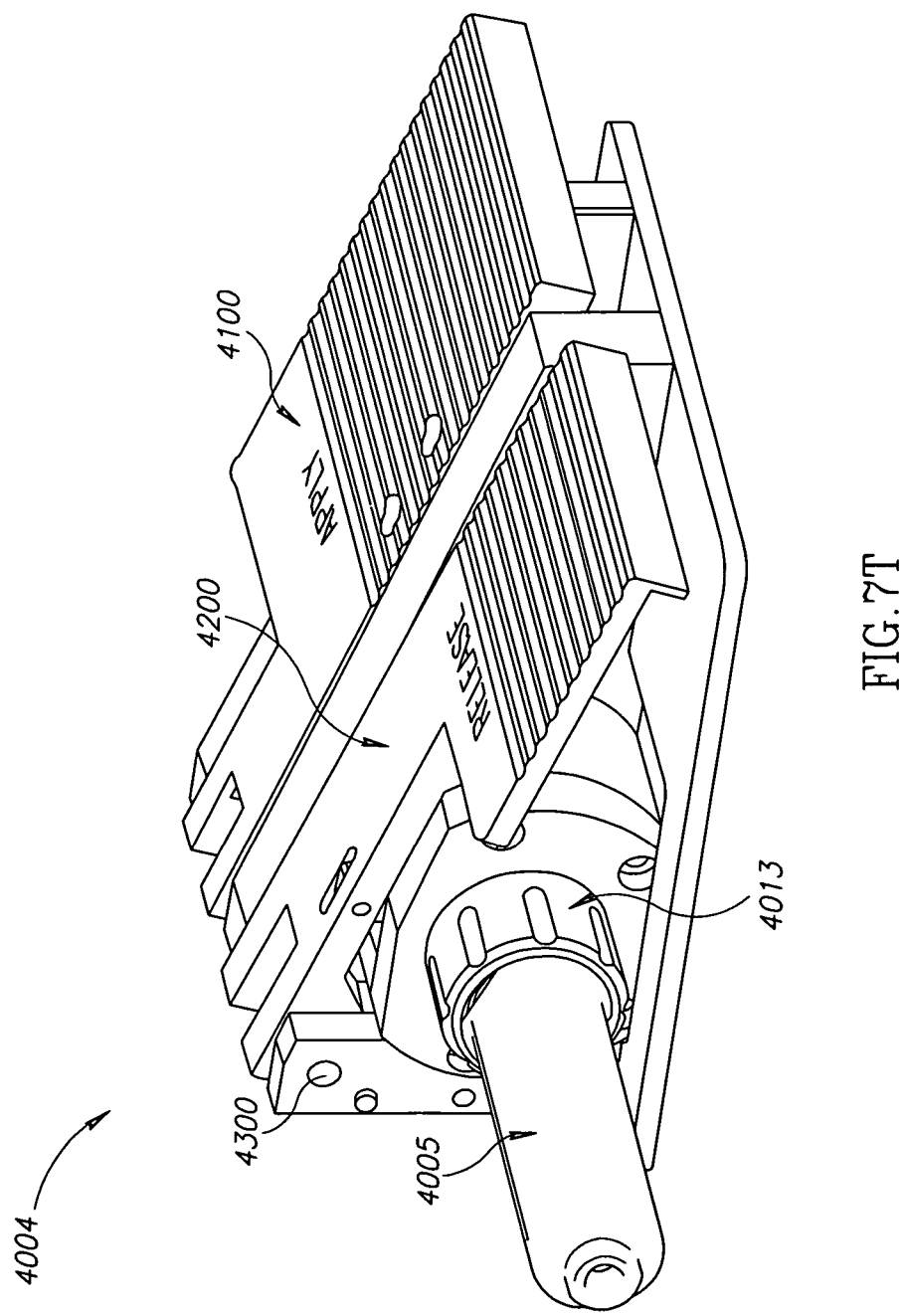
FIG. 7T is a perspective view of a foot operated actuator suitable for use in a delivery system according to some embodiments of the invention.

FIG. 7T is a perspective view of a foot operable hydraulic actuator 4004. A foot operable actuator may be used in place of a hand operable actuator. In an exemplary embodiment of the invention, a foot operated actuator permits an operator to employ both hands for other tasks and/or reduces the need for an assistant. In the figure, hydraulic reservoir 4005 is functionally similar to hydraulic reservoir 2005 as described hereinabove. Locking ring 4013 is functionally analogous to reservoir cap 2013 as described hereinabove. The pictured foot operable actuator contains a drive pedal 4100 which moves angularly with respect to an axle 4300. Each depression advances a hydraulic piston in hydraulic reservoir 4005 by a fixed increment. After pedal 4100 is depressed for actuation, it returns to a pre-actuation position automatically. This return may be achieved, for example, by use of a spring which provides a resistive force. Optionally, actuator 4004 includes an additional pedal 4200 for pressure release which moves angularly with respect to an axle 4300. In an exemplary embodiment of the invention, pedals 4100 and 4200 are clearly marked so that an operator can distinguish between them easily. Markings may be, for example, in printed symbols and/or by pedal color and/or by pedal size and/or by pedal shape and/or by pedal position.

In an exemplary embodiment of the invention, walls of hydraulic pressure chamber 4005 are transparent and marked with a scale. Optionally, the scale indicates indicating volume. Optionally, this permits an operator of the system to ascertain how much cement has been injected at any given moment. Optionally, ribs provided in the walls to add strength serve as a scale indicating volume.

Pressure inducing levers may apply increments of hydraulic pressure using any clutch/drive mechanism known in the art to advance a hydraulic piston within hydraulic reservoir 4005. Examples of suitable drive mechanisms include, but are not limited to ratchet pawl mechanisms, sprag clutches, roller ramp clutches and mechanical diodes, cam followers and roller bearing cam followers. Sprag clutches are commercially available (e.g. from JTEKT Co.; Osaka/Nagoya; Japan). Mechanical diodes are available from, for example, Epilogics (Los Gatos; Calif.; USA). One of ordinary skill in the art of mechanical engineering will be able to select a suitable commercially available drive mechanism, or construct a suitable drive mechanism from commercially available parts in consideration of desired performance characteristics for any particular contemplated embodiment of the invention.

In an exemplary embodiment of the invention, release pedal 4200 is provided to release some or all applied hydraulic force. Such a release may be desired, for example to change or replace cement reservoir 2004, at the end of a surgical procedure and/or in the event of an emergency. Optionally, release pedal 4200 may open a valve which vents hydraulic fluid from reservoir 4005. Alternatively or additionally, release pedal 4200 may act by permitting a threaded drive shaft to move backwards so that a hydraulic piston in reservoir 4005 is retracted.

Figure 7U:
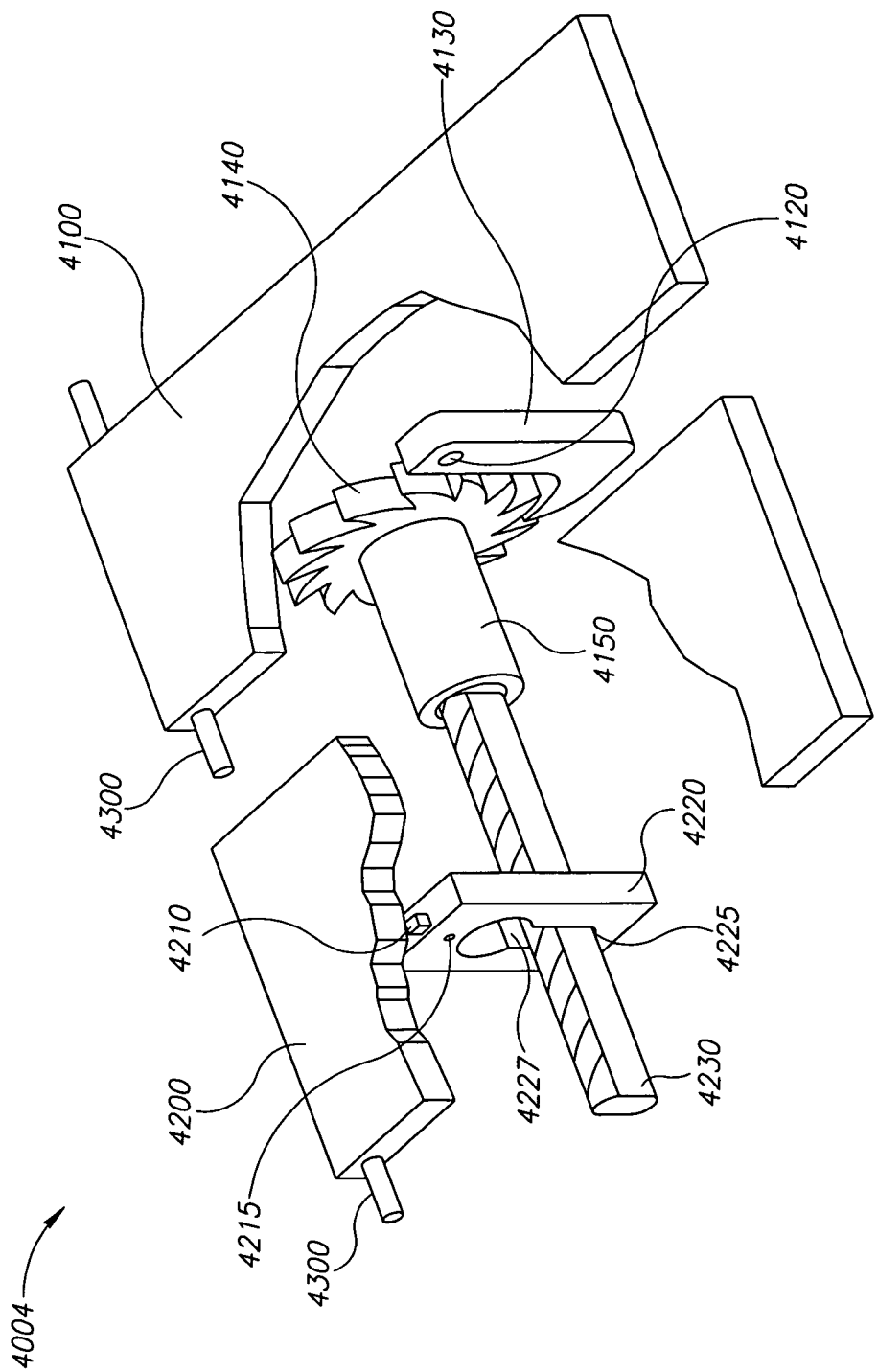
FIG. 7U is a cut away view of a foot operated actuator suitable for use in a delivery system according to some embodiments of the invention.

FIG. 7U illustrates one exemplary embodiment of a pedal operated drive mechanism with a companion release pedal.

When drive pedal 4100 is depressed by a foot, it rotates with respect to axle 4300 and depresses drive arm 4130. Drive arm 4130 engages gear 4140 causes it to rotate angularly by a single increment. The increment may be varied by varying the number of teeth on gear 4140. Gear 4140 is mounted on a drive nut 4150 so that rotation of gear 4140 causes rotation of drive nut 4150. Drive nut 4150 is equipped with an inner threading mechanism (not visible in the figure) which can advance driveshaft 4230 without rotating a distal end thereof. As drive nut 4150 is rotated it operates the inner threading mechanism and drives drive shaft 4230 outwards through a narrow portion 4225 of a hole in clutch plate 4220. Drive arm 4130 and gear 4140 are depicted to generally indicate the presence of a ratcheted gear or functionally similar mechanism and their pictured shapes should not be viewed as a limit of the invention.

When drive pedal 4100 is released, it is raised by a spring (not shown). Drive arm 4130 disengages from gear 4140. Drive arm axle 4120 permits drive arm 4130 to rotate slightly as it is raised and lowered so that it disengages and re-engages teeth of gear 4140.

A distal end of drive shaft 4230 pushes a piston (not shown in this view) in hydraulic pressure reservoir 4005 (FIG. 7T). Pressure in the reservoir tends to force drive shaft 4230 to return towards drive nut 4150.

A narrow aperture 4225 in clutch plate 4220 prevents rotation of drive shaft 4230 while drive arm 4130 is disengaged from gear 4140 and prevents the shaft from returning towards nut 4150. Clutch plate 4220 is optionally attached to pedal 4200 by rod 4210 and pin 4215.

When release lever 4200 is depressed, it lowers clutch plate 4220 so shaft 4230 passes through a wide portion 4227 of the hole. Shaft 4230 is then free to retract towards nut 4150 because it can rotate in wide portion 4227 of the hole. Optionally, shaft 4230 is constructed with sectorial threading (not pictured in this view) so that when clutch plate 4220 descends shaft 4230 rotates against a nut that defines a desired resistance.

Optionally, operation of lever 4200 releases all of the pressure in the system or only a portion of it. Optionally, release may be sudden or gradual.

Figure 7V:
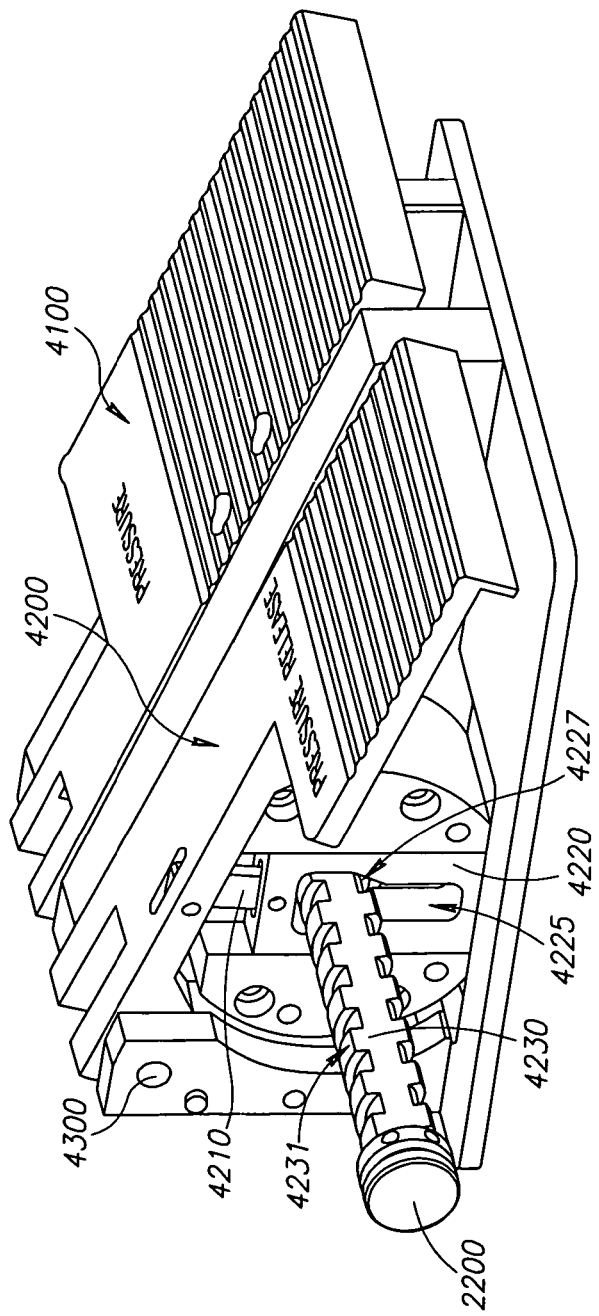
FIGS. 7V, 7W, 7X and 7Y are additional views of a foot operated actuator suitable for use in a delivery system according to some embodiments of the invention.

FIG. 7V illustrates a foot operable hydraulic actuator as seen in FIG. 7T with hydraulic reservoir 4005 removed. In this view, drive shaft 4230 is characterized by optional sectorial threading 4231. Shaft 4230 is pictured in wide portion 4227 of a hole in clutch plate 4220 so that it can retract. A distal end of shaft 4230 is fitted with a piston 2200. As shaft 4230 advances it drives piston 2200 into pressure reservoir 4005 (not pictured in this view) and increases the hydraulic pressure.

Figure 7W:
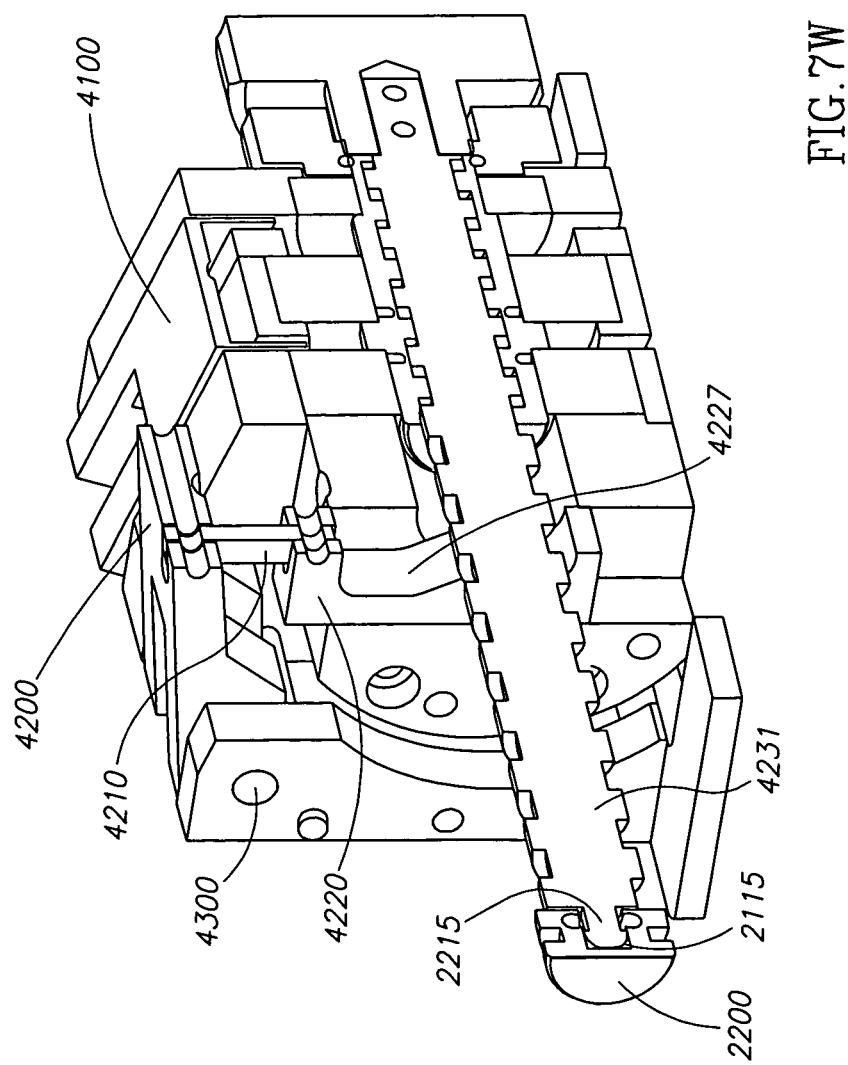

FIG. 7W is a cross sectional view of the exemplary actuator depicted in FIG. 7V. In this view release lever 4200 is raised so that wide portion 4227 of the hole in clutch plate 4220 is raised off of sectorial threads 4231 on shaft 4230. This causes the clutch plate to engage the drive shaft and prevent retraction of the drive shaft.

Figure 7X:
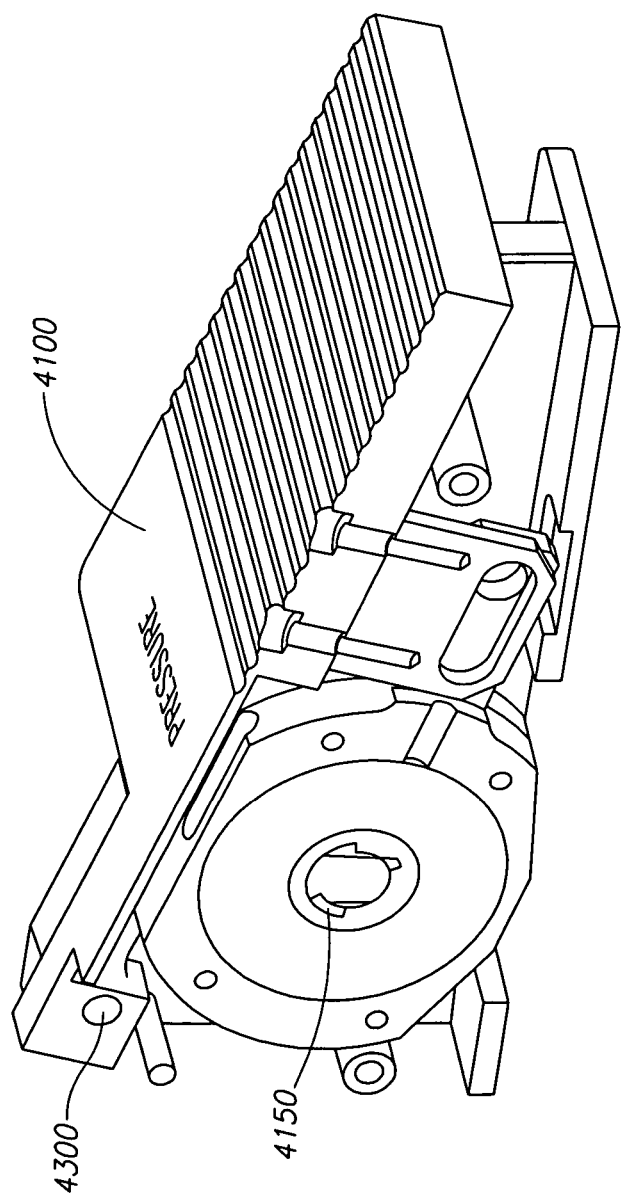

FIG. 7X illustrates an exemplary embodiment of drive nut 4150 adapted to engage and rotate sectorial threads such as those illustrated in FIGS. 7V and 7W.

Figure 7Y:
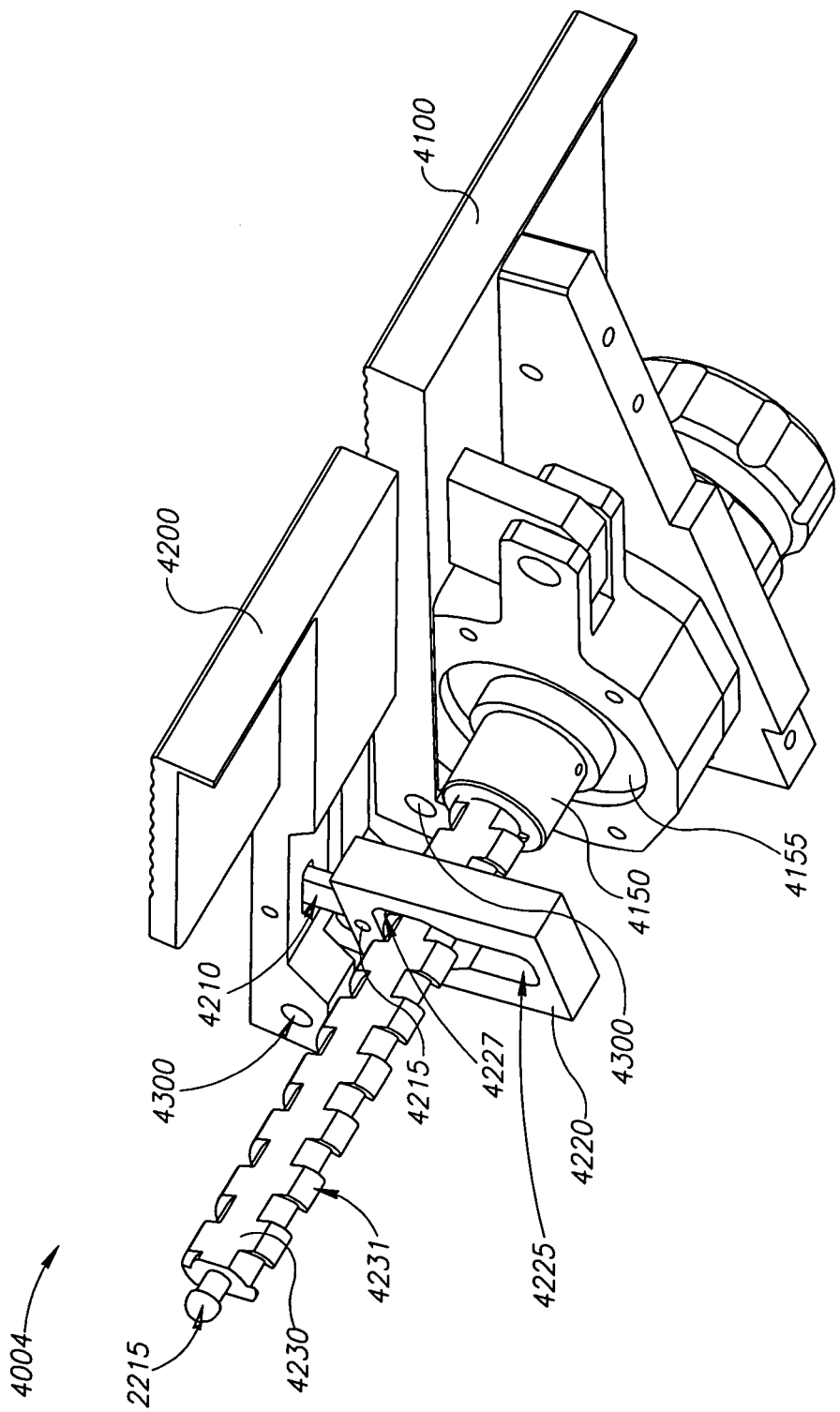

FIG. 7Y is a perspective view of the exemplary foot activated actuator depicted in FIGS. 7V; 7W and 7X from below. This view illustrates clearly a housing 4155 of the inner threading mechanism which advances shaft 4230 by engaging and turning sectorial threads 4231.

Additional Exemplary Hydraulic Mechanism

FIG. 7H illustrates an additional embodiment of a hydraulic delivery system according to the invention. In the pictured embodiment, a hydraulic pump 3000 includes a smaller syringe 3002 within a larger syringe 3004. Smaller syringe 3002 is characterized by a first volume ($V_1$) volume and a first diameter ($D_1$), and larger syringe 3004 is characterized by a second volume ($V_2$) volume and a second diameter ($D_2$); where $V_1 \ll V_2$, and $D_1 \ll D_2$.

In one embodiment of the invention, each activation of an actuator 3006 (e.g., handle rotation or foot pedal pressing) results in injection of defined amount of liquid from smaller syringe 3002 into reservoir 3010, optionally via flexible tube 3008. In an exemplary embodiment of the invention, a uni-directional valve 3012, located at the distal end of the small syringe 3002, assures that liquid flows only towards reservoir 3010. When activation of the actuator ceases, piston 3014 of the small syringe 3002 automatically returns to its original position. The automatic return of piston 3014 may be achieved, for example by use of a spring or an elastic band which applies force in a direction opposite to a direction of actuation. A second uni-directional valve 3016 is located in the wall between smaller syringe 3002 and larger syringe 3004. When piston 3014 returns to its original position, a vacuum is created inside syringe 3002. The vacuum and/or a force and/or a spring that presses piston 3018 opens valve 3016 and liquid from larger syringe 3004 flows into the barrel of the small syringe 3002. According to this embodiment of the invention, liquid in larger syringe 3004 serves as a reservoir for the refilling of the small syringe 3002. In an exemplary embodiment of the invention, a piston 3018 of larger syringe 3004 advances as $V_2$ decreases. Optionally, this embodiment can provide force amplification (if D1 is greater than an ID of 3010; see detailed explanation below) and/or facilitates delivery of small and/or defined aliquots of liquid upon each activation of actuator 3006.

In many exemplary embodiments of the invention, the system is designed to assure that the hands of an operator is outside an X-ray radiation zone of an imaging or monitoring system employed in conjunction with the cement delivery system.

Pressure Amplification

Referring again to FIG. 7G, piston 2024 of pressure source 2004 is characterized by a first diameter (D1) and piston 2018 of cement reservoir 2002 is characterized by a second diameter D2.

If hydraulic fluid is present in 2026 and in 2028, the two chambers function as a single chamber and no hydraulic amplification is achieved even if D1 and D2 are different.

In an exemplary embodiment of the invention, piston 2018 is pushed by a drive shaft (not shown) instead of by hydraulic fluid in 2028. According to this exemplary embodiment, hydraulic amplification may be calculated as follows:

The applied force (F) supplied by each piston can be calculated from relevant pressures (P) and diameters (D):

$$F = P*A; \text{where}$$

$$A = \pi*D^2/4 \text{ thus}$$

$$F = P*\pi*D^2/4$$

If pressure amplification is defined as pressure in cement reservoir 2002 (P2) divided by pressure in pressure source 20042004 (P1), the pressure amplification is equal to $(D1/D2)^2$.

In an exemplary embodiment of the invention, pressure source 2002 is a designed to be held in one hand, while a second hand operates handle 2012. This design is compatible with an internal diameter D1 of 5 cm. A typical cement reservoir has in internal diameter of 1.8 cm. This exemplary configuration produces a pressure amplification of 7.72.

For foot operated embodiments, D1 may be considerably larger (e.g. 10 cm, 15 cm, 20 cm or intermediate or larger sizes) and a greater pressure amplification may be achieved.

Alternatively or additionally, mechanical amplification applies as in any manual device that uses a rotational drive with a lever arm (e.g. handle 2012 and cap 2013 in FIG. 7G or lever 4100 and gear 4140 in FIG. 7U). These mechanical amplifiers further reduce the amount of input force required to achieve a large force to drive the piston in the cement reservoir (e.g. 2002 or 4005).

Unit Material Provision System

Figure 8A:
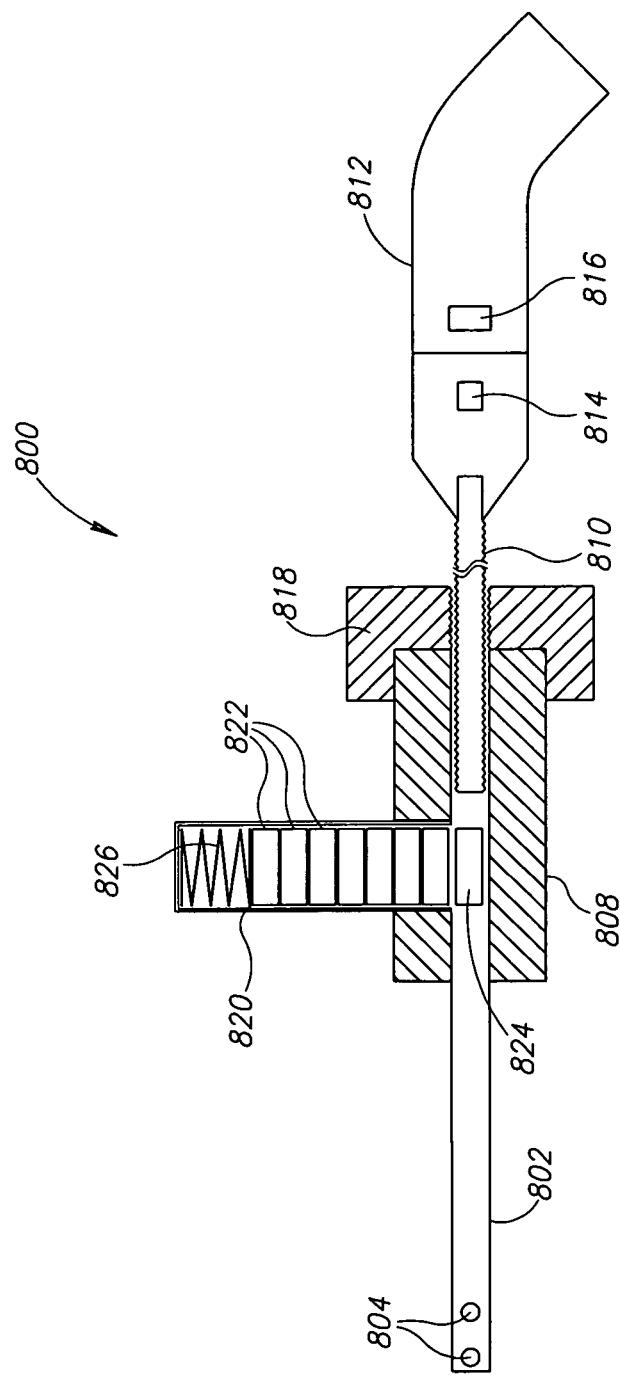
FIG. 8A shows a cassette based delivery system, in accordance with an exemplary embodiment of the invention.

FIG. 8A shows a delivery system 800 in which material is provided as discrete units, each of which is of relatively small volume, for example, 1/2, 1/4, 1/7, 1/0 or less of the amount required for treatment. One potential advantage of working in units is that an operator is more aware of the effect of his/her actions as each action can only inject one unit. Another potential advantage of working in units is that units with different material properties may be provided during a procedure. Another potential advantage is that units being small will generally exhibit a smaller friction with the delivery system.

System 800 comprises a delivery tube 802 having one or more extrusion apertures 804 at its tip. A barrel 808 on which tube 802 is mounted, also includes an optional magazine 820, described below. A body 818 with an optional nut threading is optionally attached to barrel 808. A pusher 810 lies within delivery tube 802 and/or barrel 808.

In an exemplary embodiment of the invention, a handle 812 is provided which includes a battery powered mechanism for advancing pusher 810. A hydraulic mechanism such as described above may be used instead. Optionally, one or more switches are provided, for example, an on/off switch 816 and a direction switch 814. Optionally, when pusher 810 completes its forward motion, it is automatically retracted. Optionally, only a single switch is needed, activation of which causes extrusion of one unit. In an exemplary embodiment of the invention, handle 812 is rotationally locked to body 818, for example using one or more guide pins.

In an exemplary embodiment of the invention, handle 812 comprises a motor and a battery that rotate pusher 810. An alternative mechanism is described below.

Referring to magazine 820, in an exemplary embodiment of the invention, the magazine comprises discrete units 822 of material (a unit 824 is shown inside tube 802). Optionally, a spring 826 is used to push the units towards tube 802. Optionally, the magazine is filled with a contiguous mass of material and the units are defined by the cutting action caused by pusher 810 pushing a unit of material away from the magazine.

In an exemplary embodiment of the invention, a magazine is prepared ahead of time, for example, by a manufacturer, who fills the magazine with a non-setting material.

In an exemplary embodiment of the invention, the magazine is loaded with a series of units of different properties, for example, responsive to an expected progress of a procedure, for example, first providing a soft material and then providing a harder material, or vice versa. Alternatively, a rotating magazine is used, in which a user can select which of several compartments will load barrel 808 next. This allows fine control over the injected material. In an exemplary embodiment of the invention, an operator can remove magazine 820 at any time and replace it with a different magazine. Optionally, this is done while pusher 810 is forward, so that there is no danger of backflow from the body.

Optionally, one or more of the units comprises or is an implant device (rather than an amorphous and/or homogenous mass), for example, an expanding implant or an implant whose geometry does not change. Optionally, one or more of the units comprises a cross-linked material.

In an exemplary embodiment of the invention, the delivery system used comprises two or more delivery tubes (optionally the combined geometry has a cross-section of a circle or of a figure eight). Optionally, each tube has a separate pusher mechanism and/or a separate material source (e.g., a magazine). Optionally, the two tubes are used simultaneously. Optionally, an operator can selectively use one tube. Optionally, the materials provided in each tube are components that react chemically one with another. Optionally, electronic control is provided to control the relative provision rates of the two tubes. Optionally, this allows control over the final material properties. Optionally, the use of two or more tubes allows a layered structure to be built up in the body. Optionally, one of the tubes delivers a setting material and the other tube delivers a non-setting material. In an alternative embodiment, each tube is used to provide a different component of a two component material. Optionally, the two tubes meet at their distal end, to ensure mixing of the components.

In an exemplary embodiment of the invention, the delivered material is CORTOSS by Orthovita inc. (US), a composite of Bis-GMA, Bis-EMA and TEGDMA. This material is optionally mixed along the path in the delivery tube.

In an exemplary embodiment of the invention, instead of the units being provided by a magazine or by a cutting mechanism, a partial unit behavior is provided by the motor of handle 812 stopping after every "unit" advance. Optionally, mechanical stops are provided for a hydraulic mechanism, if used. Optionally, instead of stopping, a sound is provided when a unit is injected or based on a different logic, for example, when 50% or another percentage of planned amount of material is provided. Optionally, a CPU is provided which analyzes an image provided by an imaging system and generates a signal when a sufficient and/or near sufficient and/or over-load amount of material is provided. Other circuitry may be used as well.

Optionally, circuitry is provided for controlling the rate and/or pressure of material provision. Optionally, the circuitry stops advancing if a sudden change in resistance is perceived.

In an exemplary embodiment of the invention, the delivery system includes pre-heating or pre-cooling of the injected material and/or of tube 802. In an exemplary embodiment of the invention, a Peltier cooler and/or a resistance heater are provided in barrel 808. Other cooling or heating methods, such as based on chemical reactions or phase changing materials, may be used.

In an exemplary embodiment of the invention, the magazine is a long coiled magazine. Alternatively or additionally, the deformable material is folded in the magazine. Optionally, the magazine is elongated. Optionally, separate loading and pushing mechanism are provided. In an exemplary embodiment of the invention, for loading, a unit is inserted through a slot in the side of the barrel. For pushing, the unit is advanced under a low pressure past the slot (or the slot is sealed) and only then is significant pressure required to advance the unit, for example, once the leading edge of the unit reaches the extrusion apertures.

Figure 8B:
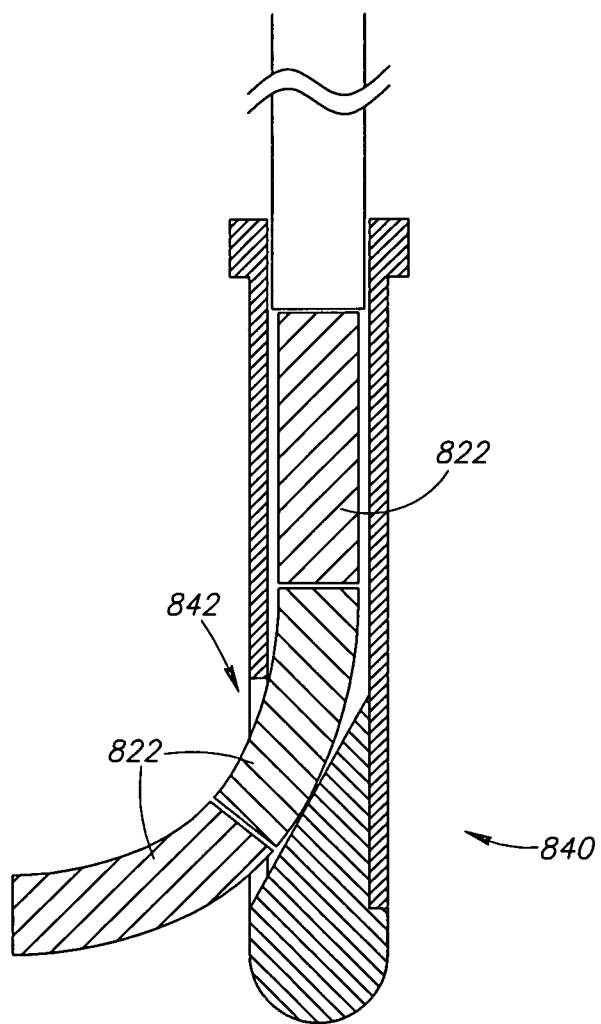
FIG. 8B is a detail showing the delivery of unit element, in accordance with an exemplary embodiment of the invention.

FIG. 8B shows the implementation of a unit delivery method even without a cassette. A delivery tip 840 of the cannula is shown with a lateral aperture 842 through which multiple units 822 are shown exiting. Optionally, an indication is provided to the user as a unit exits, for example, based on motion of a pusher used. Optionally, the system of FIG. 8A is used to load a series of units 822 into the barrel, for example, pulling back the pusher after each unit is advanced past the cassette. In an exemplary embodiment of the invention, a distal tip of the cannula is closed, optionally permanently closed, so that cement 822 is forced laterally outwards via aperture 842.

Battery Powered Pusher

Figure 9A:
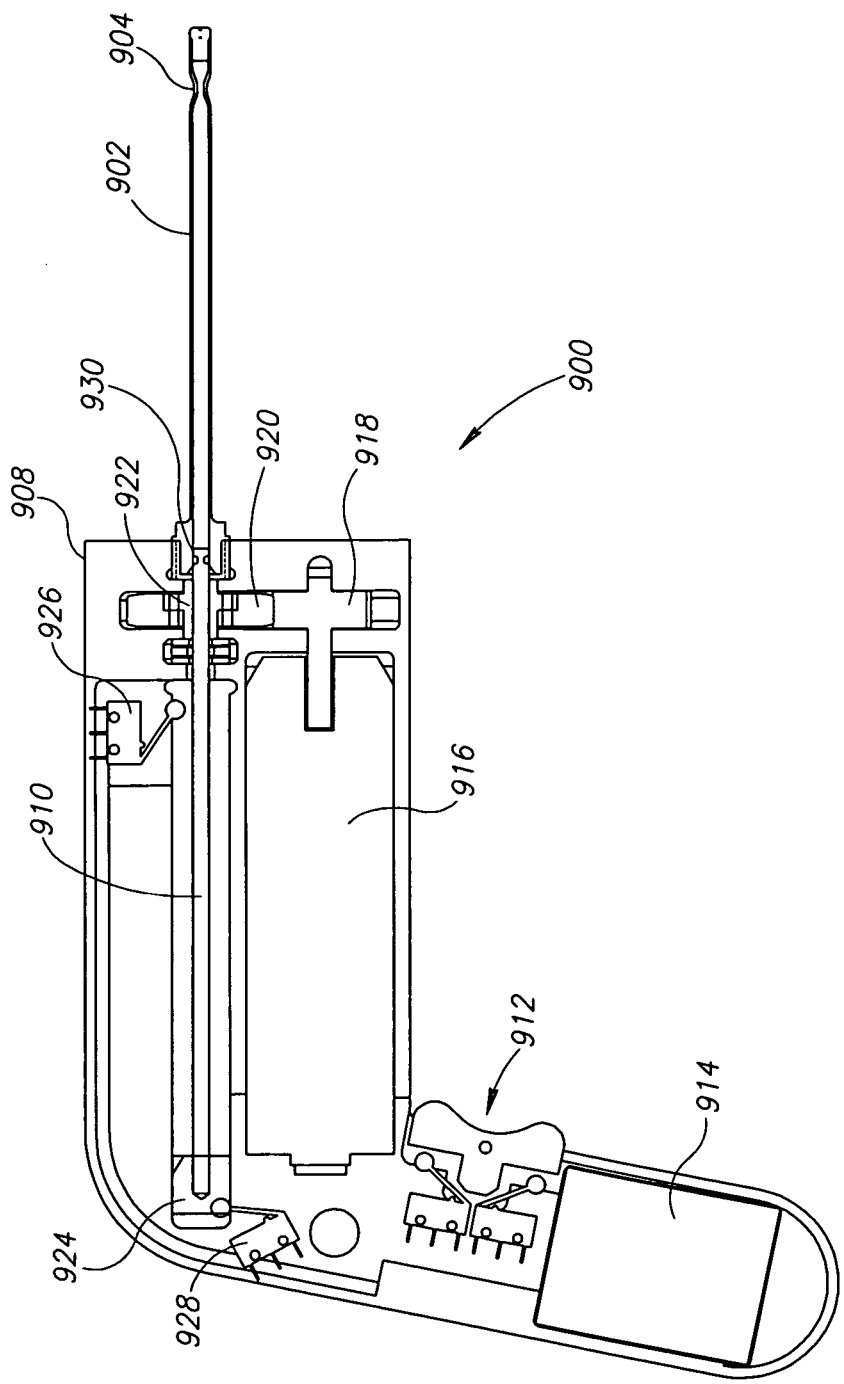
FIGS. 9A and 9B show a material pusher with reduced material twisting, in accordance with an exemplary embodiment of the invention.
Figure 9B:
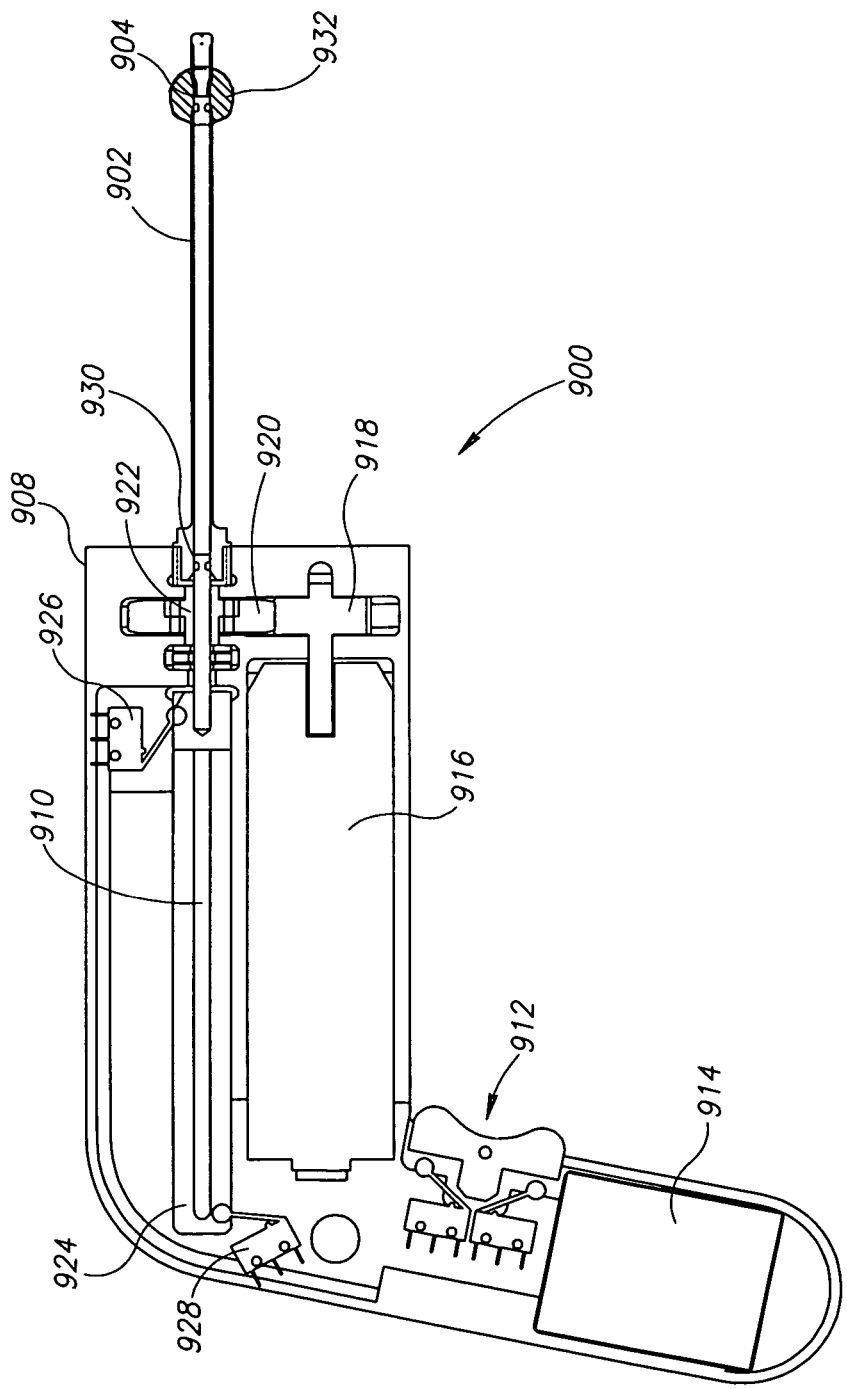

FIGS. 9A and 9B show a material pusher 900 with reduced material twisting, in accordance with an exemplary embodiment of the invention.

As in the delivery systems described above, pusher 900 comprises a delivery tube 902 having one or more apertures 904 near its end. Optionally, an offset is provided between the apertures and the far tip of tube 902, for example, to ensure centering (or other positioning) of the extruded material, for example preventing the material from being provided too close to a far end of the vertebra, if the delivery system is pushed forward.

Tube 902 is mounted (e.g., optionally replaceably) to a body 908. A pusher 910 is used to advance material through tube 902.

In an exemplary embodiment of the invention, in use, an operator presses a switch 912, for example, to select between forward, backwards and no motion of pusher 910. Power from a battery 914 (or a hydraulic or other source) is conveyed to a motor 916. Rotation of the motor causes a nut 922 to rotate relative to pusher 910. Optionally, a series of gears are used which may or may not provide a mechanical advantage, depending on the implementation. In an exemplary embodiment of the invention, motor 916 rotates a gear 918 that rotates a gear 920, which rotates nut 922 which is coaxial thereto. Optionally, a rotation preventing element 924, for example, a rectangular element 924 is mounted on pusher 910 and prevents rotation thereof.

Optionally, one or more sensors are used to detect the extremes of positions of pusher 910, when it is advanced and when it is retracted. In the example shown, a micro-switch 926 and a micro-switch 928 detect the ends of motion of pusher 910, for example, using a bump or electrically conducting section 930 (depending on the sensor type used). Alternatively or additionally, a positional encoder is used, for example, by counting rotation, or a separate encoder as known in the art of encoders.

FIG. 9B shows system 900 after extrusion is effected, showing extrusions 932. Optionally, extrusions 932 are an extension to tube 902, prior to them being cut off by pusher 910. In an exemplary embodiment of the invention, rotation of tube 902 causes extrusions 932 to act as a reamer. In an exemplary embodiment of the invention, the viscosity and shear strength of the material are selected to effect a desired limitation on the reaming abilities, for example, to prevent damage to bone.

Optionally, one or more gears are provided to rotate and/or oscillate the delivery tube as the material is advanced. Optionally, periodic or ramp axial motion is provided, by motor means. Optionally, the distal tip of the delivery tube is made soft, for example by attaching a soft tip thereto, to reduce or prevent damage to the vertebra.

Sleeve Provision System

Figure 10A:
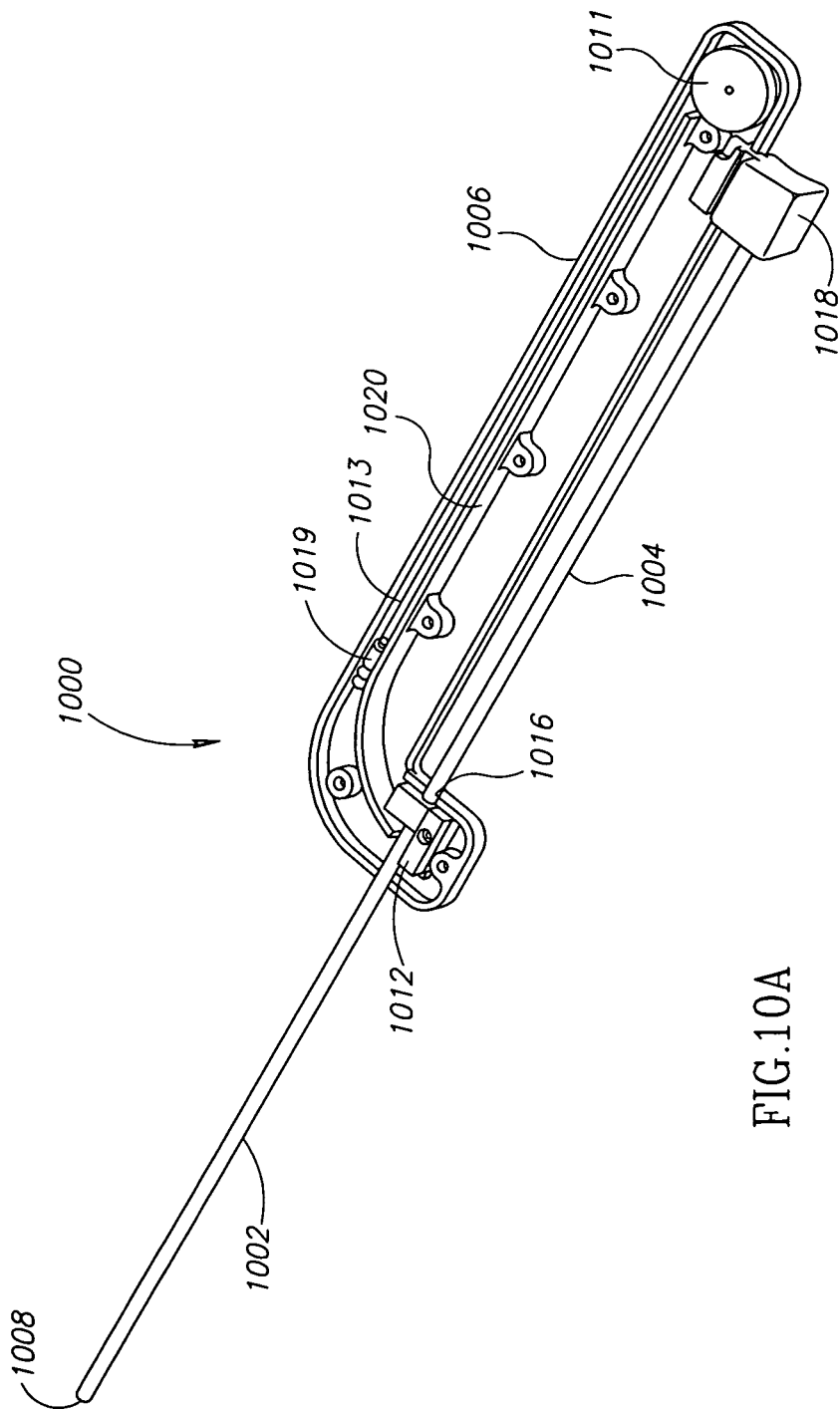
FIG. 10A-10F show sleeve based material pushers, in accordance with exemplary embodiments of the invention.
Figure 10B:
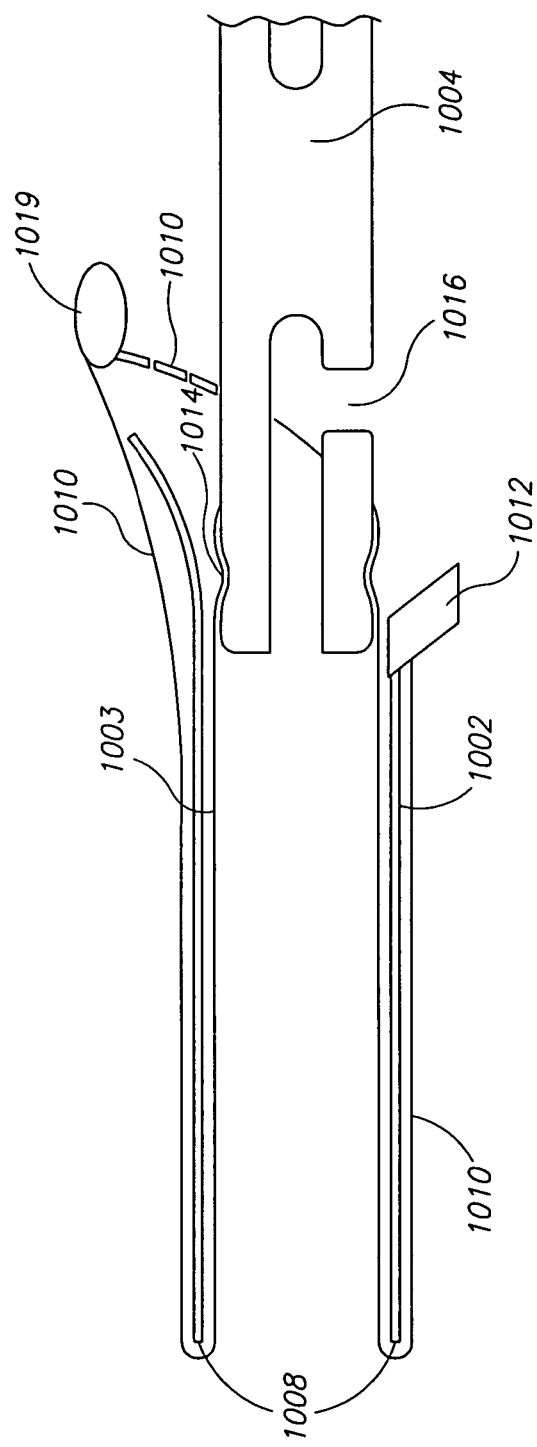

FIGS. 10A and 10B shows a sleeve based delivery system 1000, in accordance with an exemplary embodiment of the invention. FIG. 10A is a general cut-open view of system 1000, in which a sleeve 1010 is not shown. FIG. 10B shows the distal portion of system 1000, including sleeve 1010 mounted thereon.

The embodiment of FIGS. 10A-10B also illustrates a refilling mechanism by which the delivery tube includes a port to which a refill system can be connected to refill the delivery tube with material to be injected into the body.

A pusher 1004 pushes material that is found inside a delivery tube 1002. In the embodiment shown, the material is ejected past a tip 1008 of delivery tube 1002. A sleeve 1010 is provided so that the sleeve lies between the material and delivery tube 1002. An optional tube cutter 1012, such as a knife is shown to optionally split the tube after it exits the body. A pulley system 1011 for collecting the split tube is also shown.

In operation, an amount of material is either provided in tube 1002 or is injected into it, for example, via a port 1016 in pusher 1004. Advancing of pusher 1004, for example, by applying force to a knob 1018 attached thereto, for example manually, using a motor or using other mechanisms described herein, pushes against the material in tube 1002. At the same time, sleeve 1010, which is attached to pusher 1004, for example, by a crimping 1014, is pulled along with the material. Portions of sleeve 1010 reaching distal tip 1008 of tube 1002, fold back towards a body 1006 of delivery system 1000. When sleeve 1010 reaches knife 1012, it is optionally split so that it can pass over tube 1002 and pusher 1004. A thread or wire or other coupling 1013 is attached to the proximal (split) side of sleeve 1010 (e.g., via a connector 1019) and via a pulley 1011 is pulled as pusher 1004 advances. A slide 1020 is optionally provided to guide the motion of the split sleeve It should be appreciated that such a sleeve system can also be used for delivering implants rather than material. In one example, a compressed plastic implant, for example, polyurethane, which is compressed radially (and extended axially) is advanced using a sleeve system, to reduce friction. Optionally, the sleeve material is selected according to the material being used and/or the tube material. In another example, the sleeve system is used to deliver a self-expanding implant, for example, as described in WO 00/44319 or in WO 2004/110300, the disclosures of which are incorporated herein by reference.

It is noted that a sleeve system may also be flexible. Optionally, the sleeve is formed of a chain-link or a knitted material, rather than an extruded plastic polymer tube. Optionally, the sleeve is formed of multiple layers of materials, for example by extrusion or by lamination. Optionally, fibers or other strengthening means are provided to reduce elongation. Optionally, the sleeve is formed of a material that withstands heat and/or chemical byproducts caused by PMMA. Optionally, the sleeve is preformed to elastically expand when it exits the delivery tube. Optionally, the sleeve is perforated or includes a plurality of apertures therein.

Optionally, the sleeve elutes one or more treatment materials. Optionally, the sleeve elutes one or more catalysts or catalysis retarding materials, for example, to prevent or slow-down reactions in the delivery system and/or speed them up out of the delivery system.

Optionally, a layer of oil or other lubricant is provided in addition to or instead of the sleeve.

Optionally, the sleeve remains inside the body, for example, being formed of a bio-degrading materials or maintaining its form. Optionally, when degrading, strengthening fibers or other elements remain to enhance the strength of the extruded material or implant.

Figure 10C:
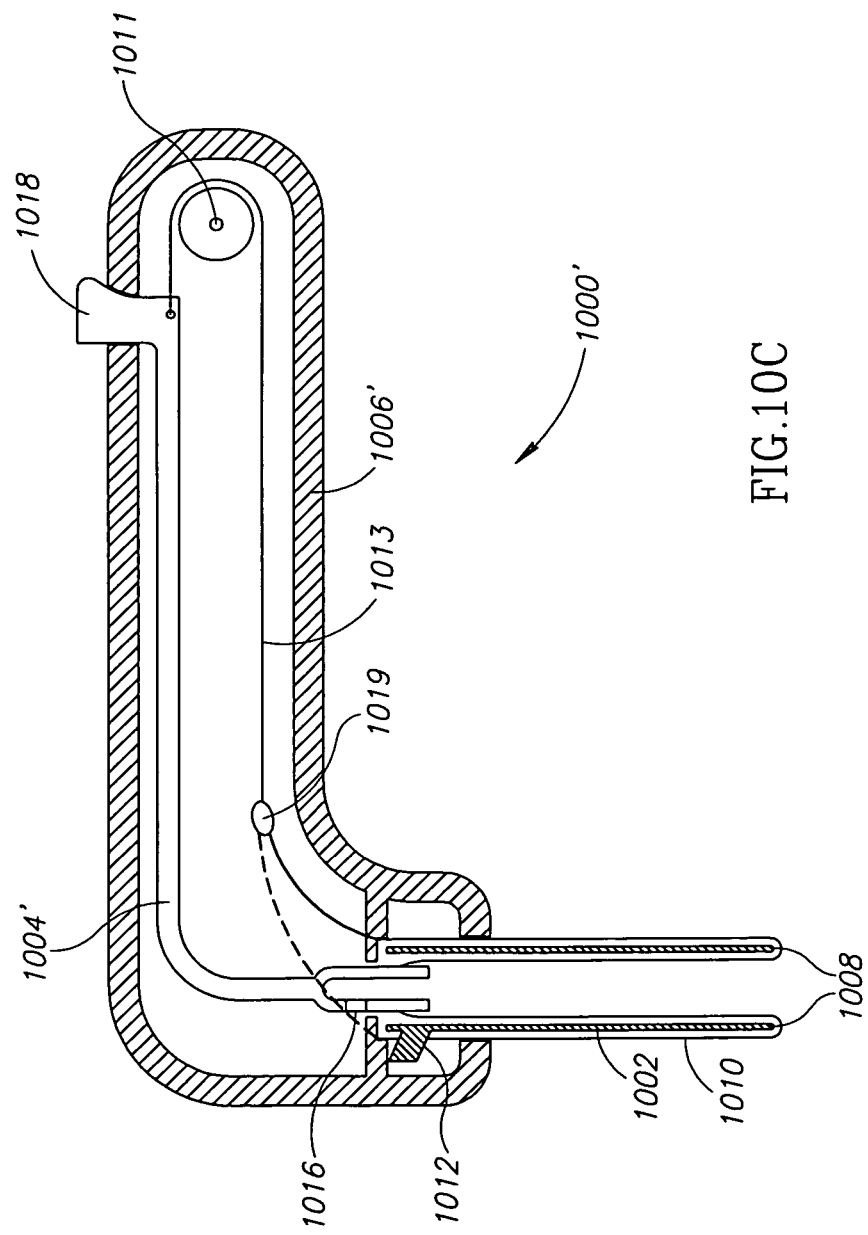

FIG. 10C is a cross-sectional view of a variant system 1000' in which a pusher 1004' is flexible enough to bend. This allows a body 1006' of the device to be manufactured in a non-linear shape, for example, in the shape of revolver, which may be easier to hold. Optionally, one or more wheels, bearings or slides (not shown) are used to guide pusher 1004'. Optionally, pusher 1004' can be made more flexible as some of the motive force used to move the material is provided by the sleeve pulling the material forward. Alternatively or additionally, some reduction is supported by the reduced friction.

Optionally, a sleeve system is used with a magazine system, for example, the units being provided through port 1016.

Optionally, the sleeve is pre-split and includes an overlap to prevent friction in the delivery tube. Optionally, this allows a magazine to load the sleeve from the side.

Figure 10D:
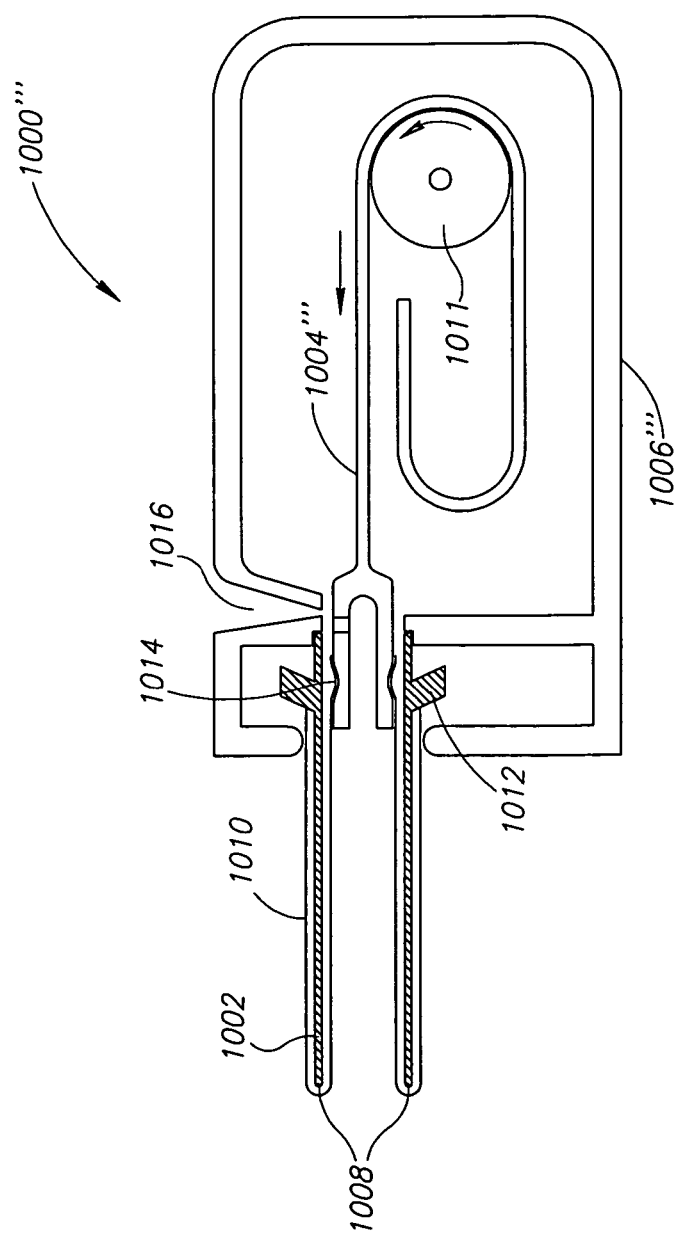

FIG. 10D shows a further, compact, variant 1000" in which a pusher 1004" is made flexible enough to fold over itself, so body 1006" can be of smaller dimensions. It should be noted that these more compact and/or non-linear embodiments can also be practiced without the sleeve feature. The sleeve pullback mechanism is not shown here.

Figure 10E:
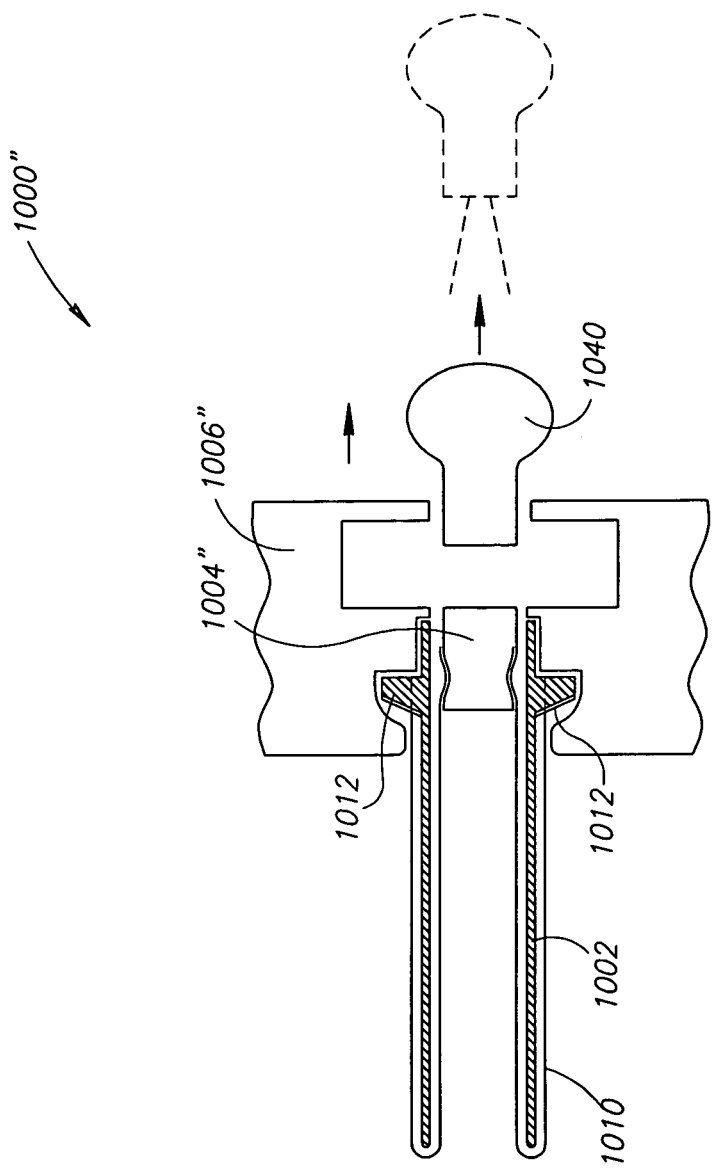

FIG. 10E shows a variant system 1000''' in which a pusher 1004''' is reduced in size axially. In this design the motive force is provided by pulling back the cut sleeve 1010 using a knob 1040 (or a motorized or mechanical gain or other means). This pulling back advances a shortened pusher 1004'''. Optionally, pusher 1004''' is provided as a sealed end of sleeve 1010. A body 1006''' of the system can be very compact, depending on the method of pulling back on knob 1040. Op two or more symmetrically positioned knifes 1012 are provided, to allow for proper mechanical support of tube 1002 by body 1006'''. Optionally, the tube is precut.

In an exemplary embodiment of the invention, it is noted that pusher 1004 is separated from the injected material by the sleeve. Optionally, a hydraulic system is used to advance the pusher, for example (in FIG. 10F) attaching a flexible tube to pusher 1004''' in tube 1002.

In an exemplary embodiment of the invention, sleeve 1010 is used to isolate the body itself from the hydraulic system, possibly allowing for a system with a higher probability of leaking.

In the embodiments shown, the material exited from the distal end 1008 of tube 1002. Optionally, a stop is provided at the end, so that the material is forced sideways. Optionally, the stop is not attached to tube 1002 at end 1008 thereof. Rather a thread, running through tube 1002 and/or outside thereof (or more than one thread) attaches the stop to the body of device 1000. Optionally, the thread runs through a narrow lumen formed in pusher 1004.

Alternatively, one or more elements which attach the stop to tube 1002, serve to split sleeve 1010, at tip 1008 of tube 1002. In an exemplary embodiment of the invention, the stop is attached to tube 1002 after the sleeve is mounted thereon. Alternatively, the sleeve is pre-split, pulled through tube 1002, past the elements and attached to connector 1019.

In an alternative embodiment of the invention, the sleeve is provided totally within the delivery tube. In one embodiment (not shown), the delivery tube comprises two coaxial tubes and the inner tube serves as shown by tube 1002 in FIGS. 10A-10E.

In another embodiment, the fact that the delivery tube is full of material is taken advantage of, in that the material (316) serves to prevent the tube from collapsing when it is simultaneously pushed from one end and pulled from the other. This may depend on the viscosity of the material and/or on the shape of the distal tip of the delivery system. Optionally, the distal end is slightly flared to define a folding over location for the sleeve.

Figure 10F:
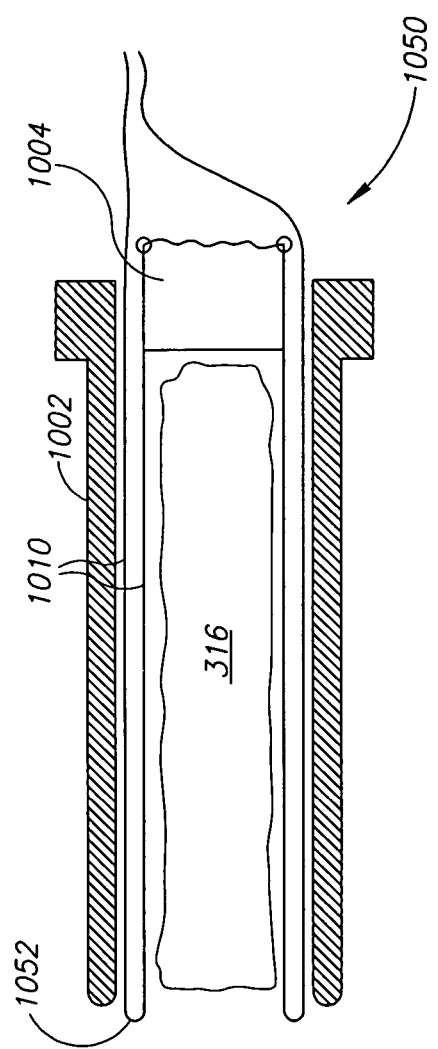

FIG. 10F shows such an embodiment, of a delivery system 1050, in which sleeve 1010 is provided within delivery tube 1002. As can be seen a folding over location 1052 for the sleeve is provided past the end of tube 1002. In an exemplary embodiment of the invention, a ring (not shown) is provided past the end of tube 1002 and around which the sleeve is folded. This ring serves as a scaffold for the folding, but due to its having a diameter greater than an inner diameter of tube 1002 (or at least being misaligned if the ring and/or tube are not circular in cross-section), cannot be pulled into the tube by retraction of sleeve 1010.

In an alternative embodiment of the invention, sleeve 1010 does not fold back towards system 1000. Rather, the sleeve is pushed into the vertebra with the material. Optionally, once out of the confines of tube 1002, the material can tear the tube. In an alternative embodiment, the sleeve remains intact and encloses the material, sausage-like, in the body. The sleeve may be formed of biocompatible, bioabsorbable and/or implant grade material.

Squeeze Based Material Provision

Figure 11A:
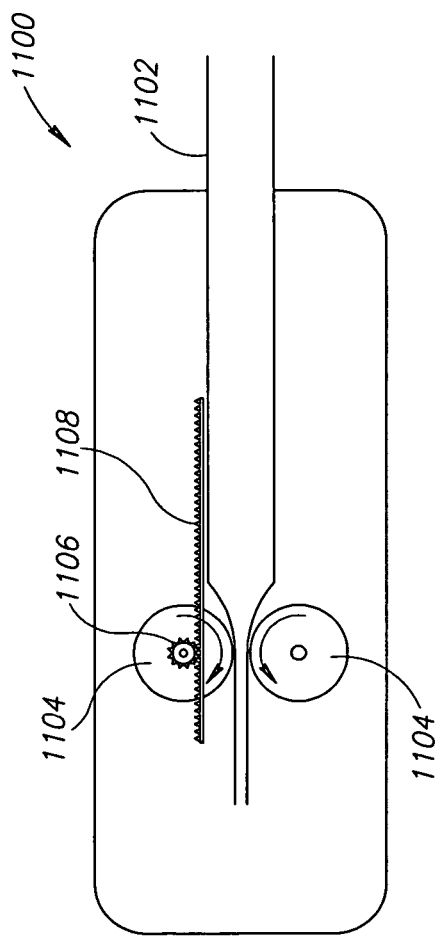
FIGS. 11A and 11B show squeeze based delivery systems, in accordance with exemplary embodiments of the invention.

In an exemplary embodiment of the invention, the material is squeezed out of the delivery system rather than pushed. FIG. 11A shows a squeeze based system 1100, in which a delivery tube 1102 is made out of a squeezable material, such as a polymer or annealed metal. A pair of rollers 1104 (or one roller and an opposing anvil, not shown) advance towards the distal side of tube 1102, squeezing it flat and forcing material that fills the tube to migrate distally. Various motion mechanism can be used. In the figure, the motion mechanism is a linear gear 1108 which engages a gear 1106 that is coaxial with roller 1104. When the roller is rotated, the linear gear advances the roller. Various power sources may be used, for example, electric motors and hydraulic power. Also, other power trains may be used. The rollers are optionally made of stainless steel.

Figure 11B:
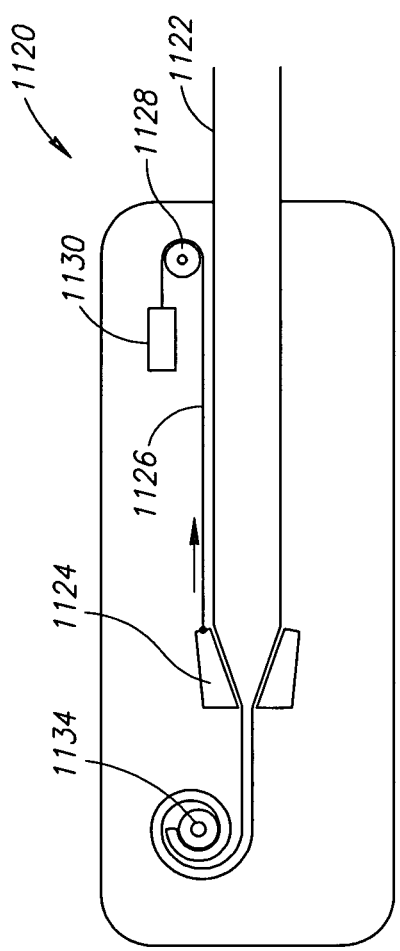

FIG. 11B shows a delivery system 1120, in which a squeeze element 1124 slides rather than rolls against a delivery tube 1122. Tube 1122 is optionally rolled around a pin 1134. Various mechanisms can be used to move squeeze element 1124, for example a motor 1130 attached to a cable 1126 via an optional pulley 1128.

Tamping Method

In an exemplary embodiment of the invention, friction is reduced by reducing the length of motion of the material inside a delivery tube. In one method, a small amount of material is provided into a distal side of a delivery tube (while outside the body). Then the distal part is inserted into the body and a tamping tool is provided into the proximal part.

This process may be repeated several times until a desired amount of material is provided into the body.

Penetrating Delivery System

In some embodiment of the invention, the delivery system also penetrates to the bone and/or penetrates the bone. Optionally, this obviates the need for a separate cannula and/or may simplify the procedure. Optionally, the delivery tube is kept in the body when it is being refilled with material to be injected.

Figure 12A:
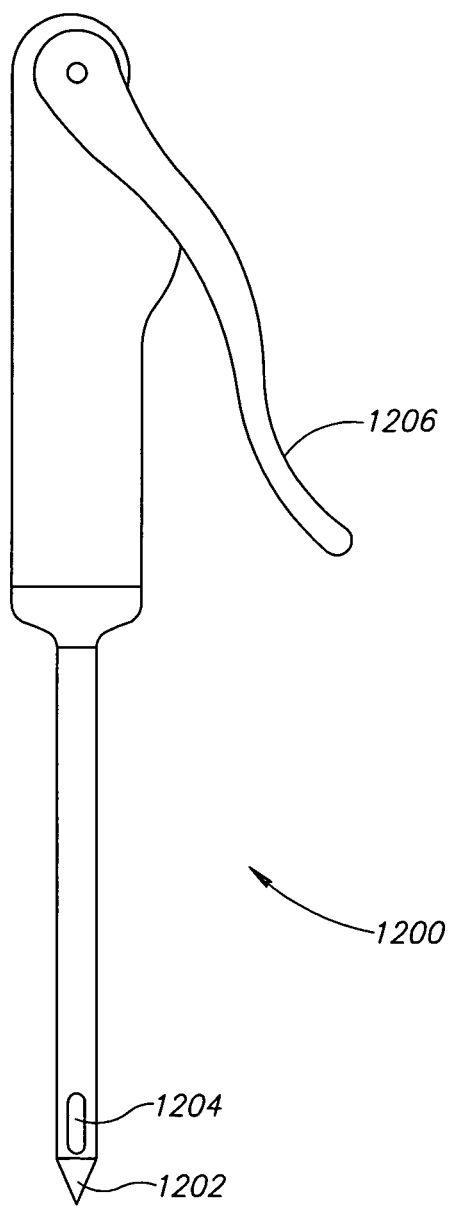
FIGS. 12A and 12B illustrate a one step access and delivery system, in accordance with an exemplary embodiment of the invention.
Figure 12B:
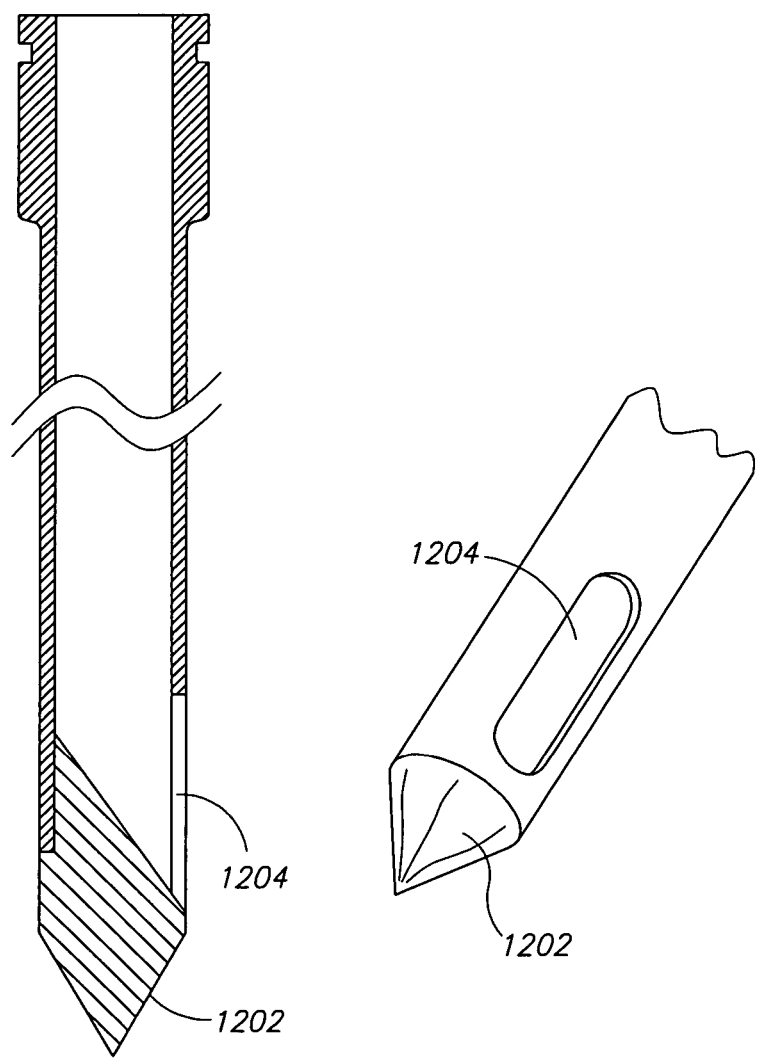

FIG. 12A shows a penetrating delivery system 1200. A distal tip 1202 is formed in a manner suitable for drilling in bone. This is shown in greater detail in FIG. 12B which illustrates one exemplary embodiment of a bone cement cannula with a lateral ejection aperture 1204 and a permanently closed distal tip 1202.

A hydraulic pump or mechanical ratchet advance mechanism is optionally used, with a handle 1206 used for pumping shown.

A potential advantage of a one piece system is that fewer parts are needed. If the system is preloaded with all the material needed, for example, at a manufacture, no equipment changes are needed. Optionally, the use of a side aperture 1204 allows the tip to be a drilling tip. Optionally, the use of smaller diameter tubes allows fewer parts to be used, as drilling is simplified.

Optionally, the proximal end of system 1200 is adapted for tapping with a mallet.

Figure 12C:
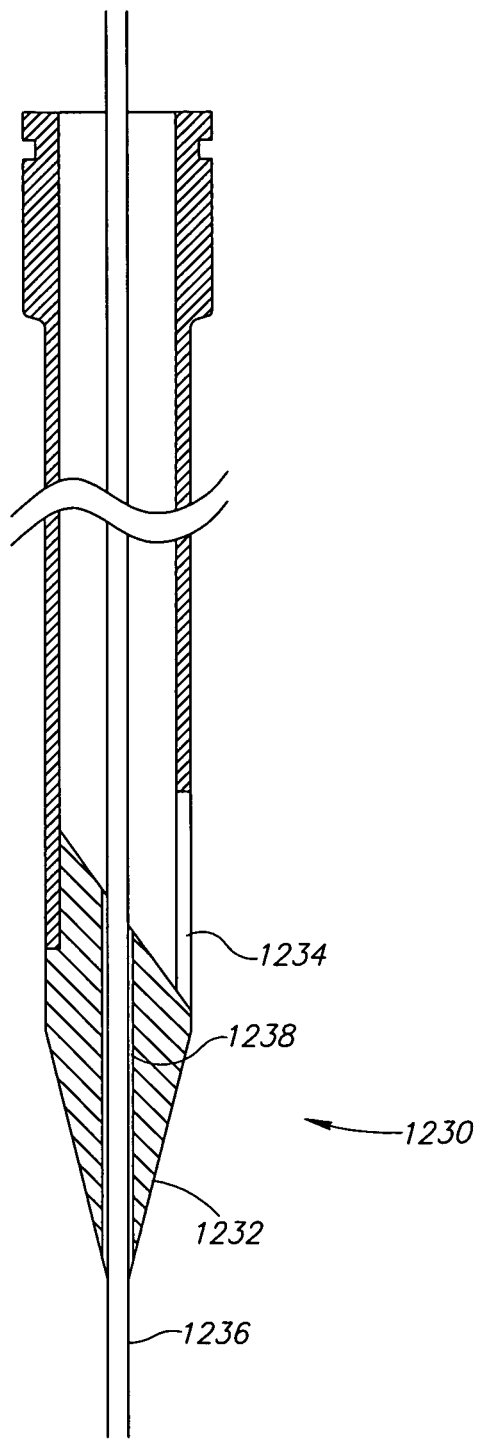
FIG. 12C shows an over-the-wire delivery system, in accordance with an exemplary embodiment of the invention.

FIG. 12C shows an alternative embodiment of a system, 1230, in which the system is adapted to ride on a guidewire 1236, for example, a K-wire. In an exemplary embodiment of the invention, a bore 1238 is formed in a drilling section 1232 of system 1230. Alternatively, the bore is to the side of the drilling head, for example, exiting through an aperture 1234 which may also be used for extruding material. Optionally, the pusher (not shown) is drilled as well. Optionally, the diameters of the drilled holes are too small for the material to exit through. Alternatively, bore 1238 is used for extruding material, after the K-wire is removed.

In an exemplary embodiment of the invention, the material is predrilled with a bore, to allow passage of the guidewire therethrough. Optionally, this bore is provided with a sleeve. It is noted that absent axial pressure on the material, the material will generally not flow into the drilled bore. Alternatively or additionally, the guidewire is coated with a suitable friction reducing coating, solid or fluid.

Optionally, the delivery tube is loaded after the delivery tube is guided into the body (and the guidewire removed), for example using a barrel storage means or a unit magazine as described above.

Optionally, a separate lumen is defined for a K-wire. Optionally, that lumen is a collapsible lumen. However, until pressure is applied to the material to be delivered, it remains un-collapsed. Once the guidewire completed its task, it is removed and pressure applied to the material, collapsing the guidewire channel and improving the flow characteristics (by increasing effective inner diameter of the delivery tube.

In an exemplary embodiment of the invention, a cannula is not needed, for example, if the delivery system rides on the guidewire or if the delivery system is used to directly penetrate the bone. Optionally, the delivery tube of the delivery system is not removed once inserted into or to the bone, for example, using a barrel or pumping mechanism as described above to reload the delivery mechanism if required. Once the system is reloaded, the pusher can advance the material into the delivery tube where it can then be advanced into the bone.

Mixing Apparatus

Figures 14A, 14B:
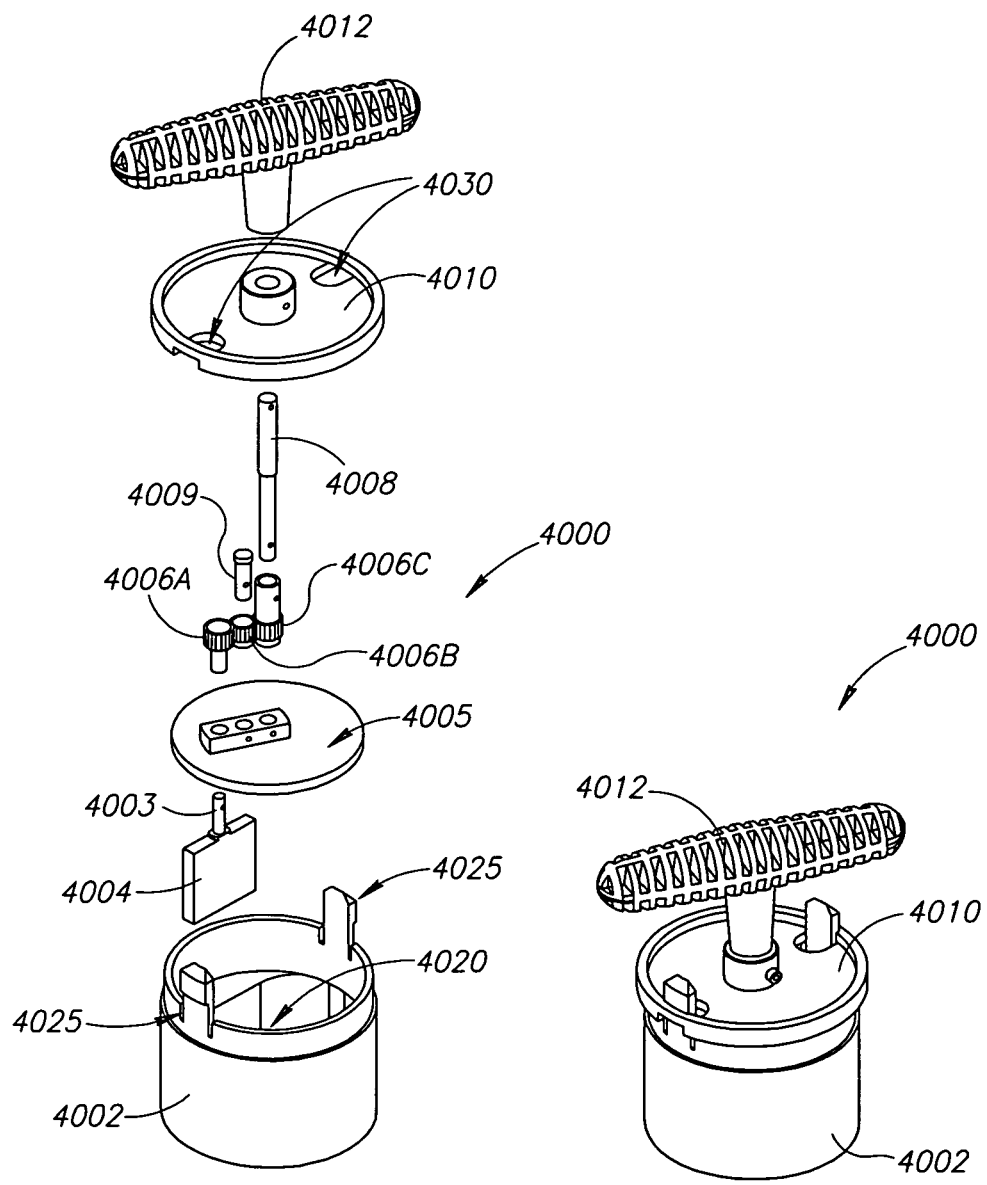
FIGS. 14A and 14B are exploded and perspective views respectively of an exemplary apparatus for mixing viscous material, in accordance with some embodiments of the invention.

FIGS. 14A-14B illustrate an exemplary high shearing force mixing apparatus 4000 adapted for mixing a viscous mixture according to an exemplary embodiment of the invention.

FIG. 14A is an exploded view of apparatus 4000 and FIG. 14B is a perspective view of the same apparatus after assembly. In an exemplary embodiment of the invention, apparatus 4000 is used for mixing the components of high viscosity bone cement.

In an exemplary embodiment of the invention, mixing apparatus 4000 comprises a container 4002, a mixing paddle 4004, a revolving plate 4005, gears 4006, axles 4008 and 4009, a cover 4010, and a handle 4012. In an exemplary embodiment of the invention, mixing element 4004 has a large surface area of 400, optionally 600, optionally 800, optionally 1000 mm$^2$ or intermediate or greater values. Optionally, mixing paddle 4004 is slotted or has holes distributed on its surface. Optionally, during operation mixing implement 4004 applies large shearing forces to a viscous mixture in well 4020. Optionally the large shearing force assures complete mixing of a liquid phase and a solid phase (e.g. powder or beads).

In an exemplary embodiment of the invention, paddle 4004 is "wiped" on walls of container 4020. Optionally, shearing forces and stresses may vary with velocity of the revolving and/or paddle surface area and/or cement volume and/or cement viscosity.

In an exemplary use scenario of mixer 4000, the cement components are inserted into a mixing well 4020 of container 4002. The cement components will typically initially include a solid phase (e.g. polymer beads or powder) and a liquid phase.

In an exemplary embodiment of the invention, closing cover 4010 by lowering it onto container 4002 so that tabs 4025 are engaged by slots 4030 prevents rotation of cover 4010 with respect to container 4002. Optionally, other rotational locking means are employed.

Revolution of handle 4012 turns axle 4008 and causes revolution of gears 4006A, 4006B and 4006C. In an exemplary embodiment of the invention, axle 4008 is rotated by an electric motor, optionally a battery powered motor.

Mixing element 4004 is attached via its axle 4003 to gear 4006A located on revolving plate 4005. When axle 4008 is turned, it causes revolution of gears 4006A, 4006B and 4006C.

Revolution of revolving plate 4005 causes axle 4003 of mixing element 4005 to revolve about a center of mixing well 4020. The revolution without rotation of mixing paddle 4004 causes the mixing element to press the mixture against each of the four wells of mixing well 4020 in turn. In an exemplary embodiment of the invention, this mixing pattern reduces an amount of un-mixed material on inner walls of well 4020.

Figure 14C:
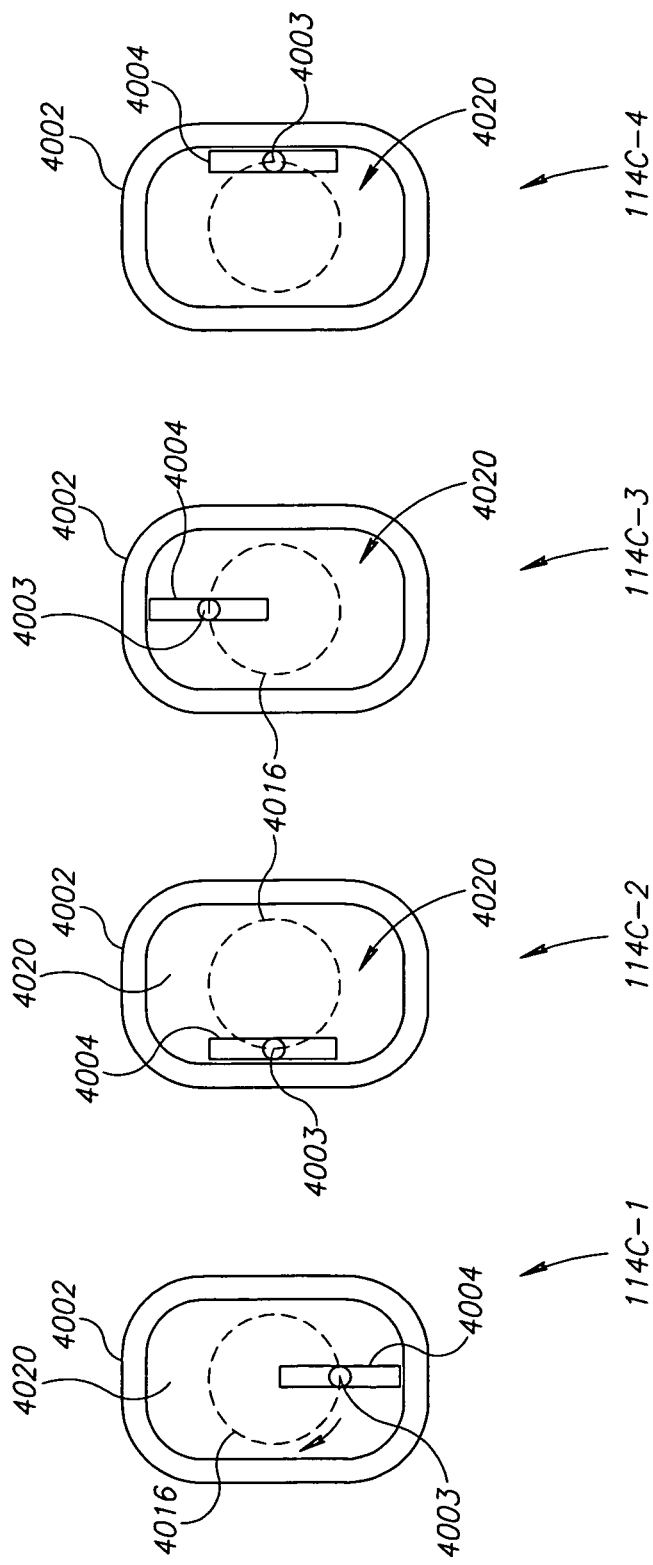

FIGS. 14C1; 14C2; 14C3 and 14C4 are top views of mixing well 4020. The described sequential views of paddle 4004 describe how the apparatus successively presses material against walls of the mixing well. In an exemplary embodiment of the invention, axle 4003 moves along round path 4016. Gears 4006A; 4006B and 4006C assure that paddle 4004 does not rotate around axis 4003. Thus, each of the four sides of the paddle 4004 always faces the same direction (relative to walls of mixing well 4020). In an exemplary embodiment of the invention, paddle 4004 revolves without rotation because gears 4006A and 4006C each have the same number of teeth. Gear 4006B is interposed between gears 4006A and 4006C to cause them to turn in a same direction. Optionally, gear 4006B has any desired number of teeth.

As illustrated in FIG. 14C1, as the paddle 4004 moves from the bottom wall towards the left wall, it applies pressure to a portion of the mixture located near the left wall presses it against the left wall of mixing well 4020 (FIG. 14C-2). The material being mixed tends to escape towards the upper and lower walls of well 4020. As paddle 4004 continues along its path (FIGS. 14C-3) it contacts the upper wall of well 4020 and then presses the mixture against the right wall (FIG. 14C-4) of well 4020. This mixing pattern provides constant flow of the material being mixed and homogeneous mixing of the mixture components, even at high viscosity.

Mixing apparatus 4000 may be constructed of a wide variety of materials. A choice of construction materials optionally considers the particular type of bone cement to be mixed, its chemical characteristics and/or viscosity. In an exemplary embodiment of the invention, mixing well 4020 and/or container 4002 are constructed at least partially of polypropylene and/or nylon. In an exemplary embodiment of the invention, paddle 4004 and/or axle 4003 are constructed of stainless steel. Gears 4006A, 4006B and 400C are optionally constructed of plastic and/or metal.

Once mixing is complete, cover 4010 can be opened and the mixed contents can be removed from mixing well 4020.

Transfer of Viscous Material

In an exemplary embodiment of the invention, mixed viscous bone cement is removed from mixing well 4020 and transferred to a reservoir of a delivery system. Optionally, the reservoir is a cement reservoir as described hereinabove. Optionally, the mixing well serves as a cement reservoir.

In an exemplary embodiment of the invention, viscous bone cement is manually manipulated into a delivery system reservoir. Optionally, manual transfer includes shaping. In an exemplary embodiment of the invention, viscous bone cement is manually shaped so that it roughly conforms to a configuration of a delivery reservoir. For example, the viscous material may be rolled into a roughly cylindrical form with a diameter slightly smaller than a delivery reservoir into which the material is to be introduced. In an exemplary embodiment of the invention, manual transfer includes use of a tool. For example, viscous bone cement is packed into a delivery reservoir using a tool. Optionally, the tool is a rod.

In an exemplary embodiment of the invention, viscous bone cement is transferred to a delivery reservoir via an aperture in mixing well 4020. Optionally, the aperture is a lateral aperture in a wall of well 4020. Optionally, the same aperture is used to introduce cement into well 4020. In an exemplary embodiment of the invention, the aperture includes a connector connectable to the delivery system reservoir. Optionally, the connector connects the mixing apparatus to the delivery system reservoir while the mixing apparatus operates.

Transfer Apparatus

FIGS. 18, 19, 20 and 21 illustrate an exemplary embodiment of a transfer apparatus 5000 for loading a viscous material into a container. In an exemplary embodiment of the invention, the container is a cement reservoir and the material is a viscous bone cement.

Figure 18:
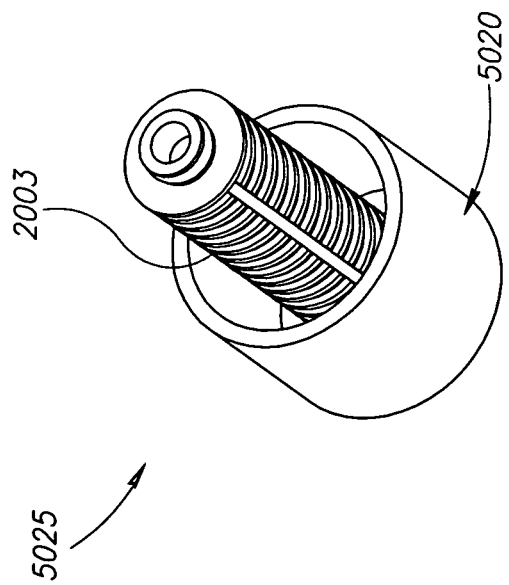

FIG. 18 illustrates cement reservoir 2003 assembled into a transfer piston 5020 to form a transfer assembly 5025.

Figure 19:
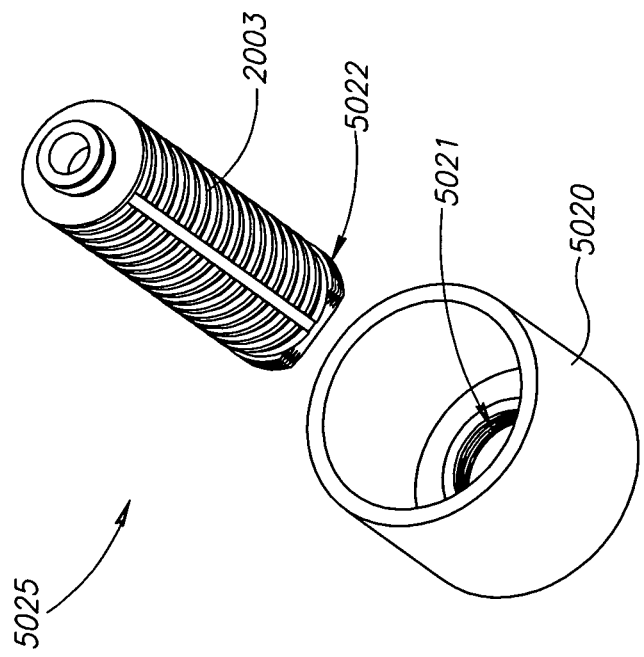

FIG. 19 illustrates that assembly of cement reservoir 2003 and transfer piston 5020 is optionally by means of matched threads 5021 and 5022.

FIG. 21 illustrates assembly of transfer assembly 5025 into a container 5011 of a mixing apparatus. Not pictured is the viscous material (optionally bone cement) in container 5011.

Transfer assembly 5025 is seated in container 5011 so that reservoir 2003 faces outwards. Cover 5030 is optionally applied to container 5011, for example using threads 5031 so that reservoir 2003 protrudes from hole 5032 as seen more clearly in FIG. 20.

Application of pressure to reservoir 2003 and/or an upper edge of piston 5020 causes piston 5020 to descend into container 5011. In an exemplary embodiment of the invention, cover 5030 applies pressure to upper edge of piston 502*o* as it is attached to container 5011. Cement in container 5011 is displaced upwards into reservoir 2003. When the reservoir is sufficiently filled, it is removed from piston 5020. In an exemplary embodiment of the invention, the reservoir is transferred to a delivery system as described hereinabove.

Figure 22:
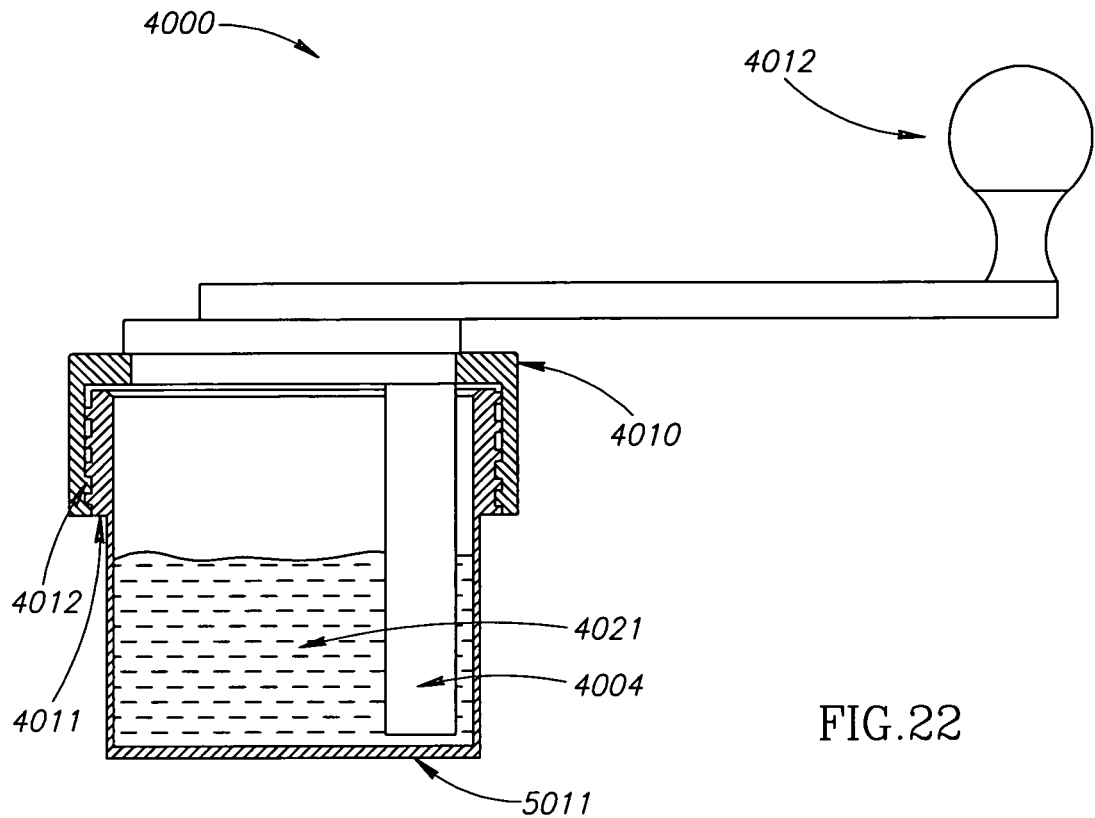
FIGS. 22; 23; 24; 25 and 26 illustrate an additional exemplary embodiment of a transfer apparatus.

FIGS. 22; 23; 24; 25 and 26 illustrate an exemplary embodiment of the invention in which container 5011 is a mixing well of a mixer 4000.

FIG. 22 is a cross sectional view of the mixer containing cement 4021. Cover 4010 is held in place by mated threads 4011 and 4012.

Figure 23:
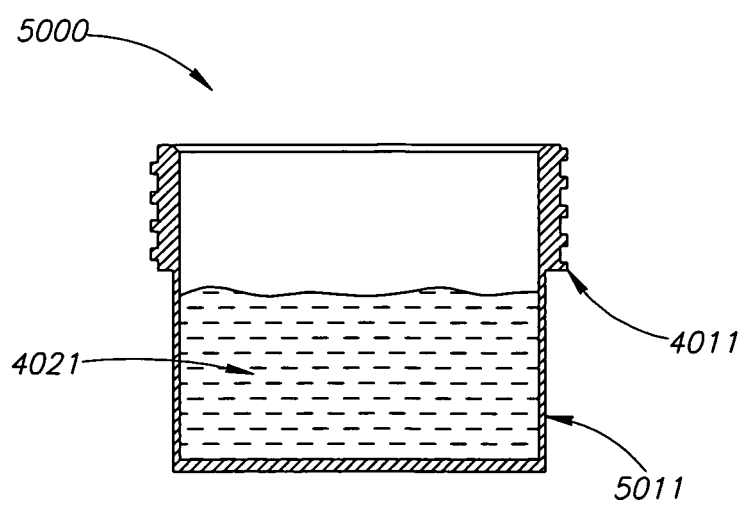

FIG. 23 is a cross sectional view of the mixer containing cement 4021 with cover 4010 removed. Mixing well 5011 becomes the basis for transfer apparatus 5000.

Figure 24:
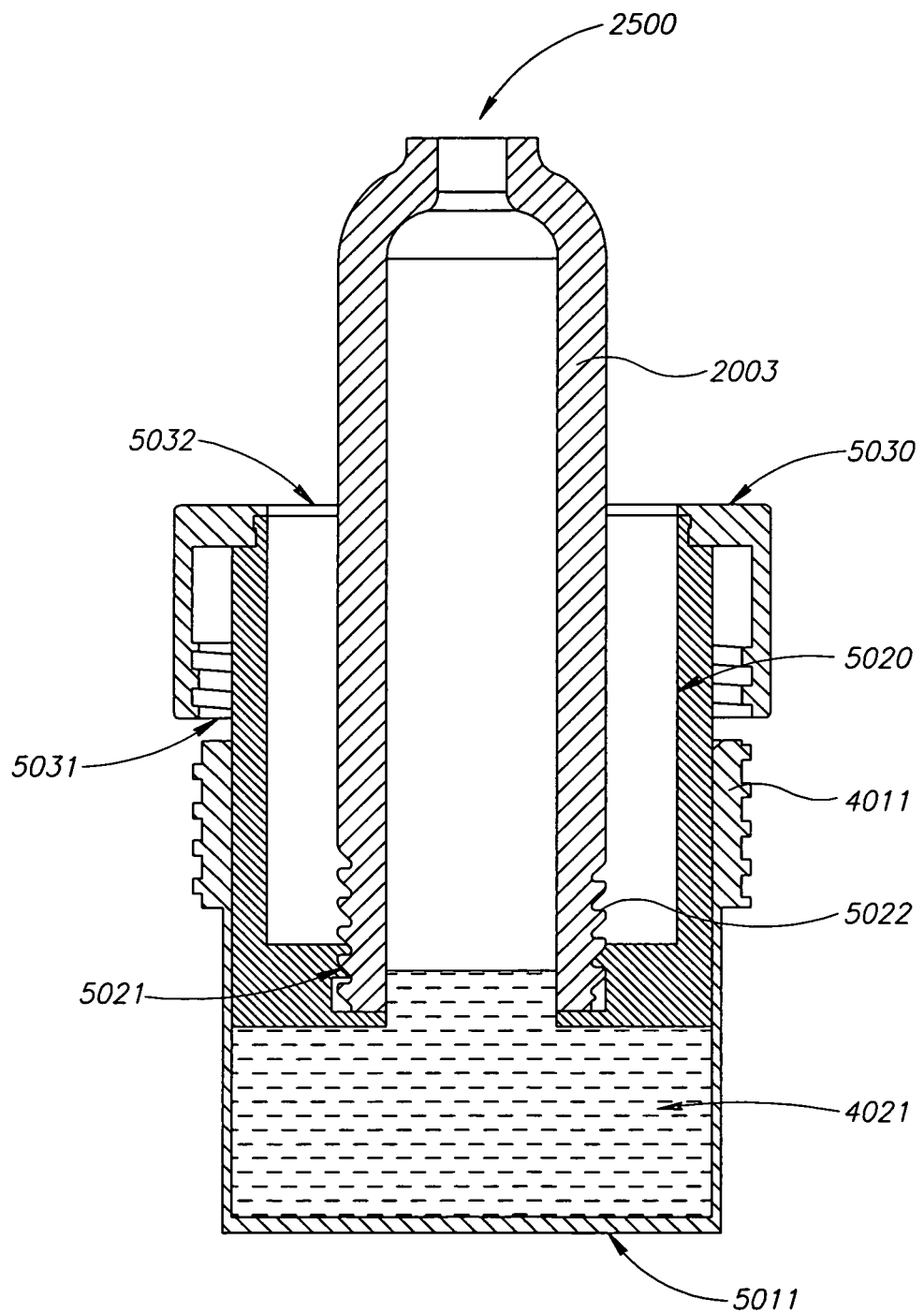
Figure 25:
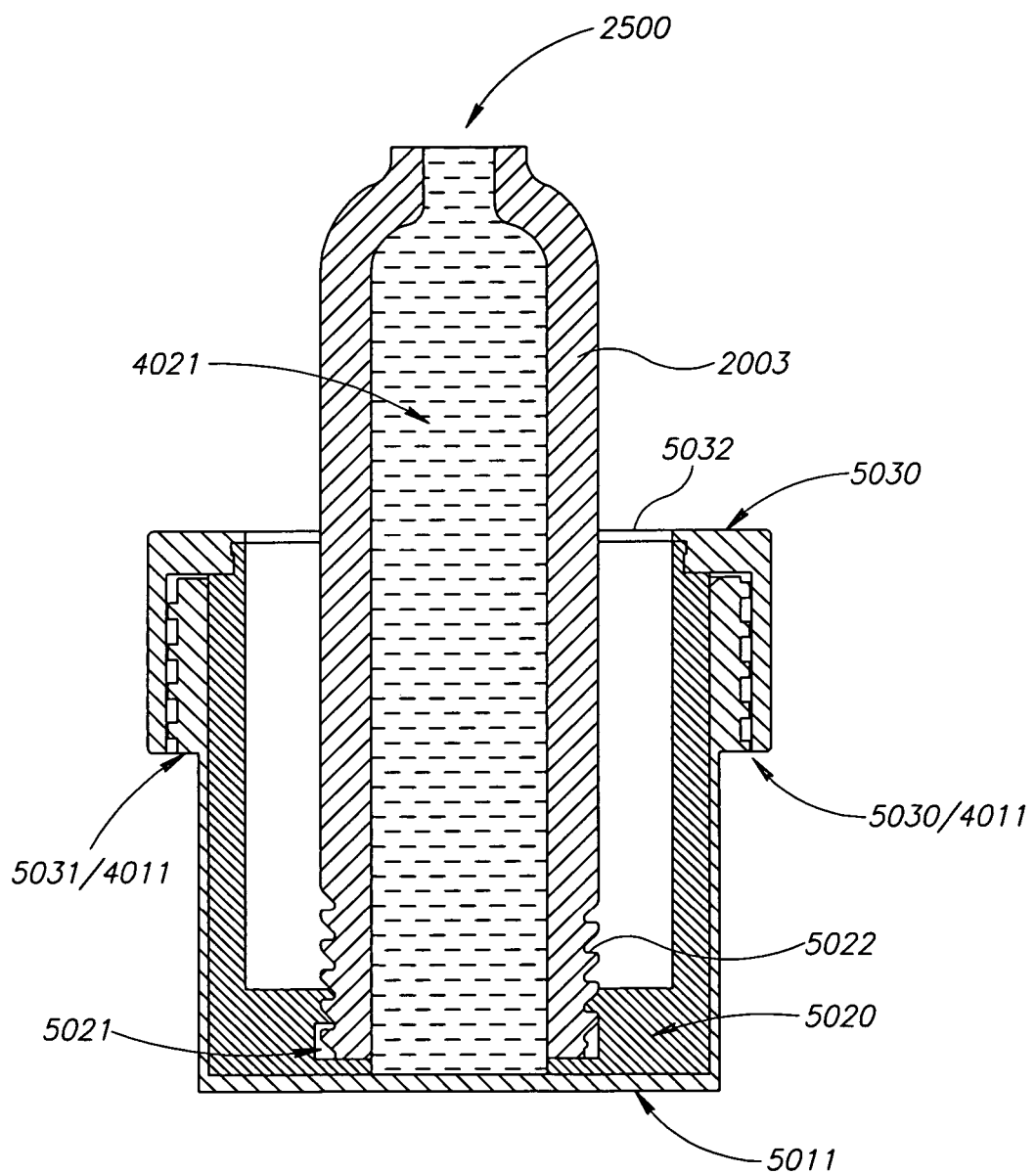

FIGS. 24 and 25 are cross sectional views illustrating assembly of cement reservoir 2003 into transfer piston 5020. Optionally, assembly is via mated threads 5022 of reservoir 2003 and 5021 of transfer piston 5020. Cover 5030 is optionally employed to force transfer piston 5020 downwards into mixing well 5011. Cover 5030 may be threaded onto mixing well 5011 via complementary threads 5031 and 4011. In an exemplary embodiment of the invention, cover 5030 is screwed onto well 5011 to force piston 5020 downwards onto cement 4021.

FIG. 25 illustrates that downward motion of piston 5020 forces cement 4021 to rise upwards into reservoir 2003 towards aperture 2500.

Figure 26:
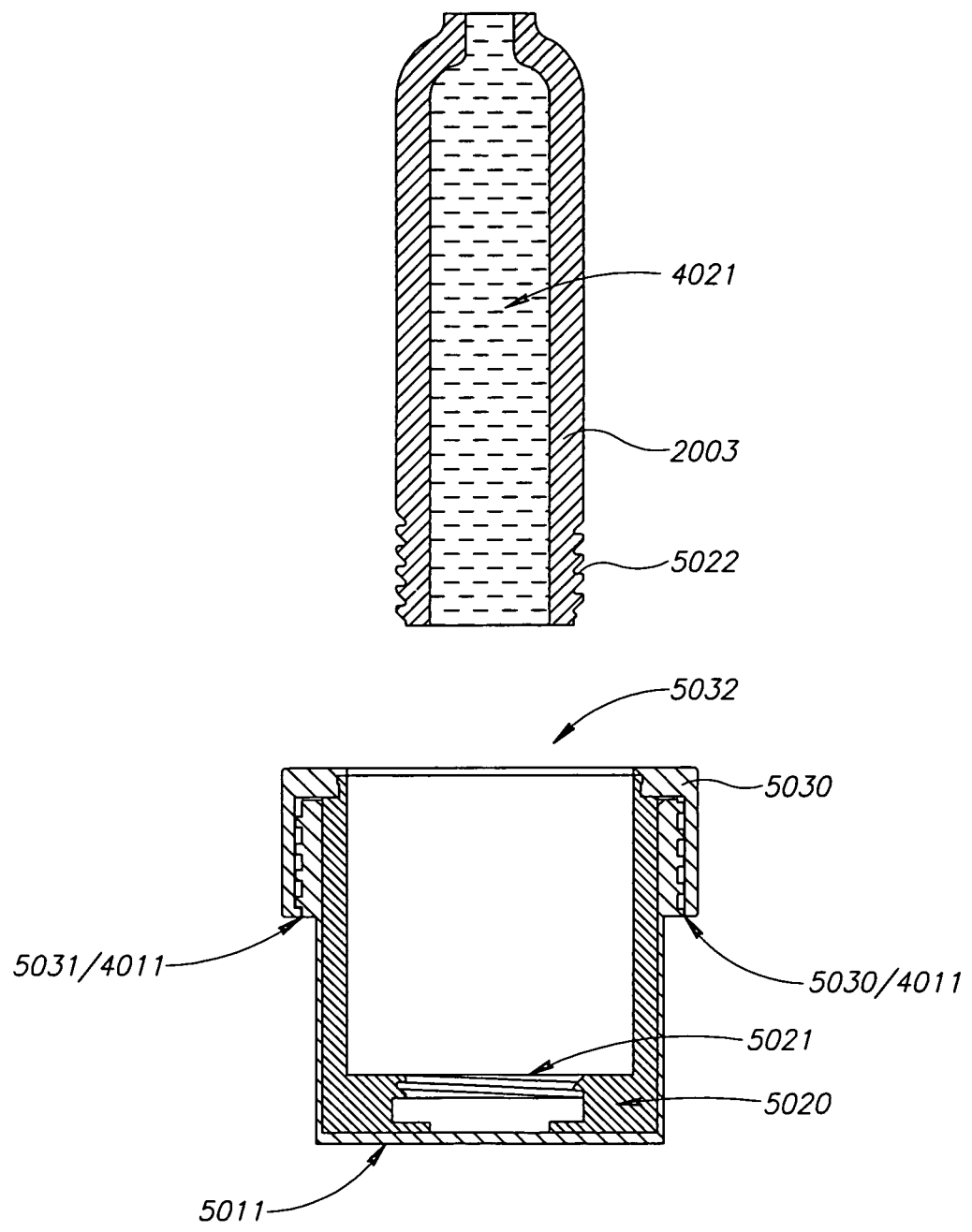

FIG. 26 illustrates removal of reservoir 2003 filled with cement 4022 by disengagement of threads 5022 from matching threads 5021. Optionally, a floor of mixing well 5011 and/or a base of transfer piston 5020 are not straight. In an exemplary embodiment of the invention, this reduces an amount of residual cement in well 5011 after transfer.

Optional Additional Therapy

In an exemplary embodiment of the invention, the provision of material is enhanced by additional therapy. Optionally, the additional therapy comprises thermal therapy. Optionally, the material is pre-heated or pre-cooled. Optionally, the pre-heating or pre-cooling also serves a purpose of controlling the material properties and/or setting behavior.

In an exemplary embodiment of the invention, the heating is by contact heat (conduction) or by radiofrequency energy or light, for example a flash lamp or a laser source. Alternatively or additionally, the delivery system radiates heat. Optionally, a microwave or other wireless heating method is used.

Optionally, heating is provided separately from material provision. In one example, a heated guidewire is provided into the vertebra. Optionally, the guidewire extends one or more protrusions, to guide thermal energy into the nearby tissue. Optionally, a thermal sensor is provided to control the temperature in the vertebra and/or prevent over heating.

In an exemplary embodiment of the invention, temperature control is applied to increase the handling and/or working time of the bone cement. Optionally, a temperature control unit operates on cement in an external reservoir and/or cement in a delivery system reservoir. In an exemplary embodiment of the invention, the temperature control unit includes a resistive coil powered by an electric power source, optionally a battery.

Exemplary Materials

Various materials are suitable for use with exemplary embodiments of the invention. Some of the materials which can be used in some embodiments of the invention are known materials, for example, PMMA, however, they may be used at unusual conditions, for example at a semi-hardened condition. Also, while putty materials may be known, they are not typically used for injection through a small bore into bone.

It should be noted that while specific examples are described it is often the case that the material composition will be varied to achieve particular desired mechanical properties. For example, different diagnoses may suggest different material viscosities.

In an exemplary embodiment of the invention, for non-hardening materials, the material can be allowed to set outside the body. After such setting the material may be washed or ventilated. In this manner, some materials with potentially hazardous by-products can be safely mixed and then used in the body. Optionally, a material is tested to make sure toxic byproducts are removed to below a safety threshold. Optionally, a testing kit is provided with the delivery system.

In an exemplary embodiment of the invention, the material is selected so that its mechanical properties match the bone in which it will be implanted. In an exemplary embodiment of the invention, the material is matched to healthy or to osteoporotic trabecular bone. Optionally, the mechanical properties of the bone are measured during access, for example, based on a resistance to advance or using sensors provided through the cannula or by taking samples, or based on x-ray densitometers measurements.

In general, PMMA is stronger and has a higher modulus than trabecular bone. For example, Trabecular bone can have a strength of between 3-20 megapascal and a Young modulus of 100-500 megapascal. Cortical bone, for example, has strength values of 170-190 gigapascal and Young modulus of 13-40 gigapascal. PMMA typically has values about half of Cortical bone.

In an exemplary embodiment of the invention, the material is selected to be less than 120% as strong and/or young modulus as the expected bone to be treated. Optionally, the values of one or both of strength and young modulus are 10%, 20%, 30%, 40% or less reduced from that of trabecular bone. It should be noted that if less of the vertebra is filled, the injected material will be supported, at least in part, by trabecular rather than cortical bone, depending for example on the method of filing of interior 308.

Exemplary Non-Hardening Material

In an exemplary embodiment of the invention, the material used is a putty like material. One example of a putty-like material is a hydroxyapatite with an increased ratio of sodium alginate. For example, the increased ratio can be 8% or 10%. While this material does harden in the body, it does not set to a hardened condition absent humidity. Thus it can be prepared ahead of time and pre-stored in a delivery system, for example by a manufacturer. In an exemplary embodiment of the invention, the added material slows down water absorption so that while sufficient water enters the material to initiate setting, not enough enters to cause dissolution. An example of this material is described in Ishikawa et al., "Non-decay fast setting Calcium phosphate cement: Hydroxyapatite putty containing an increased amount of sodium alginate", J Biomed Mater Res 36 1997, 393-399, the disclosure of which is incorporated herein by reference. More details may be found in "Effects of neutral sodium hydrogen phosphate on setting reaction and mechanical strength of hydroxyapatite putty", by Kunio Ishikawa, Youji Miyamoto, Masaaki Takechi, Yoshiya Ueyama, Kazuomi Suzuki, Masaru Nagayama and Tomohiro Matsumura, in J Biomed Mater Res, 44, 322-329, 1999, the disclosure of which is incorporated herein by reference.

Other calcium derivative cements, bone chips and/or fillers may be used as well. Bone chips, depending on processing may have a limited shelf life. Some of these materials generally harden (or combine with bone growth) after a relatively long time, such as more than a week, more than a month or more than 3 months.

Additional Exemplary Non-Hardening Material

Figure 13:
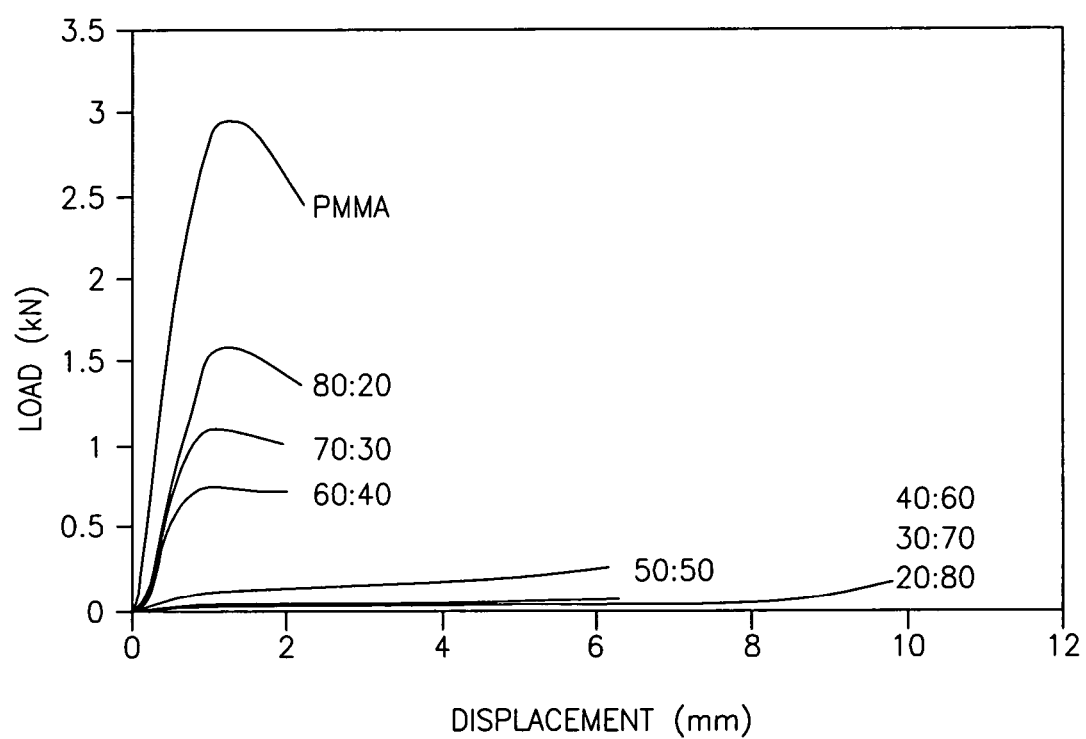
FIG. 13 is a graph showing compressibility of a material in accordance with an exemplary embodiment of the invention.

In an exemplary embodiment of the invention, the material used is a mixture of LMA (lauryl methacrylate) and MMA (methyl methacrylate). Depending on the ratio used, different mechanical properties and viscosities can be achieved. FIG. 13 is a graph showing the relative viscosities of PMMA and various ratios of the copolymer material. In the example shown, as the ratio of LCA decreases, viscosity goes down.

Diblock copolymers of MMA and LMA were synthesized by anionic polymerization using DPHLi as initiator in THF at −40° C. with the sequential addition of monomers. The molecular weight distribution of the polymers was narrow and without homopolymer contamination when LMA was added to living PMMA chain ends.

In an exemplary embodiment of the invention, the ratio used are 80:20, 70:30, 60:40, 50:50, 30:70, 20:80 or intermediate, smaller or larger ratios (by volume).

Experiment: Materials and Methods

Starting Materials

Medicinal distillate methyl methacrylate and lauryl methacrylate stabilized with 10-100 ppm of the monomethyl ether of hydroquinone were used as received from Fluka, Germany. Benzoyl peroxide (BPO) was purchased from BDH Chemicals, England. N Barium sulfate (BS) was obtained from Sigma-Aldrich (Israel). All solvents were analytical-grade from Biolab (Jerusalem, Israel) and were used as received.

Polymerization

Polymerization reactions were carried out in a single necked round bottom flask equipped with a magnetic stirring. In a typical reaction, 60 ml MMA (0.565 mol), 50 ml LMA (0.137 mol), 220 mg of Benzoyl Peroxide (0.9 mmol), and 100 ml THF were transferred. The amount of BPO was adjusted to each of the compositions according to the total amount of the monomer's mols. The amount of the THF was equal to the total volume of the monomers (table 1). The content was heated to a polymerization temperature of 70-75° C. for 20 hours, then the solution was precipitated in sufficient amount of methanol and left to mix for four hours. Finally, the polymer was dried in an oven at 110° C. under vacuum.

TABLE 1 copolymers composition

| Copolymer (MA:LMA) | MA (ml/mol) | LMA (ml/mol) | BPO (mg/mol) | THF (ml) |
|---|---|---|---|---|
| 100:0 | 100 (0.94) | 0 (0) | 285 (1.18) | 100 |
| 80:20 | 80 (0.75) | 20 (0.07) | 258 (1.06) | 100 |
| 70:30 | 70 (0.66) | 30 (0.10) | 239 (0.99) | 100 |
| 60:40 | 60 (0.56) | 40 (0.14) | 220 (0.9) | 100 |
| 50:50 | 50 (0.47) | 50 (0.17) | 201 (0.83) | 100 |
| 40:60 | 40 (0.38) | 60 (0.20) | 182 (0.75) | 100 |
| 30:70 | 30 (0.28) | 70 (0.24) | 163 (0.67) | 100 |
| 20:80 | 20 (0.19) | 80 (0.27) | 144 (0.6) | 100 |
| 0:100 | 0 (0) | 100 (0.34) | 107 (0.44) | 100 |

The dried polymer was milled to a fine powder (Hsiangtai Sample mill, model sm-1, Taiwan) and mixed with barium sulfate (30% w/w). The mixture was heated in a glass inside a sand bath to 140° C., until melting of the polymer. The mixture left to cool, and milled again. This procedure was repeated at least three times, until a homogeneous off-white polymer was received, which could be melted into loadable slugs for the delivery systems and magazines described above.

Characterization

Molecular weight and polydispersity were analyzed by Gel permeation chromatography, GPC system consisting of a Waters 1515 isocratic HPLC pump with a Waters 2410 refractive-index detector and a Rheodyne (Coatati, Calif.) injection valve with a 20-µL loop (Waters Ma). The samples were eluted with $CHCl_3$ through a linear Ultrastyragel column (Waters; 500-Å pore size) at a flow rate of 1 mL/min.

$^1$H-NMR spectra were recorded on a Varian 300 MHz instrument using $CDCl_3$, as solvents. Values were recorded as ppm relative to internal standard (TMS).

A Cannon 1C A718 Ubbelhold viscometer was used for the viscosity measurements of the polymer. The measurements were performed at 30° C. with toluene as a solvent.

Water Absorption Capacity.

Swelling behavior of acrylic bone cements was carried out from accurately weighed films of 0.8 mm thickness. Films were introduced in 0.9 wt % NaCl solution (20 ml) and kept at 37° C. The water sorption kinetics in 20 ml saline solution were evaluated in two specimens of each bone cement (containing 30% barium sulphate).

Equilibrium gain was determined gravimetrically at different periods of time. The uptake of water was recorded at 30 min intervals in the beginning and spacing out these intervals until the equilibrium was attained. At appropriate times, the samples were removed, blotted with absorbent paper to remove the water attached on its surface and weighed. The percentage of Equilibrium gain was obtained from each specimen using the following expression:

$$\text{Hydration degree (\%)} = \frac{\text{Weight of swollen specimen} - \text{initial weight of specimen}}{\text{initial weight of specimen}} \times 100$$

Results:

100% PMMA: Average 1.845% (+0.045)

Initial weight (g) 0.2156 and 0.2211

Weight of specimen at equilibrium (g) 0.2195 and 0.2253

Equilibrium gain (%): 1.8 and 1.89;

60% PMMA, 40% PLMA: Average 1.65%(+0.235)

Initial weight (g): 0.1161 and 0.1402

Weight of specimen at equilibrium (g) 0.1183 and 0.1422

Equilibrium gain (%): 1.42 and 1.89;

50% PMMA, 50% PLMA: Average: 1.02% (+0.28)

Initial weight (g): 2700 and 0.2371

Weight of specimen at equilibrium (g) 0.2720 and 0.2400

Equilibrium gain (%): 0.74 and 1.3;

Compression Testing

These tests were conducted using an Instron 4301 universal testing machine provided with a load cell of 5 kN, and at a cross-head speed of 20 mm/min. A known weight of polymer was melted in a glass inside a sand bath. The bath was heated at 150° C. for two hours, and then barium sulfate was added (30% w/w) and mixed well several times, until homogenous dough was received. Cylindrical specimens of 6 mm in diameter and 12 mm high were prepared by forcing the melted copolymers into the holes of a Teflon mold. One side of the mold was covered with Teflon plates and secured with clamps. The specimens were cooled for 20 minutes in the mold, then the upper side was cut to the mold shape, and the specimens removed from the mold, finished to a perfect cylindrical shape. The test took place at least 1 week after aging in air at 23±1° C. For each cement composition, six specimens were tested. The elastic modulus and the maximal strength force were obtained.

Results:

Molecular Weights and Viscosity Measurement

The number and weight average molecular weights of poly (La-MA), poly (MMA) and their copolymers were obtained from gel permeation chromatography. The polydispersity index varies in the range of 1.6 to 2.87. The viscosities of the polymers are obtained using Toluene as solvent at 25° C. The intrinsic viscosities ($\eta$) were obtained by extrapolating $\eta_{sp} c^{-1}$ to zero concentration. The molecular weights and viscosities are presented in Table II.

TABLE II

| Feed Ratio | | GPC analysis of polymers | | | |
|---|---|---|---|---|---|
| MMA:LMA Vol.-% (mol-%) | NMR Analysis [MMA]:[LMA] | $M_n$ | $M_w$ | Polydispersity | [$\eta$] |
| 100:0 (100:0) | 100:0 | 65190 | 119544 | 1.833 | 0.544 |
| 8:2 (91.5:8.5) | [88]:[12] | 69118 | 119194 | 1.724 | 0.421 |
| 7:3 (87:13) | 87:13 | 63006 | 112442 | 1.78 | 0.393 |
| 6:4 (84:16) | 84:16 | 73295 | 118384 | 1.615 | 0.366 |
| 1:1 (74:26) | 69:31 | 94167 | 135880 | 1.44 | 0.351 |
| 4:5 (69:31) | 70:30 | 55455 | 104711 | 1.888 | 0.316 |
| 4:6 (64:36) | 62:38 | 75648 | 134745 | 1.781 | 0.305 |
| 3:7 (56:44) | 56:44 | 35103 | 79986 | 2.27 | 0.221 |
| 2:8 (40:60) | 40:60 | 23876 | 68720 | 2.87 | 0.178 |
| 0:100 (0:100) | 0:100 | 27350 | 75146 | 2.74 | 0.083 |

Compressive Test.

The results of the compressive test are collected in Table III as a function of compressive strength and modulus. The influence on the mechanical behavior of adding lauryl methacrylate monomers can be clearly observed. The introduction of higher percentages produces a decrease that is more pronounced at 50% (v/v) LA. The compressive modulus shows a drastic decrease as the content of LA increases. This drop may be related to the structure modification of the matrix by the introduction of LMA. This drop may also limit the use of some compositions for some applications.

TABLE III

| compression test results | | |
|---|---|---|
| Composition MA:LA (V %) | Max strength (Mpa) | Modulus (Mpa) |
| 1:0 | 106.8 (9) | 2478 (220) |
| 8:2 | 82.5 (17.1) | 1100.7 (129) |
| 7:3 | 63.3 (13.2) | 634.5 (116) |
| 6:4 | 48 (11) | 550 (250) |
| 5:5 | 18.9 (4.5) | 69.6 (20) |
| 4:6 | 1.9 (0.2) | 49.5 (11.8) |
| 3:7 | 19.19 (3.42) | 8.3 (1.2) |
| 2:8 | 0.253 (0.06) | 1.71 (0.417) |

Material Modifications

Optionally, various additives are added to the materials described herein, to modify their properties. The adding can be before setting or after setting, depending on the material. Exemplary materials that can be added include fibers (e.g., carbon nanotubes or glass fibers) of various lengths and thicknesses, aggregates and/or air bubbles.

In an exemplary embodiment of the invention, if the material is manufactured to be anisotropic, it can be advanced into the body in a desired direction, for example, by selecting a delivery path (e.g., storage, tube, aperture) to reduce twisting and/or deformation. Optionally, such materials are provided as short units (FIG. 8).

Softening and Semi-hardening Materials

In an exemplary embodiment of the invention, the material used softens after provision into the body. In an exemplary embodiment of the invention, the material comprises an additive that disperses or weakness in water or body fluids, for example, salt. A softening material may be useful if the forces required for height restoration are smaller than the forces required for maintaining height. Softening times are optionally controlled by mixing in a gel material which slows down water penetration into the extruded material.

Semi-Hardening Materials

In an exemplary embodiment of the invention, the material used sets to non-hardened condition. In an exemplary embodiment of the invention, the material comprises MMA, LMA and NMP. NMP solvates in water, allowing the material to set somewhat. In an exemplary embodiment of the invention, a hardened condition is avoided, possibly preventing the induction of fractures in nearby vertebra.

Use of Hardening Materials

In an exemplary embodiment of the invention, the above described devices (e.g., delivery) are used with a material which sets to a hardened condition, for example, PMMA or other bone cements and fillers. In an exemplary embodiment of the invention, the material is provided in a kit that includes a timer and/or a viscometer, so that an operator can estimate the workability and viscosity of the material and its usefulness for height restoration without leakage. Optionally, the time includes a temperature senor and provides an estimate of workability time based on the temperature and the time the components of the PMMA were mixed.

In an exemplary embodiment of the invention, the cement includes an acrylic polymer, such as polymethylmethacrylate (PMMA). Optionally, the polymer is supplied as beads. Optionally, styrene may be added. In an exemplary embodiment of the invention, a monomer (e.g. methylmethacrylate; MMA) is mixed with the polymer beads.

In general bone cements polymerize by radical-initiated addition reactions. In an exemplary embodiment of the invention, the cement is prepared from two separate components: a powder component containing prepolymerized beads (e.g. of PMMA or a PMMA/styrene copolymer) and a liquid component containing monomers (e.g. MMA).

In an exemplary embodiment of the invention, an intiator (e.g. benzoyl peroxide (BPO) is incorporated into the powder and a chemical activator (e.g. DMPT) is incorporated into the liquid. Optionally, an easily oxidized molecule (e.g. hydroquinone) is added to the liquid component to prevent spontaneous polymerization during storage.

Optionally, cement may be rendered radiopaque, for example by adding a radio-opaque material such as adding barium sulfate and/or zirconium compounds to the powder and/or liquid component.

Optionally, the average molecular weight of PMMA in all beads is 80,000, optionally 100,000, optionally 120,000, optionally 140,000, optionally 160,000, optionally 180,000 Dalton or intermediate or lesser or greater values. In an exemplary embodiment of the invention, the average molecular weight PMMA in all beads is approximately 110,000 Dalton. Optionally, at least some of the beads include styrene. In an exemplary embodiment of the invention, styrene is added to PMMA beads in a volumetric ratio of 5-25%.

In an exemplary embodiment of the invention, at least some beads contain polymer (e,g. PMMA and/or styrene) with a higher molecular weight, Optionally, the higher molecular weight is 600,000, optionally 900,000, optionally 1,100,000 Dalton or intermediate or lesser or greater values. Optionally, polymer beads (e,g. PMMA and/or styrene) with the higher molecular weight comprise 0.25%, 0.5%, 1%, 2%, 3%, 4%, 5% or intermediate or lesser or higher of the total bead population. In an exemplary embodiment of the invention, this type of formulation provides a cement characterized by a short mixing_time and/or a cement which achieves a viscosity of 500 to 900 Pascal-second in 2 to 3 minutes from the beginning of mixing and/or which remains sufficiently flowable for injection for at least 6 to 10 minutes.

In an exemplary embodiment of the invention, higher molecular weight PMMA in the polymer beads cause the mixture to achieve a flowable plastic phase earlier than previously available cements and/or to remain in the flowable plastic phase longer than previously available alternatives. Optionally, altering the percentage of higher molecular weight PMMA in the polymer beads alters a viscosity profile of the resultant mixture.

Optionally, at least one bead of PMMA has molecular weight in the range of 700,000 Dalton to 1,000,000 Dalton. In an exemplary embodiment of the invention, approximately 3% of the beads have PMMA characterized by a molecular weight in this range.

In an exemplary embodiment of the invention, a setting material is formulated to have a high viscosity for a working window of significant duration, for example, 2, 4, 5, 8, 10 or intermediate or more minutes.

In an exemplary embodiment of the invention, the following formulation is used: a set of beads formed of PMMA/Styrene of diameter 10-200 microns and an amount of 20 cc MMA per 9.2 grams beads. In an exemplary embodiment of the invention, MMA solvates and/or encapsulates the beads and the viscosity of the mixture remains high, at the beginning due to the solvation and friction between the beads and later, as the beads dissolve, due to the progressing of polymerization. The beads may also be provided in a mixture comprising a range of sizes. It should be noted that the properties of the materials may be selected to improve a viscosity working window, even if strength of the final cement is compromised.

In an exemplary embodiment of the invention, the working viscosity is set by selecting the bead size and/or material ratios and/or molecular weights of polymer provided in the beads.

In an exemplary embodiment of the invention, the working viscosity is influenced by the presence of particles of hardened acrylic polymer added to the mixture.

Mechanical Viscosity Increasing Agents

In an exemplary embodiment of the invention, the cement includes particles characterized by a large surface which do not participate in the polymerization reaction. Examples of materials suitable for use as particles characterized by a large surface are which do not participate in the polymerization reaction include, but are not limited to Zirconium, hardened acrylic polymer and bone. Optionally, the particles characterized by a large surface which do not participate in the polymerization reaction are not X-ray transparent so that they aid in visualization of injected cement. In an exemplary embodiment of the invention, the large surface area particles impart added viscosity to the cement mixture independent of polymerization. Optionally, the added viscosity comes from friction of particles against one another in the cement.

Polymerization Reaction Kinetics

In an exemplary embodiment of the invention, mixture of polymer and monomer components produces a material with a viscosity in the range 500 to 900 Pascal-second within 120, optionally within 100, optionally within 60, optionally within 30, optionally within 15 seconds or lesser or greater or intermediate times. In an exemplary embodiment of the invention, once a high viscosity is achieved, the viscosity remains stable for 5 minutes, optionally 8 minutes, optionally 10 minutes or lesser or intermediate or greater times. In an exemplary embodiment of the invention, stable viscosity indicates a change of 10% or less in two minutes and a change of 20% or less in 8 minutes. The time during which viscosity is stable provides a window of opportunity for performance of a medical procedure.

Material with a Glass Transition Temperature

In an exemplary embodiment of the invention, a bone cement includes a material characterized by a glass transition temperature higher than 37 degrees Celsius. Heating such a material above its glass transition temperature, weakens the material. The weakening transforms the material to a dough-like or putty-like state. In an exemplary embodiment of the invention, the dough-like material is suitable for delivery using a delivery system as disclosed herein. After delivery, the dough cools to 37 degrees Celsius and hardens. Examples of materials with a glass transition temperature above 37 degrees include, but are not limited to, polycaprolactone (PCL) and/or Polylactic acid (PLA). Polymers with glass transition temperatures suitable for use in the context of the invention are commercially available, for example "Lactel absorbable polymers" (Curect Corp.; Pelham, Ala., USA).

In an exemplary embodiment of the invention, a material with a glass transition temperature above 35, optionally 40, optionally 45, optionally 50, optionally 55, optionally 60 degrees Celsius is selected.

Optionally, the delivery system is heated to maintain the material above the glass tranisition temperature. In an exemplary embodiment of the invention, a heating element is provided in and/or adjacent to the cement reservoir and/or the cannula.

Use of Bone in Bone Cement

In an exemplary embodiment of the invention, the bone cement or other dough-like material includes processed bone (from human or animals origin) and/or synthetic bone. Optionally, the cement has osteoconductive and/or osteoinductive feature. Optionally, the processing of the bone includes grinding. One of ordinary skill in the art will be capable of processing bone using known methods for use in the context of the present invention.

In an exemplary embodiment of the invention, the bone cement comprises 50%, optionally 60% optionally 70% or intermediate or greater percentages of bone powder and/or granules and/or chips.

Additional Implant Devices

Optionally, an implant is also injected into the vertebra, for example, before, during or after injection of the material. Exemplary implants are metal or polymer cage or intra ventricular devices and enclosing mesh or solid bags or balloons. Optionally, bone graft is injected. Optionally, where an implant is provided, the material is extruded through the implant, for example from an axial section thereof in a radial direction.

Optionally, devices such as, for example, those described in PCT applications PCT/IL00/00458; PCT/IL00/00058; PCT/IL00/00056; PCT/IL00/00055; PCT/IL00/00471; PCT/IL02/00077; PCT/IL03/00052; and PCT/IL2004/000508, PCT/IL2004/000527 and PCT/IL2004/000923, the disclosures of which are incorporated herein by reference, are used.

Optionally, the material is extruded into a performed cavity, for example a cavity formed using an inflatable balloon. Optionally, the material is extruded into an inter-vertebral space, for example a disc-space.

Optionally, a material which sets to a hardened condition, for example, PMMA is co-extruded with or extruded before or after material which does not so set. Optionally, the setting material comprises less than 60% of the material, for example, less than 40%, less than 20% or intermediate values.

Other Tissue and General

While the above application has focused on the spine, other tissue can be treated as well, for example, compacted tibia plate and other bones with compression fractures and for tightening implants, for example, hip implants or other bone implants that loosened, or during implantation. Optionally, for tightening an existing implant, a small hole is drilled to a location where there is a void in the bone and material is extruded into the void.

It should be noted that while the use in bones of the above methods and devices provide particular advantages for bone and vertebras in particular, optionally, non-bone tissue is treated, for example, cartilage or soft tissue in need of tightening. Optionally, the delivered material includes an encapsulated pharmaceutical and is used as a matrix to slowly release the pharmaceutical over time. Optionally, this is used as a means to provide anti-arthritis drugs to a joint, but forming a void and implanting an eluting material near the joint.

According to various embodiments of the invention, a bone cement according to the invention is injected into a bone void as a preventive therapy and/or as a treatment for a fracture, deformity, deficiency or other abnormality. Optionally, the bone is a vertebral body and/or a long bone. In an exemplary embodiment of the invention, the cement is inserted into the medullary canal of a long bone. Optionally, the cement is molded into a rod. In an exemplary embodiment of the invention, the rod serves as an intra-medular nail.

It will be appreciated that the above described methods of implanting and treating may be varied in many ways, including, changing the order of steps, which steps are performed more often and which less often, the arrangement of elements, the type and magnitude of forces applied and/or the particular shapes used. In particular, various tradeoffs may be desirable, for example, between applied forces, degree of resistance and forces that can be withstood. Further, the location of various elements may be switched, without exceeding the spirit of the disclosure, for example, the location of the power source. In addition, a multiplicity of various features, both of method and of devices have been described. It should be appreciated that different features may be combined in different ways. In particular, not all the features shown above in a particular embodiment are necessary in every similar exemplary embodiment of the invention. Further, combinations of the above features are also considered to be within the scope of some exemplary embodiments of the invention. In addition, some of the features of the invention described herein may be adapted for use with prior art devices, in accordance with other exemplary embodiments of the invention. The particular geometric forms used to illustrate the invention should not be considered limiting the invention in its broadest aspect to only those forms, for example, where a cylindrical tube is shown, in other embodiments a rectangular tube may be used. Although some limitations are described only as method or apparatus limitations, the scope of the invention also includes apparatus programmed and/or designed to carry out the methods.

Also within the scope of the invention are surgical kits which include sets of medical devices suitable for implanting a device or material and such a device. Section headers are provided only to assist in navigating the application and should not be construed as necessarily limiting the contents described in a certain section, to that section. Measurements are provided to serve only as exemplary measurements for particular cases, the exact measurements applied will vary depending on the application. When used in the following claims, the terms "comprises", "comprising", "includes", "including" or the like means "including but not limited to".

It will be appreciated by a person skilled in the art that the present invention is not limited by what has thus far been described. Rather, the scope of the present invention is limited only by the following claims.

The invention claimed is:

1. A bone cement comprising:
 a first liquid component containing MMA (methyl methacrylate) monomers; and
 a second powder component containing pre-polymerized PMMA (polymethyl methacrylate) beads having an average molecular weight and further containing a population of pre-polymerized PMMA beads having a high molecular weight,
 wherein, the average molecular weight, the high molecular weight, and the percentage of beads having the high molecular weight are selected so that contacting the first component and the second component produces a mixture which achieves a high viscosity during an initial period, has a stable viscosity during a working time, and solidifies after the working time;
 wherein the mixture attains the high viscosity of greater than 900 Pascal seconds within the initial period of about 180 seconds following initiation of mixing of the first liquid component and the second powder component,
 wherein the working time is for at least 5 minutes and the working time follows the initial period;
 wherein the viscosity of the mixture is between 900 Pascal seconds and 2000 Pascal seconds during the working time;
 wherein the viscosity of the mixture changes by less than 200 Pascal seconds during a window of at least 2 minutes after mixing; and
 wherein the mixture is suitable for in-vivo use.

2. The bone cement of claim 1, wherein the working time is at least 8 minutes long.

3. The bone cement of claim 1, wherein the initial period does not exceed 1 minute.

4. The bone cement of claim 1, wherein the initial period is less than 3 minutes and the mixture solidifies after the working time.

5. The bone cement of claim 1, wherein the viscosity of greater than 900 Pascal-second results at least partly from a polymerization reaction.

6. A bone cement comprising:
 a first liquid component containing MMA monomers; and
 a second powder component containing pre-polymerized PMMA beads having an average molecular weight and further containing a population of pre-polymerized PMMA beads having a high molecular weight,
 wherein, the average molecular weight, the high molecular weight, and the percentage of beads having the high molecular weight are selected so that contacting the first component and the second component produces a mixture which has substantially no liquid phase during an initial period, a stable viscosity during a working time, and solidifies after the working time;
 wherein the mixture attains a viscosity greater than 200 Pascal seconds within the initial period of 3 minutes following initiation of mixing of the first liquid component with the second powder component,
 wherein the viscosity of the mixture remains between 200 and 2000 Pascal seconds for a working time of at least 5 minutes after the initial period,
 wherein the viscosity of said cement is changing by less than 10% in a period of 2 minutes within said working time, and
 wherein the mixture is suitable for in-vivo use.

7. The bone cement of claim 1, wherein the initial period does not exceed 2 minutes.

8. The bone cement of claim 1, wherein the mixture produced by contacting the first component and the second component attains a viscosity greater than 1000 Pascal seconds within the initial period.

9. The bone cement of claim 6, wherein the viscosity of the mixture changes by less than 200 Pascal second during a window of at least 2 minutes after mixing.

* * * * *